United States Patent
Lapointe et al.

(10) Patent No.: US 10,344,000 B2
(45) Date of Patent: Jul. 9, 2019

(54) SUBSTITUTED BICYCLIC PYRAZOLE COMPOUNDS AS RORGAMMAT INHIBITORS AND USES THEREOF

(71) Applicant: Merck Sharp & Dohme Corp., Rahway, NJ (US)

(72) Inventors: Blair T. Lapointe, Brookline, MA (US); Peter H. Fuller, Ashland, MA (US); Hakan Gunaydin, Somerville, MA (US); Kun Liu, Needham, MA (US); Danielle F. Molinari, Brookline, MA (US); Qinglin Pu, Boston, MA (US); Mark E. Scott, Edmonton (CA); B. Wesley Trotter, Medfield, MA (US); Hongjun Zhang, Boston, MA (US)

(73) Assignee: Merck Sharp & Dohme Corp., Rahway, NJ (US)

( * ) Notice: Subject to any disclaimer, the term of this patent is extended or adjusted under 35 U.S.C. 154(b) by 0 days.

(21) Appl. No.: 15/770,255

(22) PCT Filed: Oct. 27, 2016

(86) PCT No.: PCT/US2016/059057
§ 371 (c)(1),
(2) Date: Apr. 23, 2018

(87) PCT Pub. No.: WO2017/075178
PCT Pub. Date: May 4, 2017

(65) Prior Publication Data
US 2018/0305320 A1  Oct. 25, 2018

Related U.S. Application Data

(60) Provisional application No. 62/246,918, filed on Oct. 27, 2015.

(51) Int. Cl.
```
C07D 231/56      (2006.01)
C07D 401/04      (2006.01)
C07D 491/052     (2006.01)
C07D 491/107     (2006.01)
A61P 19/02       (2006.01)
A61P 17/06       (2006.01)
A61P 29/00       (2006.01)
A61P 37/02       (2006.01)
A61P 11/06       (2006.01)
C07D 471/04      (2006.01)
```
(52) U.S. Cl.
CPC .......... *C07D 231/56* (2013.01); *A61P 11/06* (2018.01); *A61P 17/06* (2018.01); *A61P 19/02* (2018.01); *A61P 29/00* (2018.01); *A61P 37/02* (2018.01); *C07D 401/04* (2013.01); *C07D 471/04* (2013.01); *C07D 491/052* (2013.01); *C07D 491/107* (2013.01); *A61K 2121/00* (2013.01)

(58) Field of Classification Search
None
See application file for complete search history.

(56) References Cited

U.S. PATENT DOCUMENTS

| | | | |
|---|---|---|---|
| 4,670,447 A | 6/1987 | Strupczewski | |
| 4,751,235 A | 6/1988 | Anderson | |
| 5,583,152 A | 12/1996 | Bernstein et al. | |
| 5,639,780 A | 6/1997 | Lau et al. | |
| 5,985,903 A | 11/1999 | Assmann et al. | |
| 6,020,354 A | 2/2000 | Assmann et al. | |
| 6,037,367 A | 3/2000 | Christensen, IV et al. | |
| 6,133,290 A | 10/2000 | Krushinski, Jr. et al. | |
| 6,160,001 A | 12/2000 | Assmann et al. | |

(Continued)

FOREIGN PATENT DOCUMENTS

| | | |
|---|---|---|
| EP | 0429257 A2 | 5/1991 |
| EP | 0882718 A1 | 12/1998 |

(Continued)

OTHER PUBLICATIONS

U.S. Appl. No. 15/647,437, 4-Heteroaryl Substituted Benzoic Acid Compounds as RORgammaT Inhibitors and Uses Thereof, filed Jul. 12, 2017.

(Continued)

*Primary Examiner* — Kamal A Saeed
(74) *Attorney, Agent, or Firm* — Dechert LLP

(57) ABSTRACT

The present invention relates to compounds according to Formula I: and pharmaceutically acceptable salts thereof. Such compounds can be used in the treatment of RORgammaT-mediated diseases or conditions.

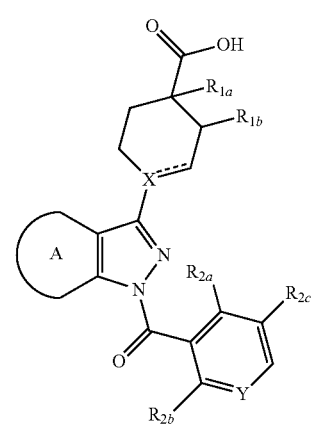

(I)

23 Claims, No Drawings

(56) References Cited

U.S. PATENT DOCUMENTS

| | | |
|---|---|---|
| 6,172,092 B1 | 1/2001 | Assmann et al. |
| 6,180,643 B1 | 1/2001 | Zablocki et al. |
| 6,348,032 B1 | 2/2002 | Sperl et al. |
| 6,352,985 B1 | 3/2002 | Yamasaki et al. |
| 6,387,939 B1 | 5/2002 | Assmann et al. |
| 6,440,973 B1 | 8/2002 | Zablocki et al. |
| 6,534,535 B1 | 3/2003 | Zhu et al. |
| 6,605,634 B2 | 8/2003 | Zablocki et al. |
| 6,638,960 B2 | 10/2003 | Assmann et al. |
| 6,683,091 B2 | 1/2004 | Asberom et al. |
| 6,828,344 B1 | 12/2004 | Seehra et al. |
| 7,084,176 B2 | 8/2006 | Morie et al. |
| 7,115,750 B1 | 10/2006 | Kato et al. |
| 7,138,401 B2 | 11/2006 | Kasibhatla et al. |
| 7,329,675 B2 | 2/2008 | Cox et al. |
| 7,355,042 B2 | 4/2008 | Edgar et al. |
| 7,420,059 B2 | 9/2008 | O'Connor et al. |
| 7,482,342 B2 | 1/2009 | D'Orchymont et al. |
| 7,514,465 B2 | 4/2009 | Kuo et al. |
| 7,569,571 B2 | 8/2009 | Dong et al. |
| 7,696,200 B2 | 4/2010 | Ackermann et al. |
| 7,696,229 B2 | 4/2010 | Dunn et al. |
| 7,713,996 B2 | 5/2010 | Ackermann et al. |
| 7,741,495 B2 | 6/2010 | Liou et al. |
| 7,772,252 B2 | 8/2010 | Hendrix et al. |
| 7,799,933 B2 | 9/2010 | Ceccarelli et al. |
| 9,095,583 B2 | 8/2015 | Karstens et al. |
| 9,266,827 B2 | 2/2016 | Aicher et al. |
| 9,273,070 B2 | 3/2016 | Knochel et al. |
| 9,487,490 B2 | 11/2016 | Barr et al. |
| 9,512,111 B2 | 12/2016 | Glick et al. |
| 9,556,168 B2 | 1/2017 | Barr et al. |
| 9,603,838 B2 | 3/2017 | Karstens et al. |
| 9,657,033 B2 | 5/2017 | Aicher et al. |
| 9,663,522 B2 | 5/2017 | Barr et al. |
| 9,745,265 B2 | 8/2017 | Barr et al. |
| 9,884,043 B2 | 2/2018 | Karstens et al. |
| 2006/0004000 A1 | 1/2006 | D'Orchymont et al. |
| 2006/0030612 A1 | 2/2006 | Steffan et al. |
| 2006/0100218 A1 | 5/2006 | Ibrahim et al. |
| 2006/0100230 A1 | 5/2006 | Bischoff et al. |
| 2007/0010537 A1 | 1/2007 | Hamamura et al. |
| 2007/0010670 A1 | 1/2007 | Hirata et al. |
| 2007/0049556 A1 | 3/2007 | Zhang et al. |
| 2007/0060567 A1 | 3/2007 | Ackermann et al. |
| 2007/0154487 A1 | 7/2007 | Littman et al. |
| 2007/0191603 A1 | 8/2007 | Ackermann et al. |
| 2007/0197782 A1 | 8/2007 | Clough et al. |
| 2007/0281922 A1 | 12/2007 | Liu et al. |
| 2008/0027100 A1 | 1/2008 | McCormick et al. |
| 2008/0058386 A1 | 3/2008 | Liou et al. |
| 2008/0153805 A1 | 6/2008 | Ceccarelli et al. |
| 2008/0305169 A1 | 12/2008 | Miki et al. |
| 2009/0005410 A1 | 1/2009 | Charvat et al. |
| 2009/0075973 A1 | 3/2009 | Newcom et al. |
| 2009/0124616 A1 | 5/2009 | Song et al. |
| 2009/0233955 A1 | 9/2009 | Frazee et al. |
| 2009/0247502 A1 | 10/2009 | Newcom et al. |
| 2009/0275586 A1 | 11/2009 | Govek et al. |
| 2010/0022515 A1 | 1/2010 | Alper et al. |
| 2010/0130484 A1 | 5/2010 | Ackermann et al. |
| 2010/0234340 A1 | 9/2010 | Schunk et al. |
| 2010/0317863 A1 | 12/2010 | Kuzmich et al. |
| 2011/0053915 A1 | 3/2011 | Ivaschenko et al. |
| 2011/0112070 A1 | 5/2011 | Baldwin et al. |
| 2011/0118246 A1 | 5/2011 | Baldwin et al. |
| 2011/0130384 A1 | 6/2011 | Setoh et al. |
| 2011/0150864 A1 | 6/2011 | Bignan et al. |
| 2011/0178063 A1 | 7/2011 | Baldwin et al. |
| 2011/0263046 A1 | 10/2011 | Deuschle et al. |
| 2014/0088094 A1 | 3/2014 | Glick et al. |
| 2015/0111877 A1 | 4/2015 | Aicher et al. |
| 2015/0126493 A1 | 5/2015 | Aicher et al. |
| 2015/0191434 A1 | 7/2015 | Barr et al. |
| 2015/0210687 A1 | 7/2015 | Barr et al. |
| 2015/0218096 A1 | 8/2015 | Barr et al. |
| 2015/0218169 A1 | 8/2015 | Barr et al. |
| 2015/0297566 A1 | 10/2015 | Karstens et al. |
| 2016/0304476 A1 | 10/2016 | Aicher et al. |
| 2016/0304505 A1 | 10/2016 | Aicher et al. |
| 2016/0311787 A1 | 10/2016 | Aicher et al. |
| 2017/0313722 A1 | 11/2017 | Aicher et al. |
| 2017/0340610 A1 | 11/2017 | Karstens et al. |
| 2018/0016239 A1 | 1/2018 | Lapointe et al. |
| 2018/0022701 A1 | 1/2018 | Barr et al. |

FOREIGN PATENT DOCUMENTS

| | | |
|---|---|---|
| EP | 1820515 A1 | 8/2007 |
| EP | 2181710 A1 | 5/2010 |
| EP | 2487159 A1 | 8/2012 |
| JP | 06250441 A | 9/1994 |
| JP | 2004307487 A | 11/2004 |
| JP | 2007238463 A | 9/2007 |
| JP | 2016-141632 A | 8/2016 |
| WO | WO-92/13856 A1 | 8/1992 |
| WO | WO-1996/37467 A1 | 11/1996 |
| WO | WO-97/01561 A1 | 1/1997 |
| WO | WO-97/48697 A1 | 12/1997 |
| WO | WO-98/22457 A1 | 5/1998 |
| WO | WO-00/17202 A1 | 3/2000 |
| WO | WO-01/012600 A1 | 2/2001 |
| WO | WO-02/100819 A1 | 12/2002 |
| WO | WO-03/014075 A2 | 2/2003 |
| WO | WO-2004/056830 A1 | 7/2004 |
| WO | WO-05/028434 A2 | 3/2005 |
| WO | WO-2005/037834 A1 | 4/2005 |
| WO | WO-2006/007486 A2 | 1/2006 |
| WO | WO-2006/026754 A2 | 3/2006 |
| WO | WO-2006/052190 A1 | 5/2006 |
| WO | WO-2006/057460 A1 | 6/2006 |
| WO | WO-2006/063167 A1 | 6/2006 |
| WO | WO-2007/024944 A1 | 3/2007 |
| WO | WO-2007/031429 A1 | 3/2007 |
| WO | WO-2007/093507 A1 | 8/2007 |
| WO | WO-2007/103308 A2 | 9/2007 |
| WO | WO-2007/125405 A2 | 11/2007 |
| WO | WO-2007/138998 A1 | 12/2007 |
| WO | WO-2007/144327 A2 | 12/2007 |
| WO | WO-2008/003703 A1 | 1/2008 |
| WO | WO-2008/045664 A2 | 4/2008 |
| WO | WO-2008/062740 A1 | 5/2008 |
| WO | WO-2008/074692 A1 | 6/2008 |
| WO | WO-2008/097428 A2 | 8/2008 |
| WO | WO-2008/132434 A2 | 11/2008 |
| WO | WO-2008/138889 A1 | 11/2008 |
| WO | WO-2008/150827 A1 | 12/2008 |
| WO | WO-2008/153858 A1 | 12/2008 |
| WO | WO-2009/015067 A2 | 1/2009 |
| WO | WO-2009/032667 A1 | 3/2009 |
| WO | WO-2009/035997 A2 | 3/2009 |
| WO | WO-2009/077956 A2 | 6/2009 |
| WO | WO-2009/147187 A1 | 12/2009 |
| WO | WO-2009/149819 A1 | 12/2009 |
| WO | WO-2009/149820 A1 | 12/2009 |
| WO | WO-2009/157196 A1 | 12/2009 |
| WO | WO-2010/017827 A1 | 2/2010 |
| WO | WO-2010/038901 A1 | 4/2010 |
| WO | WO-2010/50837 A1 | 5/2010 |
| WO | WO-2010/057101 A2 | 5/2010 |
| WO | WO-2010/059602 A2 | 5/2010 |
| WO | WO-2010/068483 A2 | 6/2010 |
| WO | WO-2010/071853 A1 | 6/2010 |
| WO | WO-2010/102958 A1 | 9/2010 |
| WO | WO-2010/117425 A1 | 10/2010 |
| WO | WO-2010/123139 A1 | 10/2010 |
| WO | WO-2010/125082 A1 | 11/2010 |
| WO | WO-2010/150837 A1 | 12/2010 |
| WO | WO-2011/14775 A1 | 2/2011 |
| WO | WO-2011/014775 A1 | 2/2011 |
| WO | WO-2011/019634 A2 | 2/2011 |
| WO | WO-2011/059839 A1 | 5/2011 |
| WO | WO-2011/067364 A1 | 6/2011 |
| WO | WO-2011/067365 A1 | 6/2011 |

(56) References Cited

FOREIGN PATENT DOCUMENTS

| WO | WO-2011/067366 A1 | 6/2011 |
|---|---|---|
| WO | WO-2011/103189 A1 | 8/2011 |
| WO | WO-2011/109059 A1 | 9/2011 |
| WO | WO-2011/146313 A1 | 11/2011 |
| WO | WO-2012/032065 A1 | 3/2012 |
| WO | WO-2012/032067 A1 | 3/2012 |
| WO | WO-2012/037108 A1 | 3/2012 |
| WO | WO-2012/064744 A2 | 5/2012 |
| WO | WO-2012/077932 A2 | 6/2012 |
| WO | WO-2012/106995 A1 | 8/2012 |
| WO | WO-2012/139775 A1 | 10/2012 |
| WO | WO-2012/176763 A1 | 12/2012 |
| WO | WO-2013/169704 A2 | 11/2013 |
| WO | WO-2014/026327 A1 | 2/2014 |
| WO | WO-2014/026328 A1 | 2/2014 |
| WO | WO-2014/026329 A1 | 2/2014 |
| WO | WO-2014/028589 A2 | 2/2014 |
| WO | WO-2014/028591 A2 | 2/2014 |
| WO | WO-2014/028597 A2 | 2/2014 |
| WO | WO-2014/028600 A2 | 2/2014 |
| WO | WO-2015/008234 A1 | 1/2015 |
| WO | WO-2015/087234 A1 | 6/2015 |
| WO | WO-2015/139621 | 9/2015 |
| WO | WO-2016/128908 A1 | 8/2016 |
| WO | WO-2016/130818 A1 | 8/2016 |

OTHER PUBLICATIONS

U.S. Appl. No. 15/549,465, Substituted Pyrazole Compounds as RORgammaT Inhibitors and Uses Thereof, filed Aug. 8, 2017.
U.S. Appl. No. 15/770,256, Substituted Indazole Compounds as RORgammaT Inhibitors and Uses Thereof, filed Apr. 23, 2018.
U.S. Appl. No. 15/770,257, Heteroaryl Substituted Benzoic Acids as RORgammaT Inhibitors and Uses Thereof, filed Apr. 23, 2018.
International Search Report from PCT/CN2012/071017, dated May 24, 2012.
Bundgaard (ed.). Design of Prodrugs, Elsevier (1985).
Buonocore et al., "Innate lymphoid cells drive interleukin-23-dependent innate intestinal pathology," 464 Nature 1371-75 (2010).
Cheng et al., "Design and synthesis of heterocyclic malonyl-CoA decarboxylase inhibitors," 16 Bioorg. Med. Chem. Lett. 695-700 (2006).
Figueroa-Vega et al., "Increased Circulating Pro-Inflammatory Cytokines and Th17 Lymphocytes in Hashimoto's Thyroiditis," 95(2) J. Clin. Endocrinol. Metab. 953-62 (2010).
Gennaro (ed.), Remington: The Science and Practice of Pharmacy, 20th edition (2000).
Higuchi et al. (eds.), Pro-drugs as Novel Delivery Systems, 14 A.C.S. Symposium Series (1975).
Hueber et al., "Cutting Edge: Mast Cells Express IL-17A in Rheumatoid Arthritis Synovium," 184 J. Immunol. 3336-40 (2010).
Jia et al., "The T helper type 17/regulatory T cell imbalance in patients with acute Kawasaki disease," 162 Clin. Exp. Immunol. 131-37 (2010).
Kastelein et al., "Discovery and Biology of IL-23 and IL-27: Related but Functionally Distinct Regulators of Inflammation," 25 Annu. Rev. Immunol. 221-42 (2007).
Louten et al., "Development and function of TH17 cells in health and disease," 123(5) J. Allergy Clin. Immunol. 1004-11 (2009).
Roche (ed.), Biorevesible Carriers in Drug Design, Pergamon Press (1987).
Zhou et al., "Use of Homogeneous Time-Resolved Fluorescence Energy Transfer in the Measurement of Nuclear Receptor Activation," 25 Methods 54-61 (2001).
Extended European Search Report, EP Application No. 12744370.3, dated Sep. 9, 2014.
Ciattini et al., "An Efficient Synthesis of 3-Substituted Indoles by Palladium-Catalyzed Coupling Reaction of 3-Tributylstannylindoles with Organic Triflates and Halides," 35(15) Tetrahedron Letters 2405-08 (1994).

Inamoto et al., "Palladium-Catalyzed C—H Activation/Intramolecular Amination Reaction: A New Route to 3-Aryl/Alkylindazoles," 9(15) Org. Letts. 2931-34 (2007).
Larhed et al., "Rapid Microwave-Assisted Suzuki Coupling on Solid-Phase," 37(45) Tetrahedron Letters 8219-22 (1996).
Reckenbeil et al., "Supramolekulare Phosphorylierung kationischer Alkohole mit 3-Arylindol-4-carboxamidin-Struktur," Liebigs Ann. Chem. 1219-29 (1994).
Chen, Hua-Sin et al., "Synthesis and antiplatelet activity of ethyl 4-(1-benzyl-1H-indazol-3-yl)benzoate (YD-3) derivatives," *Bioorganic & Medicinal Chemistry*, vol. 16, pp. 1262-1278, (2008).
Annunziato et al., "Type 17 T helper cells-origins, features and possible roles in rheumatic disease," 5 Nat. Rev. Rheumatol. 325-31 (2009).
Boaventura et al., "Human mucosal leishmaniasis: Neutrophils infiltrate areas of tissue damage that express high levels of Th17-related cytokines," 40 Eur. J. Immunol. 2830-36 (2010).
Eberl et al., "An essential function for the nuclear receptor RORγt in the generation of fetal lymphoid tissue inducer cells," 5(1) Nat. Immunol. 64-73 (2004).
He et al., "RORγt, a Novel Isoform of an Orphan Receptor, Negatively Regulates Fas Ligand Expression and IL-2 Production in T Cells," 9 Immunity 797-806 (1998).
Hirose et al., "RORγ: the third member of ROR/RZR orphan receptor subfamily that is highly expressed in skeletal muscle," 205 Biochem. Biophys. Res. Comm. 1976-83 (1994).
Ivanov et al., "The Orphan Nuclear Receptor RORγt Directs the Differentiation Program of Proinflammatory IL-17+ T Helper Cells," 126 *Cell* 1121-33 (2006).
Jin et al., "Structural Basis for Hydroxycholesterols as Natural Ligands of Orphan Nuclear Receptor RORγ," *Mol. Endocrinol.* (2010) vol. 24, No. 5, pp. 923-929.
Kurebayashi et al., "Selective LXXLL peptides antagonize transcriptional activation by the retinoid-related orphan receptor RORγ," 315 Biochem. Biophys. Res. Comm. 919-27 (2004).
Miossec et al., "Interleukin-17 and Type 17 Helper T Cells," 361(9) New Eng. J. Med. 888-98 (2009).
Sun et al., "Requirement for RORγ in Thymocyte Survival and Lymphoid Organ Development," 288 Science 2369-72 (2000).
Sutton et al., "Interleukin-1 and IL-23 Induce Innate IL-17 Production from γδ T Cells, Amplifying Th17 Responses and Autoimmunity," 31 Immunity 331-41 (2009).
Varnavas et al., "Anthranilic acid based CCK1 receptor antagonists: preliminary investigation on their second 'touch point,'" 40(6) Euro. J. Med. Chem. 563-81 (2005).
Wang et al., "Identification of SR1078, a Synthetic Agonist for the Orphan Nuclear Receptors RORα and RORγ," 5(11) ACS Chem. Biol. 1029-34 (2010).
Wang et al., "Modulation of Retinoic Acid Receptor-related Orphan Receptor α and γ Activity by 7-Oxygenated Sterol Ligands," J. Biol. Chem. (2010) vol. 285, No. 7, pp. 5013-5025.
Xie et al., "RORγt Recruits Steroid Receptor Coactivators to Ensure Thymocyte Survival," 175(6) J. Immunol. 3800-09 (2005).
Yang et al., "T Helper 17 Lineage Differentiation is programmed by Orphan Nuclear Receptors RORα and RORγ," 28 Immunity 29-39 (2008).
International Search Report and Written Opinion for PCT/US2013/054168, dated Feb. 14, 2014 (5 pages).
Lee et al., "Synthesis of 1-Benzyl-3-(5'-hydroxymethyl-2'-furyl)indazole Analogues as Novel Antiplatelet Agents," 44 J. Med. Chem. 3746-49 (2001).
André et al., "Disruption of retinoid-related orphan receptor ß changes circadian behaviour, causes retinal degeneration and leads to vacillans phenotype in mice," 17(14) The EMBO J. 3867-77 (1998).
Becker-André et al., "Identification of nuclear receptor mRNAs by RT-PCR amplification of conserved zinc-finger motif sequences," 194(3) Biochem. Biophys. Res. Comm. 1371-79 (1993).
Bernhardt et al., "Preparation of Solid Salt-Stabilized Functionalized Organozinc Compounds and their Application to Cross-Coupling and Carbonyl Addition Reactions," 50(39) Angew. Chem. Int. Ed. 9205-9209 (2011).

(56) References Cited

OTHER PUBLICATIONS

Boltze et al., "Chemische Struktur and antiphlogistische Wirkung in der Reihe der substituierten Indol-3-essigsauren," 30(8A) Arzneimittel-Forschung 1314-25 (1980).
Burris et al., "Targeting Orphan Nuclear Receptors for Treatment of Metabolic Diseases and Autoimmunity," 19(1) Chem. Biol. 51-59 (2012).
Cai, et al., "Pivotal Role of Dermal IL-17-Producing γδ T Cells in Skin Inflammation", Immunity (2011) vol. 35, pp. 596-610.
Carlberg et al., "RZRs, a new family of retinoid-related orphan receptors that function as both monomers and homodimers," 8 Mol. Endocrinol. 757-70 (1994).
D. van der Heijde, et al., "Secukinumab Provides Significant and Sustained Inhibition of Joint Structural Damage in a Phase III Study of Active Psoriatic Arthritis" Arthritis & Rheumatology Brief Report, Accepted Article DOI: 10.1002/art.39685, American College of Rheumatology, (2016) pp. 1-27.
Baeten, et al., "Secukinumab, an Interleukin-17A Inhibitor, in Ankylosing Spondylitis", The New England Journal of Medicine, (2015) vol. 373, pp. 2534-2548.
Dussault et al., "Orphan nuclear receptor RORα-deficient mice display the cerebellar defects of staggerer," 70 Mech. Develop. 147-53 (1998).
El-Sawy et al., "Synthesis, antimicrobial and anti-cancer activities of some new N-ethyl, N-benzyl and N-benzoyl-3-indolyl heterocycles," 62 Acta Pharm. 157-179 (2012).
Giguère et al., "Isoform-specific amino-terminal domains dictate DNA-binding properties of RORα, a novel family of orphan hormone nuclear receptors," 8 Genes & Develop. 538-53 (1994).
Guo et al., "Stereospecific microbial reduction of ethyl 1-benzyl-3-oxo-piperidine-4-carboxylate," 17(13) Tetrahedron: Asymmetry 2015-2020 (2006).
Hirose et al., "Benzoheterocyclic derivatives. XI. Synthesis and pharmacological actions of indoline derivatives. 2," CA76:46035 (1971).
Huh et al., "Small molecule inhibitors of RORγt: Targeting Th17 cells and other applications," 42 Eur. J. Immunol. 2232-2237 (2012).
Julia et al., "Research in the indole series. IX. Certain 3-indolylsuccinic acids and the corresponding succinimides and pyrrolidines," CA61:92261 (1964).
Krueger, "A welcome surprise in psoriasis", Nature Medicine, (2012) vol. 18, No. 12, pp. 1750-1751.
Leonardi, et al., "Anti-Interleukin-17 Monoclonal Antibody Ixekizumab in Chronic Plaque Psoriasis", The New England Journal of Medicine, (2012) vol. 366, Iss. 13, pp. 1-10.
Martinez, "Th17-biased RORγt transgenic mice become susceptible to a viral model for multiple sclerosis", Brain, Behavior, and Immunity, (2014) vol. 43, pp. 86-97.
Medvedev et al., "Cloning of a cDNA encoding the murine orphan receptor RZR/RORγ and characterization of its response element," 181 Gene 199-206 (1996).
Nakajima, et al., "IL-17A as an Inducer for Th2 Immune Responses in Murine Atopic Dermatitis Models", Journal of Investigative Dermatology, (2014) vol. 134, pp. 2122-2130.
Ortiz et al., "TOR: a new orphan receptor expressed in the thymus that can modulate retinoid and thyroid hormone signals," 9 Mol. Endocrinol. 1679-91 (1995).
Papp, et al. "Brodalumab, an Anti-Interleukin-17-Receptor Antibody for Psoriasis", The New England Journal of Medicine, (2012) vol. 366, Iss. 13, 9 pgs.
Skepner, J. et al. "Pharmacologic Inhibition of RORγt Regulates Th17 Signature Gene Expression and Suppresses Cutaneous Inflammation In Vivo," downloaded from the Internet at http://www.jimmunol.org/cgi/doi/10.4049/jimmunol.1302190 on Feb. 17, 2014, published in final edited form in *J. Immunol.* (2014) vol. 192, No. 6, pp. 2564-2575.
Smith, "The Bench-to-Bedside Story of IL-17 and the Therapeutic Efficacy of its Targeting in Spondyloarthritis", Curr Rheumatol Rep. (2016) vol. 18, pp. 1-10.

Solt et al., "Action of RORs and their ligands in (patho)physiology," 23(12) Trends in Endocrinology and Metabolism. 619-627 (2012).
Tlustochowicz, et al. "Efficacy and Safety of Subcutaneous and Intravenous Loading Dose Regimens of Secukinumab in Patients with Active Rheumatoid Arthritis: Results from a Randomized Phase II Study" The Journal of Rheumatology, (2016) vol. 43, No. 3, pp. 495-503.
Villey et al., "RORγT, a thymus-specific isoform of the orphan nuclear receptor RORγ/TOR, is up-regulated by signaling through the pre-T cell receptor and binds to the TEA promoter," 29 Eur. J. Immunol. 4072-80 (1999).
Whelligan et al., "Aminopyrazine Inhibitors Binding to an Unusual Inactive Conformation of the Mitotic Kinase Nek2: SAR and Structural Characterization," 53 J. Med. Chem. 7682-98 (2010).
Wiesenberg et al., "Transcriptional activation of the nuclear receptor RZRα by the pineal gland hormone melatonin and identification of CGP 52608 as a synthetic ligand," 23(3) Nucl. Acids Res. 327-33 (1995).
Xiao, et al., "Small-Molecule RORγt Antagonists Inhibit T Helper 17 Cell Transcriptional Network by Divergent Mechanisms", Immunity (2014) vol. 40, pp. 477-489.
International Search Report and Written Opinion for PCT/US2013/054887, dated Mar. 18, 2014 (5 pages).
International Search Report and Written Opinion for PCT/US2013/054902, dated Feb. 28, 2014 (5 pages).
International Search Report and Written Opinion for PCT/US2013/054911 dated Mar. 4, 2014 (9 pages).
Database Caplus [Online] Chemical Abstracts Service, Columbus, Ohio, US; Kusakabe, Kanekazu et al: "Preparation of condensed pyrazole compounds as TTK protein kinase inhibitors", retrieved from STN Database accession No. 2011:1578140 ; & Kusakabe, Kanekazu et al: "Preparation of condensed pyrazole compounds as TTK protein kinase inhibitors", Jpn. Kokai Tokkyo Koho, 134PP. Coden: JKXXAF.
Arisawa et al., "Development of Isomerization and Cycloisomerization with Use of a Ruthenium Hydride with N-Heterocyclic Carbene and Its Application to the Synthesis of Heterocycles," 71 J. Org. Chem. 4255-61 (2006).
Berge et al., "Pharmaceutical salts," 66(1) J. Pharm. Sci. 1-19 (1977).
Bhagawanth et al., "Room-Temperature Pd-Catalyzed Amidation of Aryl Bromides Using tert-Butyl Carbamate," 74 J. Org. Chem. 4634-37 (2009).
Boger et al., "Regiocontrolled Nucleophilic Addition to Selectively Activated p-Quinone Diimines: Alternative Preparation of a Key Intermediate Employed in the Preparation of the CC-1065 Left-Hand Subunit," 55 J. Org. Chem. 1379-90 (1990).
Carroll et al., "Synthesis, Nicotinic Acetylcholine Receptor Binding, and Antinociceptive Properties of 2-exo-2-(2',3'-Disubstituted 5'-pyridinyl)-y-azabicyclo[2.2.1]heptanes: Epibatidine Analogues," 45 J. Med. Chem. 4755-61 (2002).
Chang et al., "7-Aroyl-aminoindoline-1-sulfonamides as a Novel Class of Potent Antitubulin Agents," 49 J. Med. Chem. 6656-59 (2006).
Colbon et al., "Double Arylation of Allyl Alcohol via a One-Pot Heck Arylation—Isomerization—Acylation Cascade," 13 Org. Lett. 5456-59 (2011).
De et al., Methods in Molecular Biology 1184, second edition, Human Press (2014).
Gould, "Salt selection for basic drugs," 33 Int'l J. Pharmaceutics 201-217 (1986).
Grasa et al., "Amination Reactions of Aryl Halides with Nitrogen-Containing Reagents Mediated by Palladium/Imidazolium Salt Systems," 66 J. Org. Chem. 7729-37 (2001).
Greene & Wuts, Protective Groups in Organic Synthesis, 2d Edition (1991).
Guimond et al., "Rhodium(III)-Catalyzed Isoquinolone Synthesis: The N—O Bond as a Handle for C—N Bond Formation and Catalyst Turnover," 132(20) J. Am. Chem. Soc. 6908-09 (2010).
Hanessian et al., "A versatile protocol for the stereocontrolled elaboration of vicinal secondary and tertiary centers of relevance to natural product synthesis," 52(6) J. Org. Chem. 1170-72 (1987).

(56) References Cited

OTHER PUBLICATIONS

Hauser et al., "Relative Ease of Cyclization of 2-, 3-, and 4-Aminopyridine Derivatives. Synthesis of Naphthyridines," 15 J. Org. Chem. 1224-32 (1950).
International Search Report and Written Opinion for PCT/US2011/059788 dated May 23, 2012 (23 pages).
International Search Report and Written Opinion for PCT/US2013/039422 dated Oct. 11, 2013 (9 pages).
International Search Report and Written Opinion for PCT/US2013/039839 dated Oct. 18, 2013 (8 pages).
International Search Report and Written Opinion for PCT/US2013/040085 dated Oct. 23, 2013 (9 pages).
Ishikura et al., "An Efficient Synthesis of 3-Heteroarylpyridines via Diethyl-(3-pyridyl)-borane," Synthesis 936-38 (1984).
Jayashree et al., "Design and synthesis of 2-quinolones as antioxidants and antimicrobials: a rational approach," 19 Med. Chem. Res. 193-209 (2010).
Jiang et al., "Synthesis and Cytotoxicity Evaluation of Novel Indolylpyrimidines and Indolylpyrazines as Potential Antitumor Agents," 9 Bioorg. Med. Chem. 1149-54 (2001).
Li et al., "Chemical Libraries via Sequential C—H Functionalization of Phenols," 10 J. Comb. Chem. 170-74 (2008).
Li et al., "Synthesis and Resolution of a Novel Chiral Diamine Ligand and Application to Asymmetric Lithiation-Substitution," 2 Org. Lett. 875-78 (2000).
Liu et al., "1-Sulfonylindazoles as potent and selective 5-HT6 ligands," 19 Bioorg. Med. Chem. Lett. 2413-15 (2009).
Murase et al., "A New Concise Synthesis of Arcyriacyanin A and Its Unique Inhibitory Activity against a Panel of Human Cancer Cell Line," 48(1) Chem. Pharm. Bull. 81-84 (2000).
Ninomiya et al., "Phosphorous in Organic Synthesis—VII: Diphenyl Phosphorazidate (DPPA). A New Convenient Reagent for a Modified Curtius Reaction," 30 Tetrahedron 2151-57 (1975).
Nyrkova et al., "Synthesis of a New Heterocyclic System—3,4-Diazaphenoxazine," 1(9) J. Org. Chem. USSR, 1711-14, translating 1(9) Zh. Org. Khimii, 1688-91 (1965).
Santilli et al., "Synthesis of 5,6,7,8-Tetrahydro-5-oxopyrido[2,3-d]pyrimidine-6-carbonitriles and -6-carboxylic Acid Esters," 12 J. Het. Chem. 311-16 (1975).
Skraup, "Eine Synthese des Chinolins," 13 Berichte 2086-87 (1880).
Stefko et al., "General and Modular Synthesis of Isomeric 5-Substituted Pyridin-2-yl and 6-Substituted Pyridin-3-yl C-Ribonucleosides Bearing Diverse Alkyl, Aryl, Hetaryl, Amino, Carbamoyl, and Hydroxy Groups," 76 J. Org. Chem. 6619-35 (2011).
STN Columbus, pp. 1-40 (2011).
Takano et al., "A new synthesis of a steroid side chain via stereocontrolled protonation: synthesis of (−)-desmosterol," 14 J. Chem. Soc., Chem. Commun. 760-61 (1983).
Van Heerden et al., "Dibutylboron triflate promoted conjugate addition of benzylic and allylic organocopper reagents to chiral α,β-unsaturated N-acyl imidazolidinones" 38(10) Tet. Lett. 182-124 (1997).
Wang et al., "Synthesis of new carbon-11-labeled 7-aroyl-aminoindoline-1-sulfonamides as potential PET agents for imaging of tubulin polymerization in cancers," 51(1) J. Label. Compd. Radiopharm. 6-11 (2008).
Yeh et al., "Practical Cu-catalyzed amination of functionalized heteroaryl halides," 47(34) Tetrahedron Lett. 6011-16 (2006).
Zhu et al., "The Direct Formulation of Functionalized Alkyl(aryl)zinc halides by Oxidative Addition of Highly Reactive Zinc with Organic Halides and Their Reactions with Acid Chlorides, α,β-Unsaturated Ketones, and Allylic, Aryl, and Vinyl Halides," 56 J. Org. Chem. 1445-53 (1991).
International Search Report and Written Opinion for PCT/US2014/071671 dated Apr. 28, 2015 (10 pages).
International Search Report and Written Opinion for PCT/US2014/071663 dated Apr. 17, 2015 (6 pages).
International Search Report and Written Opinion for PCT/US2014/071656 dated Mar. 12, 2015 (8 pages).
International Search Report and Written Opinion for PCT/US2016/017566 dated May 6, 2016 (12 pages).
International Search Report and Written Opinion for PCT/US2016/059057 dated Dec. 9, 2016 (13 pages).
International Search Report and Written Opinion for PCT/US2016/059063 dated Jan. 20, 2017 (12 pages).
International Search Report and Written Opinion for PCT/US2016/059067 dated Jan. 11, 2017 (10 pages).
CAS Registry Nos. 886371-27-3 and 886370-74-7, STN entry date: Jun. 1, 2006.
Fauber Benjamin P. "Modulators of the Nuclear Receptor Retinoic Acid Receptor-Related Orphan Receptor-[gamma] (ROR[gamma] or RORc," *Journal of Medicinal Chemistry*, vol. 57, No. 14, Jul. 24, 2014 (Jul. 24, 2014), pp. 5871-5892, XP055242989.
Fauber Benjamin P. "Discovery of Imidazo[1,5-a]pyridines and -pyrimidines as potent and selective RORc inverse agonists," *Bioorganic & Medicinal Chemistry Letters*, vol. 25, No. 15, May 28, 2015 (May 28, 2015), pp. 2907-2912, XP029160601.
International Search Report and Written Opinion for PCT/US2013/054893 dated Feb. 24, 2014 (6 pages).

SUBSTITUTED BICYCLIC PYRAZOLE COMPOUNDS AS RORGAMMAT INHIBITORS AND USES THEREOF

CROSS REFERENCE TO RELATED APPLICATIONS

This application is the national stage of International (PCT) Patent Application Serial No. PCT/US2016/059057, filed Oct. 27, 2016, which claims the benefit of and priority to U.S. Provisional Patent Application Ser. No. 62/246,918, filed Oct. 27, 2015, the contents of each of which are hereby incorporated by reference.

BACKGROUND OF THE INVENTION

Upon activation by antigen-presenting cells naïve T helper cells undergo clonal expansion and will ultimately differentiate into cytokine secreting effector T cells, such as Th1 and Th2 subtypes. A third and distinct effector subset has been identified, which plays a key role in providing immunity to bacteria and fungi at mucosal surfaces (Kastelein et al., Annu. Rev. Immunol. 25: 221-242, 2007). This effector T helper cell subset can be distinguished based on its ability to produce large quantities of IL-17/F, IL-21 and IL-22, and is named Th17 (Miossec et al., New Eng. J. Med. 2361: 888-898, 2009).

Different T helper subsets are characterized by the expression of lineage specific master transcription factors. Th1 and Th2 effector cells express Tbet and GATA3, respectively. A Thymocyte/T cell specific variant of Retinoic Acid Receptor-related Orphan Receptor (ROR), RORgammaT, is highly expressed in Th17 cells (He et al., Immunity 9: 797-806, 1998). RORgammaT belongs to the nuclear hormone receptor superfamily (Hirose et al., Biochem. Biophys. Res. Comm. 205: 1976-1983, 1994). RORgammaT is a truncated form of RORgamma, lacking the first N-terminal 21 amino acids and is, in contrast to RORgamma which is expressed in multiple tissues (heart, brain, kidney, lung, liver, and muscle), exclusively expressed in cells of the lymphoid lineage and embryonic lymphoid tissue inducers (Sun et al., Science 288: 2369-2372, 2000; Eberl et al., Nat. Immunol. 5: 64-73, 2004).

Studies using heterozygous knock-in mice replacing the RORgammaT open reading frame with GFP (green fluorescent protein), revealed a constitutive expression of GFP in approximately 10% of the CD4+ T cells in the small intestinal lamina propria (LP), co-expressing the Th17 cytokines IL-17/F and IL-22 (Ivanov et al., Cell 126: 1121-1133, 2006). In mice deficient for RORgammaT, the number of Th17 cells was markedly decreased in the LP; and in vitro stimulation of CD4+ T cells under Th17 polarizing conditions resulted in a drastic decrease of IL-17 expression. These results were further substantiated via forced expression of RORgammaT in naïve CD4+ T cells, which resulted in an induction of IL-17/F and IL-22 (Ivanov et al., Cell 126: 1121-1133, 2006). The foregoing studies demonstrate the importance of RORgammaT in differentiation and stabilization of the Th17 lineage. In addition, a ROR family member, RORalpha, has been demonstrated to be involved in Th17 differentiation and stabilization (Yang et al., Immunity 28: 29-39, 2008).

Recently, RORgammaT was shown to play a crucial role in non-Th17 lymphoid cells. In these studies, RORgammaT was critically important in innate lymphoid cells expressing Thy1, SCA-1, and IL-23R proteins. Genetic disruption of RORgamma in a mouse colitis model dependent on these innate lymphoid cells prevented colitis development (Buonocore et al., Nature 464: 1371-1375, 2010). In addition, RORgammaT was shown to play a crucial role in other non-Th17 cells, such as mast cells (Hueber et al., J. Immunol. 184: 3336-3340, 2010). Finally, RORgammaT expression and secretion of Th17-type of cytokines was reported for Lymphoid Tissue Inducer cells, NK T-cells, NK cells (Eberl et al., Nat. Immunol. 5: 64-73, 2004), and gamma-delta T-cells (Sutton et al., Nat. Immunol. 31: 331-341, 2009; Louten et al., J. Allergy Clin. Immunol. 123: 1004-1011, 2009), suggesting an important function for RORgammaT in these subtypes of cells.

Based on the role of IL-17 producing cells (either Th17 or non-Th17 cells), RORgammaT has been identified as a key mediator in the pathogenesis of several diseases (Louten et al., J. Allergy Clin. Immunol. 123: 1004-1011, 2009; Annuziato et al., Nat. Rev. Rheumatol. 5: 325-331, 2009). This was confirmed using several disease models representative of autoimmune diseases. Genetic ablation of the RORgamma gene in mice prevented the development of experimental autoimmune diseases, such as experimental autoimmune encephalomyelitis (EAE) and colitis (Ivanov et al., Cell 126:1121-33, 2006; Buonocore et al., Nature 464: 1371-1375, 2010).

With RORgammaT being a critical mediator in Th17 cells and non-Th17 cells, antagonism of the transcriptional activity of RORgammaT is expected to have a beneficial effect on autoimmune diseases such as, but not limited to, rheumatoid arthritis, psoriasis, multiple sclerosis, inflammatory bowel disease, Crohn's disease, and asthma (Annunziato et al., Nat. Rev. Immunol. 5: 325-331, 2009; Louten et al., J. Allergy Clin. Immunol. 123: 1004-1011, 2009). Antagonism of RORgammaT may also be beneficial in other diseases that are characterized by increased levels of Th17 cells and/or elevated levels of Th17 hallmark cytokines such as IL-17, IL-22 and IL-23. Examples of such diseases are Kawasaki Disease (Jia et al., Clin. Exp. Immunol. 162: 131-137, 2010) and Hashimoto's thyroiditis (Figueroa-Vega et al., J Clin. Endocrinol. Metab. 95: 953-962, 2010). Other examples include various infectious diseases such as, but not limited to, mucosal leishmaniasis (Boaventura et al., Eur. J Immunol. 40: 2830-2836, 2010). In each of the above examples the inhibition may be enhanced by simultaneous inhibition of RORalpha.

Compounds modulating RORgammaT have been reported. Examples of agonists include T0901317 and SR1078 (Wang et al., ACS Chem. Biol. 5:1029-1034, 2010). In addition, antagonists have been reported such as 7-oxygenated sterols (Wang et al., J. Biol. Chem. 285: 5013-5025, 2009) and compounds described in EP2181710 A1.

Numerous immune and inflammatory disorders continue to afflict millions of patients worldwide. Although significant advances have been made in treating these disorders, current therapies do not provide satisfactory results for all patients due to, for example, detrimental side effects or insufficient efficacy. One exemplary immune disorder in need of better therapy is psoriasis. Various therapeutics have been developed in an attempt to treat psoriasis. However, the traditional therapies for psoriasis often have toxic adverse effects. An exemplary inflammatory disorder in need of better treatment is rheumatoid arthritis. Numerous therapeutics have been developed in an attempt to treat this disorder. However, some patients develop resistance to current therapies. Another exemplary disorder in need of better therapy is cancer.

Accordingly, a need exists for improved treatments for immune disorders and inflammatory disorders. The present invention addresses this need and provides other related advantages.

SUMMARY OF THE INVENTION

The present invention provides compounds that alter the interaction of coregulator proteins with RORgammaT (and thereby, as commonly observed for nuclear hormone receptors, antagonize RORgammaT-mediated transcriptional activity; see e.g. "Differential Biochemical and Cellular Actions of Premarin Estrogens: Distinct Pharmacology of Bazedoxifene-Conjugate Estrogens Combination". Berrodin, T. J., Chang, K. C. N., Komm, B. S., Freedman, L. P., Nagpal, S. Molecular Endocrinology, January 2009, 23(1): 74-85) and are useful for the treatment of RORgammaT-mediated diseases or conditions, in particular autoimmune diseases and inflammatory diseases, as well as pharmaceutical compositions comprising such compounds and pharmaceutical carriers.

DETAILED DESCRIPTION OF THE INVENTION

Definitions

The terms used herein have their ordinary meaning and the meaning of such terms is independent at each occurrence thereof. That notwithstanding, and except where stated otherwise, the following definitions apply throughout the specification and claims. Chemical names, common names, and chemical structures may be used interchangeably to describe the same structure.

As used herein, and throughout this disclosure, the following terms, unless otherwise indicated, shall be understood to have the following meanings:

The term "alkyl" as used herein, refers to an aliphatic hydrocarbon group having one of its hydrogen atoms replaced with a bond having the specified number of carbon atoms. In an embodiment, an alkyl group contains, for example, from 1 to 4 carbon atoms ($C_{1-4}$)alkyl. Non-limiting examples of alkyl groups include methyl, ethyl, n-propyl, isopropyl, n-butyl, sec-butyl, isobutyl and tert-butyl. In one embodiment, an alkyl group is linear. In another embodiment, an alkyl group is branched.

The term "spirocyclic" as used herein, refers to a spiro ring system which is a bicyclic ring wherein the two rings are joined through a common ring carbon atom. Nonlimiting examples of a spirocyclic moiety include azaspiro[4.4]nonane, azaspiro[3.4]octane and so on.

The term "halogen" (or "halo") refers to fluorine, chlorine, bromine and iodine (alternatively referred to as fluoro (F), chloro (Cl), bromo (Br), and iodo (I)). In one embodiment, a halogen is F or Cl. In another embodiment, halogen is F.

When any variable occurs more than one time in any constituent or in any formula depicting and describing compounds of the invention, its definition on each occurrence is independent of its definition at every other occurrence. Also, combinations of substituents and/or variables are permissible only if such combinations result in stable compounds.

The term "substituted" means that one or more hydrogens on the designated atom/atoms is/are replaced with a selection from the indicated group, provided that the designated atom's normal valency under the existing circumstances is not exceeded, and that the substitution results in a stable compound. Combinations of substituents and/or variables are permissible only if such combinations result in stable compounds. "Stable compound" or "stable structure" is defined as a compound or structure that is sufficiently robust to survive isolation to a useful degree of purity from a reaction mixture, and formulation into an efficacious therapeutic agent.

The term "optionally substituted" means that a substitution with the specified groups, radicals, or moieties may or may not be made on the specified group.

When any substituent or variable occurs more than one time in any constituent or in the compound of Formulas (I-III), its definition on each occurrence is independent of its definition at every other occurrence, unless otherwise indicated.

The term "purified" as used herein, refers to the physical state of a compound after the compound has been isolated through a synthetic process (e.g., from a reaction mixture), from a natural source, or a combination thereof. The term "purified" also refers to the physical state of a compound after the compound has been obtained from a purification process or processes described herein or well-known to the skilled artisan (e.g., chromatography, recrystallization, and the like), in sufficient purity to be characterizable by standard analytical techniques described herein or well-known to the skilled artisan.

The term "amount" or "effective amount" as used herein refers to an amount of the compound of Formulas (I-III) and/or an additional therapeutic agent, or a composition thereof, that is effective in producing the desired therapeutic, ameliorative, inhibitory or preventative effect when administered to a subject suffering from an RORgammaT-mediated disease or disorder. In the combination therapies of the present invention, as effective amount can refer to each individual agent or to the combination as a whole, wherein the amounts of all agents administered are together effective, but wherein the component agent of the combination may not be present individually in an effective amount.

A "subject" is a human or non-human mammal. In one embodiment, a subject is a human.

It should be noted that any carbon as well as heteroatom with unsatisfied valences in the text, schemes, examples and tables herein is assumed to have the sufficient number of hydrogen atom(s) to satisfy the valences.

Compounds of the Invention

The present invention provides a compound according to Formula I

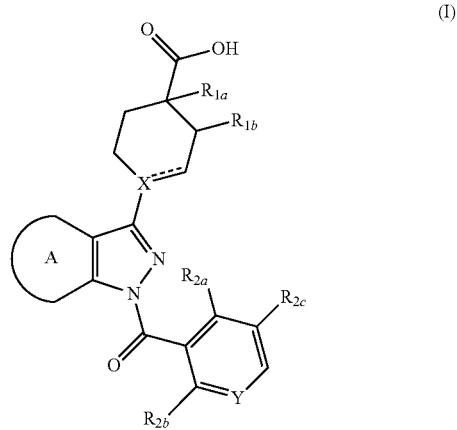

(I)

wherein:
Ring A is selected from:

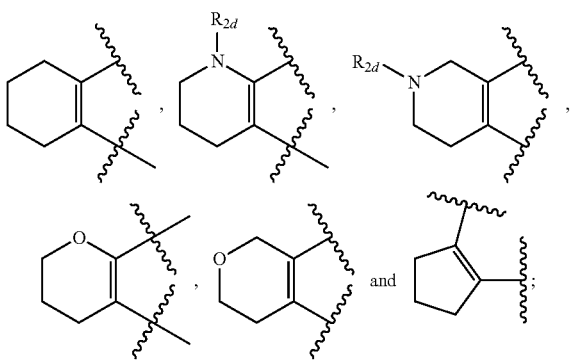

each optionally substituted with one or two substituents independently selected from OH, halogen, $(C_{1-4})$alkyl and $(C=O)O(C_{1-4})$alkyl, wherein a carbon in the $(C_{1-4})$alkyl chain may bond to a carbon on Ring A and form a spirocyclic moiety, wherein $(C_{1-4})$alkyl is optionally substituted with OH, methylpyrrolidine, $NH_2$ or oxo;
X is N or C, wherein when X is N then the dashed line is absent and when X is C the dashed line represents a double bond;
Y is N or CH;
$R_{1a}$ is H or $(C_{1-4})$alkyl;
$R_{1b}$ is H, OH or $(C_{1-4})$alkyl;
$R_{2a}$ is Cl or $(C_{1-4})$alkyl;
$R_{2b}$ is cyclopropyl, cyclobutyl, oxetane or azetidine, each optionally substituted with $(C_{1-4})$alkyl, F, $CF_3$, $CHF_2$ or CN;
$R_{2c}$ is H or F; and
$R_{2d}$ is H or $(C_{1-4})$alkyl;
or a pharmaceutically acceptable salt thereof.

The group

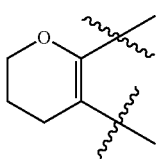 [SMILES: *C1=C(*)OCCC1]

in the definition of Ring A is meant to encompass compounds embraced by both of the following formulae:

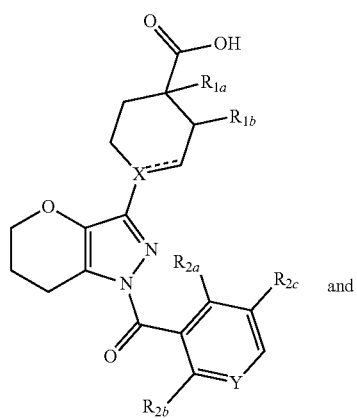

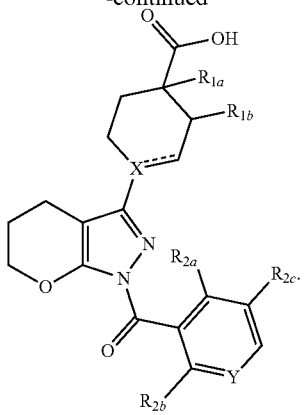

The groups

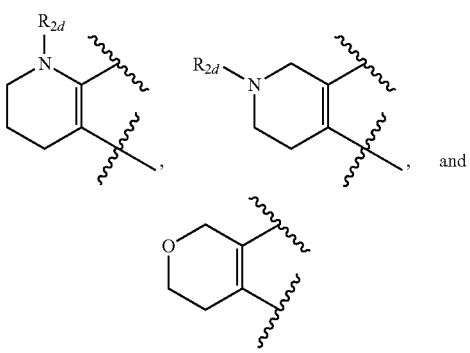

in the definition of Ring A in Formula I are similarly understood to encompass regioisomers permitted by the two orientations of attachment allowed by the definition of Ring A.

In another embodiment, the present invention provides a compound according to Formula I, wherein:
Ring A is selected from:

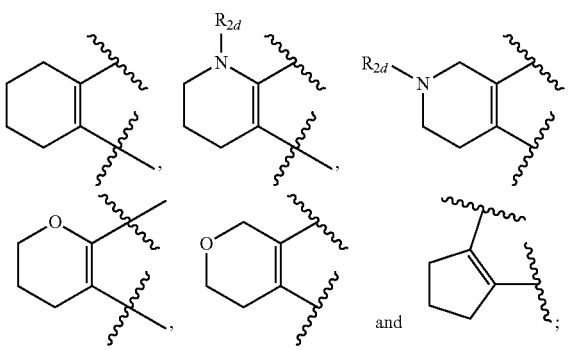

each optionally substituted with one or two substituents independently selected from OH, halogen, $(C_{1-4})$alkyl and $(C=O)O(C_{1-4})$alkyl, wherein a carbon in the $(C_{1-4})$alkyl chain may bond to a carbon on Ring A and form a spirocyclic moiety, wherein $(C_{1-4})$alkyl is optionally substituted with OH, methylpyrrolidinyl, $NH_2$ or oxo;
X is N or C, wherein when X is N then the dashed line is absent and when X is C the dashed line represents a double bond;

Y is N or CH;
R$_{1a}$ is H or (C$_{1-4}$)alkyl;
R$_{1b}$ is H, OH or (C$_{1-4}$)alkyl;
R$_{2a}$ is Cl or (C$_{1-4}$)alkyl;
R$_{2b}$ is cyclopropyl, cyclobutyl, oxetanyl or azetidinyl, each optionally substituted with (C$_{1-4}$)alkyl, F, CF$_3$, CHF$_2$ or CN;
R$_{2c}$ is H or F; and
R$_{2d}$ is H or (C$_{1-4}$)alkyl;
or a pharmaceutically acceptable salt thereof.

In another embodiment, the present invention provides a compound according to Formula I, wherein:
Ring A is selected from:

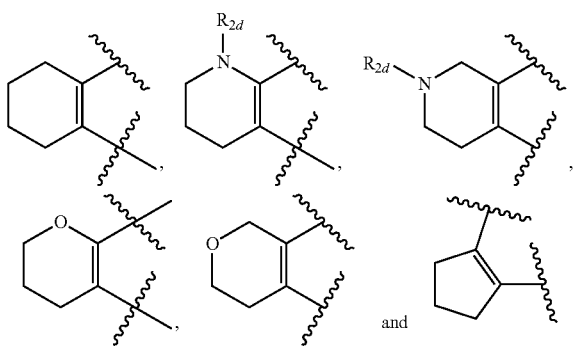

each optionally substituted with one or two substituents independently selected from OH, F, (C$_{1-4}$)alkyl and (C=O)O(C$_{1-4}$)alkyl, wherein a carbon in the (C$_{1-4}$)alkyl chain may bond to a carbon on Ring A and form a spirocyclic moiety, wherein (C$_{1-4}$)alkyl is optionally substituted with OH, methylpyrrolidine, NH$_2$ or oxo;
X is N or C, wherein when X is N then the dashed line is absent and when X is C the dashed line represents a double bond;
Y is N or CH;
R$_{1a}$ is H or methyl;
R$_{1b}$ is H, OH or methyl;
R$_{2a}$ is Cl or methyl;
R$_{2b}$ is cyclopropyl, cyclobutyl, oxetane or azetidine, each optionally substituted with methyl, F, CF$_3$, CHF$_2$ and CN;
R$_{2c}$ is H or F; and
R$_{2d}$ is H or (C$_{1-4}$)alkyl;
or a pharmaceutically acceptable salt thereof.

In another embodiment, the present invention provides a compound according to Formula I, wherein:
Ring A is selected from:

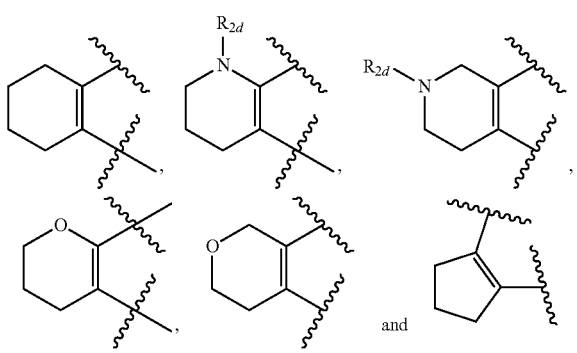

each optionally substituted with one or two substituents independently selected from OH, F, (C$_{1-4}$)alkyl and (C=O)O(C$_{1-4}$)alkyl, wherein a carbon in the (C$_{1-4}$)alkyl chain may bond to a carbon on Ring A and form a spirocyclic moiety, wherein (C$_{1-4}$)alkyl is optionally substituted with OH, methylpyrrolidinyl, NH$_2$ or oxo;
X is N or C, wherein when X is N then the dashed line is absent and when X is C the dashed line represents a double bond;
Y is N or CH;
R$_{1a}$ is H or methyl;
R$_{1b}$ is H, OH or methyl;
R$_{2a}$ is Cl or methyl;
R$_{2b}$ is cyclopropyl, cyclobutyl, oxetanyl or azetidinyl, each optionally substituted with methyl, F, CF$_3$, CHF$_2$ and CN;
R$_{2c}$ is H or F; and
R$_{2d}$ is H or (C$_{1-4}$)alkyl;
or a pharmaceutically acceptable salt thereof.

A more specific collection of compounds may be described according to the following definitions for certain variables for Formula I. In certain embodiments, X is C. In certain embodiments, Y is CH. In certain embodiments, R$_{1a}$ is H. In certain embodiments, Rib is H or OH. In certain embodiments, R$_{2a}$ is Cl. In certain embodiments, R$_{2b}$ is cyclopropyl optionally substituted with CF$_3$. In certain embodiments, R$_{2c}$ is H. In certain embodiments, R$_{2d}$ is H. In certain embodiments, Ring A is selected from:

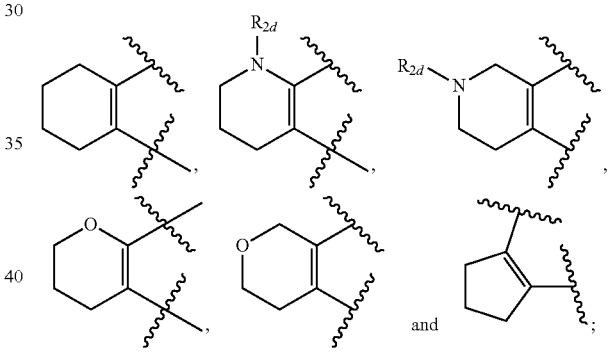

each optionally substituted with one or two substituents independently selected from OH, halogen, (C$_{1-4}$)alkyl and (C=O)O(C$_{1-4}$)alkyl, wherein (C$_{1-4}$)alkyl is optionally substituted with OH, methylpyrrolidine, or NH$_2$. In certain embodiments, Ring A is selected from:

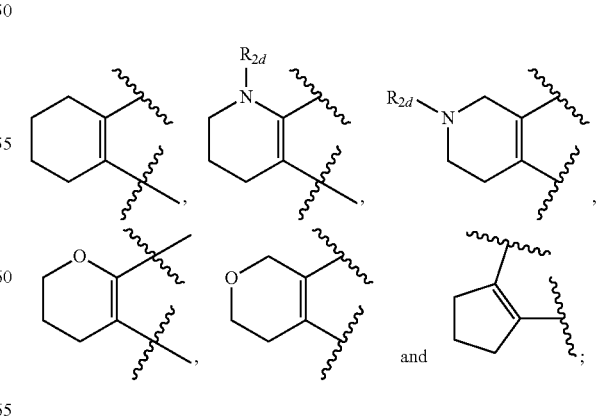

each optionally substituted with one or two substituents independently selected from OH, halogen, (C$_{1-4}$)alkyl and (C=O)O(C$_{1-4}$)alkyl, wherein (C$_{1-4}$)alkyl is optionally substituted with OH, methylpyrrolidinyl, or NH$_2$. In certain embodiments, Ring A is

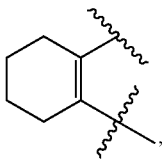

optionally substituted with one or two substituents independently selected from halogen and (C$_{1-4}$)alkyl, wherein the (C$_{1-4}$)alkyl is optionally substituted with OH or NH$_2$. In certain embodiments, the compound is in the form of a free acid. The invention embraces all combinations of such embodiments, such as where X is C, Y is CH, R$_{1a}$ is H, R$_{2a}$ is Cl, and R$_{2b}$ is cyclopropyl optionally substituted with CF$_3$.

In another embodiment, the present invention provides a compound according to Formula II:

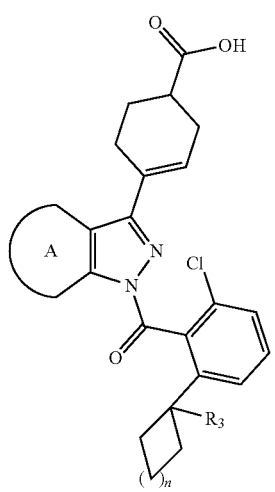

(II)

wherein:
Ring A is selected from:

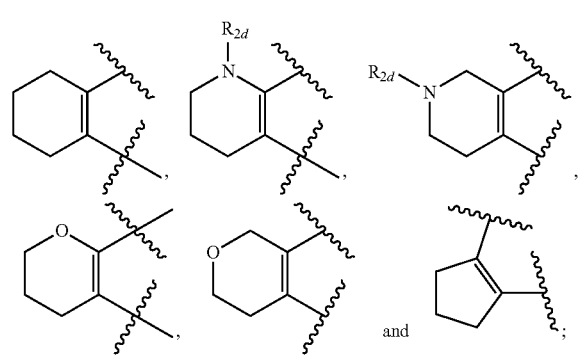

each optionally substituted with one or two substituents independently selected from OH, F, (C$_{1-4}$)alkyl and (C=O)O(C$_{1-4}$)alkyl, wherein a carbon in the (C$_{1-4}$)alkyl chain may bond to a carbon on Ring A and form a spirocyclic moiety, wherein (C$_{1-4}$)alkyl is optionally substituted with OH, methylpyrrolidine, NH$_2$ or oxo;

n is 0 or 1; and

R$_{2d}$ is H or (C$_{1-4}$)alkyl; and

R$_3$ is methyl, F, CF$_3$, CHF$_2$ or CN;

or a pharmaceutically acceptable salt thereof.

In another embodiment, the present invention provides a compound according to Formula II, wherein:

Ring A is selected from:

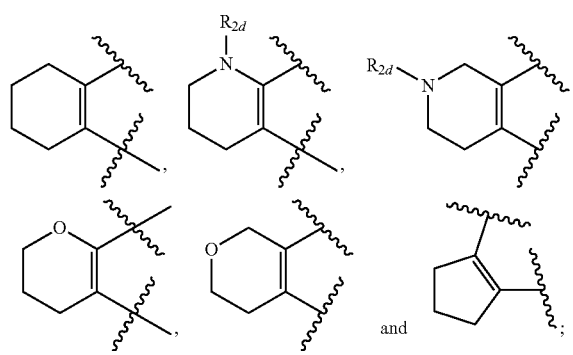

each optionally substituted with one or two substituents independently selected from OH, F, (C$_{1-4}$)alkyl and (C=O)O(C$_{1-4}$)alkyl, wherein a carbon in the (C$_{1-4}$)alkyl chain may bond to a carbon on Ring A and form a spirocyclic moiety, wherein (C$_{1-4}$)alkyl is optionally substituted with OH, methylpyrrolidinyl, NH$_2$ or oxo;

n is 0 or 1; and

R$_{2d}$ is H or (C$_{1-4}$)alkyl; and

R$_3$ is methyl, F, CF$_3$, CHF$_2$ or CN;

or a pharmaceutically acceptable salt thereof.

A more specific collection of compounds may be described according to the following definitions for certain variables for Formula II. In certain embodiments, Ring A is selected from:

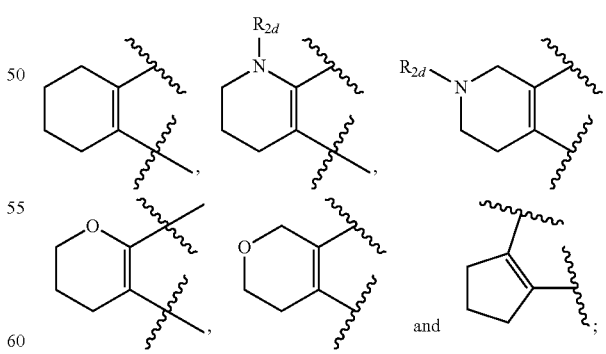

each optionally substituted with one or two substituents independently selected from OH, halogen, (C$_{1-4}$)alkyl and (C=O)O(C$_{1-4}$)alkyl, wherein (C$_{1-4}$)alkyl is optionally substituted with OH, methylpyrrolidine, or NH$_2$. In certain embodiments, Ring A is selected from:

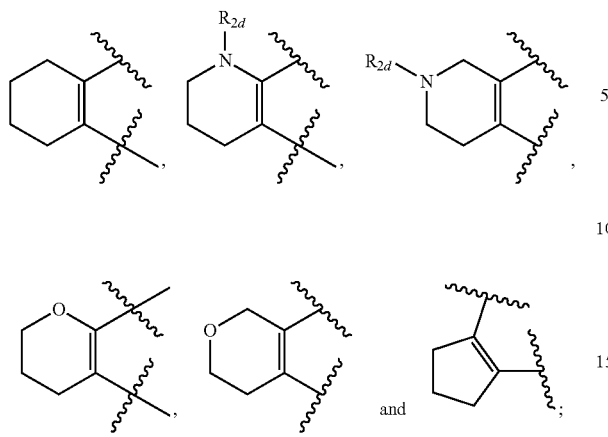

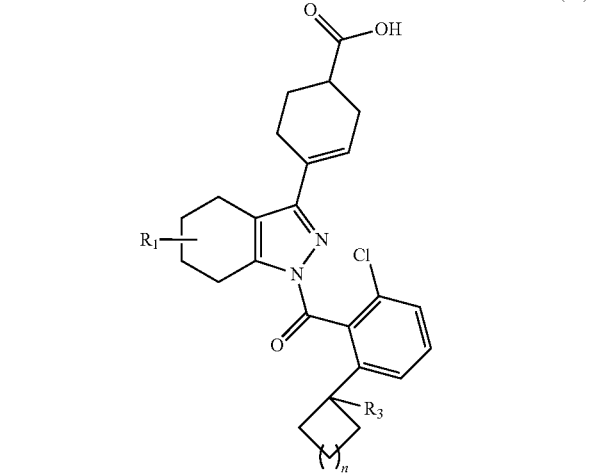

(III)

each optionally substituted with one or two substituents independently selected from OH, halogen, $(C_{1-4})$alkyl and $(C=O)O(C_{1-4})$alkyl, wherein $(C_{1-4})$alkyl is optionally substituted with OH, methylpyrrolidinyl, or $NH_2$. In certain embodiments, Ring A is

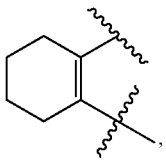 [SMILES: *C1=C(*)CCCC1]

optionally substituted with one or two substituents independently selected from halogen and $(C_{1-4})$alkyl, wherein the $(C_{1-4})$alkyl is optionally substituted with OH or $NH_2$. In certain embodiments, n is 0. In certain embodiments, $R_3$ is $CF_3$. In certain embodiments, the compound is in the form of a free acid. The invention embraces all combinations of such embodiments, such as where Ring A is

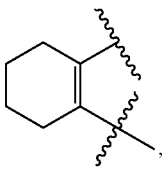 [SMILES: *C1=C(*)CCCC1]

optionally substituted with one or two substituents independently selected from halogen and $(C_{1-4})$alkyl, wherein the $(C_{1-4})$alkyl is optionally substituted with OH or $NH_2$, n is 0, and $R_3$ is $CF_3$.

In another embodiment, the present invention provides a compound according to Formula III:

wherein:
$R_1$ is independently selected from OH, F, $(C_{1-4})$alkyl and $(C=O)O(C_{1-4})$alkyl, wherein a carbon in the $(C_{1-4})$alkyl chain may bond to a carbon on the cyclohexyl ring and form a spirocyclic moiety, wherein $(C_{1-4})$alkyl is optionally substituted with OH, methylpyrrolidine, $NH_2$ or oxo;
n is 0 or 1; and
$R_3$ is methyl, F, $CF_3$, $CHF_2$ or CN;
or a pharmaceutically acceptable salt thereof.

In another embodiment, the present invention provides a compound according to Formula III, wherein:
$R_1$ is independently selected from OH, F, $(C_{1-4})$alkyl and $(C=O)O(C_{1-4})$alkyl, wherein a carbon in the $(C_{1-4})$alkyl chain may bond to a carbon on the cyclohexyl ring and form a spirocyclic moiety, wherein $(C_{1-4})$alkyl is optionally substituted with OH, methylpyrrolidinyl, $NH_2$ or oxo;
n is 0 or 1; and
$R_3$ is methyl, F, $CF_3$, $CHF_2$ or CN;
or a pharmaceutically acceptable salt thereof.

A more specific collection of compounds may be described according to the following definitions for certain variables for Formula III. In certain embodiments, $R_1$ is independently selected from OH, F, and $(C_{1-4})$alkyl, wherein $(C_{1-4})$alkyl is optionally substituted with OH, methylpyrrolidine, or $NH_2$. In certain embodiments, $R_1$ is independently selected from OH, F, and $(C_{1-4})$alkyl, wherein $(C_{1-4})$alkyl is optionally substituted with OH, methylpyrrolidinyl, or $NH_2$. In certain embodiments, $R_1$ is independently selected from $(C_{1-4})$alkyl optionally substituted with OH or $NH_2$. In certain embodiments, n is 0. In certain embodiments, $R_3$ is $CF_3$. In certain embodiments, the compound is in the form of a free acid. The invention embraces all combinations of such embodiments, such as where $R_1$ is independently selected from $(C_{1-4})$alkyl optionally substituted with OH or $NH_2$, n is 0, and $R_3$ is $CF_3$.

Exemplary specific compounds according to the instant invention include, for example:
4-(1-(2-chloro-6-cyclopropylbenzoyl)-4,5,6,7-tetrahydro-1H-indazol-3-yl)cyclohex-3-ene-1-carboxylic acid;
4-{1-[(2-chloro-6-cyclopropylphenyl)carbonyl]-1,4,5,7-tetrahydropyrano[3,4-c]pyrazol-3-yl}cyclohex-3-ene-1-carboxylic acid;
4-{1-[(2-chloro-6-cyclopropylphenyl)carbonyl]-1,4,5,6-tetrahydrocyclopenta[c]pyrazol-3-yl}cyclohex-3-ene-1-carboxylic acid;

4-(1-{[2-chloro-6-(1-methylcyclopropyl)phenyl]carbonyl}-1,4,5,7-tetrahydropyrano[3,4-c]pyrazol-3-yl)cyclohex-3-ene-1-carboxylic acid;

4-(1-{[2-chloro-6-(1-methylcyclopropyl)phenyl]carbonyl}-1,4,5,6-tetrahydrocyclopenta[c]pyrazol-3-yl)cyclohex-3-ene-1-carboxylic acid;

4-(1-{[2-chloro-6-(1-cyanocyclobutyl)phenyl]carbonyl}-1,4,5,6-tetrahydrocyclopenta[c]pyrazol-3-yl)cyclohex-3-ene-1-carboxylic acid;

(S)-4-(1-(2-Chloro-6-cyclobutylbenzoyl)-1,4,5,7-tetrahydropyrano[3,4-c]pyrazol-3-yl)cyclohex-3-ene-1-carboxylic acid;

(R)-4-(1-(2-Chloro-6-cyclobutylbenzoyl)-1,4,5,7-tetrahydropyrano[3,4-c]pyrazol-3-yl)cyclohex-3-ene-1-carboxylic acid;

(1R or S)-4-(1-{[2-chloro-6-(1-cyanocyclopropyl)phenyl]carbonyl}-1,4,5,7-tetrahydropyrano[3,4-c]pyrazol-3-yl)cyclohex-3-ene-1-carboxylic acid;

(1R or S)-4-(1-{[2-chloro-6-(1-cyanocyclobutyl)phenyl]carbonyl}-1,4,5,7-tetrahydropyrano[3,4-c]pyrazol-3-yl)cyclohex-3-ene-1-carboxylic acid;

4-((R or S)-1-(2-chloro-6-cyclopropylbenzoyl)-4-methyl-4,5,6,7-tetrahydro-1H-indazol-3-yl)cyclohex-3-ene-1-carboxylic acid;

4-((R or S)-1-(2-chloro-6-cyclopropylbenzoyl)-6-(methoxycarbonyl)-4,5,6,7-tetrahydro-1H-indazol-3-yl)cyclohex-3-ene-1-carboxylic acid;

4-(1'-(2-chloro-6-cyclopropylbenzoyl)-2-oxo-1',4,4',5,5',7'-hexahydro-2H-spiro[furan-3,6'-indazol]-3'-yl)cyclohex-3-ene-1-carboxylic acid;

4-((R or S)-1-(2-chloro-6-cyclopropylbenzoyl)-6-(hydroxymethyl)-4,5,6,7-tetrahydro-1H-indazol-3-yl)cyclohex-3-ene-1-carboxylic acid;

4-((R or S)-1-(2-chloro-6-cyclopropylbenzoyl)-6-(hydroxymethyl)-4,5,6,7-tetrahydro-1H-indazol-3-yl)cyclohex-3-ene-1-carboxylic acid;

4-((R or S)-1-(2-chloro-6-cyclopropyl-3-fluorobenzoyl)-6-(hydroxymethyl)-4,5,6,7-tetrahydro-1H-indazol-3-yl)cyclohex-3-ene-1-carboxylic acid;

4-((R or S)-1-(2-chloro-6-(oxetan-3-yl)benzoyl)-6-(hydroxymethyl)-4,5,6,7-tetrahydro-1H-indazol-3-yl)cyclohex-3-ene-1-carboxylic acid;

4-((R or S)-1-(2-chloro-6-(1-(trifluoromethyl)cyclopropyl)benzoyl)-6-(hydroxymethyl)-4,5,6,7-tetrahydro-1H-indazol-3-yl)cyclohex-3-ene-1-carboxylic acid;

4-((R or S)-1-(2-chloro-6-cyclopropylbenzoyl)-6-((R or S)-1-hydroxyethyl)-4,5,6,7-tetrahydro-1H-indazol-3-yl)cyclohex-3-ene-1-carboxylic acid;

4-((R or S)-1-(2-chloro-6-cyclopropylbenzoyl)-6-(hydroxymethyl)-6-methyl-4,5,6,7-tetrahydro-1H-indazol-3-yl)cyclohex-3-ene-1-carboxylic acid;

4-((R or S)-1-(2-chloro-6-cyclopropylbenzoyl)-6-hydroxy-4,5,6,7-tetrahydro-1H-indazol-3-yl)cyclohex-3-ene-1-carboxylic acid;

4-(1-(2-chloro-6-cyclopropylbenzoyl)-6-fluoro-4,5,6,7-tetrahydro-1H-indazol-3-yl)cyclohex-3-ene-1-carboxylic acid;

4-(1-(2-chloro-6-(1-(trifluoromethyl)cyclopropyl)benzoyl)-4,5,6,7-tetrahydro-1H-pyrazolo[4,3-b]pyridin-3-yl)cyclohex-3-ene-1-carboxylic acid;

(R or S)-4-((R or S)-1-(2-chloro-6-cyclopropylbenzoyl)-6-(hydroxymethyl)-4,5,6,7-tetrahydro-1H-indazol-3-yl)-1-methylcyclohex-3-ene-1-carboxylic acid;

4-((R or S)-6-(aminomethyl)-1-(2-chloro-6-cyclopropylbenzoyl)-4,5,6,7-tetrahydro-1H-indazol-3-yl)cyclohex-3-ene-1-carboxylic acid;

4-(1-(2-chloro-6-cyclopropylbenzoyl)-1,5,6,7-tetrahydropyrano[3,2-c]pyrazol-3-yl)cyclohex-3-ene-1-carboxylic acid;

1-(1-(2-chloro-6-cyclopropylbenzoyl)-4,5,6,7-tetrahydro-1H-indazol-3-yl)piperidine-4-carboxylic acid;

Trans-(3R or S,4R or S)-1-(1-(2-chloro-6-cyclopropylbenzoyl)-4,5,6,7-tetrahydro-1H-indazol-3-yl)-3-hydroxypiperidine-4-carboxylic acid;

Trans-(3R or S,4R or S)-1-(1-(2-chloro-6-(1-(trifluoromethyl)cyclopropyl)benzoyl)-4,5,6,7-tetrahydro-1H-indazol-3-yl)-3-hydroxypiperidine-4-carboxylic acid; and cis 1-(1-(2-chloro-6-cyclopropylbenzoyl)-4,5,6,7-tetrahydro-1H-indazol-3-yl)-3-hydroxypiperidine-4-carboxylic acid;

or a pharmaceutically acceptable salt thereof.

Collections of compounds defined by Formulae I, II, and III may be more specifically described according to the following embodiments specifying certain definitions (where present in Formula I, II, or III) for variables Ring A and X. In an embodiment, Ring A is

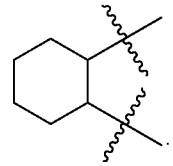 [SMILES: *C1CCCCC1*]

In an embodiment, Ring A is

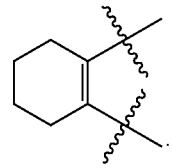

In an embodiment, Ring A of Formula I is optionally substituted with one or two substituents independently selected from OH, F, aminomethyl, COOH, methyl, (C═O)O-methyl, spirofuran, said spirofuran substituted with oxo, hydroxymethyl, hydroxyethyl, and (C═O)O-pyrrolidine, said pyrrolidine substituted with methyl. In an embodiment, Ring A of Formula I is unsubstituted. In an embodiment, X is C.

The invention also provides a compound of Formulas I-III, or a pharmaceutically acceptable salt thereof in purified form.

In certain embodiments, a compound of Formula I, II, or III is provided in the form of a free base or free acid (i.e, not a salt form).

The invention includes prodrugs, hydrates or solvates of the compounds described herein. The use of the terms "prodrug", "hydrate", "salt", "solvate", "ester", and the like is intended to equally apply to the salt, solvate, ester, and prodrug of enantiomers, stereoisomers, rotamers, tautomers, positional isomers, racemates, or prodrugs of the inventive compounds.

Optical Isomers—Diastereomers—Geometric Isomers—Tautomers

The compounds of Formulas (I-III) may contain asymmetric or chiral centers, and, therefore, exist in different stereoisomeric forms. It is intended that all stereoisomeric forms of the compounds of Formulas (I-III) as well as mixtures thereof, including racemic mixtures, form part of the present invention. In addition, the present invention embraces all geometric and positional isomers. For example, if a compound of Formulas (I-III) incorporates a double bond or a fused ring, both the cis- and trans-forms, as well as mixtures, are embraced within the scope of the invention.

Compounds described herein may contain an asymmetric center and may thus exist as enantiomers. Where the compounds according to the invention possess two or more asymmetric centers, they may additionally exist as diastereomers. The present invention includes all such possible stereoisomers as substantially pure resolved enantiomers, racemic mixtures thereof, as well as mixtures of diastereomers. The above Formulas (I-III) are shown without a definitive stereochemistry at certain positions. The present invention includes all stereoisomers of Formulas (I-III) and pharmaceutically acceptable salts thereof.

Diastereoisomeric pairs of enantiomers may be separated by, for example, fractional crystallization from a suitable solvent, and the pair of enantiomers thus obtained may be separated into individual stereoisomers by conventional means, for example by the use of an optically active acid or base as a resolving agent or on a chiral HPLC column. Further, any enantiomer or diastereomer of a compound of the general Formulas (I-III) may be obtained by stereospecific synthesis using optically pure starting materials or reagents of known configuration.

When compounds described herein contain olefinic double bonds, unless specified otherwise, such double bonds are meant to include both E and Z geometric isomers.

Some of the compounds described herein may exist with different points of attachment of hydrogen. Such compounds are referred to as tautomers. For example, compounds including carbonyl —$CH_2C(O)$— groups (keto forms) may undergo tautomerism to form hydroxyl —CH=C(OH)— groups (enol forms). Both keto and enol forms, individually as well as mixtures thereof, are included within the scope of the present invention. The compounds of Formulas I-III may exist in different tautomeric forms, and all such forms are embraced within the scope of the invention. Also, for example, imine-enamine forms of the compounds are included in the invention.

Diastereomeric mixtures can be separated into their individual diastereomers on the basis of their physical chemical differences by methods well known to those skilled in the art, such as, for example, by chromatography and/or fractional crystallization. Enantiomers can be separated by converting the enantiomeric mixture into a diastereomeric mixture by reaction with an appropriate optically active compound (e.g. chiral auxiliary such as a chiral alcohol or Mosher's acid chloride), separating the diastereomers and converting (e.g. hydrolyzing) the individual diastereomers to the corresponding pure enantiomers. Also, some of the compounds of Formulas (I-III) may be atropisomers (e.g. substituted biaryls) and are considered as part of this invention. Enantiomers can also be separated by use of chiral HPLC column.

All stereoisomers (for example, geometric isomers, optical isomers and the like) of the present compounds (including those of the salts, solvates, esters, and prodrugs of the compounds as well as the salts, solvates, and esters of the prodrugs), such as those that may exist due to asymmetric carbons on various substituents, including enantiomeric forms (which may exist even in the absence of asymmetric carbons), rotameric forms, atropisomers, and diastereomeric forms, are contemplated within the scope of this invention, as are positional isomers. Individual stereoisomers of the compounds of the invention may, for example, be substantially free of other isomers, or may be admixed, for example, as racemates or with all other, or other selected, stereoisomers. The chiral centers of the present invention can have the S or R configuration as defined by the IUPAC 1974 Recommendations.

Salts

The term "pharmaceutically acceptable salts" refers to salts prepared from pharmaceutically acceptable non-toxic bases or acids. When the compound of the present invention is acidic, its corresponding salt can be conveniently prepared from pharmaceutically acceptable non-toxic bases, including inorganic bases and organic bases. Salts derived from such inorganic bases include aluminum, ammonium, calcium, copper (ic and ous), ferric, ferrous, lithium, magnesium, manganese (-ic and -ous), potassium, sodium, zinc and the like salts. Preferred are the ammonium, calcium, magnesium, potassium and sodium salts. Salts prepared from pharmaceutically acceptable organic non-toxic bases include salts of primary, secondary, and tertiary amines derived from both naturally occurring and synthetic sources. Pharmaceutically acceptable organic non-toxic bases from which salts can be formed include, for example, arginine, betaine, caffeine, choline, N,N'-dibenzylethylenediamine, diethylamine, 2-diethylaminoethanol, 2-dimethylaminoethanol, ethanolamine, ethylenediamine, N-ethyl-morpholine, N-ethylpiperidine, glucamine, glucosamine, histidine, hydrabamine, isopropylamine, dicyclohexylamine, lysine, methylglucamine, morpholine, piperazine, piperidine, polyamine resins, procaine, purines, theobromine, triethylamine, trimethylamine, tripropylamine, tromethamine and the like.

When the compound of the present invention is basic, its corresponding salt can be conveniently prepared from pharmaceutically acceptable non-toxic inorganic and organic acids. Such acids include, for example, acetic, benzenesulfonic, benzoic, camphorsulfonic, citric, ethanesulfonic, fumaric, gluconic, glutamic, hydrobromic, hydrochloric, isethionic, lactic, maleic, malic, mandelic, methanesulfonic, mucic, nitric, pamoic, pantothenic, phosphoric, succinic, sulfuric, tartaric, p-toluenesulfonic acid and the like. Preferred are citric, hydrobromic, hydrochloric, maleic, phosphoric, sulfuric, and tartaric acids.

The compounds of Formulas I-III can form salts which are also within the scope of this invention. Reference to a compound of Formulas I-III herein is understood to include reference to salts thereof, unless otherwise indicated.

The term pharmaceutically acceptable salt represents those salts that are, within the scope of medical judgment, suitable for use in contact for the tissues of humans and lower animals without undue toxicity, irritation, allergic response and the like, and are commensurate with a reasonable benefit/risk ratio. Pharmaceutically acceptable salts are well known in the art. They may be obtained during the final isolation and purification of the compounds of the invention, or separately by reacting the free base function with a suitable mineral acid such as hydrochloric acid, phosphoric acid, or sulfuric acid, or with an organic acid such as for example ascorbic acid, citric acid, tartaric acid, lactic acid, maleic acid, malonic acid, fumaric acid, glycolic acid, succinic acid, propionic acid, acetic acid, methanesulfonic acid, and the like. The acid function can be reacted with an organic or a mineral base, like sodium hydroxide, potassium hydroxide, calcium hydroxide, calcium carbonate, ammonium (e.g. diethylamine) or lithium hydroxide.

Solvates

The present invention includes within its scope solvates of compounds of Formulas (I-III). As used herein, the term "solvate" refers to a complex of variable stoichiometry formed by a solute (i.e., a compound of Formulas (I-III)) or a pharmaceutically acceptable salt thereof and a solvent that does not interfere with the biological activity of the solute. Examples of solvents include but are not limited to water, ethanol, and acetic acid. When the solvent is water, the solvate is known as hydrate; hydrate includes, but is not limited to, hemi-, mono, sesqui-, di- and trihydrates.

The compounds of the invention may form hydrates or solvates. It is known to those of skill in the art that charged compounds form hydrated species when lyophilized with water, or form solvated species when concentrated in a solution with an appropriate organic solvent. One or more compounds of the invention may exist in unsolvated as well as solvated forms with pharmaceutically acceptable solvents such as water, ethanol, and the like, and it is intended that the invention embrace both solvated and unsolvated forms. "Solvate" may also mean a physical association of a compound of this invention with one or more solvent molecules. This physical association involves varying degrees of ionic and covalent bonding, including hydrogen bonding. In certain instances the solvate will be capable of isolation, for example when one or more solvent molecules are incorporated in the crystal lattice of the crystalline solid. "Solvate" encompasses both solution-phase and isolatable solvates. Non-limiting examples of suitable solvates include ethanolates, methanolates, and the like. "Hydrate" is a solvate wherein the solvent molecule is $H_2O$.

Prodrugs

The present invention includes within its scope the use prodrugs of the compounds of this invention. In general, such prodrugs will be functional derivatives of the compounds of this invention which are readily convertible in vivo into the required compound. Thus, in the methods of treatment of the present invention, the term "administering" shall encompass the treatment of the various conditions described with a compound of Formulas I-III or with a compound that may not be a compound of Formulas I-III, but that converts to a compound of Formulas I-III in vivo after administration to the patient. Conventional procedures for the selection and preparation of suitable prodrug derivatives are described, for example, in "Design of Prodrugs," ed. H. Bundgaard, Elsevier, 1985.

The term "prodrug" means a compound (e.g., a drug precursor) that is transformed in vivo to yield a compound of Formulas I-III or a pharmaceutically acceptable salt, hydrate or solvate of the compound. The transformation may occur by various mechanisms (e.g., by metabolic or chemical processes), such as, for example, through hydrolysis in blood. A discussion of prodrugs and the use of prodrugs is provided by T. Higuchi and W. Stella, "Prodrugs as Novel Delivery Systems," Vol. 14 of the A.C.S. Symposium Series, 1987; and in Bioreversible Carriers in Drug Design, ed. Edward B. Roche, American Pharmaceutical Association and Pergamon Press, 1987.

Isotopes

In the compounds of generic Formulas (I-III), the atoms may exhibit their natural isotopic abundances, or one or more of the atoms may be artificially enriched in a particular isotope having the same atomic number, but an atomic mass or mass number different from the atomic mass or mass number predominantly found in nature. The present invention is meant to include all suitable isotopic variations of the compounds of generic Formulas I-III. For example, different isotopic forms of hydrogen (H) include protium ($^1H$) and deuterium ($^2H$). Protium is the predominant hydrogen isotope found in nature. Enriching for deuterium may afford certain therapeutic advantages, such as increasing in vivo half-life or reducing dosage requirements, or may provide a compound useful as a standard for characterization of biological samples. In light of the present disclosure, isotopically-enriched compounds within generic Formulas (I-III) can be prepared without undue experimentation by conventional techniques well known to those skilled in the art or by processes analogous to those described in the Schemes and Examples herein using appropriate isotopically-enriched reagents and/or intermediates.

Utilities

Compounds of the present invention alter the interaction of coregulator proteins with Retinoic Acid Receptor-related Orphan Receptor gamma t (RORgammaT) and thereby antagonize RORgammaT-mediated transcriptional activity, and as such are useful in the treatment of diseases and conditions in which inhibition of RORgammaT is desirable, such as autoimmune and inflammatory diseases and disorders.

Accordingly, another embodiment of the present invention provides a method for treating a disease or condition mediated by RORgammaT in a subject comprising administering to the subject an amount of a compound having Formulas I-III, or a pharmaceutically acceptable salt thereof, that is effective for treating the disease or condition mediated by RORgammaT in the subject.

The compounds according to the invention can be used in therapy.

A further aspect of the invention resides in the use of compounds according to the invention or a pharmaceutically acceptable salt thereof for the treatment of RORgammaT-mediated diseases or RORgammaT mediated conditions.

Another aspect of the invention resides in the use of compounds or a pharmaceutically acceptable salt thereof having the general Formulas (I-III) for the treatment of autoimmune diseases, in particular those diseases in which Th17 cells and non-Th17 cells, which express Th17 hallmark cytokines, play a prominent role. These include, but are not limited to, the treatment of rheumatoid arthritis, psoriasis, inflammatory bowel disease, Crohn's disease, ankylosing spondylitis and multiple sclerosis.

In another aspect, compounds or a pharmaceutically acceptable salt thereof having the general Formulas (I-III) can be used for treatment of inflammatory diseases in which Th17 cells and/or non-Th17 cells, which express Th17 hallmark cytokines, play a prominent role, such as but not limited to respiratory diseases, osteoarthritis and asthma. Also, compounds or a pharmaceutically acceptable salt thereof having the general Formulas (I-III) can be used for treatment of infectious diseases in which Th17 cells and/or non-Th17 cells, which express Th17 hallmark cytokines, play a prominent role, such as but not limited to mucosal leishmaniasis.

Accordingly, in certain embodiments, the invention provides a method of treating a disorder selected from the group consisting of an autoimmune disorder and an inflammatory disorder, where the method comprises administering to a subject in need thereof a therapeutically effective amount of a compound described herein (e.g., a compound of Formula I, II, or III) to treat the disorder. In certain embodiments, the disorder is an autoimmune disorder. In certain embodiments, the autoimmune disorder is rheumatoid arthritis, psoriasis, Crohn's disease, inflammatory bowel disease, multiple sclerosis, psoriasis, ankylosing spondylitis, systemic lupus erythematosus, chronic graft-versus-host disease, acute graft-versus-host disease, Celiac Sprue, idiopathic thrombocytopenic thrombotic purpura, myasthenia gravis, Sjogren's syndrome, scleroderma, ulcerative colitis, or epidermal hyperplasia. In certain other embodiments, the autoimmune disorder is rheumatoid arthritis, psoriasis, Crohn's disease, inflammatory bowel disease, multiple sclerosis, or psoriasis. In certain embodiments, the disorder is an inflammatory disorder. In certain embodiments, the inflammatory disorder is a respiratory disease or osteoarthritis. In certain other embodiments, the inflammatory disorder is osteoarthritis or asthma.

Compounds or a pharmaceutically acceptable salt thereof having the general Formulas (I-III) can also be used for treatment of other diseases in which Th17 cells and/or non-Th17 cells, which express Th17 hallmark cytokines, play a prominent role, such as but not limited to Kawasaki disease and Hashimoto's thyroiditis.

In one aspect the disease or condition is an autoimmune disease or an inflammatory disease. The disease or condition includes, but is not limited to, multiple sclerosis, inflammatory bowel disease, Crohn's disease, ankylosing spondylitis, psoriasis, rheumatoid arthritis, asthma, osteoarthritis, Kawasaki disease, Hashimoto's thyroiditis or mucosal leishmaniasis.

In another aspect, the compounds according to the invention can be used in therapies to treat or prevent multiple sclerosis, inflammatory bowel disease, Crohn's disease, psoriasis, rheumatoid arthritis, asthma, osteoarthritis, Kawasaki disease, Hashimoto's thyroiditis and mucosal leishmaniasis.

In another aspect the compounds according to the invention can be used to treat or prevent psoriasis.

In yet another aspect the compounds according to the invention can be used to treat inflammatory bowel disease.

In yet another aspect the compounds according to the invention can be used to treat cancer. The term cancer includes, but is not limited to, colorectal, lung, and pancreatic cancer. Additional exemplary cancers contemplated for treatment include, for example, ovarian cancer, a melanoma, breast cancer, prostate cancer, renal cell carcinoma, testicular cancer, uterine cancer, brain cancer, bladder cancer, leukemia, a B-cell lymphoma, and non-Hodgkin lymphoma.

In another aspect the compounds according to the invention can be used to treat colorectal cancer.

In another aspect the compounds according to the invention can be used to treat lung cancer.

In another aspect the compounds according to the invention can be used to treat pancreatic cancer.

Another aspect of the inventin provides a method of inhibiting the activity of RORγ. The method comprises exposing a RORγ to an effective amount of a compound described herein (e.g., a compound of Formula I, II, or III) to inhibit the activity of said RORγ.

Another aspect of the present invention further includes the use of a compound of Formulas I-III, or a pharmaceutically acceptable salt thereof, in the manufacture of a medicament for the treatment of a disease or condition mediated by RORgammaT.

Route of Administration/Dosage

The compounds of this invention can be administered for the treatment or prevention of afflictions, diseases and illnesses according to the invention by any means that effects contact of the active ingredient compound with the site of action in the body of a warm-blooded animal. For example, administration can be oral, topical, including transdermal, ocular, buccal, intranasal, inhalation, intravaginal, rectal, intracisternal and parenteral. The term "parenteral" as used herein refers to modes of administration that include subcutaneous, intravenous, intramuscular, intraarticular injection or infusion, intrasternal and intraperitoneal. For the purpose of this disclosure, a warm-blooded animal is a member of the animal kingdom possessed of a homeostatic mechanism and includes mammals and birds.

The compounds can be administered by any conventional means available for use in conjunction with pharmaceuticals, either as individual therapeutic agents or in a combination of therapeutic agents. They can be administered alone, but are generally administered with a pharmaceutical carrier selected on the basis of the chosen route of administration and standard pharmaceutical practice.

The dosage administered will be dependent on the age, health and weight of the recipient, the extent of disease, kind of concurrent treatment, if any, frequency of treatment and the nature of the effect desired. Usually, a daily dosage of active ingredient compound will be from about 1.0-2000 milligrams per day. Ordinarily, from 10 to 500 milligrams per day in one or more applications is effective to obtain desired results. These dosages are the effective amounts for the treatment and prevention of afflictions, diseases and illnesses described above, e.g., autoimmune and inflammatory diseases and disorders.

Compositions include e.g. those suitable for oral, sublingual, subcutaneous, intravenous, intramuscular, nasal, local, or rectal administration, and the like, all in unit dosage forms for administration.

For oral administration, the active ingredient may be presented as discrete units, such as tablets, capsules, powders, granulates, solutions, suspensions, and the like. For parenteral administration, the pharmaceutical composition of the invention may be presented in unit-dose or multi-dose containers, e.g. injection liquids in predetermined amounts, for example in sealed vials and ampoules, and may also be stored in a freeze dried (lyophilized) condition requiring only the addition of sterile liquid carrier, e.g. water, prior to use.

Mixed with such pharmaceutically acceptable auxiliaries, e.g. as described in the standard reference, Gennaro, A. R. et al., Remington: *The Science and Practice of Pharmacy*(20th Edition, Lippincott Williams & Wilkins, 2000, see especially Part 5: Pharmaceutical Manufacturing), the active agent may be compressed into solid dosage units, such as pills, tablets, or be processed into capsules or suppositories. By means of pharmaceutically acceptable liquids the active agent can be applied as a fluid composition, e.g. as an injection preparation, in the form of a solution, suspension, emulsion, or as a spray, e.g. a nasal spray.

For making solid dosage units, the use of conventional additives such as fillers, colorants, polymeric binders and the like is contemplated. In general any pharmaceutically acceptable additive that does not interfere with the function of the active compounds can be used. Suitable carriers with which the active agent of the invention can be administered as solid compositions include lactose, starch, cellulose derivatives and the like, or mixtures thereof, used in suitable amounts. For parenteral administration, aqueous suspensions, isotonic saline solutions and sterile injectable solutions may be used, containing pharmaceutically acceptable dispersing agents and/or wetting agents, such as propylene glycol or butylene glycol.

Pharmaceutical Compositions

Another aspect of the present invention provides pharmaceutical compositions comprising a compound of Formulas (I-III), or a pharmaceutically acceptable salt thereof, and one or more pharmaceutically acceptable excipients or carriers. The term "excipient" and "carrier" may be used interchangeably. The term "composition", as in pharmaceutical composition, is intended to encompass a product comprising the active ingredient(s), and the inert ingredient(s) (pharmaceutically acceptable excipients) that make up the carrier, as well as any product that results, directly or indirectly, from combination, complexation or aggregation of any two or more of the ingredients, or from dissociation of one or more of the ingredients, or from other types of reactions or interactions of one or more of the ingredients. Accordingly, the pharmaceutical compositions of the present invention encompass any composition made by admixing a compound of Formulas I-III, additional active ingredient(s), and pharmaceutically acceptable excipients.

The pharmaceutical compositions of the present invention comprise a compound represented by Formulas I-III (or pharmaceutically acceptable salts thereof) as an active ingredient, a pharmaceutically acceptable carrier and optionally other therapeutic ingredients or adjuvants. The compositions include compositions suitable for oral, rectal, topical, and parenteral (including subcutaneous, intramuscular, and intravenous) administration, although the most suitable route in any given case will depend on the particular host, and nature and severity of the conditions for which the active ingredient is being administered. The pharmaceutical compositions may be conveniently presented in unit dosage form and prepared by any of the methods well known in the art of pharmacy.

The active ingredient can be administered orally in solid dosage forms, such as capsules, tablets, troches, dragées, granules and powders, or in liquid dosage forms, such as elixirs, syrups, emulsions, dispersions, and suspensions. The active ingredient can also be administered parenterally, in sterile liquid dosage forms, such as dispersions, suspensions or solutions. Other dosages forms that can also be used to administer the active ingredient as an ointment, cream, drops, transdermal patch or powder for topical administration, as an ophthalmic solution or suspension formation, i.e., eye drops, for ocular administration, as an aerosol spray or powder composition for inhalation or intranasal administration, or as a cream, ointment, spray or suppository for rectal or vaginal administration.

Gelatin capsules contain the active ingredient and powdered carriers, such as lactose, starch, cellulose derivatives, magnesium stearate, stearic acid, and the like. Similar diluents can be used to make compressed tablets. Both tablets and capsules can be manufactured as sustained release products to provide for continuous release of medication over a period of hours. Compressed tablets can be sugar coated or film coated to mask any unpleasant taste and protect the tablet from the atmosphere, or enteric coated for selective disintegration in the gastrointestinal tract.

Liquid dosage forms for oral administration can contain coloring and flavoring to increase patient acceptance.

In general, water, a suitable oil, saline, aqueous dextrose (glucose), and related sugar solutions and glycols such as propylene glycol or polyethylene glycols are suitable carriers for parenteral solutions. Solutions for parenteral administration preferably contain a water soluble salt of the active ingredient, suitable stabilizing agents, and if necessary, buffer substances. Antioxidizing agents such as sodium bisulfite, sodium sulfite, or ascorbic acid, either alone or combined, are suitable stabilizing agents. Also used are citric acid and its salts and sodium EDTA. In addition, parenteral solutions can contain preservatives, such as benzalkonium chloride, methyl- or propylparaben, and chlorobutanol.

Suitable pharmaceutical carriers are described in *Remington's Pharmaceutical Sciences*, A. Osol, a standard reference text in this field.

For administration by inhalation, the compounds of the present invention may be conveniently delivered in the form of an aerosol spray presentation from pressurized packs or nebulizers. The compounds may also be delivered as powders which may be formulated and the powder composition may be inhaled with the aid of an insufflation powder inhaler device. The preferred delivery system for inhalation is a metered dose inhalation (MDI) aerosol, which may be formulated as a suspension or solution of a compound of Formulas I-III in suitable propellants, such as fluorocarbons or hydrocarbons.

For ocular administration, an ophthalmic preparation may be formulated with an appropriate weight percent solution or suspension of the compounds of Formulas I-III in an appropriate ophthalmic vehicle, such that the compound is maintained in contact with the ocular surface for a sufficient time period to allow the compound to penetrate the corneal and internal regions of the eye.

Useful pharmaceutical dosage-forms for administration of the compounds of this invention include, but are not limited to, hard and soft gelatin capsules, tablets, parenteral injectables, and oral suspensions.

A large number of unit capsules may be prepared by filling standard two-piece hard gelatin capsules each with 100 milligrams of powdered active ingredient, 150 milligrams of lactose, 50 milligrams of cellulose, and 6 milligrams magnesium stearate.

A mixture of active ingredient in a digestible oil such as soybean oil, cottonseed oil or olive oil may be prepared and injected by means of a positive displacement pump into gelatin to form soft gelatin capsules containing 100 milligrams of the active ingredient. The capsules may be washed and dried.

A large number of tablets may be prepared by conventional procedures so that the dosage unit is 100 milligrams of active ingredient, 0.2 milligrams of colloidal silicon dioxide, 5 milligrams of magnesium stearate, 275 milligrams of microcrystalline cellulose, 11 milligrams of starch and 98.8 milligrams of lactose. Appropriate coatings may be applied to increase palatability or delay absorption.

A parenteral composition suitable for administration by injection may be prepared by stirring 1.5% by weight of active ingredient in 10% by volume propylene glycol. The solution may be made to volume with water for injection and sterilized.

An aqueous suspension may be prepared for oral administration so that each 5 milliliters contain 100 milligrams of finely divided active ingredient, 100 milligrams of sodium carboxymethyl cellulose, 5 milligrams of sodium benzoate, 1.0 grams of sorbitol solution, U.S.P., and 0.025 milliliters of vanillin.

The same dosage forms can generally be used when the compounds of this invention are administered stepwise or in conjunction with another therapeutic agent. When drugs are administered in physical combination, the dosage form and administration route should be selected depending on the compatibility of the combined drugs. Thus the term coadministration is understood to include the administration of the two agents concomitantly or sequentially, or alternatively as a fixed dose combination of the two active components.

The present invention also relates to a pharmaceutical composition comprising compounds or pharmaceutically acceptable salts thereof having the general Formulas I-III in admixture with pharmaceutically acceptable auxiliaries and optionally other therapeutic agents. The auxiliaries must be "acceptable" in the sense of being compatible with the other ingredients of the composition and not deleterious to the recipients thereof.

The invention further includes a pharmaceutical composition, as hereinbefore described, in combination with packaging material suitable for said composition, said packaging material including instructions for the use of the composition for the use as hereinbefore described.

The exact dose and regimen of administration of the active ingredient, or a pharmaceutical composition thereof, may vary with the particular compound, the route of administration, and the age and condition of the individual subject to whom the medicament is to be administered.

In general parenteral administration requires lower dosages than other methods of administration which are more dependent upon absorption. However, a dosage for humans preferably contains 0.0001-100 mg per kg body weight. The desired dose may be presented as one dose or as multiple subdoses administered at appropriate intervals throughout the day. The dosage as well as the regimen of administration may differ between a female and a male recipient.

Combination Therapy

Compounds of the present invention, and their salts and solvates, and physiologically functional derivatives thereof, may be employed alone or in combination with other therapeutic agents for the treatment of diseases and conditions associated with inappropriate IL-17 pathway activity. Combination therapies according to the present invention thus comprise the administration of at least one compound of formulas (I-III) or a pharmaceutically acceptable salt thereof, or a physiologically functional derivative thereof, and the use of at least one other pharmaceutically active agent. The compound(s) of formulas (I-III) and the other pharmaceutically active agent(s) may be administered together or separately and, when administered separately this may occur simultaneously or sequentially in any order. The amounts of the compound(s) of formulas (I-III) and the other pharmaceutically active agent(s) and the relative timings of administration will be selected in order to achieve the desired combined therapeutic effect. For the treatment of the inflammatory and autoimmune diseases, rheumatoid arthritis, psoriasis, inflammatory bowel disease, ankylosing spondylitis, SLE, uveitis, atopic dermatitis, COPD, asthma and allergic rhinitis a compound of Formulas (I-III) may be combined with one or more other active agents such as: (1) TNF-a inhibitors; (2) non-selective COX-I/COX-2 inhibitors; (3) COX-2 inhibitors; (4) other agents for treatment of inflammatory and autoimmune diseases including glucocorticoids, methotrexate, leflunomide, sulfasalazine, azathioprine, cyclosporin, tacrolimus, penicillamine, bucillamine, actarit, mizoribine, lobenzarit, ciclesonide, hydroxychloroquine, d-penicillamine, aurothiomalate, auranofin or parenteral or oral gold, cyclophosphamide, Lymphostat-B, BAFF/APRIL inhibitors and CTLA-4-Ig or mimetics thereof; (5) leukotriene biosynthesis inhibitor, 5-lipoxygenase (5-LO) inhibitor or 5-lipoxygenase activating protein (FLAP) antagonist; (6) LTD4 receptor antagonist; (7) PDE4 inhibitor; (8) antihistamine HI receptor antagonists; (9) a1- and a2-adrenoceptor agonist; (10) anticholinergic agents; (11) β-adrenoceptor agonists; (12) insulin-like growth factor type I (IGF-1) mimetic; (13) glucocorticosteroids; (14) kinase inhibitors such as inhibitors of the Janus Kinases (JAK 1 and/or JAK2 and/or JAK 3 and/or TYK2), p38 MAPK and IKK2; (15) B-cell targeting biologies such as rituximab; (16) selective costimulation modulators such as abatacept; (17) interleukin inhibitors, such as IL-1 inhibitor anakinra, IL-6 inhibitor tocilizumab, and IL12/IL-23 inhibitor ustekinumab. It could also be combined with anti-IL17 antibodies to obtain additive/synergistic responses for the treatment of inflammatory and autoimmune diseases.

Compounds of the present invention, and their salts and solvates, and physiologically functional derivatives thereof, may be employed alone or in combination with other anti-cancer agents for the treatment of cancer.

It will be clear to a person skilled in the art that, where appropriate, the other therapeutic ingredient(s) may be used in the form of salts, for example as alkali metal or amine salts or as acid addition salts, or prodrugs, or as esters, for example lower alkyl esters, or as solvates, for example hydrates, to optimize the activity and/or stability and/or physical characteristics, such as solubility, of the therapeutic ingredient. It will be clear also that, where appropriate, the therapeutic ingredients may be used in optically pure form.

The combinations referred to above may conveniently be presented for use in the form of a pharmaceutical composition and thus pharmaceutical compositions comprising a combination as defined above together with a pharmaceutically acceptable diluent or carrier represent a further aspect of the invention. These combinations are of particular interest in respiratory diseases and are conveniently adapted for inhaled or intranasal delivery.

The individual compounds of such combinations may be administered either sequentially or simultaneously in separate or combined pharmaceutical compositions. Preferably, the individual compounds will be administered simultaneously in a combined pharmaceutical composition. Appropriate doses of known therapeutic agents will be readily appreciated by those skilled in the art.

Accordingly, the pharmaceutical compositions of the present invention include those that also comprise at least one additional therapeutically active agent, in addition to the compound of Formulas I-III.

The invention further includes a compound of Formulas I-III in combination with one or more other drug(s).

Methods of Preparing the Compounds of Formulas (I-III)

Methods for preparing the compounds of this invention are illustrated in the following schemes and examples. Other synthetic protocols will be readily apparent to those skilled in the art in light of the present disclosure. The examples illustrate the preparation of the compounds of Formulas (I-III) and as such are not to be considered as limiting the invention set forth in the claims appended hereto. Unless otherwise indicated, all variables are as previously defined.

All the end products of the Formulas (I-III) were analyzed by NMR and/or LCMS. Intermediates were analyzed by NMR and/or TLC and/or LCMS. Most compounds were purified by reverse phase HPLC, MPLC on silica gel, recrystallization and/or swish (suspension in a solvent followed by filtration of the solid). The course of the reactions was followed by thin layer chromatography (TLC) and/or LCMS and/or NMR and reaction times are given for illustration only.

Abbreviations used herein are as follows: EtOAc: Ethyl acetate; PE: Petroleum ether; EA: Ethyl acetate; DCM: Dichloro methane; Dppf: 1,1'-Bis(diphenylphosphino) ferrocene; AcOH: Acetic acid; DMAC: N,N-Dimethylacetamide; $Pd(PPh_3)_4$: Tetrakis(Triphenylphosphine)Palladium (0); $Pd(dppf)Cl_2$: [1,1'-Bis(diphenylphosphino) ferrocene]dichloropalladium (II); $Ac_2O$: Acetic anhydride; LiHMDS: Lithium bis(trimethylsilyl)amide; $PhNTf_2$: N-Phenyl-bis(trifluoromethanesulfonimide); S-Phos: 2-Dicyclohexylphosphino-2',6'-dimethoxybiphenyl; X-Phos: 2-Dicyclohexylphosphino-2',4',6'-triisopropylbiphenyl; CPME: Cyclopentyl methyl ether; DMAP: 4-Dimethylaminopyridine; TEA: Triethylamine; THF: Tetrahydrofuran; PYAOP: (7-Azabenzotriazol-1-yloxy)tripyrrolidinophosphonium hexafluorophosphate.

Schemes

Scheme 1 illustrates a general method toward the preparation of compounds of the instant invention. Starting with the halogenation of compound A followed by N-acylation with either carboxylic acids or acid chlorides in the presence of base led to the formation of compound C. Subsequent cross coupling followed by ester hydrolysis afforded the final product I.

Scheme 2 illustrates a general method toward the preparation of compounds of the instant invention. Starting with the halogenation of compound A followed by a Suzuki cross coupling yielded compound C. N-acylation with either carboxylic acids or acid chlorides in the presence of base led to the formation of compound D. Ester hydrolysis led to the final product II.

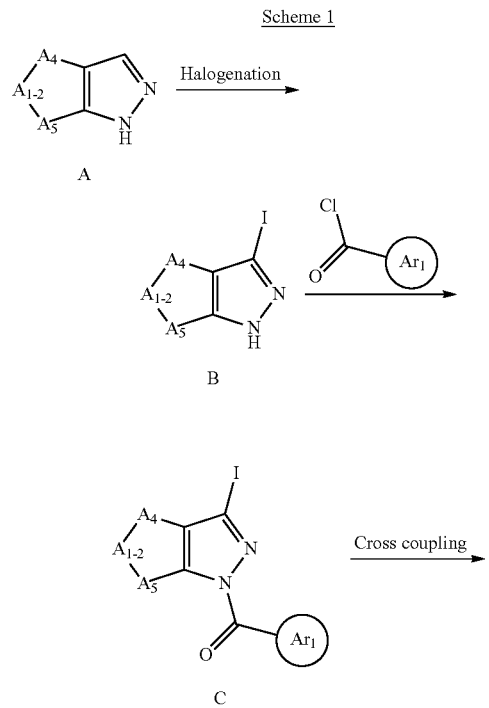

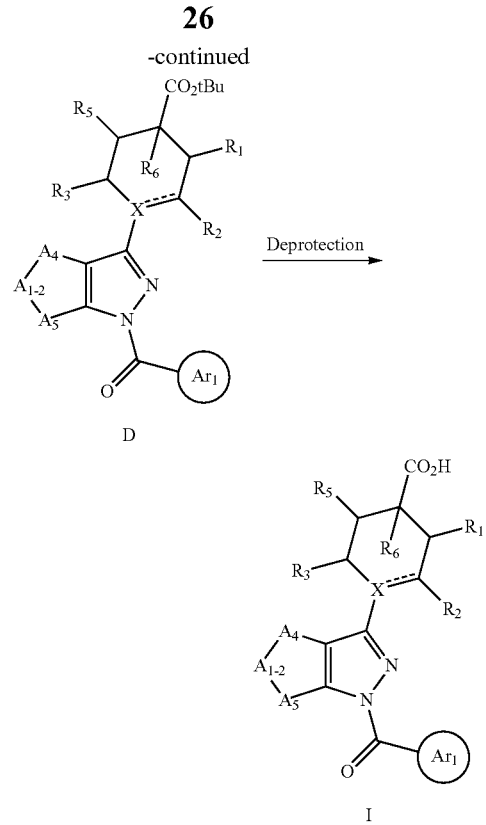

-continued

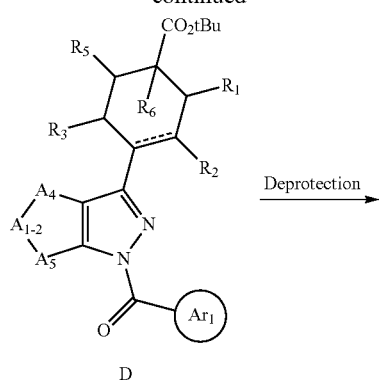

D

Deprotection →

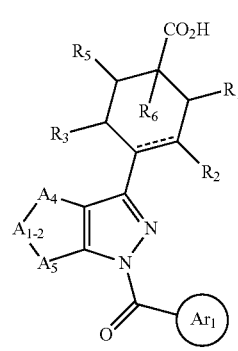

II

Commercially Available/Previously Described Materials

The following table lists commercial sources, and previously disclosed synthetic routes for chemical materials employed in the synthesis of intermediates, and examples of the instant invention. The list is not intended to be exhaustive, exclusive, or limiting in any way.

| Structure | Source |
|---|---|
| methyl 2-bromo-6-chlorobenzoate | Matrix Scientific |
| 2-chloro-6-fluorobenzoic acid | Sigma Aldrich |
| (2-chloro-6-iodophenyl)methanol | Spectra Group Limited Inc |
| 2-bromo-6-chlorobenzoic acid | Sigma Aldrich |
| 2-chloro-4-bromo-1-fluorobenzene | Sigma Aldrich |
| methyl 4-oxocyclohexanecarboxylate | Matrix Scientific |
| tert-butyl 4-oxocyclohexanecarboxylate | Astatech Inc |
| ethyl 4-oxocyclohexanecarboxylate | Sigma Aldrich |
| 2,4,5,6-tetrahydrocyclopenta[c]pyrazole | Matrix Scientific |
| methyl 3-iodo-4,5,6,7-tetrahydro-1H-indazole-6-carboxylate | Enamine |
| 1,4,6,7-tetrahydropyrano[4,3-c]pyrazole | Anichem Inc |

| Structure | Source |
|---|---|
| (4,5,6,7-tetrahydro-1H-indazol-6-ol with HO) | Enamine |
| (Boc-protected tetrahydropyrazolopyridine) | Combi-Blocks Inc |
| (BocN tetrahydropyrazolopyridine) | Enovation Chemicals Llc |
| (4,5,6,7-tetrahydro-1H-indazole) | Sigma Aldrich |
| (6,7-dihydro-1H-indazol-4(5H)-one) | Chembridge Corporation |

INTERMEDIATES

Intermediate i-1

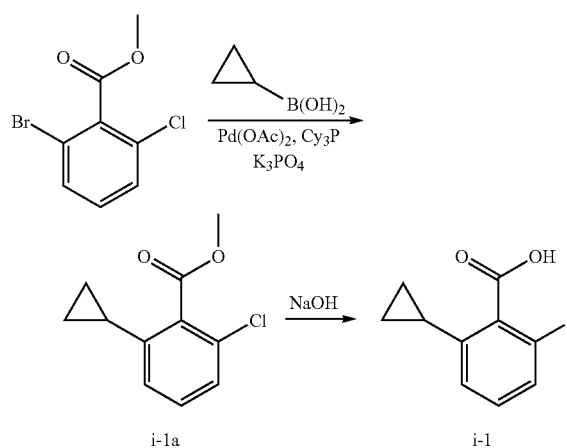

i-1a → i-1

2-chloro-6-cyclopropylbenzoic Acid

Step 1. Preparation of methyl 2-chloro-6-cyclopropylbenzoate (i-1a)

Methyl 2-bromo-6-chlorobenzoate (1.0 g, 4.0 mmol), cyclopropylboronic acid (516 mg, 6.0 mmol), Pd(OAc)$_2$ (90 mg, 0.4 mmol), Cy$_3$P (224 mg, 0.8 mmol) and K$_3$PO$_4$ (2.5 g, 12.0 mmol) were mixed in toluene (20 mL) and H$_2$O (2.5 mL). The mixture was stirred at 100° C. for 14 h under N$_2$ atmosphere. The mixture was cooled down and poured into water. The mixture was extracted with EtOAc and the organic layer was dried over Na$_2$SO$_4$ and concentrated. The residue was purified by flash chromatography (Petroleum/EtOAc 15/1) to give the title compound. MS: 211 (M+1).

Step 2. Preparation of 2-chloro-6-cyclopropylbenzoic Acid (i-1)

NaOH (380 mg, 9.5 mmol) was added to a solution of methyl 2-chloro-6-cyclopropylbenzoate (200 mg, 0.95 mmol) in EtOH (15 mL) and H$_2$O (6 mL). The resultant solution was stirred at 80° C. overnight. The mixture was cooled down and acidified with 2N HCl to pH=2~3. Then the mixture was extracted with EtOAc. The organic layer was dried over Na$_2$SO$_4$ and concentrated to afford the title compound. MS: 197 (M+1).

Intermediate i-2

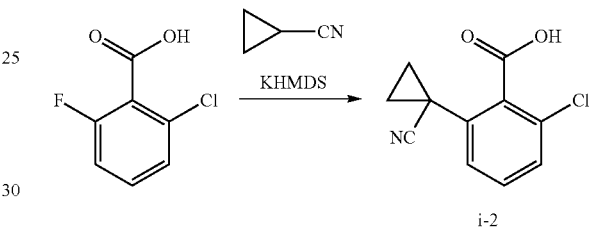

i-2

2-chloro-6-(1-cyanocyclopropyl)benzoic Acid

To a solution of 2-chloro-6-fluorobenzoic acid (5.00 g, 28.6 mmol) and cyclopropanecarbonitrile (20.0 g, 298 mmol) in THF (5 mL) at −40 OC was added KHMDS (75 mL, 1.0M in THF 75 mmol) drop wise. The reaction mixture was slowly warmed up and heated at 70° C. for 16 hrs, then cooled to room temperature. The reaction was acidified with 1N HCl, extracted with EtOAc. The combined organic layers were concentrated and the residue was purified by chromatography (0-80% ethyl acetate/Pentanes) and re-purified by prep. HPLC (CH$_3$CN/H$_2$O+0.1% TFA) to afford 2-chloro-6-(1-cyanocyclopropyl)benzoic acid. MS: 222 (M+1). $^1$H NMR (600 MHz, DMSO-d6): δ 12.9-13.1 (brs, 1H), 7.53 (dd, 1H, J=8.4, 1.2 Hz), 7.48 (dd, 1H, J=8.4, 1.2 Hz), 7.45 (t, 1H, J=8.4 Hz), 1.60-1.63 (m, 2H), 1.35-1.38 (m, 2H).

Intermediate i-3

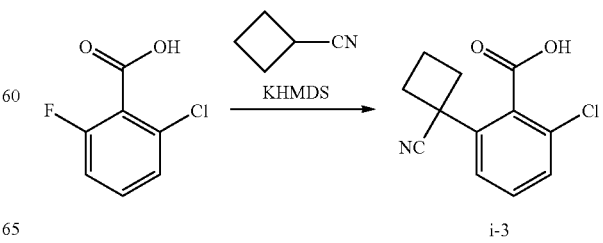

i-3

2-chloro-6-(1-cyanocyclobutyl)benzoic Acid

To a mixture of cyclobutanecarbonitrile (0.70 g, 8.6 mmol) and 2-chloro-6-fluorobenzoic acid (0.5 g, 2.9 mmol) in THF (9.6 mL) at 0° C. was added KHMDS (0.5M in toluene, 12.6 mL, 6.3 mmol). The resulting mixture was heated at 70° C. for 3 h, then cooled down, concentrated in vacuo. The residue was taken up in 20 mL $H_2O$, and extracted with $Et_2O$ for three times. The aqueous layer was acidified with 2N HCl, and extracted with $CHCl_3$/i-PrOH (3:1). The combined organics were dried over $Na_2SO_4$, concentrated. The crude residue was used directly. MS: 236 (M+1). $^1$H NMR (600 MHz, DMSO-d6): δ 12.9-13.1 (brs, 1H), 7.51 (dd, 1H, J=8.4, 1.2 Hz), 7.46 (t, 1H, J=8.4 Hz), 7.30 (dd, 1H, J=8.4, 1.2 Hz), 2.56-2.68 (m, 4H), 2.22-2.32 (m, 1H), 1.84-1.90 (m, 1H).

Intermediate i-4

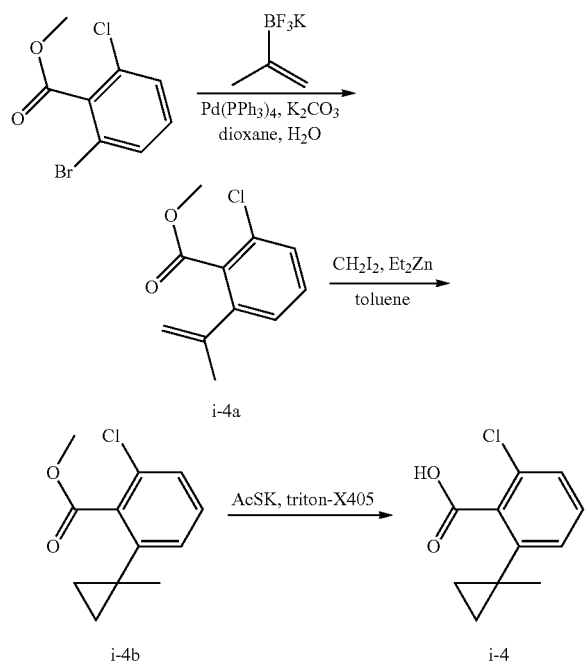

2-chloro-6-(1-methylcyclopropyl)benzoic Acid

Step 1. Preparation of 2-chloro-6-(prop-1-en-2-yl) benzoate (i-4a)

To a solution of methyl 2-bromo-6-chlorobenzoate (5.00 g, 20.0 mmol) and potassium trifluoro(prop-1-en-2-yl)borate (4.00 g, 27.0 mmol) in dioxane (30 mL) and water (5 mL) was added Pd(PPh$_3$)$_4$ (460 mg, 0.40 mmol) under N$_2$ atmosphere. The resulting mixture was stirred at 100° C. for 16 h, then cooled to room temperature, filtered and washed with DCM and water. The organic layer was washed with brine, dried over Na$_2$SO$_4$, filtered and concentrated. The residue was purified by flash chromatography (0-5% EtOAc in petroleum ether) to give the title compound. $^1$H NMR (400 MHz, CDCl$_3$) δ 7.25-7.31 (m, 2H), 7.11-7.17 (m, 1H), 5.13 (s, 1H), 4.95 (s, 1H), 3.85 (s, 3H), 2.04 (s, 3H).

Step 2. Preparation of methyl 2-chloro-6-(1-methylcyclopropyl)benzoate (i-4b)

To a solution of methyl 2-chloro-6-(prop-1-en-2-yl)benzoate (2.00 g, 9.50 mmol) in toluene (6 mL) at 0° C. was added diiodomethane (4.0 mL, 47.5 mmol), followed by the addition of 1.0 M Et$_2$Zn (47.4 mL, 47.4 mmol) under N$_2$ atmosphere. The reaction mixture was warmed to room temperature, stirred for 1 h, then heated at 60° C. for 2 days. The reaction mixture was then cooled to 0° C., additional diiodomethane (4.0 mL, 47.5 mmol) was added, followed by Et$_2$Zn (47.4 mL, 47.4 mmol) under N$_2$ atmosphere. The reaction was then heated at 60° C. overnight. The reaction mixture was cooled down, quenched with NH$_4$Cl solution, and extracted with EtOAc. The organic layer washed with brine, dried over Na$_2$SO$_4$, filtered and concentrated, the residue was purified by flash chromatography (0 to 10% EtOAc in petroleum ether) to afford crude product containing some starting material. The product was dissolved in CH$_3$CN (10 mL) and water (1 mL), followed by the addition of NMO (500 mg, 4.27 mmol) and potassium osmate(vi) dihydrate (20 mg, 0.05 mmol) at 0° C. The resulting mixture was warmed to room temperature, stirred for 24 h, quenched with Na$_2$SO$_3$ solution, extracted with EtOAc. The organic layer was washed with brine, dried over Na$_2$SO$_4$, filtered and concentrated. The residue was purified by flash chromatography (0-10% EtOAc in petroleum ether) and then preparative TLC (petroleum ether:EtOAc=20:1) to give the title compound. MS: 225 (M+1). $^1$H NMR (400 MHz, CDCl$_3$) δ 7.23-7.28 (m, 2H), 7.08-7.15 (m, 1H), 3.90 (m, 3H), 1.28 (s, 3H), 0.71-0.74 (m, 2H), 0.55-0.60 (m, 2H).

Step 3. Preparation of 2-chloro-6-(1-methylcyclopropyl)benzoic Acid (i-4)

To a solution of methyl 2-chloro-6-(1-methylcyclopropyl)benzoate (320 mg, 1.42 mmol) in DMF (5 mL) was added potassium thioacetate (651 mg, 5.70 mmol), followed by polyethylene glycol tert-octylphenyl ether (73 mg, 0.14 mmol). The resulting mixture was stirred at 130° C. for 5 h, cooled to room temperature, diluted with water and extracted with EtOAc. The organic layer was washed with brine, dried over MgSO$_4$, filtered and concentrated. The residue was purified by preparative TLC (EtOAc:DCM=2:1) and then preparative HPLC to give the title compound. MS: 211 (M+1). $^1$H NMR (400 MHz, CDCl$_3$) δ 7.31-7.36 (m, 1H), 7.25-7.29 (m, 2H), 1.39 (s, 3H), 0.85-0.90 (m, 2H), 0.67-0.74 (m, 2H).

Intermediate i-5

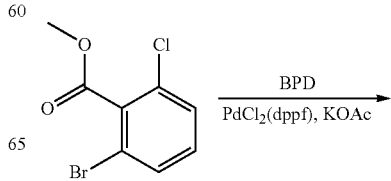

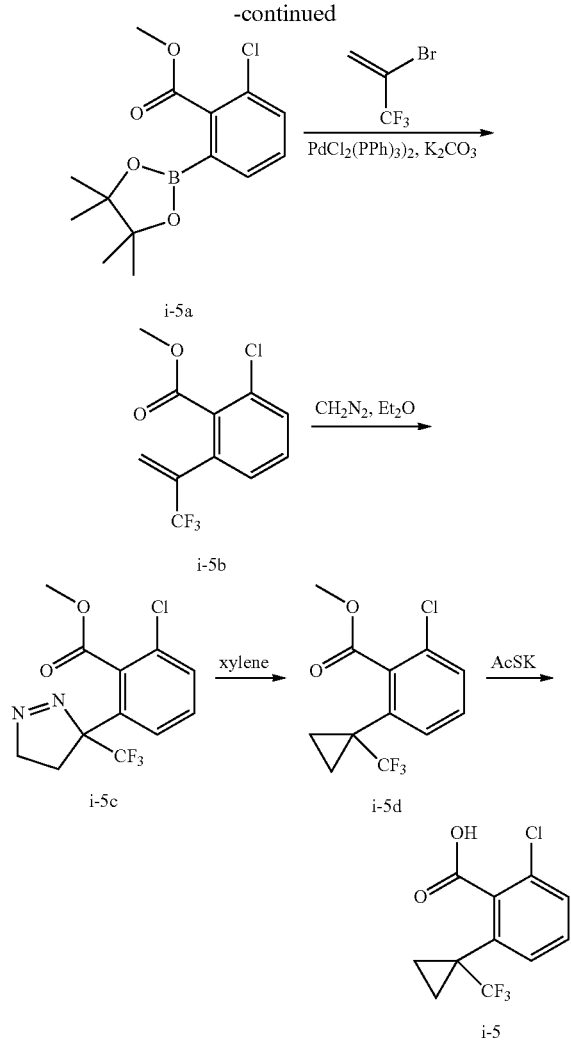

2-chloro-6-(1-(trifluoromethyl)cyclopropyl)benzoic Acid

Step 1. Preparation of methyl 2-chloro-6-(4,4,5,5-tetramethyl-1,3,2-dioxaborolan-2-yl)benzoate (i-5a)

To a solution of methyl 2-bromo-6-chlorobenzoate (7.50 g, 30.1 mmol) in dioxane (65 mL) was added BPD (15.3 g, 60.3 mmol), AcOK (3.54 g, 36.1 mmol) and PdCl$_2$(dppf) (0.66 g, 0.90 mmol) under N$_2$ atmosphere, then the resulting mixture was stirred at 100° C. for 18 h, cooled to room temperature, filtered and concentrated, and the residue was purified by chromatography (0-3% EtOAc in petroleum ether) to give the title compound. MS: 297 (M+1). $^1$H NMR (400 MHz, CDCl$_3$) δ 7.67 (d, J=7.4 Hz, 1H), 7.46 (d, J=7.8 Hz, 1H), 7.29-7.39 (m, 1H), 3.92 (s, 3H), 1.32 (s, 12H).

Step 2. Preparation of methyl 2-chloro-6-(3,3,3-trifluoroprop-1-en-2-yl)benzoate (i-5b)

Bis(triphenylphosphine)palladium(ii) dichloride (120 mg, 0.171 mmol) was added to a solution of methyl 2-chloro-6-(4,4,5,5-tetramethyl-1,3,2-dioxaborolan-2-yl)benzoate (2.00 g, 6.74 mmol), 2-bromo-3,3,3-trifluoroprop-1-ene (3.54 g, 20.23 mmol) and K$_2$CO$_3$ (1.86 g, 13.49 mmol) in THF (25 mL) and water (2 mL). The resultant mixture was stirred at 70° C. for 5 h. The mixture was concentrated in vacuo and purified by chromatography (0-5% EtOAc in petroleum ether) to give the title compound. $^1$H NMR (400 MHz, CDCl$_3$) δ 7.43-7.49 (m, 1H), 7.37 (t, J=7.8 Hz, 1H), 7.27-7.32 (m, 1H), 6.08 (s, 1H), 5.66 (s, 1H), 3.86 (s, 3H).

Step 3. Preparation of methyl 2-chloro-6-(3-(trifluoromethyl)-4,5-dihydro-3H-pyrazol-3-yl)benzoate (i-5c)

Diazomethane (300 mL, 75.0 mmol in Et$_2$O) was added to a solution of methyl 2-chloro-6-(3,3,3-trifluoroprop-1-en-2-yl)benzoate (1.03 g, 3.89 mmol) in DCM (10 mL). The resultant mixture was stirred at 0° C. for 24 h, and quenched with AcOH (1 mL). Then the reaction mixture was concentrated in vacuo and purified by column chromatography on silica gel (0-10% EtOAc in petroleum ether) to give the title compound. MS: 307 (M+1). $^1$H NMR (400 MHz, CDCl$_3$) δ 7.60 (d, J=7.8 Hz, 1H), 7.46-7.52 (m, 1H), 7.43 (d, J=7.8 Hz, 1H), 4.83-4.96 (m, 1H), 4.63 (td, J=17.8 Hz, 8.7 Hz, 1H), 3.93 (s, 3H), 2.45 (m, 1H), 1.94-2.06 (m, 1H).

Step 4. Preparation of methyl 2-chloro-6-(1-(trifluoromethyl)cyclopropyl)benzoate (i-5d)

A solution of methyl 2-chloro-6-(3-(trifluoromethyl)-4,5-dihydro-3H-pyrazol-3-yl)benzoate (900 mg, 2.93 mmol) in xylene (5.0 mL) was heated at 130° C. for 6 h, then cooled to room temperature, purified by chromatography on silica gel (petroleum ether:EtOAc=10:1) to give the title compound. $^1$H NMR (400 MHz, CDCl$_3$) δ 7.45 (d, J=7.8 Hz, 1H), 7.38-7.43 (m, 1H), 7.35 (d, J=7.8 Hz, 1H), 3.95 (s, 3H), 1.33-1.40 (m, 2H), 1.11-1.19 (m, 2H).

Step 5. Preparation of 2-chloro-6-(1-(trifluoromethyl)cyclopropyl)benzoic Acid (i-5)

To a solution of methyl 2-chloro-6-(1-(trifluoromethyl)cyclopropyl)benzoate (600 mg, 2.15 mmol) in DMF (1 mL) was added potassium thioacetate (984 mg, 8.61 mmol), followed by Polyethylene glycol-tert-octylphenyl ether (111 mg, 0.22 mmol). The resulting mixture was heated at 130° C. for 2 h, and then cooled to room temperature. The mixture was purified by Prep-HPLC to give the title compound. $^1$H NMR (400 MHz, CDCl$_3$) δ 7.36-7.48 (m, 2H), 7.28-7.36 (m, 1H), 1.32-1.41 (m, 2H), 1.15-1.19 (m, 2H).

Intermediate i-6

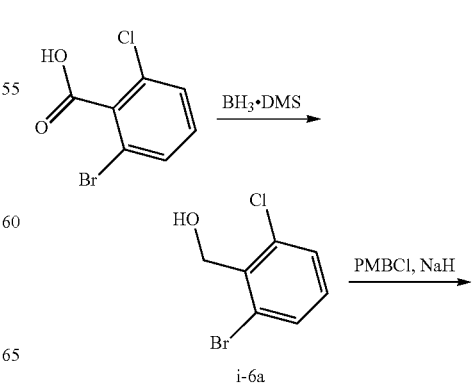

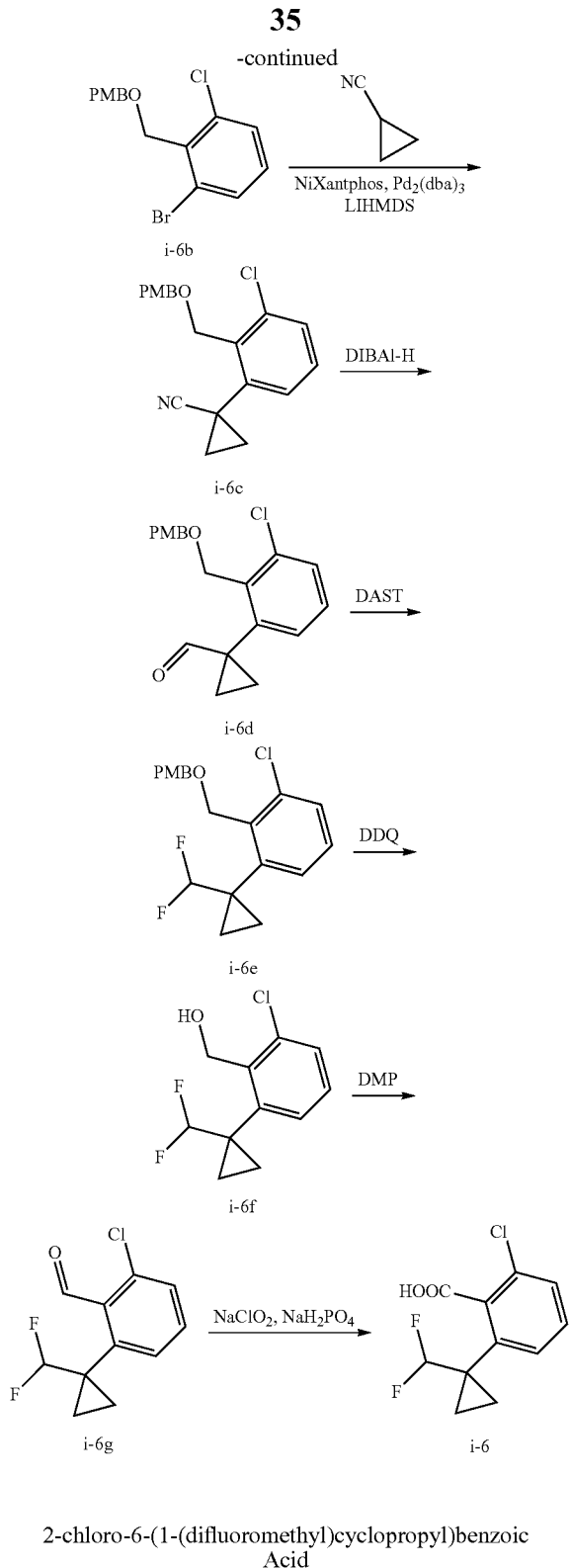

then most of THF and MeOH were removed under reduced pressure and the remaining aqueous phase was filtered. The filtrate was extracted with EtOAc (4×30 mL). The combined organic layers were washed with brine (50 mL), dried over $Na_2SO_4$, filtered and concentrated in vacuo. The residue was purified by silica gel column chromatography (petroleum ether:EtOAc=50:1-20:1) to give the title compound. $^1$H NMR (400 MHz, $CDCl_3$) δ 7.52 (d, J=8.0 Hz, 1H), 7.38 (d, J=8.0 Hz, 1H), 7.12 (t, J=8.0 Hz, 1H), 4.99 (d, J=3.5 Hz, 2H), 2.08-2.29 (m, 1H).

Step 2. Preparation of 1-bromo-3-chloro-2-(((4-methoxybenzyl)oxy)methyl)benzene (i-6b)

To a solution of (2-bromo-6-chlorophenyl)methanol (18.41 g, 83 mmol) in THF (200 mL) was added NaH (60%, 4.99 g, 125 mmol) at 0° C. After the mixture was stirred for 0.5 h, 1-(chloromethyl)-4-methoxybenzene (15.62 g, 100 mmol) was added. The mixture was stirred at 0° C. for 3 h and then at room temperature for 17 h. The mixture was quenched with $H_2O$ (80 mL), extracted with EtOAc (3×100 mL). The combined organic layers were washed with brine (80 mL), dried over $Na_2SO_4$, filtered and concentrated in vacuo. The residue was purified by silica gel column chromatography (petroleum ether:EtOAc=100:1-50:1) to give the title compound. $^1$H NMR (400 MHz, $CDCl_3$) δ 7.51 (d, J=8.0 Hz, 1H), 7.30-7.43 (m, 3H), 7.07-7.15 (m, 1H), 6.89 (d, J=8.6 Hz, 2H), 4.80 (s, 2H), 4.58 (s, 2H), 3.81 (s, 3H).

Step 3. Preparation of 1-(3-chloro-2-(((4-methoxybenzyl)oxy)methyl)phenyl)-cyclopropanecarbonitrile (i-6c)

4, 6-Bis(diphenylphosphino)-10H-phenoxazine (1.94 g, 3.51 mmol) and $Pd_2(dba)_3$ (1.61 g, 1.76 mmol) was dissolved in THF (100 mL). The mixture was stirred at room temperature for 30 min under $N_2$. 1-bromo-3-chloro-2-(((4-methoxybenzyl)oxy)methyl)benzene (12 g, 35.13 mmol) and cyclopropanecarbonitrile (2.88 g, 42.85 mmol) was added. Then LHMDS (52.8 mL, 52.8 mmol) (1.0 M in THF) was added immediately. The mixture was stirred at 80° C. for 18 h under $N_2$. The mixture was cooled and quenched with sat. $NH_4Cl$ (100 mL) and the mixture was extracted with ethyl acetate (4×60 mL). The combined organic fractions were washed with brine (50 mL), dried over $Na_2SO_4$, filtered and the solvent was evaporated under reduced pressure. The residue was purified by silica gel column flash chromatography, eluting with EtOAc/petroleum ether=0-20% to give the title compound. $^1$H NMR (400 MHz, $CDCl_3$) δ 7.35-7.42 (m, 3H), 7.27-7.32 (m, 1H), 7.21-7.26 (m, 1H), 6.92 (d, J=8.6 Hz, 2H), 4.80-4.91 (m, 2H), 4.65 (s, 2H), 3.77-3.91 (m, 3H), 1.57-1.60 (m, 2H), 1.38-1.45 (m, 2H).

Step 4. Preparation of 1-(3-chloro-2-(((4-methoxybenzyl)oxy)methyl)phenyl)-cyclopropanecarbaldehyde (i-6d)

Diisobutylaluminum hydride (55 mL, 55.0 mmol) (1.0 M in toluene) was added to a stirred mixture of 1-(3-chloro-2-(((4-methoxybenzyl)oxy)methyl)phenyl)-cyclopropanecarbonitrile (9 g, 27.5 mmol) in toluene (60 mL) at room temperature and the mixture was stirred at room temperature for 2 h. The mixture was cooled to 0° C., i-PrOH (12 mL) was added. After stirring at 0° C. for 30 min, hydrochloric acid (1 M, 60 mL) was added and the mixture was extracted with ethyl acetate (4×50 mL). The combined organic frac- 2-chloro-6-(1-(difluoromethyl)cyclopropyl)benzoic Acid Step 1. Preparation of (2-bromo-6-chlorophenyl)methanol (i-6a)

To a solution of 2-bromo-6-chlorobenzoic acid (20 g, 85 mmol) in THF (200 mL) was added $BH_3$.DMS (42.5 mL, 425 mmol) slowly at 0° C. The resulting solution was heated at 80° C. for 17 h. The reaction was cooled and quenched with MeOH (100 mL) and NaClO (aq., 100 mL) carefully, tions were washed with brine (saturated, 50 mL), dried (Na$_2$SO$_4$), filtered and the solvent was evaporated under reduced pressure. The residue was purified by silica gel column flash chromatography, (EtOAc/petroleum ether=0-10%) to give the title compound. $^1$H NMR (400 MHz, CDCl$_3$) δ 9.16 (s, 1H), 7.39 (d, J=7.5 Hz, 1H), 7.31 (d, J=8.4 Hz, 2H), 7.23 (d, J=7.9 Hz, 1H), 7.16-7.22 (m, 1H), 6.89 (d, J=8.6 Hz, 2H), 4.61 (s, 2H), 4.52 (s, 2H), 3.82 (s, 3H), 1.58 (d, J=2.9 Hz, 2H), 1.38-1.47 (m, 2H).

Step 5. Preparation of methyl 1-chloro-3-(1-(difluoromethyl)cyclopropyl)-2-(((4-methoxybenzyl)oxy) methyl)benzene (i-6e)

DAST (2.80 mL, 21.16 mmol) was added to a stirred mixture of 1-(3-chloro-2-(((4-methoxybenzyl)oxy)methyl) phenyl)cyclopropanecarbaldehyde (3.5 g, 10.58 mmol) in DCM (40 mL) at room temperature and the mixture was stirred at 30° C. for 18 h. The mixture was concentrated to dryness. The residue was purified by silica gel column flash chromatography, (EtOAc/petroleum ether=0-5%) to give the title compound. $^1$H NMR (400 MHz, CDCl$_3$) δ 7.29-7.40 (m, 4H), 7.19-7.25 (m, 1H), 6.89-6.93 (m, 2H), 5.57-5.91 (m, 1H), 4.71-4.82 (m, 2H), 4.61 (s, 2H), 3.82 (s, 3H), 1.17 (s, 2H), 1.04 (d, J=2.3 Hz, 2H).

Step 6. Preparation of (2-chloro-6-(1-(difluoromethyl)cyclopropyl)phenyl)methanol (i-6f)

DDQ (1.930 g, 8.50 mmol) was added to a stirred mixture of 1-chloro-3-(1-(difluoromethyl)cyclopropyl)-2-(((4-methoxybenzyl)oxy)methyl)benzene (2 g, 5.67 mmol) in DCM (12 mL) and water (2 mL) at room temperature and the mixture was stirred at room temperature for 18 h. The mixture was filtered and the filter cake was washed with dichloromethane (30 mL), the combined organic fractions were washed with Na$_2$SO$_3$ (Saturated, 2×20 mL), dried (Na$_2$SO$_4$), filtered and concentrated. The residue was dissolved in MeOH (10 mL), added NaBH$_4$ (0.643 g, 17.01 mmol) at 0° C. After the mixture was stirred at 0° C. for 2 h, water (5 mL) was added. The mixture was concentrated in vacuo to remove the most of MeOH, and then extracted with ethyl acetate (3×15 mL). The combined organic fractions were washed with brine (20 mL), dried over Na$_2$SO$_4$, filtered and the solvent was evaporated under reduced pressure. The residue was purified by silica gel column flash chromatography, (EtOAc/petroleum ether=0-15%) to give the title compound. $^1$H NMR (400 MHz, CDCl$_3$) δ 7.38 (dd, J=14.0 Hz, 7.8 Hz, 2H), 7.22-7.27 (m, 1H), 5.52-5.87 (m, 1H), 4.93-5.13 (m, 2H), 2.10-2.21 (m, 1H), 1.30 (s, 2H), 1.09 (brs, 2H).

Step 7. Preparation of 2-chloro-6-(1-(difluoromethyl)cyclopropyl)benzaldehyde (i-6g)

DMP (3.10 g, 7.31 mmol) was added to a stirred mixture of (2-chloro-6-(1-(difluoromethyl)cyclopropyl)phenyl) methanol (0.85 g, 3.65 mmol) in DCM (10 mL) at room temperature and the mixture was stirred at room temperature for 5 h. The mixture was diluted with DCM (20 mL), filtered and the filter cake was washed with dichloromethane (20 mL). The filtrate was concentrated and purified by silica gel column flash chromatography, (EtOAc/petroleum ether=0-10%) to give the title compound. $^1$H NMR (400 MHz, CDCl$_3$) δ 10.61 (s, 1H), 7.41-7.55 (m, 3H), 5.97-6.28 (m, 1H), 1.33-1.39 (m, 2H), 0.80 (brs, 2H).

Step 8. Preparation of 2-chloro-6-(1-(difluoromethyl)cyclopropyl)benzoic Acid (i-6)

2-Methylbut-2-ene (1.672 g, 23.85 mmol) was added to a stirred mixture of 2-chloro-6-(1-(difluoromethyl)cyclopropyl)benzaldehyde (0.55 g, 2.385 mmol) in t-BuOH (10 mL) at room temperature. Then sodium dihydrogenphosphate (0.515 g, 4.29 mmol) in H$_2$O (3 mL) and sodium chlorite (0.324 g, 3.58 mmol) in H$_2$O (2 mL) was added. The mixture was stirred at room temperature for 18 h, diluted with ethyl acetate (20 mL) and hydrochloric acid (1 M, 3 mL). The mixture was extracted with ethyl acetate (4×15 mL), washed with brine (20 mL), dried over Na$_2$SO$_4$, filtered and the solvent was evaporated under reduced pressure. The residue was purified by preparative HPLC (reverse phase C-18 column), eluting with Acetonitrile/Water+0.1% HCOOH to give the title compound. $^1$H NMR (400 MHz, CDCl$_3$) δ 7.29-7.72 (m, 3H), 5.96-6.32 (m, 1H), 1.30 (brs, 2H), 1.02 (brs, 2H).

Intermediate i-7

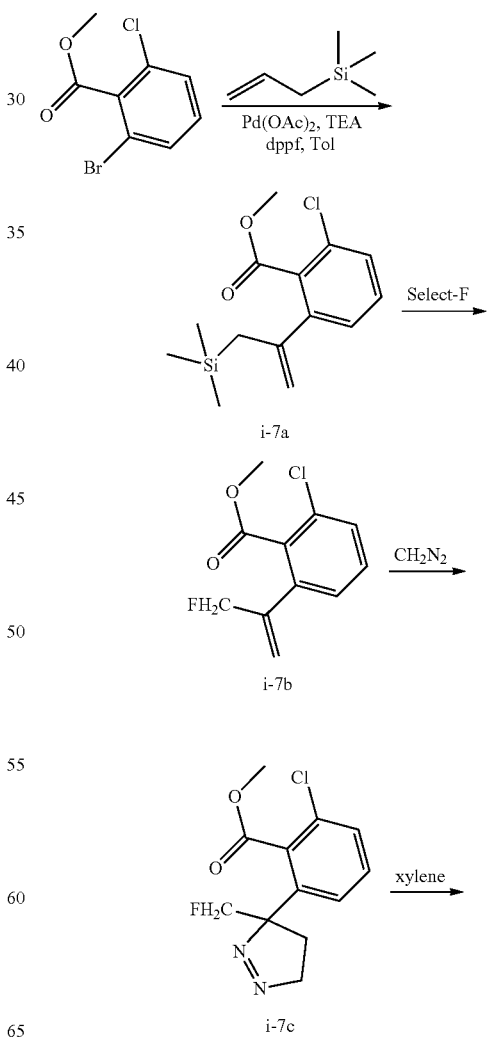

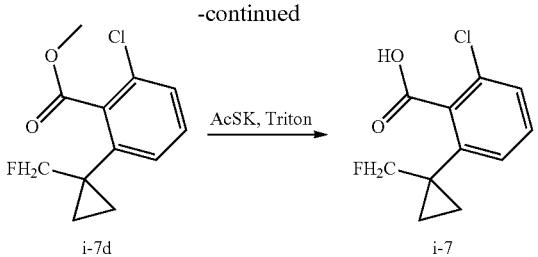

2-chloro-6-(1-(fluoromethyl)cyclopropyl)benzoic Acid

Step 1. Preparation of methyl 2-chloro-6-(3-(trimethylsilyl)prop-1-en-2-yl)benzoate (i-7a)

To a mixture of methyl 2-bromo-6-chlorobenzoate (4.6 g, 18.44 mmol), TEA (7.71 mL, 55.3 mmol) and allyltrimethylsilane (2.74 g, 23.97 mmol) in toluene (150 mL) was added Pd(OAc)$_2$ (0.207 g, 0.922 mmol) and DPPF (1.022 g, 1.844 mmol). The mixture was stirred at 130° C. for 18 h under N$_2$. TLC showed most of starting material was remained. allyltrimethylsilane (2.74 g, 23.97 mmol), TEA (7.71 mL, 55.3 mmol), Pd(OAc)$_2$ (0.207 g, 0.922 mmol) and DPPF (1.022 g, 1.844 mmol) was added and the mixture was stirred for an additional 18 h. Then the above operation was repeated after another 18 h. The mixture was cooled, diluted with water (100 mL) and extracted with EtOAc (3*150 mL). The organic layers were concentrated in vacuo. The residue was purified by column chromatography on silica gel, eluting with petroleum ether to give the title compound. $^1$H NMR (400 MHz, CDCl$_3$) δ 7.30 (brs, 1H), 7.22 (s, 1H), 7.13 (d, J=3.5 Hz, 1H), 4.97 (d, J=7.8 Hz, 2H), 3.89 (s, 3H), 1.90 (s, 2H),–0.07 (s, 9H).

Step 2. Preparation of methyl 2-chloro-6-(3-fluoroprop-1-en-2-yl)benzoate (i-7b)

To a solution of methyl 2-chloro-6-(3-(trimethylsilyl)prop-1-en-2-yl)benzoate (4.5 g, 15.91 mmol) in MeCN (100 mL) was added Selectfluor (14.09 g, 39.8 mmol). The mixture was stirred at room temperature for 24 h. The mixture was concentrated in vacuo. The residue was purified by flash column chromatography on silica gel (100% petroleum ether) to give the title compound. $^1$H NMR (400 MHz, CDCl$_3$) δ 7.31-7.43 (m, 2H), 7.20 (d, J=7.4 Hz, 1H), 5.52 (s, 1H), 5.29 (s, 1H), 5.09 (s, 1H), 4.98 (s, 1H), 3.81-3.92 (m, 3H).

Step 3. Preparation of methyl 2-chloro-6-(3-(fluoromethyl)-4,5-dihydro-3H-pyrazol-3-yl)benzoate (i-7c)

To a solution of methyl 2-chloro-6-(3-fluoroprop-1-en-2-yl)benzoate (1 g, 4.37 mmol) in Et$_2$O (10 mL) was added diazomethane (43.7 mL, 21.87 mmol) (~0.5 Min Et$_2$O) at 0-5° C. The mixture was stand at room temperature for 18 h, then the mixture was concentrated in vacuo. The residue was purified by flash column chromatography on silica gel (petroleum ether:EtOAc=4:1) to give the title compound. MS: 271 (M+1).

Step 4. Preparation of methyl 2-chloro-6-(1-(fluoromethyl)cyclopropyl)benzoate (i-7d)

A solution of methyl 2-chloro-6-(3-(fluoromethyl)-4,5-dihydro-3H-pyrazol-3-yl)benzoate (700 mg, 2.59 mmol) in xylene (50 mL) was stirred at 150° C. for 18 h. The mixture was cooled to room temperature and concentrated in vacuo. The residue was purified by Prep-TLC on silica gel (petroleum ether:EtOAc=1:20) to give the title compound. $^1$H NMR (400 MHz, CDCl$_3$) δ 7.39 (d, J=6.6 Hz, 1H), 7.29-7.36 (m, 2H), 4.45 (s, 1H), 4.33 (s, 1H), 3.95 (s, 3H), 0.95 (s, 4H).

Step 5. Preparation of 2-chloro-6-(1-(fluoromethyl)cyclopropyl)benzoic Acid (i-7)

Potassium thioacetate (424 mg, 3.71 mmol) was added to a stirred mixture of methyl 2-chloro-6-(1-(fluoromethyl)cyclopropyl)benzoate (300 mg, 1.236 mmol) and TRITON®X-114 (63 mg, 0.122 mmol) in DMF (20 mL) and the mixture was stirred at 130° C. for 2 h. The mixture was cooled, hydrochloric acid (1 M, 8 mL) was added and the mixture was extracted with ethyl acetate (3×50 mL). The combined organics were evaporated under reduced pressure and purified by preparative HPLC (reverse phase C-18 column), eluting with Acetonitrile/Water+0.1% TFA to give the title compound. $^1$H NMR (400 MHz, CDCl$_3$) δ 7.44 (d, J=6.8 Hz, 1H), 7.31-7.41 (m, 2H), 4.50 (s, 1H), 4.38 (s, 1H), 1.04 (d, J=7.3 Hz, 4H).

Intermediate i-8

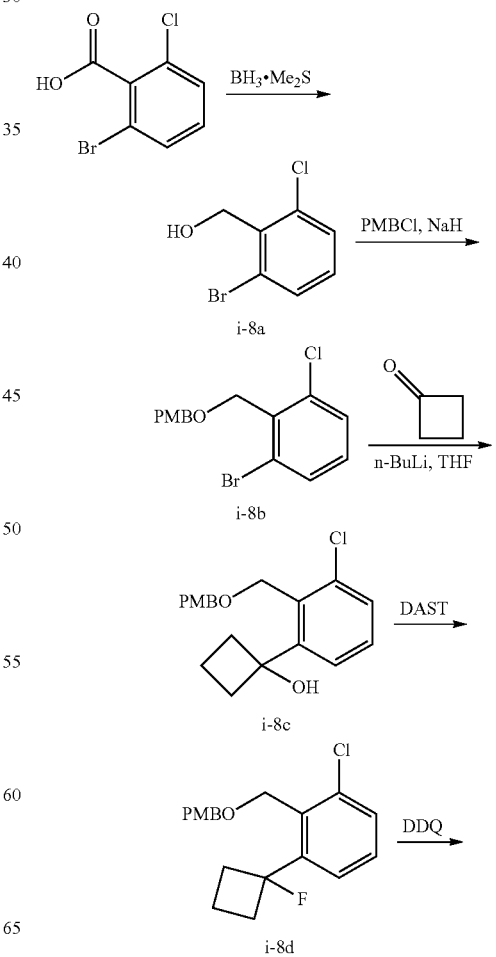

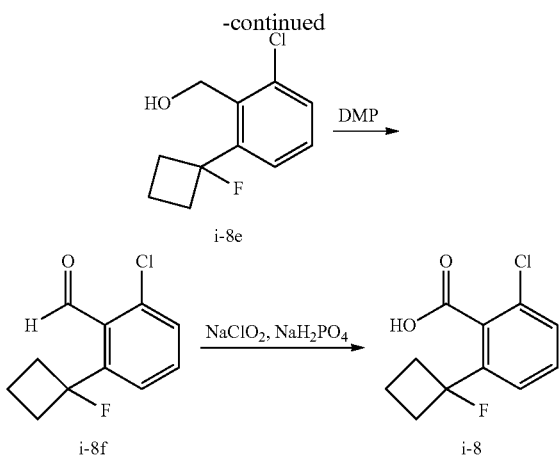

2-chloro-6-(1-fluorocyclobutyl)benzoic Acid

Step 1. Preparation of
(2-bromo-6-chlorophenyl)methanol (i-8a)

BH$_3$.Me$_2$S (31.9 mL, 10 mol/L) was added drop wise to a stirred solution of 2-bromo-6-chlorobenzoic acid (15.00 g, 63.7 mmol) in anhydrous THF (60 mL) at 5° C. The resulting mixture was stirred at 5° C. for 2 h, warmed up slowly and stirred at 70° C. for 16 h. The mixture was cooled in ice-water bath, quenched by dropping addition of saturated NH$_4$Cl (50 mL) slowly. The resulting suspension was filtered and the filter cake was washed with EtOAc (100 mL). The filtrate was concentrated in vacuo to give the title compound. $^1$H NMR (400 MHz, CDCl$_3$) δ 7.56 (d, J=7.8 Hz, 1H), 7.44 (d, J=7.8 Hz, 1H), 7.23-7.17 (m, 1H), 5.19 (brs, 1H), 4.67 (s, 2H).

Step 2. Preparation of 1-bromo-3-chloro-2-(((4-methoxybenzyl)oxy)methyl)benzene (i-8b)

Sodium hydride (60%, 3.29 g, 82 mmol) was added in small portions to a stirred solution of (2-bromo-6-chlorophenyl)methanol (14.00 g, 63.2 mmol) in anhydrous DMF (140 mL) at 5° C. After stirring for 30 min, 1-(chloromethyl)-4-methoxybenzene (10.3 mL, 76 mmol) was added drop wise. The resulting mixture was stirred at 5° C. for 30 min, then warmed up and stirred at room temperature for 2 h. The mixture was cooled to 5° C., quenched by slow addition of saturated aqueous NH$_4$Cl (150 mL). The mixture was extracted with EtOAc (200 mL*3), the combined organic phase was washed with brine (100 mL*4), dried over Na$_2$SO$_4$, filtered and concentrated. The residue was purified via column chromatography (EtOAc in petroleum ether: 0 to 10%) to give the title compound. $^1$H NMR (400 MHz, CDCl$_3$) δ 7.50 (d, J=7.9 Hz, 1H), 7.29-7.38 (m, 3H), 7.05-7.13 (m, 1H), 6.88 (d, J=8.6 Hz, 2H), 4.79 (s, 2H), 4.57 (s, 2H), 3.80 (s, 3H).

Step 3. Preparation of 1-(3-chloro-2-(((4-methoxybenzyl)oxy)methyl)phenyl)cyclobutanol (i-8c)

n-Butyllithium (9.2 mL, 23.00 mmol) (2.5 Min hexane) was added drop wise to a stirred solution of 1-bromo-3-chloro-2-(((4-methoxybenzyl)oxy)methyl)benzene (6.00 g, 17.56 mmol) in anhydrous THF (40 mL) at −65° C. under nitrogen atmosphere. After stirring at −65° C. for 1 h, cyclobutanone (2.0 mL, 26.8 mmol) was added drop wise. The resulting mixture was stirred at −65° C. for another 2 h, then warmed up slowly and stirred at room temperature for 15 h. The mixture was diluted with EtOAc (50 mL), quenched by slow addition of saturated NH$_4$Cl (30 mL) and brine (30 mL). The organic phase was separated and the aqueous phase was extracted with EtOAc (50 mL*2). The combined organic phase was washed with brine (20 mL), dried over Na$_2$SO$_4$, filtered and concentrated. The residue was purified via column chromatography (EtOAc in petroleum ether: 0 to 15%) to give the title compound. $^1$H NMR (400 MHz, CDCl$_3$) δ 7.31-7.33 (m, 1H), 7.22-7.29 (m, 4H), 6.86 (d, J=8.2 Hz, 2H), 4.85 (s, 2H), 4.49-4.56 (m, 2H), 4.43 (brs, 1H), 3.78 (s, 3H), 2.50-2.61 (m, 2H), 2.33-2.43 (m, 2H), 2.15-2.27 (m, 1H), 1.67-1.75 (m, 1H).

Step 4. Preparation of 1-chloro-3-(1-fluorocyclobutyl)-2-(((4-methoxybenzyl)oxy)methyl)-benzene (i-8d)

DAST (0.50 mL, 3.78 mmol) was added in small drops to a stirred solution of 1-(3-chloro-2-(((4-methoxybenzyl)oxy)methyl)phenyl)cyclobutanol (1.00 g, 3.00 mmol) in anhydrous DCM (20 mL) at 5° C. under N$_2$. The resulting mixture was stirred at 5° C. for 1 h. The reaction was quenched by dropping addition of saturated aqueous NaHCO$_3$ (10 mL) with vigorous stirring. The organic phase was separated and concentrated, the residue was purified via column chromatography (EtOAc in petroleum ether: 0 to 6%) to give the title compound. $^1$H NMR (400 MHz, CDCl$_3$) δ 7.34 (d, J=7.5 Hz, 1H), 7.20-7.28 (m, 3H), 7.14-7.19 (m, 1H), 6.80 (d, J=8.5 Hz, 2H), 4.56 (s, 2H), 4.49 (s, 2H), 3.73 (s, 3H), 2.65-2.79 (m, 2H), 2.47-2.62 (m, 2H), 1.95-2.08 (m, 1H), 1.53-1.63 (m, 1H).

Step 5. Preparation of (2-chloro-6-(1-fluorocyclobutyl)phenyl)methanol (i-8e)

The mixture of 1-chloro-3-(1-fluorocyclobutyl)-2-(((4-methoxybenzyl)oxy)methyl)benzene (1.25 g, 3.73 mmol) and 4,5-dichloro-3,6-dioxocyclohexa-1,4-diene-1,2-dicarbonitrile (1.70 g, 7.49 mmol) in DCM (10 mL) and water (1 mL) was stirred at room temperature for 3 h. The suspension was filtered and washed with DCM (10 mL). The filtrate was washed with saturated aqueous NaHCO$_3$ (5 mL) and concentrated. The residue was purified via column chromatography (EtOAc in petroleum ether: 0 to 20%) to give a mixture of (2-chloro-6-(1-fluorocyclobutyl)phenyl)methanol and 4-methoxybenzaldehyde. This mixture was dissolved in MeOH (5 mL), NaBH$_4$ (130 mg, 3.44 mmol) was added. The resulting mixture was stirred at room temperature for 1 h. The mixture was concentrated and the residue was purified via column chromatography (EtOAc in petroleum ether: 0 to 35%) to give the title compound. $^1$H NMR (400 MHz, CDCl$_3$) δ 7.43 (d, J=7.8 Hz, 1H), 7.30-7.36 (m, 1H), 7.22-7.30 (m, 1H), 4.83 (d, J=5.9 Hz, 2H), 2.63-2.81 (m, 4H), 2.28 (d, J=4.3 Hz, 1H), 2.05-2.15 (m, 1H), 1.62-1.72 (m, 1H).

Step 6. Preparation of
2-chloro-6-(1-fluorocyclobutyl)benzaldehyde (i-8f)

The mixture of (2-chloro-6-(1-fluorocyclobutyl)phenyl)methanol (200 mg, 0.932 mmol) and Dess-Martin periodinane (593 mg, 1.40 mmol) in DCM (5 mL) was stirred at room temperature for 2 h. The reaction suspension was filtered and the filter cake was washed with DCM (5 mL), the filtrate was concentrated. The residue was purified via column chromatography (EtOAc in petroleum ether: 0 to 15%) to give the title compound. $^1$H NMR (400 MHz, CDCl$_3$) δ 10.47 (d, J=3.9 Hz, 1H), 7.36-7.48 (m, 3H), 2.60-2.74 (m, 4H), 2.05-2.15 (m, 1H), 1.67-1.78 (m, 1H).

Step 7. Preparation of 2-chloro-6-(1-fluorocyclobutyl)benzoic Acid (i-8)

A mixture of 2-chloro-6-(1-fluorocyclobutyl)benzaldehyde (200 mg, 0.941 mmol), sodium dihydrogen phosphate (226 mg, 1.881 mmol), 2-methylbut-2-ene (1.0 mL, 9.44 mmol) in t-BuOH (5 mL) was stirred at room temperature for 30 min. A solution of sodium chlorite (128 mg, 1.411 mmol) in water (1 mL) was added dropwise at 5° C., and then the reaction mixture was stirred at room temperature for 16 h. The mixture was concentrated and diluted with water (5 mL), extracted with EtOAc (10 mL*5). The combined organic phase was dried over Na$_2$SO$_4$, filtered and concentrated to give the title compound. $^1$H NMR (400 MHz, CDCl$_3$) δ 7.32-7.46 (m, 3H), 4.87 (brs, 1H), 2.60-2.78 (m, 4H), 2.08-2.19 (m, 1H), 1.73-1.84 (m, 1H).

Intermediate i-9

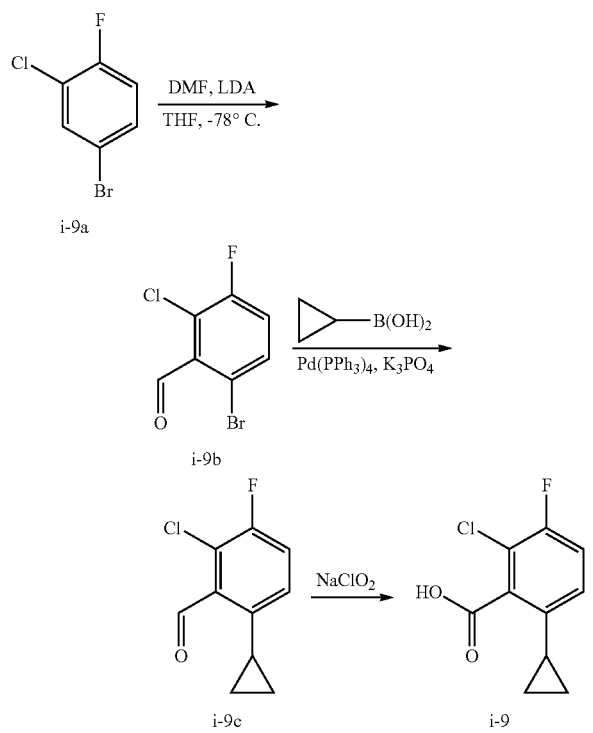

2-chloro-6-cyclopropyl-3-fluorobenzoic Acid

Step 1. Preparation of 6-bromo-2-chloro-3-fluorobenzaldehyde (i-9b)

To a solution of 4-bromo-2-chloro-1-fluorobenzene (5.00 g, 23.9 mmol) in THF (40 mL) was added lithium diisopropylamide (14.3 mL, 28.6 mmol) drop wise at −78° C. The resultant mixture was stirred at −78° C. for 2 h and then DMF (2.70 mL, 35.8 mmol) was added. The reaction mixture was warmed to room temperature, quenched with aq. NH$_4$Cl, and extracted with EtOAc (3×100 mL). The combined organic layers were concentrated and purified by chromatography (0-10% EtOAc in petroleum ether) to give the title compound. $^1$H NMR (400 MHz, CDCl$_3$) δ 10.27-10.33 (m, 1H), 7.56 (dd, J=8.6 Hz, 4.3 Hz, 1H), 7.18-7.26 (m, 1H).

Step 2. Preparation of 2-chloro-6-cyclopropyl-3-fluorobenzaldehyde (i-9c)

To a mixture of 6-bromo-2-chloro-3-fluorobenzaldehyde (2.00 g, 8.42 mmol) and cyclopropylboronic acid (1.09 g, 12.7 mmol) in toluene (20 mL) and water (2 mL) was added K$_3$PO$_4$ (3.58 g, 16.8 mmol) and tetrakis(triphenylphosphine) palladium (0.97 g, 0.84 mmol). The resultant mixture was stirred at 100° C. for 3 h under N$_2$. The reaction mixture was cooled to room temperature and concentrated in vacuo. The residue was purified by chromatography (0-10% EtOAc in petroleum ether) to give the title compound. $^1$H NMR (400 MHz, CDCl$_3$) δ 10.63-10.74 (m, 1H), 7.23 (t, J=8.4 Hz, 1H), 7.00 (dd, J=8.6 Hz, 4.7 Hz, 1H), 2.53-2.65 (m, 1H), 1.02-1.09 (m, 3H), 0.66 (q, J=5.5 Hz, 3H).

Step 3. Preparation of 2-chloro-6-cyclopropyl-3-fluorobenzoic Acid (i-9)

2-Methylbut-2-ene (2.54 g, 36.2 mmol) was added to the solution of 2-chloro-6-cyclopropyl-3-fluorobenzaldehyde (800 mg, 4.03 mmol) in t-BuOH (3 mL). Then an aqueous solution of sodium chlorite (474 mg, 5.24 mmol) and sodium dihydrogen phosphate (628 mg, 5.24 mmol) was added slowly to the reaction mixture. The resultant mixture was stirred at room temperature for 16 h. The solution was concentrated in vacuo and acidified to pH 2 with 1 M HCl aq., extracted with EtOAc (3×20 mL). The combined organic layers were concentrated to give the title compound. $^1$H NMR (400 MHz, MeOD) δ 7.16 (t, J=8.8 Hz, 1H), 6.98 (dd, J=8.6 Hz, 4.7 Hz, 1H), 1.89-1.96 (m, 1H), 0.91-0.97 (m, 2H), 0.68 (q, J=5.2 Hz, 2H).

Intermediate i-10

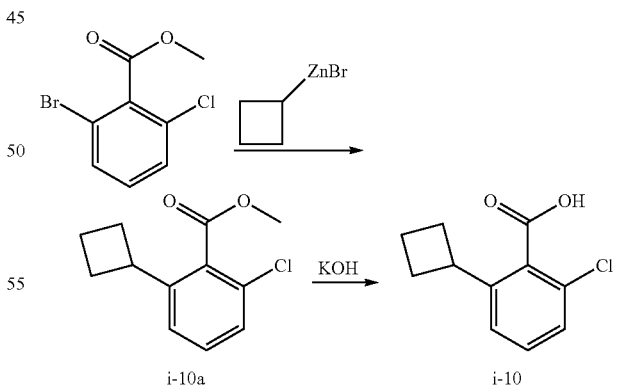

Step 1. Preparation of methyl 2-chloro-6-cyclobutylbenzoate (i-10a)

A mixture of methyl 2-bromo-6-chlorobenzoate (750 mg, 3 mmol), (PPh$_3$)$_4$Pd (345 mg, 0.3 mmol) and cyclobutylzinc bromide (0.5M in THF, 12 mL) were mixed under N$_2$ protection. The mixture was stirred at 70° C. for 12 h under N₂. The mixture was extracted with EtOAc and water. The organic phase was washed with brine, dried over Na₂SO₄, filtered, and concentrated. The residue was purified with flash chromatography (PE:EtOAc=50:1) to give the title compound. MS: 225 (M+1).

Step 2. Preparation of 2-chloro-6-cyclobutylbenzoic Acid (i-10)

To a solution of methyl 2-chloro-6-cyclobutylbenzoate (350 mg, 1 mmol) in EtOH (2 mL), was added 0.2M KOH (1.5 mL, 3 mmol). The mixture was stirred at 100° C. for 12 h, acidified with 3N HCl and extracted with EtOAc. The organic phase was washed with brine, dried over Na₂SO₄, filtered and concentrated. The residue was purified with prep-HPLC (ACN: H₂O) to give the title compound. MS: 211 (M+1).

Intermediate i-11

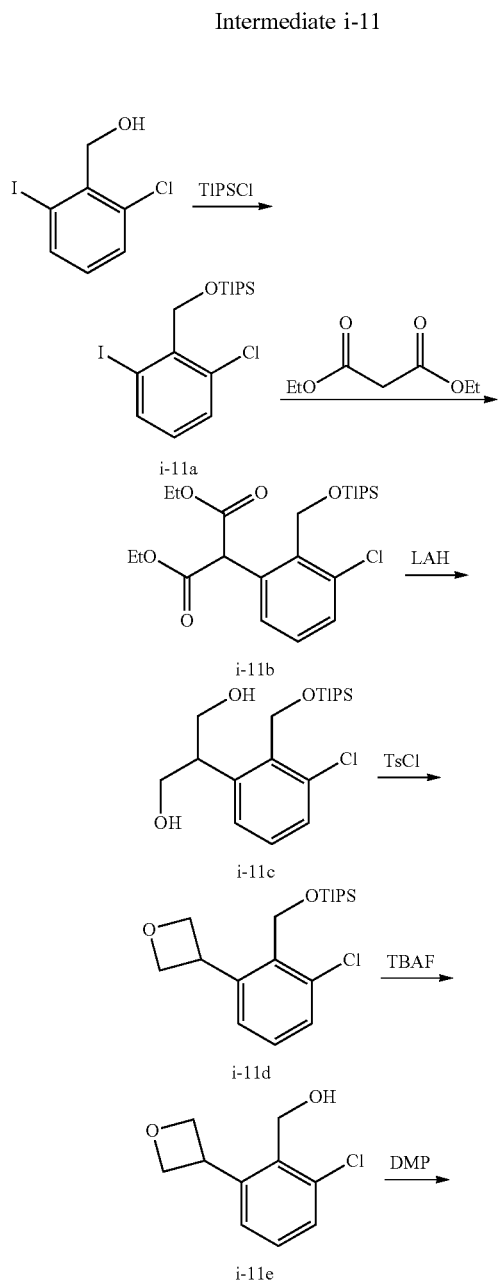

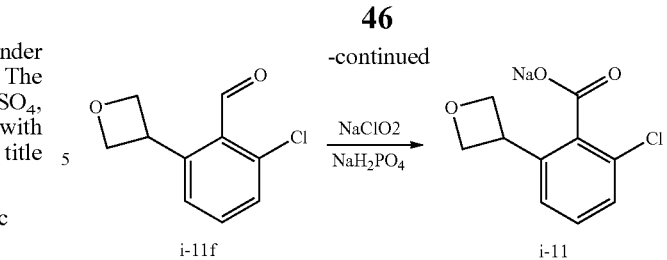

Sodium 2-chloro-6-(oxetan-3-yl)benzoate

Step 1. Preparation of ((2-chloro-6-iodobenzyl)oxy)triisopropylsilane (i-11a)

Into a 10 L flask, was charged (2-chloro-6-iodophenyl) methanol (610 g, 2272 mmol), 1H-imidazole (351 g, 5156 mmol) and DMF (3050 mL). Chlorotriisopropylsilane (498 g, 2583 mmol) was added drop wise at r.t over 1 h. The mixture was stirred overnight at room temperature. TLC showed reaction completed. Water (7000 mL) was added. The solution was extracted with EA (5 L×3). The combined organic layers were washed with brine, dried with Na₂SO₄, filtered and concentrated to obtain title compound.

Step 2. Preparation of diethyl 2-(3-chloro-2-(((triisopropylsilyl)oxy)methyl)phenyl)malonate (i-11b)

Into a 20 L flask, was charged ((2-chloro-6-iodobenzyl) oxy)triisopropylsilane (1000 g, 2354 mmol), diethyl malonate (754 g, 4708 mmol), cesium carbonate (1153 g, 3539 mmol) and THF (5 L). The mixture was degased for 15 min. Copper(I) iodide (68 g, 357 mmol) and [1,1'-biphenyl]-2-ol (80 g, 471 mmol) was added. The resulting mixture was heated to reflux overnight. LCMS showed reaction completed. The suspension was cooled to room temperature and H₂O (10 L) was added. The mixture was extracted with EA (3000 mL×2). The combined organic layers were dried with Na₂SO₄, filtered and concentrated to obtain the crude product, which was purified on silica gel eluting with PE/EA gradient from 100:0 to 30:1 to afford title compound.

Step 3. Preparation of 2-(3-chloro-2-(((triisopropylsilyl)oxy)methyl)phenyl)propane-1,3-diol (i-11c)

To a solution of LAH (56.1 g, 1477 mmol) in THF (1500 mL) at −10 OC was added drop wise diethyl 2-(3-chloro-2-(((triisopropylsilyl)oxy)methyl)phenyl)malonate (300 g, 492 mmol) in THF (1500 mL). The mixture was stirred at room temperature for 3 h, then water (500 mL) was dropwise at −10 OC and extracted with EtOAc. The organic layer was separated, dried over Na₂SO₄, filtered and concentrated. The residue was applied onto a silica gel column with ethyl acetate/petroleum ether (1:1) to give title compound.

Step 4. Preparation of ((2-chloro-6-(oxetan-3-yl) benzyl)oxy)triisopropylsilane (i-11d)

Into a 10 L flask, was charged 2-(3-chloro-2-(((triisopropylsilyl)oxy)methyl)phenyl) propane-1,3-diol (190 g, 509 mmol), THF (1900 mL). The solution was cooled to −78° C., butyllithium (224 mL, 560 mmol) was added drop wise at −78° C. over 15 min. The solution was slowly warmed to 10 OC and stirred for 30 min. The mixture was cooled to −20° C., a solution of 4-methylbenzene-1-sulfonyl chloride (97 g, 509 mmol) in THF (200 mL) was added by batch wise at 0° C. over 5 min. The solution was stirred for a further 30 min at 0° C. LCMS showed the reaction completed conversion. The solution was cooled to −60° C., and additional butyllithium (224 mL, 560 mmol) was added. The reaction mixture was warmed to 35° C. for 30 min. Saturated NH₄Cl (1000 mL) was added slowly at 0° C. The mixture was extracted with EA (1000 mL×3). The combined organic layers were washed with brine and dried with Na₂SO₄, filtered and concentrated to obtain crude product which was purified on silica gel eluting with PE/EA (50:1 to 20:1) to afford title compound.

Step 5. Preparation of (2-chloro-6-(oxetan-3-yl) phenyl)methanol (i-11e)

To a flask containing ((2-chloro-6-(oxetan-3-yl)benzyl) oxy)triisopropylsilane (36 g, 101 mmol) in THF (360 mL) at 25° C. was added tetrabutylammonium fluoride (29.2 g, 112 mmol). The mixture was stirred at room temperature for 1 h. TLC showed the reaction completed. The mixture was diluted with sat. NaHCO₃ and extracted with EtOAc. The organic layer was separated, washed with brine, dried over Na₂SO₄. The residue was used for next step without purification.

Step 6. Preparation of 2-chloro-6-(oxetan-3-yl)benzaldehyde (i-11f)

To a solution of (2-chloro-6-(oxetan-3-yl)phenyl)methanol (35 g, 88 mmol, crude) in CH₂Cl₂ (350 mL) at 15° C. was added sodium bicarbonate (22.20 g, 264 mmol) and Dess-Martin Periodinane (74.7 g, 176 mmol). The mixture was stirred at room temperature for 1 h. TLC showed no SM left. The mixture was diluted with sat NaHCO₃ and extracted with EtOAc. The organic layer was dried over Na₂SO₄, and concentrated. The residue was purified by flash chromatography (0-30% EtOAc/hexanes) to afford title compound.

Step 7. Preparation of Sodium 2-Chloro-6-(Oxetan-3-Yl)Benzoate (i-11)

To a solution of 2-chloro-6-(oxetan-3-yl)benzaldehyde (20 g, 102 mmol) in t-Butanol (200 mL) at room temperature was added 2-methylbut-2-ene (35.7 g, 509 mmol). This was followed by the addition of a pre-mixed solution of sodium chlorite (18.40 g, 203 mmol) and sodium dihydrogen phosphate (24.41 g, 203 mmol) in Water (100 mL). The mixture was stirred at room temperature for 1 h. LCMS showed product formation as major and no SM left. The mixture was acidified with 4 N HCl to PH=1-2, extracted with MTBE. Then the combined organic layers were re-extracted with a solution of 10% Na₂CO₃ (100 mL). The aqueous layer was lyophilized to give sodium 2-chloro-6-(oxetan-3-yl)benzoate. MS: 213 (M+1). ¹H NMR (400 MHz, D₂O) δ 7.54 (1H, d), 7.36 (2H, m), 5.10 (2H, m), 4.77 (2H, m), 4.28 (1H, m).

Intermediate i-12a

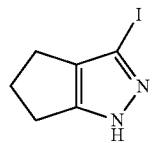

3-iodo-1,4,5,6-tetrahydrocyclopenta[c]pyrazole

A mixture of 1,4,5,6-tetrahydrocyclopenta[c]pyrazole (200 mg, 1.85 mmol) and NIS (416 mg, 1.85 mmol) in DMF (2.3 mL) was stirred at room temperature overnight. The reaction mixture was diluted with water and EtOAc. The organic layer was separated and washed twice with aqueous NaHCO₃ and once with brine. Aqueous layers were back extracted once with EtOAc, combined organic layers were dried with Na₂SO₄, filtered and the solvent was evaporated under reduced pressure. The residue was purified by silica gel chromatography (EtOAc/Hexane 25-90%) to afford the title compound. MS: 235 (M+1).

The following examples shown in Table 1 were prepared following similar procedures described can be achieved by those of ordinary skill in the art of organic synthesis.

TABLE 1

| Intermediate | Structure | IUPAC Name | MS (M + 1) |
| --- | --- | --- | --- |
| i-12b | 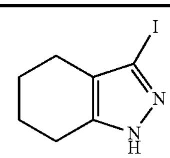 | 3-iodo-4,5,6,7-tetrahydro-1H-indazole | 249 |
| i-12c | 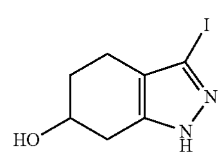 [SMILES: OC1CCc2c(I)n[nH]c2C1] | 3-iodo-4,5,6,7-tetrahydro-1H-indazol-6-ol | 264 |
| i-12d | 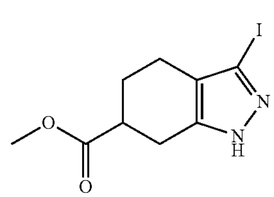 | methyl 3-iodo-4,5,6,7-tetrahydro-1H-indazole-6-carboxylate | 307 |

TABLE 1-continued

| Intermediate | Structure | IUPAC Name | MS (M + 1) |
|---|---|---|---|
| i-12e | 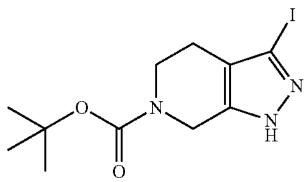 [SMILES: CC(C)(C)OC(=O)N1CCc2c(I)n[nH]c2C1] | tert-butyl 3-iodo-1,4,5,7-tetrahydro-6H-pyrazolo[3,4-c]pyridine-6-carboxylate | 350 |
| i-12f | 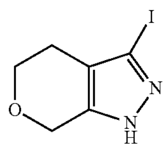 | 3-iodo-1,4,5,7-tetrahydropyrano[3,4-c]pyrazole | 251 |
| i-12g | 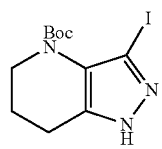 [SMILES: CC(C)(C)OC(=O)N1CCCc2[nH]nc(I)c21] | tert-butyl 3-iodo-1,5,6,7-tetrahydro-4H-pyrazolo[4,3-b]pyridine-4-carboxylate | 350 |

Intermediate i-13a

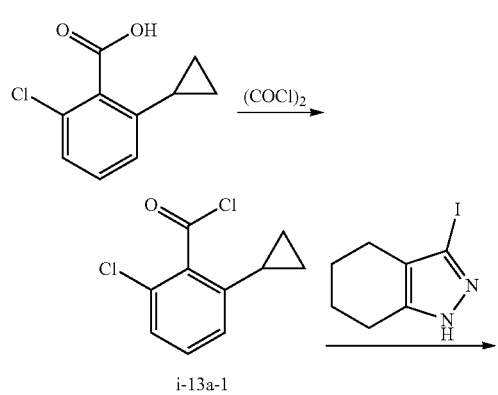

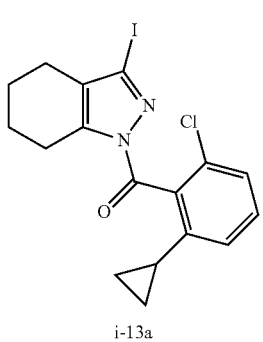

(2-chloro-6-cyclopropylphenyl)(3-iodo-4,5,6,7-tetrahydro-1H-indazol-1-yl)methanone Step 1: 2-chloro-6-cyclopropylbenzoyl chloride (i-13a-1)

A mixture of 2-chloro-6-cyclopropylbenzoic acid (1.0 g, 5.1 mmol), oxalyl chloride (1.1 mL, 12.7 mmol) and DMF (0.039 mL, 0.51 mmol) in DCM (10.2 mL) was allowed to stir at room temperature for 30 minutes. The mixture was concentrated in vacuum to give the crude title compound, which was directly used to next step without further purification.

Step 2: (2-chloro-6-cyclopropylphenyl)(3-iodo-4,5,6,7-tetrahydro-1H-indazol-1-yl)methanone (i-13a)

To a stirred solution of 3-iodo-4,5,6,7-tetrahydro-1H-indazole (950 mg, 3.83 mmol), DMAP (468 mg, 3.83 mmol) and TEA (5.3 mL, 38.3 mmol) in DMF (5 mL) was added 2-chloro-6-cyclopropylbenzoyl chloride (1318 mg, 6.13 mmol) drop wise. The solution was allowed to stir at room temperature overnight. The reaction mixture was diluted with ethyl acetate. The organic layer was separated and washed twice with aqueous sodium hydrogen carbonate and once with brine. The combined organic layers were dried with $Na_2SO_4$, filtered and the solvent was evaporated under reduced pressure. The residue was purified by silica gel chromatography (EtOAc/Hexane 5-50%) to afford the title compound. MS: 427 (M+1).

The following examples shown in Table 2 were prepared following similar procedures described can be achieved by those of ordinary skill in the art of organic synthesis.

TABLE 2

| Intermediate | Structure | IUPAC Name | MS (M + 1) |
|---|---|---|---|
| i-13b | 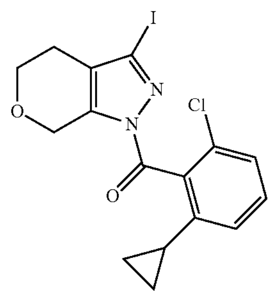 [SMILES: O=C(c1c(Cl)cccc1C1CC1)n1nc(I)c2c1COCC2] | (2-chloro-6-cyclopropylphenyl)(3-iodo-4,7-dihydropyrano[3,4-c]pyrazol-1(5H)-yl)methanone | 429 |
| i-13c | 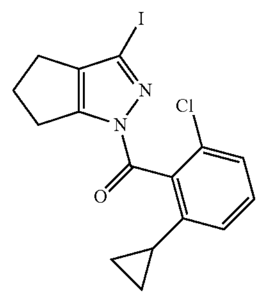 [SMILES: O=C(c1c(Cl)cccc1C1CC1)n1nc(I)c2c1CCC2] | (2-chloro-6-cyclopropylphenyl)(3-iodo-5,6-dihydrocyclopenta[c]pyrazol-1(4H)-yl)methanone | 412.9 |
| i-13g | 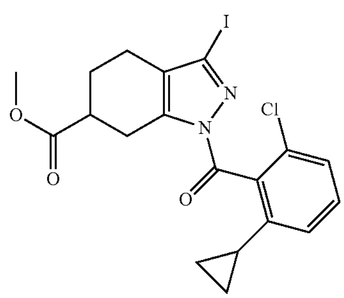 [SMILES: COC(=O)C1CCc2c(I)nn(C(=O)c3c(Cl)cccc3C3CC3)c2C1] | methyl 1-(2-chloro-6-cyclopropylbenzoyl)-3-iodo-4,5,6,7-tetrahydro-1H-indazole-6-carboxylate | 485 |
| i-13h | 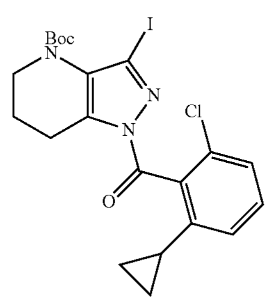 [SMILES: CC(C)(C)OC(=O)N1CCCc2c1c(I)nn2C(=O)c1c(Cl)cccc1C1CC1] | tert-butyl 1-(2-chloro-6-cyclopropylbenzoyl)-3-iodo-1,5,6,7-tetrahydro-4H-pyrazolo[4,3-b]pyridine-4-carboxylate | 528 |
| i-13j | 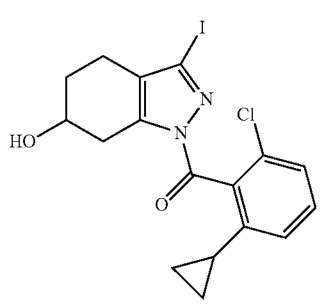 [SMILES: O=C(c1c(Cl)cccc1C1CC1)n1nc(I)c2c1CC(O)CC2] | (2-chloro-6-cyclopropylphenyl)(6-hydroxy-3-iodo-4,5,6,7-tetrahydro-1H-indazol-1-yl)methanone | 443 |

TABLE 2-continued

| Intermediate | Structure | IUPAC Name | MS (M + 1) |
|---|---|---|---|
| i-13k | 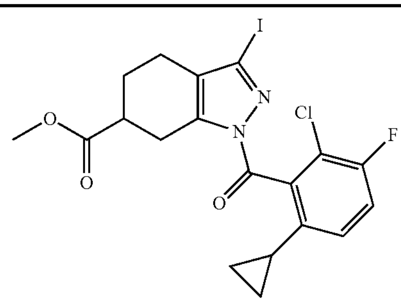 | methyl 1-(2-chloro-6-cyclopropyl-3-fluorobenzoyl)-3-iodo-4,5,6,7-tetrahydro-1H-indazole-6-carboxylate | 503 |
| i-13l | 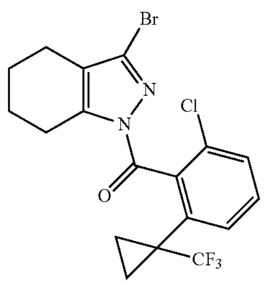 [SMILES: O=C(c1c(Cl)cccc1C1(C(F)(F)F)CC1)n1nc(Br)c2c1CCCC2] | (2-chloro-6-(1-(trifluoromethyl)cyclopropyl)phenyl)(3-iodo-4,5,6,7-tetrahydro-1H-indazol-1-yl)methanone | 447 |

Intermediate i-14A and i-14B methyl (6R)-3-iodo-4,5,6,7-tetrahydro-1H-indazole-6-carboxylate and methyl (6S)-3-iodo-4,5,6,7-tetrahydro-1H-indazole-6-carboxylate The mixture of the two stereoisomers was purified by chiral SFC (AD-H column, 30%/70% Methanol/CO$_2$) to afford i-14A (faster eluting): MS: 307 (M+1). i-14B (slower eluting): MS: 307 (M+1).

The following examples shown in Table 3 were prepared using i-14A and following similar procedures described in i-13a can be achieved by those of ordinary skill in the art of organic synthesis.

TABLE 3

| Intermediate | Structure | IUPAC Name | MS (M + 1) |
|---|---|---|---|
| i-15A | 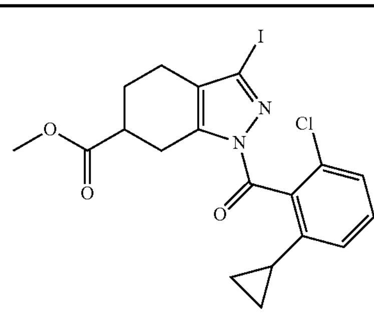 | methyl (R or S)-1-(2-chloro-6-cyclopropylbenzoyl)-3-iodo-4,5,6,7-tetrahydro-1H-indazole-6-carboxylate | 485 |

TABLE 3-continued

| Intermediate | Structure | IUPAC Name | MS (M + 1) |
|---|---|---|---|
| i-16A | 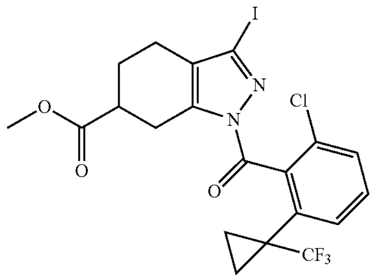 [SMILES: COC(=O)C1CCc2c(I)nn(C(=O)c3c(Cl)cccc3C3(C(F)(F)F)CC3)c2C1] | methyl (R or S)-1-(2-chloro-6-(1-(trifluoromethyl)cyclopropyl)benzoyl)-3-iodo-4,5,6,7-tetrahydro-1H-indazole-6-carboxylate | 553 |

The following examples shown in Table 4 were prepared using i-14B and following similar procedures described in i-13a can be achieved by those of ordinary skill in the art of organic synthesis.

TABLE 4

| Intermediate | Structure | IUPAC Name | Spectral Data |
|---|---|---|---|
| i-15B | 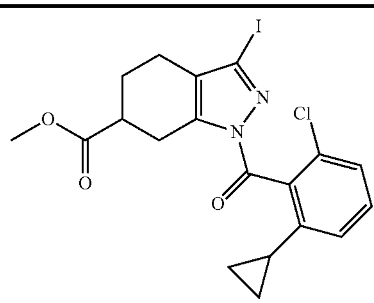 | methyl (R or S)-1-(2-chloro-6-cyclopropylbenzoyl)-3-iodo-4,5,6,7-tetrahydro-1H-indazole-6-carboxylate | MS: 485 (M + 1) |
| i-19B | 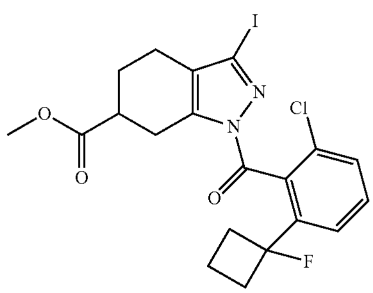 [SMILES: COC(=O)C1CCc2c(I)nn(C(=O)c3c(Cl)cccc3C3(F)CCC3)c2C1] | methyl (R or S)-1-(2-chloro-6-(1-fluorocyclobutyl)benzoyl)-3-iodo-4,5,6,7-tetrahydro-1H-indazole-6-carboxylate | $^1$H NMR (400 MHz, CDCl$_3$) δ 7.35-7.48 (m, 3H), 3.76 (s, 3H), 3.50-3.61 (m, 1H), 3.24-3.36 (m, 1H), 2.79-2.89 (m, 1H), 2.52-2.70 (m, 4H), 2.35-2.49 (m, 3H), 2.20-2.29 (m, 1H), 1.88-1.99 (m, 1H), 1.75-1.84 (m, 1H). |

Intermediate i-20A and i-20B

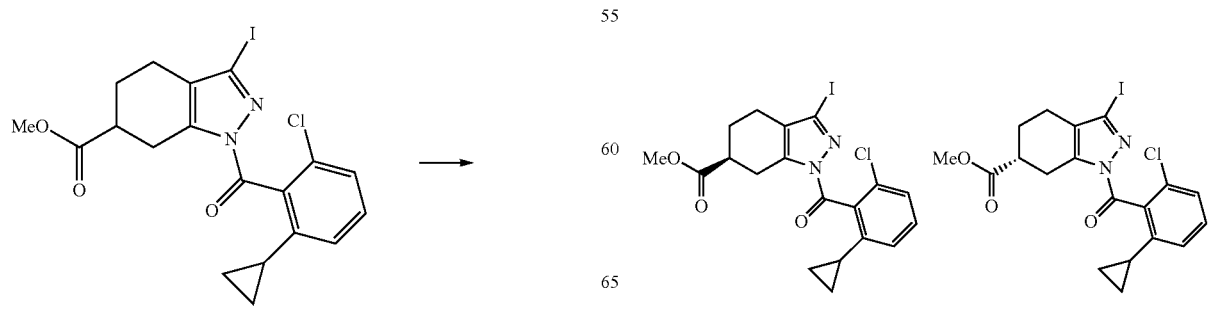

methyl (S)-1-(2-chloro-6-cyclopropylbenzoyl)-3-iodo-4,5,6,7-tetrahydro-1H-indazole-6-carboxylate and methyl (R)-1-(2-chloro-6-cyclopropylbenzoyl)-3-iodo-4,5,6,7-tetrahydro-1H-indazole-6-carboxylate The mixture of the two stereoisomers was purified by chiral SFC (OJ-H column, 20%/80% Methanol with 0.25% DME/CO$_2$) to afford i-20A (faster eluting): MS: 485 (M+1). i-20B (slower eluting): MS: 485 (M+1).

Intermediate i-21A and i-21B

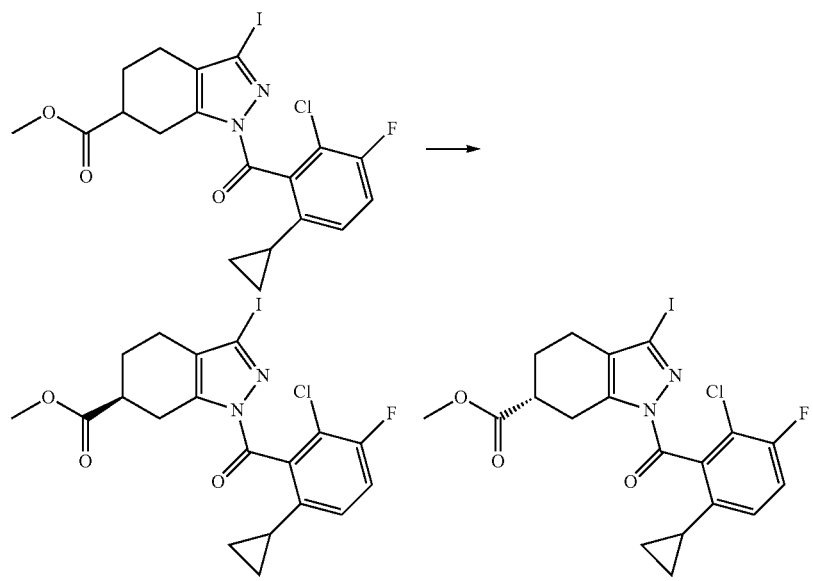

methyl (R)-1-(2-chloro-6-cyclopropyl-3-fluorobenzoyl)-3-iodo-4,5,6,7-tetrahydro-1H-indazole-6-carboxylate and methyl (S)-1-(2-chloro-6-cyclopropyl-3-fluorobenzoyl)-3-iodo-4,5,6,7-tetrahydro-1H-indazole-6-carboxylate The mixture of the two stereoisomers was purified by chiral SFC (OJ-H column, 15%/85% Methanol with 0.25% DMEA/CO$_2$) to afford i-21A (faster eluting): MS: 503 (M+1). i-21B (slower eluting): MS: 503 (M+1).

Intermediate i-22a

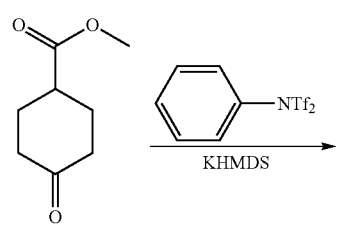

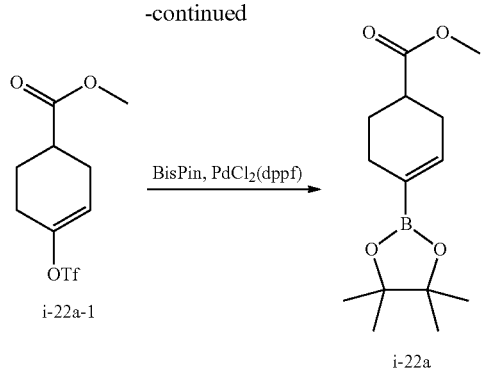

methyl 4-(4,4,5,5-tetramethyl-1,3,2-dioxaborolan-2-yl)cyclohex-3-ene-1-carboxylate Step 1. Preparation of methyl 4-(((trifluoromethyl)sulfonyl)oxy)cyclohex-3-ene-1-carboxylate (i-22a-1)

Into a 100 mL 3-necked, round bottomed flask, purged and maintained with an inert atmosphere of nitrogen was placed KHMDS (9.1 g, 21%), followed by the addition of a solution of methyl 4-oxocyclohexanecarboxylate (1 g, 6.40 mmol, 1.00 equiv) in THF (10 mL) dropwise with stirring, while cooling to a temperature of −70~−80° C. The resulting solution was stirred for 2 hours at −70~−78° C., then added a solution of PhN(Tf)₂ (2.75 g, 7.70 mmol, 1.20 equiv) in THF (10 mL) dropwise with stirring at −70~−80° C. The resulting solution was stirred for 2 hours at −70~−78° C. The reaction progress was monitored by TLC (EtOAc/PE=1:2). The reaction mixture was then quenched by adding 10 mL of H₂O, followed by extraction three times with 50 mL of EtOAc. The organic layers were combined, washed 3 times with 50 mL of 10% NaHCO₃ solution, dried over MgSO₄ and concentrated under vacuum. The residue was purified by eluting through a silica gel column with a 1:100 EtOAc/PE solvent system to afford methyl 4-(trifluoromethylsulfonyloxy)cyclohex-3-enecarboxylate.

Step 1. Preparation of methyl 4-(4,4,5,5-tetramethyl-1,3,2-dioxaborolan-2-yl)cyclohex-3-ene-1-carboxylate (i-22a)

Into a 1000 mL 3-necked, round bottomed flask, purged and maintained with an inert atmosphere of nitrogen, were placed a solution of methyl 4-(trifluoromethylsulfonyloxy)cyclohex-3-enecarboxylate (76.3 g, 264.93 mmol, 1.00 equiv) in 1,4-dioxane (800 mL), 4,4,5,5-tetramethyl-2-(4,4,5,5-tetramethyl-1,3,2-dioxaborolan-2-yl)-1,3,2-dioxaborolane (74 g, 308.46 mmol, 1.10 equiv), PdCl₂(dppf) (8.5 g, 10.41 mmol, 0.04 equiv) and AcOK (76.3 g, 777.46 mmol, 3.00 equiv). The resulting solution was stirred overnight at 80-90° C. in an oil bath. The reaction progress was monitored by TLC (EtOAc/PE=1:5). After cooled to room temperature, the reaction mixture was filtered. The filtrate was diluted with 800 mL of water, then extracted three times with 800 mL of EtOAc. The organic layers were combined, washed with brine, dried over MgSO₄ and concentrated under vacuum. This resulted in 36 g (51%) of methyl 4-(4,4,5,5-tetramethyl-1,3,2-dioxaborolan-2-yl)cyclohex-3-enecarboxylate. MS: 267 (M+1). ¹H NMR (400 MHz, CDCl₃) δ 1.41 (12H, m), 1.58 (1H, m), 2.04 (1H, m), 2.14 (1H, m), 2.30 (3H, m), 2.53 (1H, m), 3.68 (3H, s), 6.5 (1H, s).

The following examples shown in Table 5 were prepared following similar procedures described can be achieved by those of ordinary skill in the art of organic synthesis.

TABLE 5

| Intermediate | Structure | IUPAC Name | NMR |
|---|---|---|---|
| i-22b | 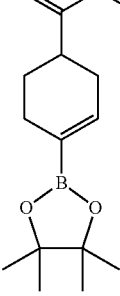 | ethyl 4-(4,4,5,5-tetramethyl-1,3,2-dioxaborolan-2-yl)cyclohex-3-ene-1-carboxylate | ¹HNMR (400 MHz, CDCl₃, ppm): δ 6.55-6.56 (1H, s), 4.18-4.16 (2H, m), 2.49-2.54 (1H, s), 2.26-2.37 (3H, m), 2.01-2.17 (2H, m), 1.59-1.67 (1H, m), 1.26-1.29 (15H, m). |
| i-22c | 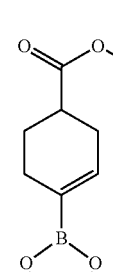 | tert-butyl 4-(4,4,5,5-tetramethyl-1,3,2-dioxaborolan-2-yl)cyclohex-3-ene-1-carboxylate | ¹HNMR (400 MHz, CDCl₃, ppm): δ 6.56 (m, 1H), 2.41 (m, H), 2.28 (m, 3H), 2.12 (m, 1H), 1.98 (m, 1H), 1.58 (m, 1H), 1.45 (s, 9H), 1.25 (s, 12H). |

Intermediate i-23

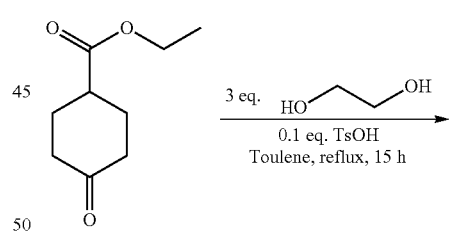

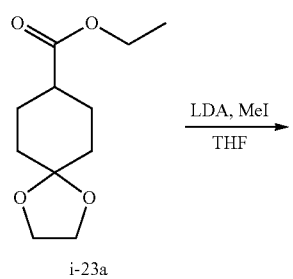

i-23a

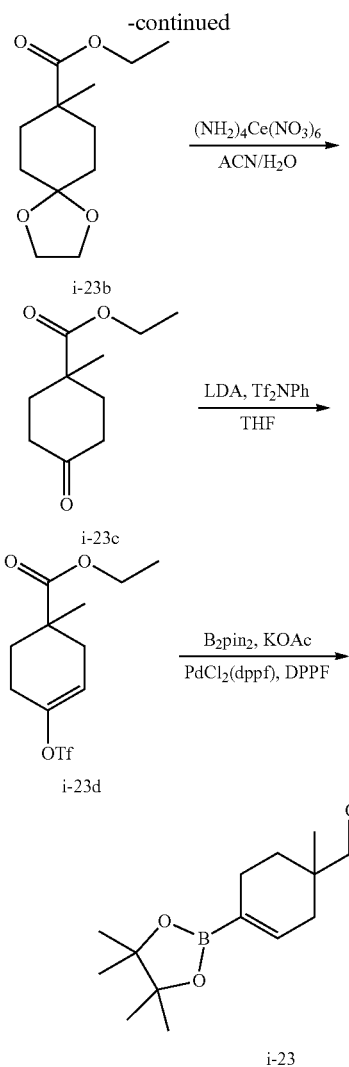

ethyl 1-methyl-4-(4,4,5,5-tetramethyl-1,3,2-dioxaborolan-2-yl)cyclohex-3-enecarboxylate Step 1. Preparation of ethyl 1,4-dioxaspiro[4.5]decane-8-carboxylate (i-23a)

To a solution of ethyl 4-oxocyclohexanecarboxylate (25 g, 147 mmol) in toluene (300 mL) were added p-toluenesulfonic acid (2.53 g, 14.69 mmol) and ethylene glycol (27.3 g, 441 mmol). The mixture was stirred at 120° C. and refluxed with water knockout trap for 16 h. The reaction mixture was concentrated under reduced pressure and the residue was diluted in EtOAc (100 mL), washed with NaHCO$_3$ (aq.) (200 mL) and brine (200 mL), dried over Na$_2$SO$_4$, filtered and concentrated. The residue was purified by column chromatography on silica gel (Petro. Ether: EtOAc=100:1~50:1) to afford the title compound. $^1$H NMR (CD$_3$OD, 400 MHz) δ 4.10 (q, J=7.2 Hz, 2H), 3.92 (s, 4H), 2.23-2.35 (m, 1H), 1.89-1.93 (m, 2H), 1.70-1.84 (m, 4H), 1.47-1.58 (m, 2H), 1.22 (t, J=7.2 Hz, 3H).

Step 2. Preparation of ethyl 8-methyl-1,4-dioxaspiro[4.5]decane-8-carboxylate (i-23b)

To a solution of ethyl 1,4-dioxaspiro[4.5]decane-8-carboxylate (11 g, 51.3 mmol) in THF (200 mL) cooled at −78° C. was added LDA (38.5 mL, 2.0 M in THF, 77 mmol) drop wise. The resultant yellow mixture was stirred at −78° C. for 20 min. MeI (9.6 mL, 154 mmol) was added at this temperature. The mixture was stirred at −78° C. for 2 h. The mixture was quenched with NH$_4$Cl (aq.) (50 mL), extracted with EtOAc (50 mL*3), washed with brine (100 mL*2), dried over Na$_2$SO$_4$, filtered and concentrated. The residue was purified by column chromatography on silica gel (Petro. ether:EtOAc=100:1~50:1) to afford the title compound. $^1$H NMR (CD$_3$OD, 400 MHz) δ 4.14 (q, J=7.2 Hz, 2H), 3.93 (s, 4H), 2.13 (d, J=12.8 Hz, 2H), 1.58-1.64 (m, 4H), 1.45-1.54 (m, 2H), 1.25 (t, J=7.2 Hz, 3H), 1.18 (s, 3H).

Step 3. Preparation of ethyl 1-methyl-4-oxocyclohexanecarboxylate (i-23c)

To a solution of ethyl 8-methyl-1,4-dioxaspiro[4.5]decane-8-carboxylate (7.3 g, 32.0 mmol) in MeCN (50 mL) and water (50 mL) was added CAN (2.11 g, 3.85 mmol). The mixture was heated to 70° C. and stirred for 2 h. The reaction mixture was cooled to room temperature, and partitioned between water (50 mL) and EtOAc (50 mL). The aqueous layer was extracted with EtOAc (50 mL*2). The combined organic layers were washed with brine (50 mL*2), dried over Na$_2$SO$_4$, filtered and concentrated under reduced pressure to afford the title compound (5 g, 85%) as yellow oil, which was used for next step without further purification.

Step 4. Preparation of ethyl 1-methyl-4-(((trifluoromethyl)sulfonyl)oxy)cyclohex-3-enecarboxylate (i-23d)

To a solution of LDA (20.4 mL, 2.0 M in THF, 40.8 mmol) in THF (30 mL) cooled at −78 OC was added ethyl 1-methyl-4-oxocyclohexanecarboxylate (5.00 g, 27.1 mmol) in THF (10 mL) drop wise. After stirring at this temperature for 30 min, N,N-bis(trifluoromethylsulfonyl)aniline (10.67 g, 29.9 mmol) in THF (20 mL) was added. The mixture was warmed to room temperature and stirred for 16 h. The mixture was quenched with NH$_4$Cl (aq.) (30 mL), extracted with EtOAc (30 mL*3). The combined organic layers were washed with brine (40 mL*2), dried over Na$_2$SO$_4$, filtered and concentrated. The residue was purified by column chromatography on silica gel (Petro. ether:EtOAc=100:1~50:1) to afford the title compound. $^1$H NMR (CD$_3$OD, 400 MHz) δ 5.71 (s, 1H), 4.04-4.21 (m, 2H), 2.62-2.75 (m, 1H), 2.27-2.48 (m, 2H), 2.01-2.19 (m, 2H), 1.68-1.75 (m, 1H), 1.14-1.25 (m, 6H).

Step 5. Preparation of ethyl 1-methyl-4-(4,4,5,5-tetramethyl-1,3,2-dioxaborolan-2-yl)cyclohex-3-enecarboxylate (i-23)

To a solution of ethyl 1-methyl-4-(((trifluoromethyl)sulfonyl)oxy)cyclohex-3-enecarboxylate (3.6 g, 11.38 mmol), bis(pinacolato)diboron (3.47 g, 13.66 mmol), potassium acetate (3.35 g, 34.1 mmol) in dioxane (40 mL) were added DPPF (0.631 g, 1.138 mmol) and PdCl$_2$(dppf) (0.833 g, 1.138 mmol). The mixture was stirred at 80° C. for 18 h under N$_2$, cooled to room temperature, diluted with water (20 mL), and extracted with EtOAc (20 mL*3). The combined organic layers were washed with brine (20 mL*2), dried over Na$_2$SO$_4$, filtered and concentrated. The residue was purified by column chromagraphy on silica gel (Petro. ether:EtOAc=100:1~30:1) to afford the title compound. $^1$H NMR (CDCl$_3$, 400 MHz) δ 6.47-6.55 (m, 1H), 4.08-4.15 (m, 2H), 2.59-2.65 (m, 1H), 2.14-2.19 (m, 2H), 1.95-2.00 (m, 1H), 1.86-1.92 (m, 1H), 1.53-1.58 (m, 1H), 1.21-1.26 (m, 15H), 1.18 (s, 3H). MS: 295 (M+1).

Intermediate i-24A

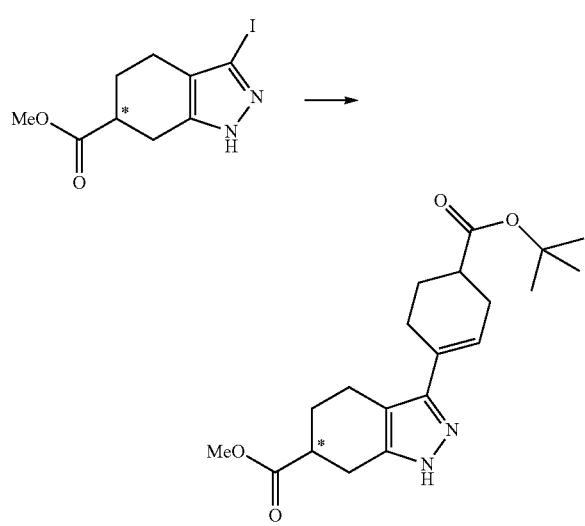

methyl (6R or S)-3-(4-(tert-butoxycarbonyl)cyclo-hex-1-en-1-yl)-4,5,6,7-tetrahydro-1H-indazole-6-carboxylate Step 1. Preparation of methyl (6R or S)-3-(4-(tert-butoxycarbonyl)cyclohex-1-en-1-yl)-4,5,6,7-tetrahydro-1H-indazole-6-carboxylate (i-24A)

A mixture of tert-butyl 4-(4,4,5,5-tetramethyl-1,3,2-dioxaborolan-2-yl)cyclohex-3-enecarboxylate (6.04 g, 19.60 mmol), (R or S)-methyl 3-iodo-4,5,6,7-tetrahydro-1H-indazole-6-carboxylate i-14A (3 g, 9.80 mmol), 1,1'-bis(diphenylphosphino)ferrocene-palladium(ii)dichloride dichloromethane complex (1.601 g, 1.960 mmol), and potassium acetate (2.89 g, 29.4 mmol) in dioxane (16.33 mL) was thoroughly degassed with argon. Water (3.27 mL) was then added and the reaction mixture was stirred at 90° C. overnight. The reaction was cooled and diluted with EtOAc. The organic layer was washed twice with aqueous NaHCO₃ and once with brine, dried with Na₂SO₄, filtered, and concentrated under reduced pressure. The residue was purified by silica gel chromatography (0-100% EtOAc/Hexane) to afford the title compound. MS: 361 (M+1).

Intermediate i-24B

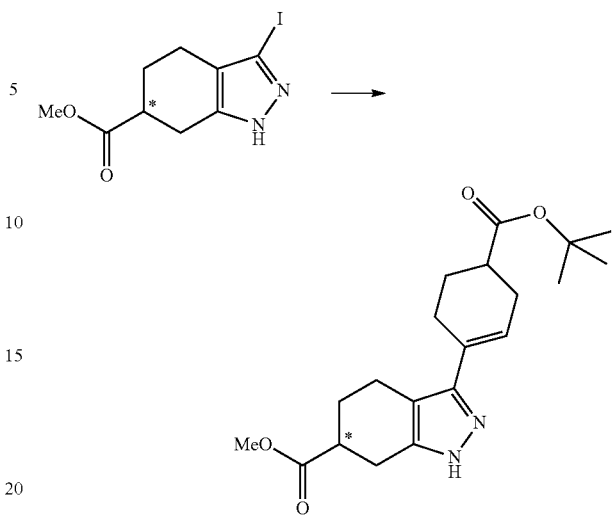

methyl (6R or S)-3-(4-(tert-butoxycarbonyl)cyclo-hex-1-en-1-yl)-4,5,6,7-tetrahydro-1H-indazole-6-carboxylate Step 1. Preparation of methyl (6R or S)-3-(4-(tert-butoxycarbonyl)cyclohex-1-en-1-yl)-4,5,6,7-tetrahydro-1H-indazole-6-carboxylate (i-24B)

A mixture of tert-butyl 4-(4,4,5,5-tetramethyl-1,3,2-dioxaborolan-2-yl)cyclohex-3-enecarboxylate (201 mg, 0.653 mmol), (R or S)-methyl 3-iodo-4,5,6,7-tetrahydro-1H-indazole-6-carboxylate i-14B (100 mg, 0.33 mmol), potassium carbonate (135 mg, 0.980 mmol), and 1,1'-bis(diphenylphosphino)ferrocene-palladium(ii)dichloride dichloromethane complex (40.0 mg, 0.049 mmol) in dioxane (907 µL) and water (181 µL) was thoroughly degassed under argon. The reaction mixture was stirred at 90° C. overnight. The reaction was cooled and diluted with EtOAc. The organic layer was washed twice with aqueous NaHCO₃ and once with brine, dried with Na₂SO₄, filtered, and concentrated under reduced pressure. The residue was purified by silica gel chromatography (0-100% EtOAc/Hexane) to afford the title compound. MS: 361 (M+1).

The following examples shown in Table 6 were prepared following similar procedures described can be achieved by those of ordinary skill in the art of organic synthesis.

TABLE 6

| Intermediate | Structure | IUPAC Name | MS (M + 1) |
|---|---|---|---|
| i-25A | 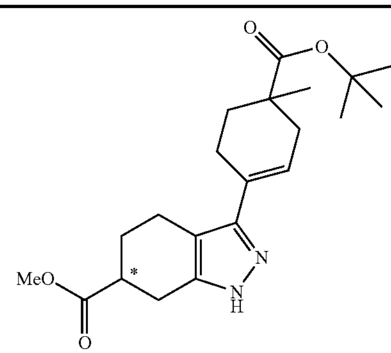 | methyl (6R or S)-3-(4-(tert-butoxycarbonyl)-4-methylcyclohex-1-en-1-yl)-4,5,6,7-tetrahydro-1H-indazole-6-carboxylate | 375 |

TABLE 6-continued

| Intermediate | Structure | IUPAC Name | MS (M + 1) |
| --- | --- | --- | --- |
| i-25B | 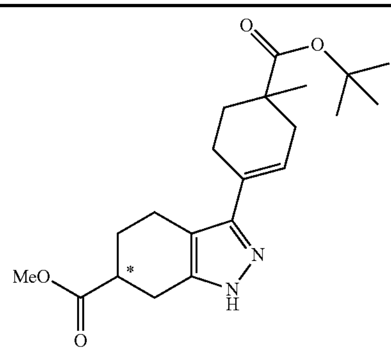 | methyl (6R or S)-3-(4-(tert-butoxycarbonyl)-4-methylcyclohex-1-en-1-yl)-4,5,6,7-tetrahydro-1H-indazole-6-carboxylate | 375 |

Intermediate i-26A and i-26R

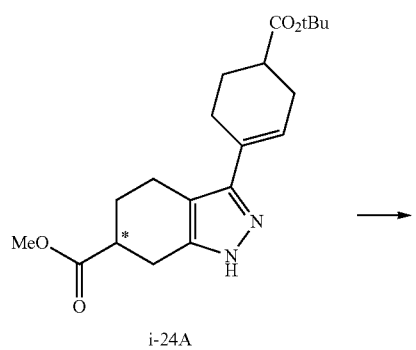

Intermediate i-27A and i-27B

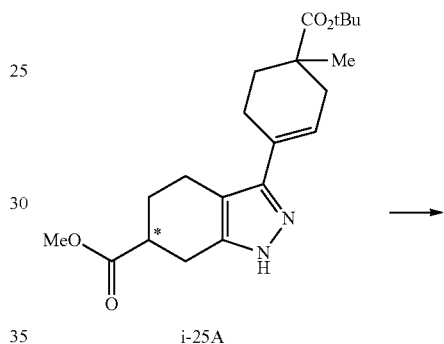

methyl (R or S)-3-((R or S)-4-(tert-butoxycarbonyl)cyclohex-1-en-1-yl)-4,5,6,7-tetrahydro-1H-indazole-6-carboxylate and methyl (R or S)-3-((R or S)-4-(tert-butoxycarbonyl)cyclohex-1-en-1-yl)-4,5,6,7-tetrahydro-1H-indazole-6-carboxylate The mixture of the two stereoisomers of i-24A was purified by chiral SFC (AD-H column, 40%/60% EtOH+ DEA/$CO_2$) to afford i-26A (faster eluting): MS: 361 (M+1). i-26B (slower eluting): MS: 361 (M+1).

methyl (R or S)-3-((R or S)-4-(tert-butoxycarbonyl)-4-methylcyclohex-1-en-1-yl)-4,5,6,7-tetrahydro-H-indazole-6-carboxylate and methyl (R or S)-3-((R or S)-4-(tert-butoxycarbonyl)-4-methylcyclohex-1-en-1-yl)-4,5,6,7-tetrahydro-1H-indazole-6-carboxylate The mixture of the two stereoisomers of i-25A were purified by chiral SFC (OJ-H column, 7.5%/92.5% MeOH+ 0.25% DMEA/$CO_2$) to afford i-27A (faster eluting): MS: 375 (M+1). i-27B (slower eluting): MS: 375 (M+1).

Intermediate i-28

Intermediate i-29A, i-29B, i-29C, and i-29D

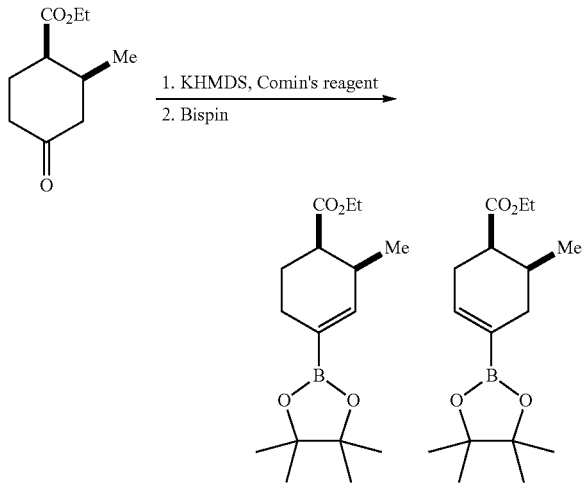

racemic ethyl (cis)-2-methyl-4-(4,4,5,5-tetramethyl-1,3,2-dioxaborolan-2-yl)cyclohex-3-ene-1-carboxylate and racemic ethyl (cis)-6-methyl-4-(4,4,5,5-tetramethyl-1,3,2-dioxaborolan-2-yl)cyclohex-3-ene-1-carboxylate Step 1. Preparation of racemic ethyl (cis)-2-methyl-4-(4,4,5,5-tetramethyl-1,3,2-dioxaborolan-2-yl)cyclohex-3-ene-1-carboxylate and racemic ethyl (cis)-6-methyl-4-(4,4,5,5-tetramethyl-1,3,2-dioxaborolan-2-yl)cyclohex-3-ene-1-carboxylate To a solution of racemic ethyl (cis)-2-methyl-4-oxocyclohexane-1-carboxylate (1 g, 5.43 mmol) in THF (11 mL) at −78° C. was added KHMDS (6.5 mL, 1.0M in THF, 6.5 mmol. The mixture was stirred for 15 min, followed by the addition of 2-[N,N-bis(trifluoromethanesulfonyl)amino]-5-chloropyridine (2.35 g, 5.97 mmol) (dissolved in 3 mL THF). The mixture was kept stirring at −78° C. for 30 min, and then warmed up and stirred at room temperature for 2 h. The mixture was quenched with H$_2$O, and extracted with EtOAc. The combined organics were washed with brine, dried over Na$_2$SO$_4$, filtered and concentrated in vacuo. The residue was purified by flash chromatography (0-40% EtOAc/hexanes) to give the desired vinyl triflate as a mixture of two double bond regio-isomers (ratio ~1:1).

To a solution of the triflate (a mixture of two regio-isomers) from previous step in dioxane (16 mL) were added bis(pinacolato)diboron (1.51 g, 5.9 mmol), potassium acetate (1.16 g, 11.9 mmol). The mixture was degassed for 5 min, followed by the addition of Chloro(2-dicyclohexylphosphino-2′,4′,6′-triisopropyl-1,1′-biphenyl)[2-(2′-amino-1,1′-biphenyl)]palladium(II) (0.16 g, 0.20 mmol). The mixture was heated at 90° C. for 14 h, cooled down, filtered through celite, concentrated. The residue was purified by flash chromatography (0-40% EtOAc/hexanes) to give final product as a mixture of two inseparable regio-isomers, ethyl (1R,2S or 1S, 2R)-2-methyl-4-(4,4,5,5-tetramethyl-1,3,2-dioxaborolan-2-yl)cyclohex-3-ene-1-carboxylate and ethyl (1R,6S or 1S, 6R)-6-methyl-4-(4,4,5,5-tetramethyl-1,3,2-dioxaborolan-2-yl)cyclohex-3-ene-1-carboxylate. MS: 295 (M+1)

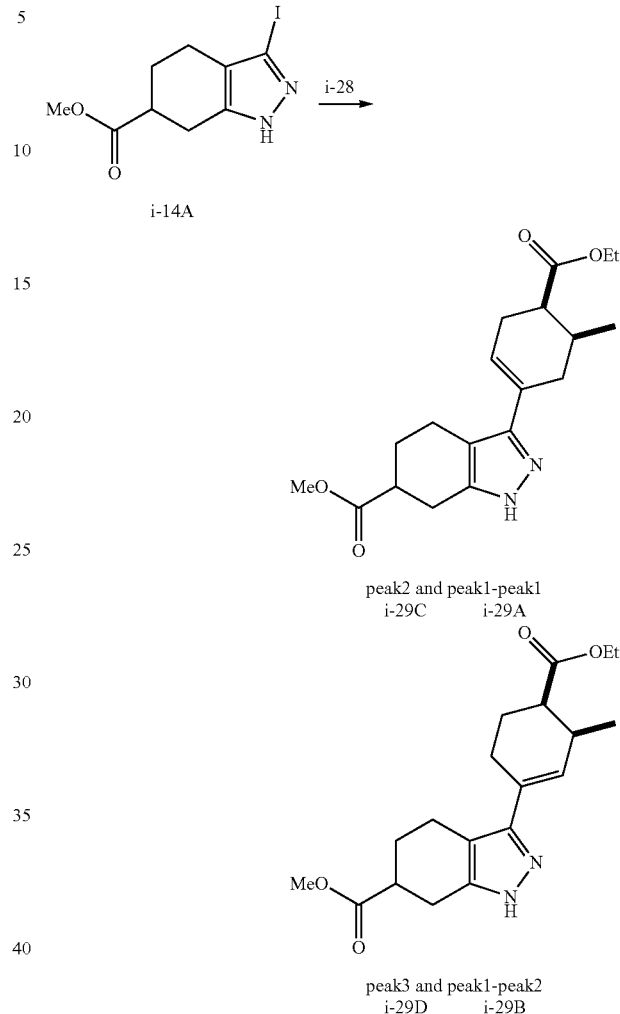

Step 1. Preparation of methyl (R or S)-3-((3S,4R or 3R, 4S)-4-(ethoxycarbonyl)-3-methylcyclohex-1-en-1-yl)-4,5,6,7-tetrahydro-1H-indazole-6-carboxylate i-29D (peak 3)/i-29B (peak 1-peak 2) and methyl (R or S)-3-((4R,5S or 4S,5R)-4-(ethoxycarbonyl)-5-methylcyclohex-1-en-1-yl)-4,5,6,7-tetrahydro-1H-indazole-6-carboxylate i-29C (peak 2)/i-29A (peak 1-peak 1)

To a microwave reaction vial containing a ~1:1 mixture of methyl ethyl (cis)-2-methyl-4-(4,4,5,5-tetramethyl-1,3,2-dioxaborolan-2-yl)cyclohex-3-ene-1-carboxylate and ethyl (cis)-6-methyl-4-(4,4,5,5-tetramethyl-1,3,2-dioxaborolan-2-yl)cyclohex-3-ene-1-carboxylate (i-28) (1.48 g, 5.03 mmol) were added methyl (R or S)-3-iodo-4,5,6,7-tetrahydro-1H-indazole-6-carboxylate i-14A (1.4 g, 4.57 mmol), dioxane (15 mL), and sodium carbonate (3.43 mL, 6.86 mmol). The mixture was degassed for 5 min, followed by the addition of 1,1′-bis(diphenylphosphino) ferrocene-palladium(ii)dichloride dichloromethane complex (0.37 g, 0.46 mmol). The vial was sealed and heated at 90° C. for 14 h. The reaction mixture was cooled down, diluted with H$_2$O, and extracted with EtOAc. The organic layer was separated, washed with brine, dried over MgSO₄, and concentrated. The residue was purified by flash chromatography (50-100% EtOAc/hexanes) to give 1.1 g of final compound as a mixture of four diastereomers.

The mixture of the isomers was purified by chiral SFC (OJ-H column, 10%/90% Methanol+0.25% Dimethyl Ethyl Amine/CO₂) to afford three separate peaks. Peaks two and three each contain a single diastereomer, peak 2 yielding i-29C and peak 3 yielding i-29D. The first peak contains two diastereomers and was resubmitted through chiral SFC (Phenomenex, Lux-2 column, 25%/75% Methanol+0.25% Dimethyl Ethyl Amine/CO₂) to afford i-29A (faster eluting peak) and i-29B (slower eluting peak)

NMR confirmed that i-29D (peak 3) and i-29B (peak 1-peak 2) possess the same regio-chemistry for cyclohexenyl moiety (Methyl at allyic position), while i-29C (peak 2) and i-29A (peak 1-peak 1) also possess the same regio-chemistry for cyclohexenyl moiety (Methyl at homoallyic position)

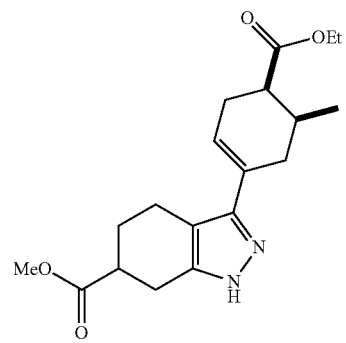 [SMILES: CCOC(=O)[C@@H]1CC=C(c2n[nH]c3c2CCC(C(=O)OC)C3)C[C@@H]1C]

i-29C (peak 2): $^1$H NMR (CDCl₃, 600 MHz) δ 5.98 (brs, 1H), 4.04-4.28 (m, 2H), 3.70 (s, 3H), 2.86-2.94 (m, 1H), 2.62-2.84 (m, 5H), 2.42-2.60 (m, 2H), 2.30-2.40 (m, 1H), 2.14-2.20 (m, 1H), 1.90-2.00 (m, 1H), 1.74-1.86 (m, 2H), 1.24 (t, J=7.2 Hz, 3H), 0.94 (d, J=7.2 Hz, 3H). MS: 347 (M+1).

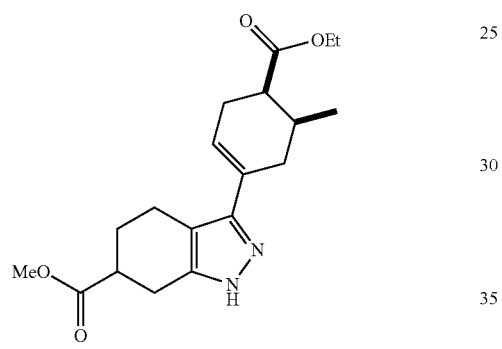

i-29A (peak 1-peak 1): $^1$H NMR (CDCl₃, 600 MHz) δ 5.99 (brs, 1H), 4.08-4.28 (m, 2H), 3.70 (s, 3H), 2.80-2.98 (m, 2H), 2.62-2.76 (m, 4H), 2.42-2.60 (m, 3H), 2.32-2.39 (m, 1H), 2.26-2.32 (m, 1H), 2.14-2.22 (m, 1H), 1.76-1.84 (m, 1H), 1.24 (t, J=7.2 Hz, 3H), 0.94 (d, J=7.2 Hz, 3H). MS: 347 (M+1).

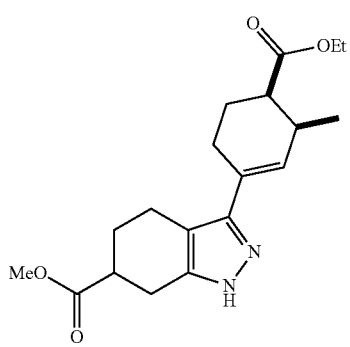 [SMILES: CCOC(=O)[C@@H]1CCC(c2n[nH]c3c2CCC(C(=O)OC)C3)=C[C@@H]1C]

i-29D (peak 3): $^1$H NMR (CDCl₃, 600 MHz) δ 5.97 (brs, 1H), 4.04-4.20 (m, 2H), 3.70 (s, 3H), 2.86-2.94 (m, 2H), 2.62-2.84 (m, 3H), 2.30-2.60 (m, 6H), 2.10-2.20 (m, 1H), 1.70-1.84 (m, 1H), 1.24 (t, J=7.2 Hz, 3H), 0.94 (d, J=7.2 Hz, 3H). MS: 347 (M+1).

Example 1A

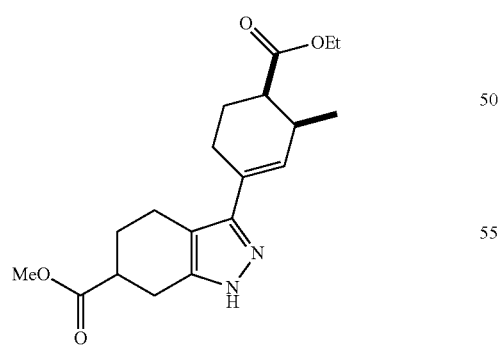

i-29B (peak 1-peak 2): $^1$H NMR (CDCl₃, 600 MHz) δ 5.94-5.98 (m, 1H), 4.08-4.22 (m, 2H), 3.73 (s, 3H), 2.90-2.96 (m, 1H), 2.77-2.87 (m, 2H), 2.66-2.76 (m, 3H), 2.54-2.64 (m, 2H), 2.26-2.33 (m, 1H), 2.16-2.22 (m, 1H), 1.94-1.99 (m, 1H), 1.76-1.88 (m, 2H), 1.26 (t, J=7.2 Hz, 3H), 0.95 (d, J=7.2 Hz, 3H). MS: 347 (M+1).

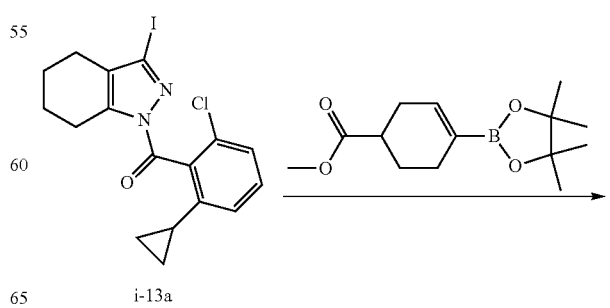

i-13a

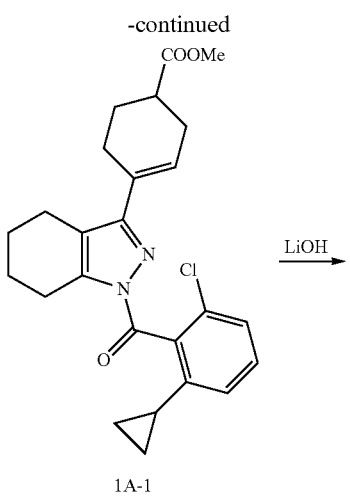

1A-1

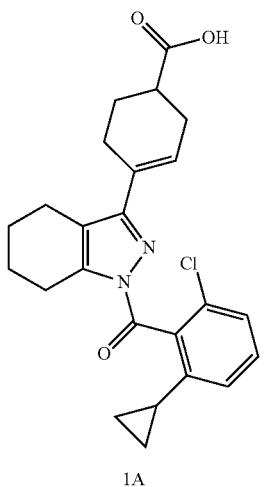

1A

4-(1-(2-chloro-6-cyclopropylbenzoyl)-4,5,6,7-tetrahydro-1H-indazol-3-yl)cyclohex-3-ene-1-carboxylic Acid Step 1. Preparation of methyl 4-(1-(2-chloro-6-cyclopropylbenzoyl)-4,5,6,7-tetrahydro-1H-indazol-3-yl)cyclohex-3-ene-1-carboxylate (1A-1)

To a flask vial were added (2-chloro-6-cyclopropylphenyl)(3-iodo-4,5,6,7-tetrahydro-1H-indazol-1-yl)methanone (50 mg, 0.117 mmol), 4-(4,4,5,5-tetramethyl-1,3,2-dioxaborolan-2-yl)-3-cyclohexene-1-carboxylic acid methyl ester (62.4 mg, 0.234 mmol), potassium acetate (34.5 mg, 0.352 mmol), dioxane (977 μL), water (195 μL). The mixture was degassed by bubbling argon for 5 min, followed by the addition of [1,1'-bis(diphenylphosphino)ferrocene]dichloropalladium(II) (17.15 mg, 0.023 mmol), sealed and then heated at 80° C. for 14 h. The mixture was diluted with saturated aqueous NH$_4$Cl, extracted with EtOAc. The organics were washed with brine, dried, and concentrated. The residue was purified by flash chromatography (0-40% EtOAc/hexanes) to give desired product.

Step 2. Preparation of 4-(1-(2-chloro-6-cyclopropylbenzoyl)-4,5,6,7-tetrahydro-1H-indazol-3-yl)cyclohex-3-ene-1-carboxylic Acid (1A)

To a solution of methyl 4-(1-(2-chloro-6-cyclopropylbenzoyl)-4,5,6,7-tetrahydro-1H-indazol-3-yl)cyclohex-3-enecarboxylate racemic (12 mg, 0.027 mmol) in THF (0.5 mL)/MeOH (0.5 mL) was added LiOH (0.137 mL, 0.273 mmol). The mixture was stirred at room temperature overnight, acidified with 2N HCl, extracted with EtOAc. The organic layer was washed with brine, dried, and concentrated. The mixture was filtered and purified by mass triggered reverse phase HPLC (ACN/water with 0.1% TFA modifier) to afford the title compound. $^1$H NMR (DMSO-d6, 600 MHz) δ 12.14 (brs, 1H), 7.34 (t, J=7.8 Hz, 1H), 7.30 (d, J=7.8 Hz, 1H), 6.98 (d, J=7.8 Hz, 1H), 6.16 (brs, 1H), 2.98-3.04 (m, 2H), 2.48-2.54 (m, 2H), 2.30-2.44 (m, 2H), 2.14-2.28 (m, 2H), 1.98-2.10 (m, 1H), 1.83-1.90 (m, 1H), 1.60-1.80 (m, 4H), 1.54-1.60 (m, 1H), 1.46-1.53 (m, 1H), 0.77-0.83 (m, 1H), 0.66-0.73 (m, 1H), 0.60-0.65 (m, 1H), 0.53-0.59 (m, 1H). MS: 425 (M+1).

The following examples shown in Table 7 were prepared following similar procedures described above.

TABLE 7

| Example No. | Structure | IUPAC Name | Exact Mass [M + H]+ |
| --- | --- | --- | --- |
| 1B | 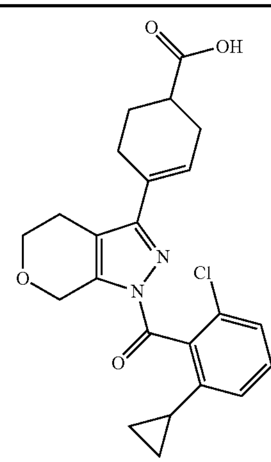 | 4-{1-[(2-chloro-6-cyclopropylphenyl)carbonyl]-1,4,5,7-tetrahydropyrano[3,4-c]pyrazol-3-yl}cyclohex-3-ene-1-carboxylic acid | 427 |

TABLE 7-continued

| Example No. | Structure | IUPAC Name | Exact Mass [M + H]+ |
| --- | --- | --- | --- |
| 1C | 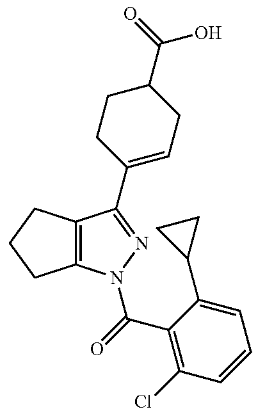 [SMILES: O=C(O)C1CC=C(c2nn(C(=O)c3c(Cl)cccc3C3CC3)c3c2CCC3)CC1] | 4-{1-[(2-chloro-6-cyclopropylphenyl)carbonyl]-1,4,5,6-tetrahydrocyclopenta[c]pyrazol-3-yl}cyclohex-3-ene-1-carboxylic acid | 411 |
| 1D | 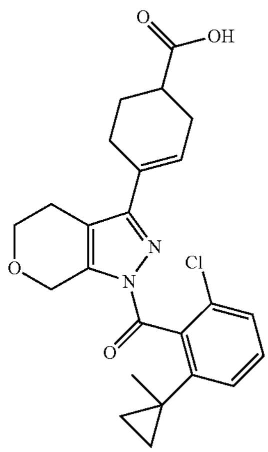 [SMILES: CC1(c2cccc(Cl)c2C(=O)n2nc(C3=CCC(C(=O)O)CC3)c3c2COCC3)CC1] | 4-(1-{[2-chloro-6-(1-methylcyclopropyl)phenyl]carbonyl}-1,4,5,7-tetrahydropyrano[3,4-c]pyrazol-3-yl)cyclohex-3-ene-1-carboxylic acid | 441 |
| 1E | 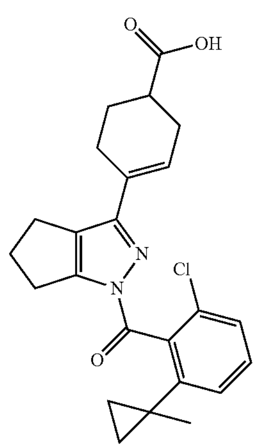 [SMILES: CC1(c2cccc(Cl)c2C(=O)n2nc(C3=CCC(C(=O)O)CC3)c3c2CCC3)CC1] | 4-(1-{[2-chloro-6-(1-methylcyclopropyl)phenyl]carbonyl}-1,4,5,6-tetrahydrocyclopenta[c]pyrazol-3-yl)cyclohex-3-ene-1-carboxylic acid | 425 |

TABLE 7-continued

| Example No. | Structure | IUPAC Name | Exact Mass [M + H]+ |
|---|---|---|---|
| 1F | 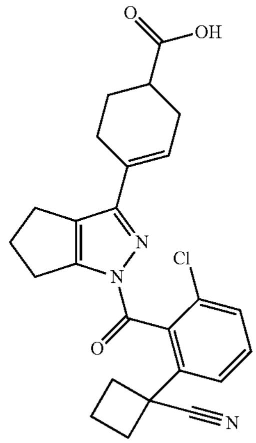 [SMILES: N#CC1(c2cccc(Cl)c2C(=O)n2nc(C3=CCC(C(=O)O)CC3)c3c2CCC3)CCC1] | 4-(1-{[2-chloro-6-(1-cyanocyclobutyl)phenyl]carbonyl}-1,4,5,6-tetrahydrocyclopenta[c]pyrazol-3-yl)cyclohex-3-ene-1-carboxylic acid | 450 |

Examples 2A-A and 2A-B

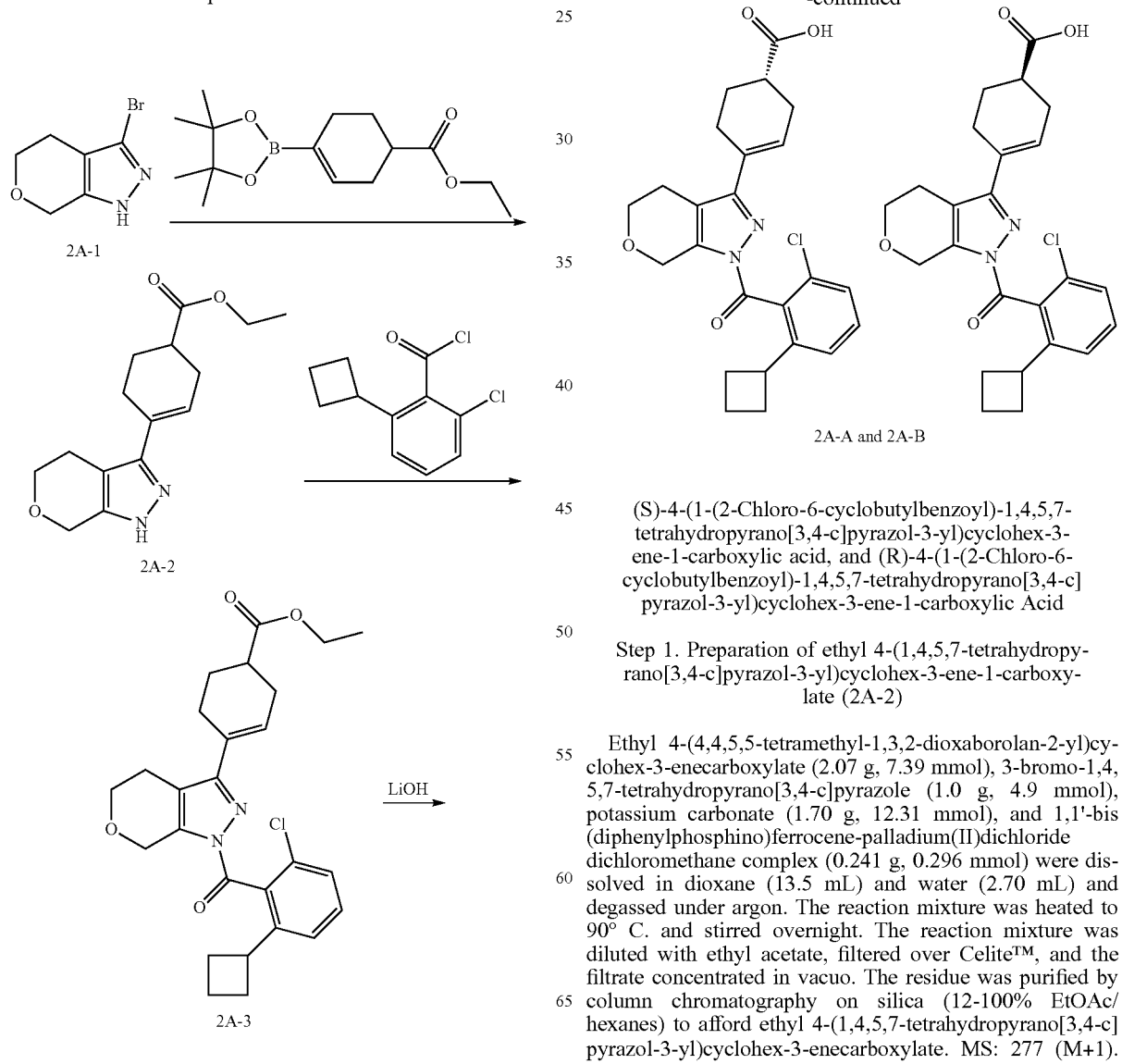

(S)-4-(1-(2-Chloro-6-cyclobutylbenzoyl)-1,4,5,7-tetrahydropyrano[3,4-c]pyrazol-3-yl)cyclohex-3-ene-1-carboxylic acid, and (R)-4-(1-(2-Chloro-6-cyclobutylbenzoyl)-1,4,5,7-tetrahydropyrano[3,4-c]pyrazol-3-yl)cyclohex-3-ene-1-carboxylic Acid Step 1. Preparation of ethyl 4-(1,4,5,7-tetrahydropyrano[3,4-c]pyrazol-3-yl)cyclohex-3-ene-1-carboxylate (2A-2)

Ethyl 4-(4,4,5,5-tetramethyl-1,3,2-dioxaborolan-2-yl)cyclohex-3-enecarboxylate (2.07 g, 7.39 mmol), 3-bromo-1,4,5,7-tetrahydropyrano[3,4-c]pyrazole (1.0 g, 4.9 mmol), potassium carbonate (1.70 g, 12.31 mmol), and 1,1′-bis(diphenylphosphino)ferrocene-palladium(II)dichloride dichloromethane complex (0.241 g, 0.296 mmol) were dissolved in dioxane (13.5 mL) and water (2.70 mL) and degassed under argon. The reaction mixture was heated to 90° C. and stirred overnight. The reaction mixture was diluted with ethyl acetate, filtered over Celite™, and the filtrate concentrated in vacuo. The residue was purified by column chromatography on silica (12-100% EtOAc/hexanes) to afford ethyl 4-(1,4,5,7-tetrahydropyrano[3,4-c]pyrazol-3-yl)cyclohex-3-enecarboxylate. MS: 277 (M+1).

Step 2. Preparation of ethyl 4-(1-(2-chloro-6-cyclobutylbenzoyl)-1,4,5,7-tetrahydropyrano[3,4-c]pyrazol-3-yl)cyclohex-3-ene-1-carboxylate (2A-3)

To a solution of ethyl 4-(1,4,5,7-tetrahydropyrano[3,4-c]pyrazol-3-yl)cyclohex-3-enecarboxylate (200 mg, 0.72 mmol) in THF (2.0 mL) at 0° C. was added NaH (60% in mineral oil; 57.9 mg, 1.45 mmol) and the reaction mixture was stirred at 0° C. for 30 min. 2-Chloro-6-cyclobutylbenzoyl chloride (249 mg, 1.09 mmol) in DCM (1 mL) were added, and the reaction mixture was warmed to room temperature and stirred overnight. The mixture was diluted with ethyl acetate and washed with saturated ammonium chloride then brine. The organic layer was dried over sodium sulfate, filtered, and concentrated in vacuo. The residue was purified by column chromatography on silica (2-20% EtOAc/hexanes) to afford ethyl 4-(1-(2-chloro-6-cyclobutylbenzoyl)-1,4,5,7-tetrahydropyrano[3,4-c]pyrazol-3-yl)cyclohex-3-enecarboxylate. MS: 469 (M+1).

Step 3. Preparation of (S)-4-(1-(2-Chloro-6-cyclobutylbenzoyl)-1,4,5,7-tetrahydropyrano[3,4-c]pyrazol-3-yl)cyclohex-3-ene-1-carboxylic acid, and (R)-4-(1-(2-Chloro-6-cyclobutylbenzoyl)-1,4,5,7-tetrahydropyrano[3,4-c]pyrazol-3-yl)cyclohex-3-ene-1-carboxylic Acid (2A-A and 2A-B)

To a solution of ethyl 4-(1-(2-chloro-6-cyclobutylbenzoyl)-1,4,5,7-tetrahydropyrano[3,4-c]pyrazol-3-yl)cyclohex-3-enecarboxylate (167.8 mg, 0.358 mmol) in THF (1.8 mL) and water (1.8 mL) was added LiOH (42.8 mg, 1.79 mmol). The reaction mixture was stirred at room temperature overnight, diluted with ethyl acetate, and washed with HCl (2N aq.) and brine. The organic layer was dried over sodium sulfate, filtered, and concentrated in vacuo. The residue was purified by column chromatography on silica (10-80% EtOAc/hexanes) to afford 4-(1-(2-chloro-6-cyclobutylbenzoyl)-1,4,5,7-tetrahydropyrano[3,4-c]pyrazol-3-yl)cyclohex-3-enecarboxylic acid. The mixture of the two stereoisomers was purified by chiral SFC (AD-H column, 20%/80% Isopropanol+0.25% Dimethyl Ethyl Amine/CO$_2$) to afford isomer A (faster eluting): MS: 441 (M+1). $^1$H NMR (500 MHz, d-DMSO) δ 7.50 (t, J=7.9 Hz, 1H), 7.40 (d, J=7.6 Hz, 2H), 6.26 (s, 1H), 5.06-4.91 (m, 2H), 3.90-3.81 (m, 2H), 2.80-2.65 (m, 2H), 2.41-2.35 (m, 3H), 2.32-2.24 (m, 2H), 2.18-2.08 (m, 3H), 1.98-1.80 (m, 4H), 1.73-1.66 (m, 1H), 1.56-1.50 (m, 1H). Isomer B (slower eluting): MS: 441 (M+1). $^1$H NMR (500 MHz, d-DMSO) δ 7.50 (t, J=7.9 Hz, 1H), 7.40 (d, J=7.6 Hz, 2H), 6.26 (s, 1H), 5.06-4.91 (m, 2H), 3.90-3.81 (m, 2H), 2.80-2.65 (m, 2H), 2.41-2.35 (m, 3H), 2.32-2.24 (m, 2H), 2.18-2.08 (m, 3H), 1.98-1.80 (m, 4H), 1.73-1.66 (m, 1H), 1.56-1.50 (m, 1H).

The following examples shown in Table 8 were prepared following similar procedures described above.

TABLE 8

| Example No. | Structure | IUPAC Name | Exact Mass [M + H]+ |
|---|---|---|---|
| 2B-A | (structure) | (1R or S)-4-(1-{[2-chloro-6-(1-cyanocyclopropyl)phenyl]carbonyl}-1,4,5,7-tetrahydropyrano[3,4-c]pyrazol-3-yl)cyclohex-3-ene-1-carboxylic acid | 452 |
| 2B-B | (structure) | (1R or S)-4-(1-{[2-chloro-6-(1-cyanocyclopropyl)phenyl]carbonyl}-1,4,5,7-tetrahydropyrano[3,4-c]pyrazol-3-yl)cyclohex-3-ene-1-carboxylic acid | 452 |

TABLE 8-continued
| Example No. | Structure | IUPAC Name | Exact Mass [M + H]+ |
|---|---|---|---|
| 2C-A | 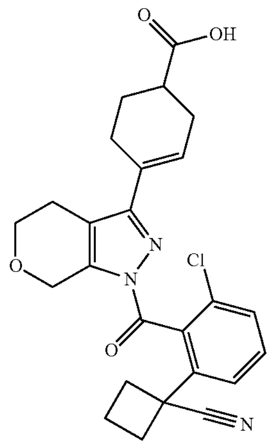 [SMILES: N#CC1(c2cccc(Cl)c2C(=O)n2nc(C3=CCC(C(=O)O)CC3)c3c2COCC3)CCC1] | (1R or S)-4-(1-{[2-chloro-6-(1-cyanocyclobutyl)phenyl]carbonyl}-1,4,5,7-tetrahydropyrano[3,4-c]pyrazol-3-yl)cyclohex-3-ene-1-carboxylic acid | 466 |
| 2C-B | 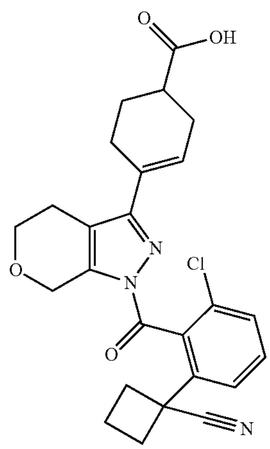 [SMILES: N#CC1(c2cccc(Cl)c2C(=O)n2nc(C3=CCC(C(=O)O)CC3)c3c2COCC3)CCC1] | (1R or S)-4-(1-{[2-chloro-6-(1-cyanocyclobutyl)phenyl]carbonyl}-1,4,5,7-tetrahydropyrano[3,4-c]pyrazol-3-yl)cyclohex-3-ene-1-carboxylic acid | 466 |
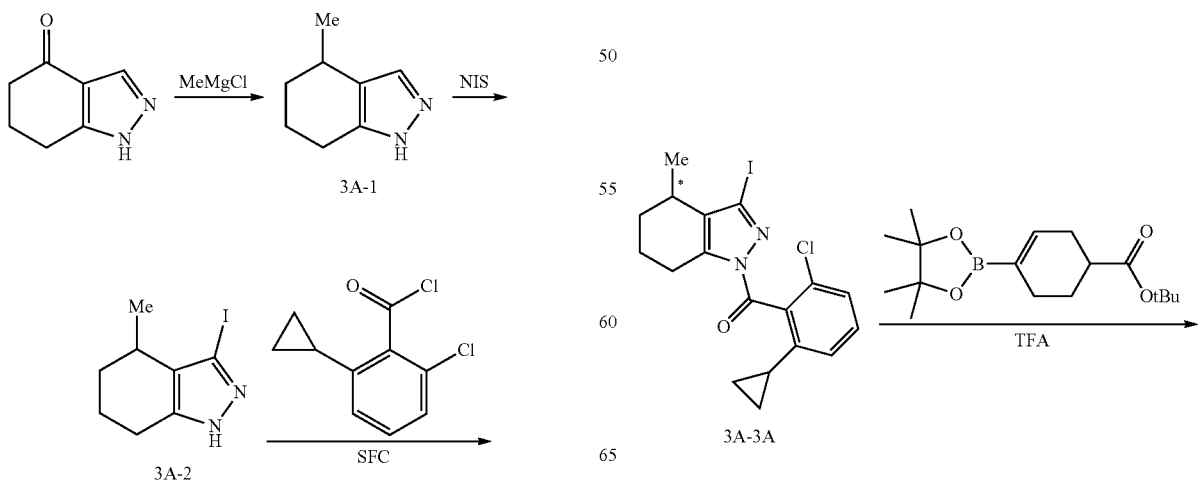

4-((R or S)-1-(2-chloro-6-cyclopropylbenzoyl)-4-methyl-4,5,6,7-tetrahydro-1H-indazol-3-yl)cyclohex-3-ene-1-carboxylic Acid

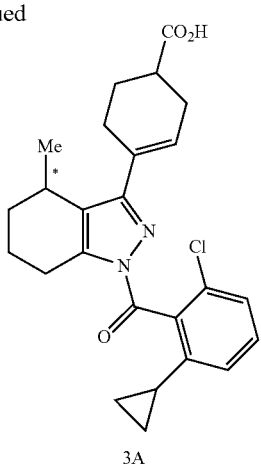

3A

Step 1. Preparation of 4-methyl-4,5,6,7-tetrahydro-1H-indazole (3A-1)

To an oven dried round bottom flask equipped with magnetic stir bar under an atmosphere of $N_2$, 6,7-dihydro-1H-indazol-4(5H)-one (2.5 g, 18.4 mmol, 1 equiv), and THF (12.2 mL, 0.5 M) were added. The solution was cooled to −78° C. followed by the addition of methyl magnesium chloride (18.4 mL, 3.00 M in THF, 3 equiv). The reaction mixture was warmed to 0° C. over 2 h, then quenched with saturated aqueous $NH_4Cl$ (50 mL) and diluted with EtOAc (50 mL). After warming to room temperature, the layers were separated, and the aqueous layer was extracted with EtOAc (3×30 mL). The combined organic layers were washed with brine (30 mL), dried over $Na_2SO_4$, and concentrated in vacuo. The crude oil was taken up in DCE (12.2 mL, 0.5 M), and treated with triethylsilane (14.66 mL, 92 mmol, 5 equiv) and trifluoroacetic acid (14.2 mL, 184 mmol, 10 equiv). The reaction mixture was heated to 65° C. for 12 h. The reaction mixture was then cooled to room temperature, and concentrated in vacuo. The resulting oil was purified using $SiO_2$ gel chromatography to afford the title compound. MS: 137 (M+1).

Step 2. Preparation of 3-iodo-4-methyl-4,5,6,7-tetrahydro-1H-indazole (3A-2)

To an oven dried round bottom flask equipped with magnetic stir bar under an atmosphere of $N_2$, 4-methyl-4,5,6,7-tetrahydro-1H-indazole (2.5 g, 18.4 mmol, 1 equiv), DMF (61.2 mL, 0.3 M), and N-iodosuccinimide (6.2 g, 27.5 mmol, 1.5 equiv) were added. The reaction mixture was heated to 80° C. for 3 h. Upon cooling to room temperature, the mixture was diluted with water (50 mL) and EtOAc (50 mL). The layers were separated, and the aqueous layer was extracted with EtOAc (3×50 mL). The combined organic layers were washed with aqueous $NaHCO_3$ (30 mL), brine (30 mL), dried over $Na_2SO_4$, and concentrated in vacuo. The crude oil was purified using $SiO_2$ gel chromatography to afford the title compound. MS: 263 (M+1).

Step 3. Preparation of (R or S)-(2-chloro-6-cyclopropylphenyl)(3-iodo-4-methyl-4,5,6,7-tetrahydro-1H-indazol-1-yl)methanone (3A-3A)

To an oven dried round bottom flask equipped with magnetic stir bar under an atmosphere of $N_2$, racemic 3-iodo-4-methyl-4,5,6,7-tetrahydro-1H-indazole (3 g, 11.5 mmol, 1 equiv), DCM (38.2 mL, 0.3 M), triethylamine (4.79 mL, 34.3 mmol, 3 equiv), and DMAP (280 mg, 2.29 mmol, 0.2 equiv) were added. The reaction was stirred at room temperature for 5 minutes followed by the addition of 2-chloro-6-cyclopropylbenzoyl chloride (3.7 g, 17.2 mmol, 1.5 equiv). After 12 h, the reaction was concentrated in vacuo, and purified using $SiO_2$ gel chromatography to afford a mixture of isomers. MS: 441 (M+1).

The mixture of stereoisomers were purified by chiral SFC (OJ-H column, 35%/65% MeOH+0.25% $DEA/CO_2$) to afford Isomer 3A-3A (faster eluting): MS: 411 (M+1). Isomer 3A-3B (slower eluting): MS: 411 (M+1).

Step 3. Preparation of 4-((R or S)-1-(2-chloro-6-cyclopropylbenzoyl)-4-methyl-4,5,6,7-tetrahydro-1H-indazol-3-yl)cyclohex-3-ene-1-carboxylic acid (3A)

To an oven dried microwave vial equipped with magnetic stir bar under an atmosphere of $N_2$, (R or S)-(2-chloro-6-cyclopropylphenyl)(3-iodo-4-methyl-4,5,6,7-tetrahydro-1H-indazol-1-yl)methanone Isomer 3A-3A (50 mg, 0.11 mmol, 1 equiv), Chloro(2-dicyclohexylphosphino-2',6'-dimethoxy-1,1'-biphenyl)[2-(2'-amino-1,1'-biphenyl)]palladium(II) (8.2 mg, 0.11 mmol, 0.1 equiv), racemic tert-butyl 4-(4,4,5,5-tetramethyl-1,3,2-dioxaborolan-2-yl)cyclohex-3-enecarboxylate (70 mg, 0.23 mmol, 2 equiv), and dioxane (567 µL, 0.2 M) were added, followed by potassium phosphate tribasic (340 µL, 1M, 3 equiv). The reaction mixture was heated to 80° C. for 24 h, and then cooled to room temperature. The crude reaction mixture was diluted with EtOAc (50 mL), filtered through celite, and concentrated in vacuo. The resulting oil was taken up in DCM (1 mL), and trifluoroacetic acid (1 mL). After stirring for 3 h at room temperature, the solution was concentrated in vacuo, and purified using mass directed reverse phase chromatography to afford the title compound. MS: 439 (M+1). $^1$H NMR (DMSO-d6) δ (ppm): 7.36-7.29 (m, 2H), 6.98 (m, 1H), 6.10 (s, 1H), 3.1 (m, 1H), 2.98-2.87 (m, 2H), 2.43 (m, 1H), 2.32-2.23 (m, 3H), 2.12-1.98 (m, 3H), 1.87-1.75 (m, 3H), 1.56 (m, 1H), 1.54-1.51 (m, 2H), 1.08 (m, 3H), 0.80 (m, 1H), 0.70-0.54 (m, 3H).

Example 3B

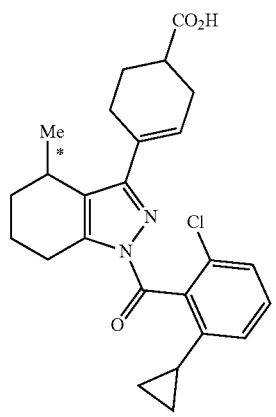 [SMILES: CC1CCCc2c1c(C1=CCC(C(=O)O)CC1)nn2C(=O)c1c(Cl)cccc1C1CC1]

4-((R or S)-1-(2-chloro-6-cyclopropylbenzoyl)-4-methyl-4,5,6,7-tetrahydro-1H-indazol-3-yl)cyclohex-3-ene-1-carboxylic Acid Step 1. Preparation of 4-((R or S)-1-(2-chloro-6-cyclopropylbenzoyl)-4-methyl-4,5,6,7-tetrahydro-1H-indazol-3-yl)cyclohex-3-ene-1-carboxylic Acid (3B)

To an oven dried microwave vial equipped with magnetic stir bar under an atmosphere of $N_2$, (R or S)-(2-chloro-6-cyclopropylphenyl)(3-iodo-4-methyl-4,5,6,7-tetrahydro-1H-indazol-1-yl)methanone Isomer 3A-3B (50 mg, 0.11 mmol, 1 equiv), Chloro(2-dicyclohexylphosphino-2',6'-dimethoxy-1,1'-biphenyl)[2-(2'-amino-1,1'-biphenyl)]palladium(II) (8.2 mg, 0.11 mmol, 0.1 equiv), racemic tert-butyl 4-(4,4,5,5-tetramethyl-1,3,2-dioxaborolan-2-yl)cyclohex-3-enecarboxylate (70 mg, 0.23 mmol, 2 equiv), and dioxane (567 µL, 0.2 M) were added, followed by potassium phosphate tribasic (340 µL, 1M, 3 equiv). The reaction mixture was heated to 80° C. for 24 h, and then cooled to room temperature. The crude reaction mixture was diluted with EtOAc (50 mL), filtered through celite, and concentrated in vacuo. The resulting oil was taken up in DCM (1 mL), and trifluoroacetic acid (1 mL). After stirring for 3 h at room temperature, the solution was concentrated in vacuo, and purified using mass directed reverse phase chromatography to afford title compound. MS: 439 (M+1). $^1$H NMR (DMSO-d6) δ (ppm): 7.36-7.29 (m, 2H), 6.98 (m, 1H), 6.10 (s, 1H), 3.1 (m, 1H), 2.98-2.87 (m, 2H), 2.43 (m, 1H), 2.32-2.23 (m, 3H), 2.12-1.98 (m, 3H), 1.87-1.75 (m, 3H), 1.56 (m, 1H), 1.54-1.51 (m, 2H), 1.08 (m, 3H), 0.80 (m, 1H), 0.70-0.54 (m, 3H).

Example 4A

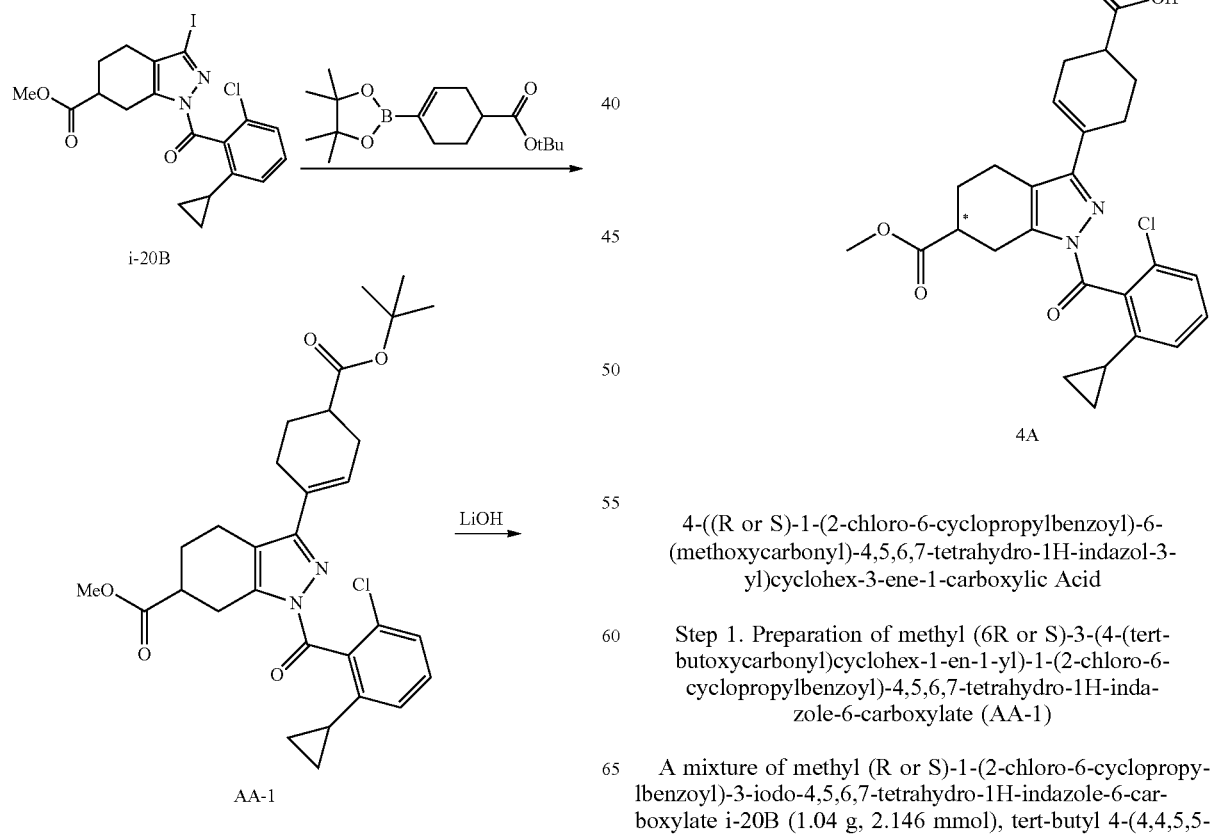

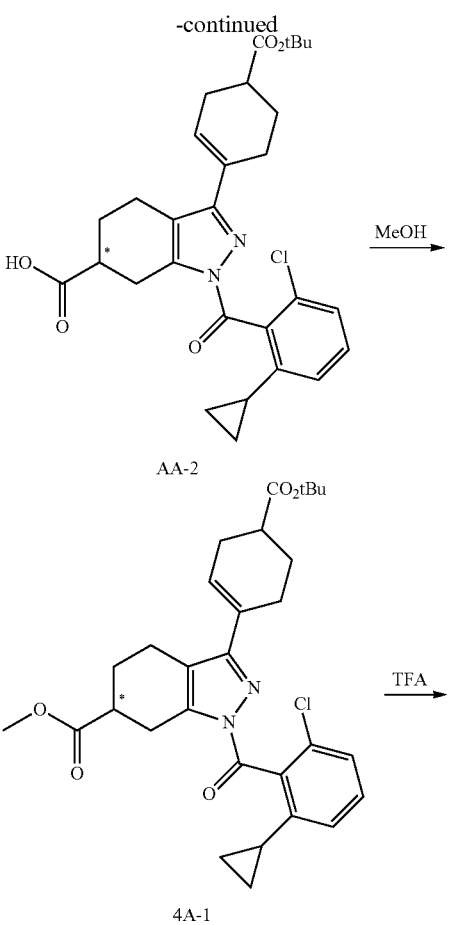

4-((R or S)-1-(2-chloro-6-cyclopropylbenzoyl)-6-(methoxycarbonyl)-4,5,6,7-tetrahydro-1H-indazol-3-yl)cyclohex-3-ene-1-carboxylic Acid Step 1. Preparation of methyl (6R or S)-3-(4-(tert-butoxycarbonyl)cyclohex-1-en-1-yl)-1-(2-chloro-6-cyclopropylbenzoyl)-4,5,6,7-tetrahydro-1H-indazole-6-carboxylate (AA-1)

A mixture of methyl (R or S)-1-(2-chloro-6-cyclopropylbenzoyl)-3-iodo-4,5,6,7-tetrahydro-1H-indazole-6-carboxylate i-20B (1.04 g, 2.146 mmol), tert-butyl 4-(4,4,5,5- tetramethyl-1,3,2-dioxaborolan-2-yl)cyclohex-3-enecarboxylate (1.058 g, 3.43 mmol), PdCl$_2$(dppf)-CH$_2$Cl$_2$ (0.350 g, 0.429 mmol), potassium acetate (0.632 g, 6.44 mmol), and THF (8.58 mL) was thoroughly degassed with argon for 5 minutes. Water (2.146 mL) was then added and the reaction was heated at 80° C. overnight. The reaction was cooled and diluted with EtOAc. The organic layer was separated and washed twice with aqueous NaHCO$_3$ and once with brine. The combined organic layers were dried with Na$_2$SO$_4$, filtered, and concentrated in vacuo. The residue was purified by silica gel chromatography (0-100% EtOAc/Hexane) to afford the title compound. MS: 539 (M+1).

Step 2. Preparation of (6R or S)-3-(4-(tert-butoxycarbonyl)cyclohex-1-en-1-yl)-1-(2-chloro-6-cyclopropylbenzoyl)-4,5,6,7-tetrahydro-1H-indazole-6-carboxylic Acid (AA-2)

A mixture of methyl 3-(4-(tert-butoxycarbonyl)cyclohex-1-en-1-yl)-1-(2-chloro-6-cyclopropylbenzoyl)-4,5,6,7-tetrahydro-1H-indazole-6-carboxylate (747 mg, 1.386 mmol) and LiOH (498 mg, 20.79 mmol) in THF (4619 μL) and water (2310 μL) was stirred overnight at room temperature. The reaction was diluted with EtOAc and the organic layer was washed twice with saturated ammonium chloride. The organic layer was dried with Na$_2$SO$_4$, filtered, and concentrated in vacuo. The crude product thus obtained was used in the next step without further purification. MS: 525 (M+1).

Step 3. Preparation of methyl (6R or S)-3-(4-(tert-butoxycarbonyl)cyclohex-1-en-1-yl)-1-(2-chloro-6-cyclopropylbenzoyl)-4,5,6,7-tetrahydro-1H-indazole-6-carboxylate (4A-1)

A mixture of 3-(4-(tert-butoxycarbonyl)cyclohex-1-en-1-yl)-1-(2-chloro-6-cyclopropylbenzoyl)-4,5,6,7-tetrahydro-1H-indazole-6-carboxylic acid AA-2 (50 mg, 0.095 mmol), methanol (7.71 μL, 0.190 mmol), HATU (72.4 mg, 0.190 mmol), TEA (66.4 μL, 0.476 mmol), and DMF (952 μL) was allowed to stir at room temperature for 3 hours. The reaction was then diluted with water and DCM and the organic layer was extracted with phase separator column and concentrated to afford the title compound. MS: 539 (M+1).

Step 4. Preparation of 4-((R or S)-1-(2-chloro-6-cyclopropylbenzoyl)-6-(methoxycarbonyl)-4,5,6,7-tetrahydro-1H-indazol-3-yl)cyclohex-3-ene-1-carboxylic Acid (4A)

A mixture of methyl 3-(4-(tert-butoxycarbonyl)cyclohex-1-en-1-yl)-1-(2-chloro-6-cyclopropylbenzoyl)-4,5,6,7-tetrahydro-1H-indazole-6-carboxylate (51 mg, 0.095 mmol), DCM (1 mL) and TFA (73.4 μL, 0.952 mmol) was allowed to stir at room temperature overnight. The reaction was then concentrated and then brought up in methanol. The mixture was filtered and purified by mass triggered reverse phase HPLC (ACN/water with 0.1% TFA modifier) to afford the title compound. MS: 483 (M+1). $^1$H NMR (600 MHz, DMSO) δ 7.39-7.26 (m, 2H), 7.00 (dd, J=7.6, 13.2, 1H), 6.16 (s, 1H), 3.64 (d, J=3.1, 3H), 3.43-3.30 (m, 1H), 3.20-3.08 (m, 1H), 2.96-2.84 (m, 1H), 2.65-2.52 (m, 2H), 2.44-2.30 (m, 2H), 2.30-1.94 (m, 4H), 1.91-1.67 (m, 2H), 1.64-1.42 (m, 2H), 0.86-0.76 (m, 1H), 0.75-0.49 (m, 3H)

Example 5A

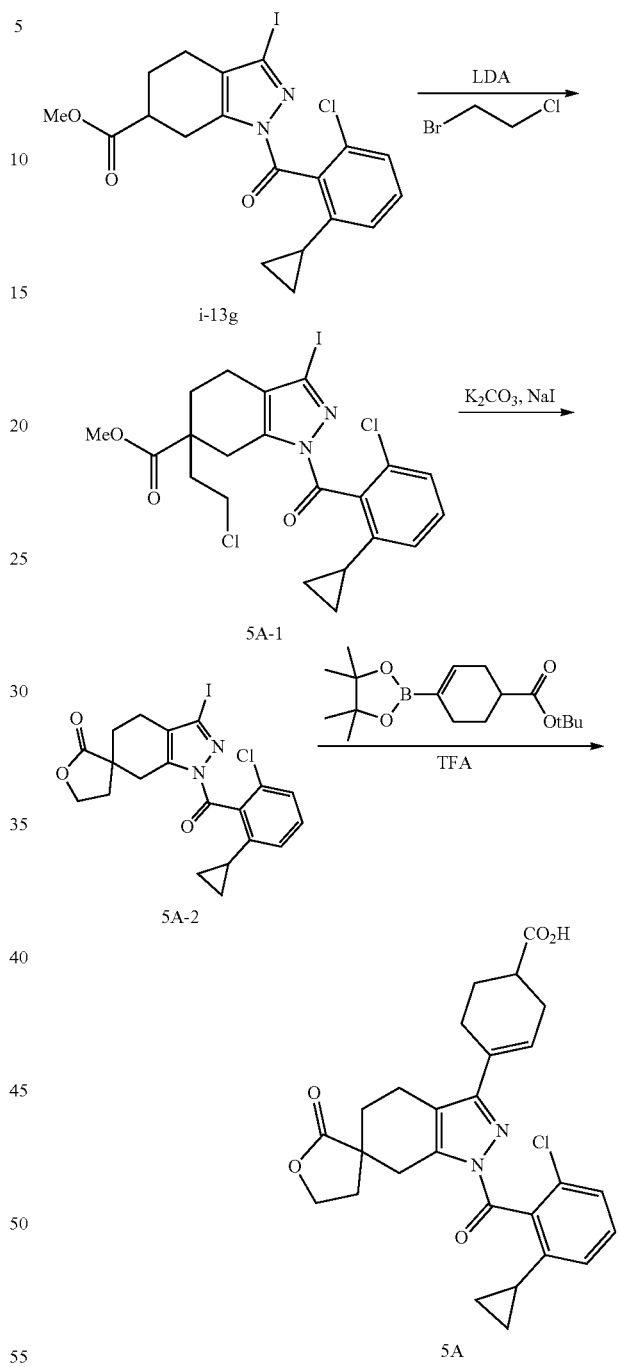

4-(1'-(2-chloro-6-cyclopropylbenzoyl)-2-oxo-1',4,4',5,5',7'-hexahydro-2H-spiro[furan-3,6'-indazol]-3'-yl)cyclohex-3-ene-1-carboxylic Acid Step 1. Preparation of methyl 1-(2-chloro-6-cyclopropylbenzoyl)-6-(2-chloroethyl)-3-iodo-4,5,6,7-tetrahydro-1H-indazole-6-carboxylate (5A-1)

To an oven dried round bottom flask equipped with magnetic stir bar under an atmosphere of N$_2$, racemic methyl 1-(2-chloro-6-cyclopropylbenzoyl)-3-iodo-4,5,6,7-tetrahydro-1H-indazole-6-carboxylate (530 mg, 1.1 mmol, 1 equiv), and THF (5.5 mL, 0.2 M) were added. The reaction flask was cooled to −78° C., followed by the addition of lithium diisopropyl amide (0.82 mL, 2M in THF, 1.64 mmol, 1.50 equiv). The reaction mixture was stirred for 30 minutes followed by the addition of 1-bromo-2-chloroethane (220 μL, 2.64 mmol, 2.4 equiv). The reaction mixture was slowly warmed to room temperature over 16 h, and then quenched with saturated $NH_4Cl$ (25 mL) and diluted with EtOAc (25 mL). The layers were separated, and the resulting aqueous layer was extracted with EtOAc (3×25 mL). The combined organic layers were washed with brine, dried over $Na_2SO_4$, and concentrated in vacuo. The crude oil was purified using $SiO_2$ gel chromatography to afford the title compound. MS: 547 (M+1).

Step 2. Preparation of 1'-(2-chloro-6-cyclopropylbenzoyl)-3'-iodo-1',4,4',5,5',7'-hexahydro-2H-spiro[furan-3,6'-indazol]-2-one (5A-2)

To an oven dried round bottom flask equipped with magnetic stir bar under an atmosphere of $N_2$, racemic methyl 1-(2-chloro-6-cyclopropylbenzoyl)-6-(2-chloroethyl)-3-iodo-4,5,6,7-tetrahydro-1H-indazole-6-carboxylate (270 mg, 0.5 mmol, 1 equiv), and DMSO (1.65 mL, 0.3 M) were added, followed by $K_2CO_3$ (273 mg, 1.97 mmol, 4 equiv), NaI (74 mg, 0.5 mmol, 1 equiv), and $NH_4Cl$ (53 mg, 1.0 mmol, 2 equiv). The reaction mixture was stirred at room temperature for 24 h, and then heated to 120° C. for 3 h. The reaction mixture was cooled to room temperature, and then quenched with saturated $NH_4Cl$ (15 mL) and diluted with EtOAc (15 mL). The layers were separated, and the resulting aqueous layer was extracted with EtOAc (3×25 mL). The combined organic layers were washed with brine, dried over $Na_2SO_4$, and concentrated in vacuo. The crude oil was purified using $SiO_2$ gel chromatography to afford the title compound. MS: 497 (M+1).

Step 3. Preparation of 4-(1'-(2-chloro-6-cyclopropylbenzoyl)-2-oxo-1',4,4',5,5',7'-hexahydro-2H-spiro[furan-3,6'-indazol]-3'-yl)cyclohex-3-ene-1-carboxylic Acid (5A)

To an oven dried microwave vial equipped with magnetic stir bar under an atmosphere of $N_2$, racemic 1'-(2-chloro-6-cyclopropylbenzoyl)-3'-iodo-1',4,4',5,5',7'-hexahydro-2H-spiro[furan-3,6'-indazol]-2-one (56 mg, 0.11 mmol, 1 equiv), $2^{nd}$ Gen Sphos Precatalyst (8.1 mg, 0.11 mmol, 0.1 equiv), racemic tert-butyl 4-(4,4,5,5-tetramethyl-1,3,2-dioxaborolan-2-yl)cyclohex-3-enecarboxylate (70 mg, 0.23 mmol, 2 equiv), and dioxane (564 L, 0.2 M) were added, followed by potassium phosphate tribasic (338 μL, 1M, 3 equiv). The reaction mixture was heated to 80° C. for 24 h, and then cooled to room temperature. The crude reaction mixture was diluted with EtOAc (50 mL), filtered through celite, and concentrated in vacuo. The resulting oil was taken up in DCM (1 mL), and trifluoroacetic acid (1 mL). After stirring for 3 h at room temperature, the solution was concentrated in vacuo, and purified using mass directed reverse phase chromatography to afford title compound. MS: 495 (M+1). $^1H$ NMR (DMSO-d6) δ (ppm): 7.65 (m, 1H), 7.35 (m, 1H), 7.00 (m, 1H), 6.22 (s, 1H), 4.34 (m, 1H), 3.58-3.12 (m, 5H), 2.65 (m, 1H), 2.53-2.32 (m, 4H), 2.23 (m, 1H), 2.11 (m, 1H), 1.87 (m, 1H), 1.60 (m, 1H), 1.49 (m, 1H), 0.96-0.86 (m, 2H), 0.79 (m, 1H), 0.73-0.61 (m, 2H), 0.52 (m, 1H).

Example 6A

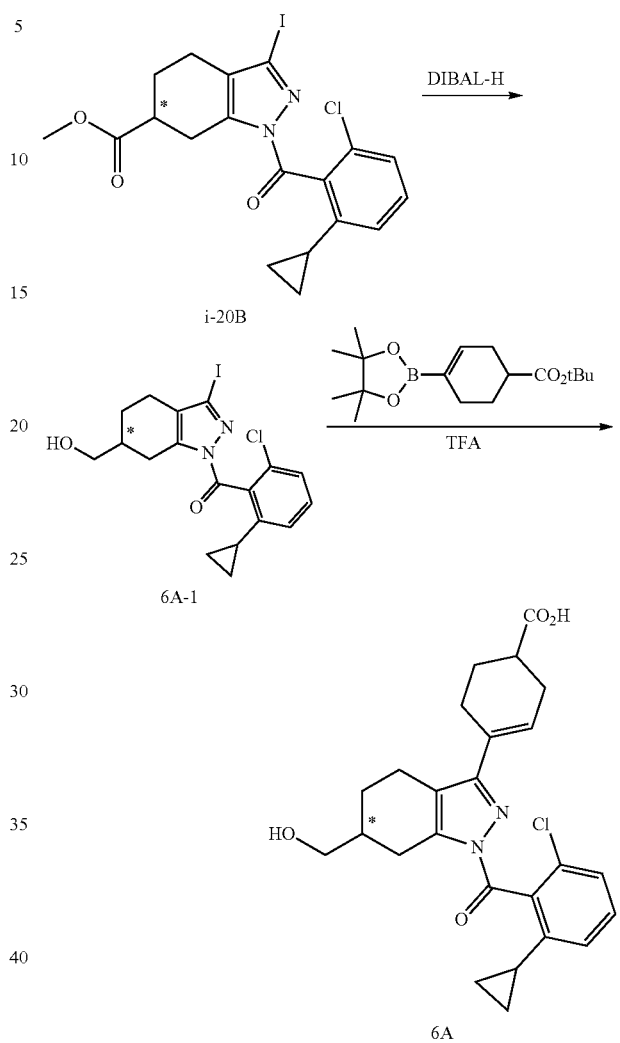

4-((R or S)-1-(2-chloro-6-cyclopropylbenzoyl)-6-(hydroxymethyl)-4,5,6,7-tetrahydro-1H-indazol-3-yl)cyclohex-3-ene-1-carboxylic Acid Step 1. Preparation of (R or S)-(2-chloro-6-cyclopropylphenyl)(6-(hydroxymethyl)-3-iodo-4,5,6,7-tetrahydro-1H-indazol-1-yl)methanone (6A-1)

To an oven dried microwave vial equipped with magnetic stir bar under an atmosphere of $N_2$, methyl (R or S)-1-(2-chloro-6-cyclopropylbenzoyl)-3-iodo-4,5,6,7-tetrahydro-1H-indazole-6-carboxylate i-20B (250 mg, 0.52 mmol, 1 equiv) and DCM (1.79 mL, 0.3 M) were added. The reaction mixture was cooled to −78° C., and diisobutylaluminum hydride (1.547 mL, 1 M in THF, 3 equiv) was added. The reaction mixture was warmed to 0° C. over 1 h, and then was quenched with 1 HCl (5 mL), and diluted with EtOAc (20 mL). The mixture was stirred vigorously for 1 h at room temperature. The layers were separated, the aqueous layer was extracted with EtOAc (3×25 mL). The combined organic layers were washed with brine, filtered through celite, and then concentrated in vacuo. The resulting oil was purified using SiO$_2$ gel chromatography to afford the title compound. MS: 457 (M+1).

Step 2. Preparation of 4-((R or S)-1-(2-chloro-6-cyclopropylbenzoyl)-6-(hydroxymethyl)-4,5,6,7-tetrahydro-1H-indazol-3-yl)cyclohex-3-ene-1-carboxylic Acid (6A)

To an oven dried microwave vial equipped with magnetic stir bar under an atmosphere of N$_2$, (R or S)-(2-chloro-6-cyclopropylphenyl)(6-(hydroxymethyl)-3-iodo-4,5,6,7-tetrahydro-1H-indazol-1-yl)methanone (40 mg, 0.09 mmol, 1 equiv), 2$^{nd}$ Gen Sphos Precatalyst (6.3 mg, 8.76 µmol, 0.1 equiv), racemic tert-butyl 4-(4,4,5,5-tetramethyl-1,3,2-dioxaborolan-2-yl)cyclohex-3-enecarboxylate (54 mg, 0.18 mmol, 2 equiv), and dioxane (438 µL, 0.2 M) were added, followed by potassium phosphate tribasic (263 µL, 1M, 3 equiv). The reaction mixture was heated to 80° C. for 24 h, and then cooled to room temperature. The crude reaction mixture was diluted with EtOAc (50 mL), filtered through celite, and concentrated in vacuo. The resulting oil was taken up in DCM (1 mL), and trifluoroacetic acid (1 mL). After stirring for 3 h at room temperature, the solution was concentrated in vacuo, and purified using mass directed reverse phase chromatography to afford the title compound. MS: 455 (M+1). $^1$H NMR (DMSO-d6) δ (ppm): 12.14 (s, 1H), 7.34-7.31 (m, 2H), 6.99 (m, 1H), 6.17 (s, 1H), 3.45-3.41 (m, 2H), 3.38-3.18 (m, 2H), 2.63 (m, 1H), 2.52-2.18 (m, 5H), 2.12 (m, 1H), 2.04 (m, 1H), 1.95-1.77 (m, 3H), 1.62-1.52 (m, 2H), 1.32 (m, 1H), 0.89-0.51 (m, 4H).

Examples 7A

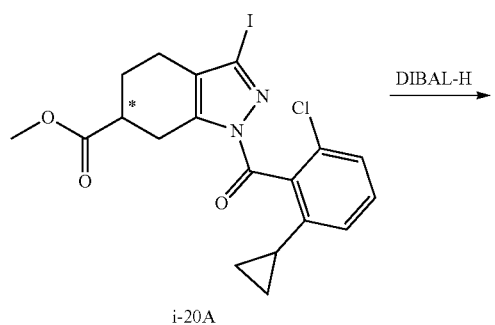

i-20A

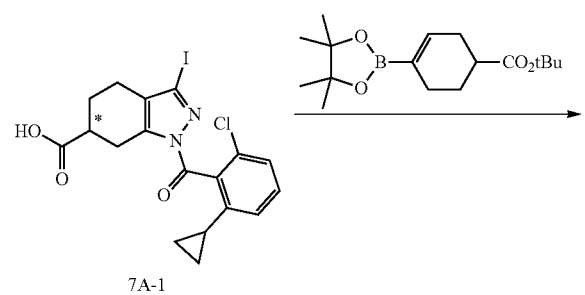

7A-1

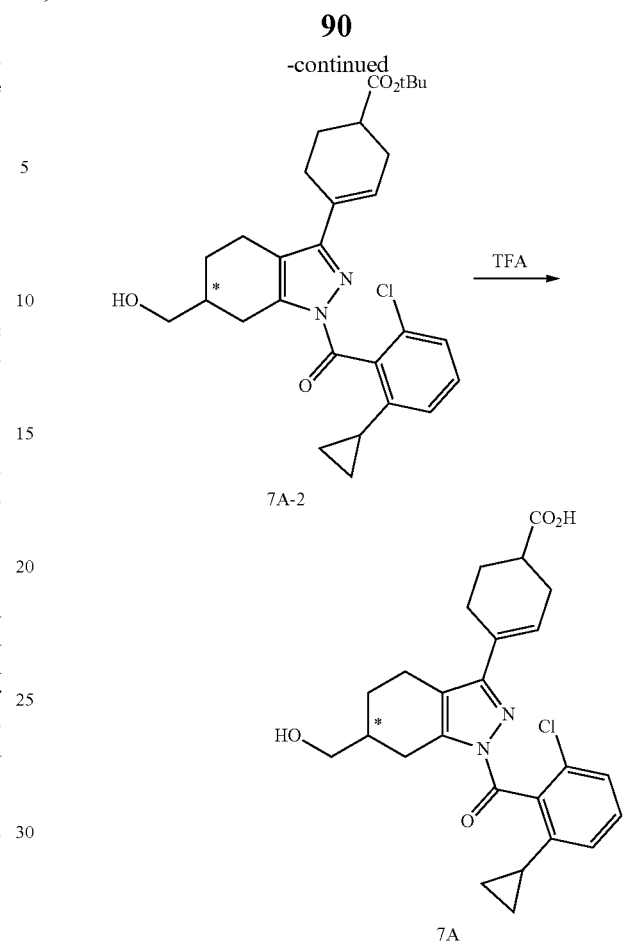

4-((R or S)-1-(2-chloro-6-cyclopropylbenzoyl)-6-(hydroxymethyl)-4,5,6,7-tetrahydro-1H-indazol-3-yl)cyclohex-3-ene-1-carboxylic Acid Step 1. Preparation of (R)-(2-chloro-6-cyclopropylphenyl)(6-(hydroxymethyl)-3-iodo-4,5,6,7-tetrahydro-1H-indazol-1-yl)methanone (7A-1)

To an oven dried microwave vial equipped with magnetic stir bar under an atmosphere of N$_2$, methyl (R or 5)-1-(2-chloro-6-cyclopropylbenzoyl)-3-iodo-4,5,6,7-tetrahydro-1H-indazole-6-carboxylate i-20A (1 g, 2.06 mmol, 1 equiv) and DCM (6.9 mL, 0.3 M) were added. The reaction mixture was cooled to −78° C., and diisobutylaluminum hydride (6.19 mL, 1 M in THF, 3 equiv) was added. The reaction mixture was warmed to 0° C. over 1 h, and then quenched with 1 HCl (25 mL), and diluted with EtOAc (50 mL). The mixture was stirred vigorously for 1 h at room temperature. The layers were separated, the aqueous layer was extracted with EtOAc (3×50 mL). The combined organic layers were washed with brine, filtered through celite, and then concentrated in vacuo. The resulting oil was purified using SiO$_2$ gel chromatography to afford the title compound. MS: 457 (M+1).

Step 2. Preparation of tert-butyl 4-((R or S)-1-(2-chloro-6-cyclopropylbenzoyl)-6-(hydroxymethyl)-4,5,6,7-tetrahydro-1H-indazol-3-yl)cyclohex-3-ene-1-carboxylate (7A-2)

To an oven dried microwave vial equipped with magnetic stir bar under an atmosphere of N$_2$, (R or S)-(2-chloro-6- cyclopropylphenyl)(6-(hydroxymethyl)-3-iodo-4,5,6,7-tetrahydro-1H-indazol-1-yl)methanone (150 mg, 0.33 mmol, 1 equiv), 2$^{nd}$ Gen Sphos Precatalyst (23.7 mg, 0.03 mmol, 0.1 equiv), racemic tert-butyl 4-(4,4,5,5-tetramethyl-1,3,2-dioxaborolan-2-yl)cyclohex-3-enecarboxylate (202 mg, 0.66 mmol, 2 equiv), and dioxane (1.64 mL, 0.2 M) were added, followed by potassium phosphate tribasic (985 μL, 1M, 3 equiv). The reaction mixture was heated to 80° C. for 24 h, and then cooled to room temperature. The crude reaction mixture was diluted with EtOAc (50 mL), filtered through celite, and concentrated in vacuo. The resulting oil was purified using SiO$_2$ gel chromatography to afford the title compound. MS: 511 (M+1).

Step 3. Preparation of 4-((R or S)-1-(2-chloro-6-cyclopropylbenzoyl)-6-(hydroxymethyl)-4,5,6,7-tetrahydro-1H-indazol-3-yl)cyclohex-3-ene-1-carboxylic Acid (7A)

To an oven dried microwave vial equipped with magnetic stir bar under an atmosphere of N$_2$, tert-butyl 4-((R or S)-1-(2-chloro-6-cyclopropylbenzoyl)-6-(hydroxymethyl)-4,5,6,7-tetrahydro-1H-indazol-3-yl)cyclohex-3-ene-1-carboxylate (30 mg, 0.06 mmol, 1 equiv), and DCM (391 μL, 0.1 M) were added, followed by trifluoroacetic acid (196 μL, 0.1 M). The reaction mixture was stirred at room temperature for 1 h, and concentrated in vacuo. The resulting oil was purified using mass directed reverse phase chromatography to afford the title compound. MS: 455 (M+1). $^1$H NMR (DMSO-d6) δ (ppm): 12.14 (s, 1H), 7.34-7.31 (m, 2H), 6.99 (m, 1H), 6.17 (s, 1H), 3.45-3.41 (m, 2H), 3.38-3.18 (m, 2H), 2.63 (m, 1H), 2.52-2.18 (m, 5H), 2.12 (m, 1H), 2.04 (m, 1H), 1.95-1.77 (m, 3H), 1.62-1.52 (m, 2H), 1.32 (m, 1H), 0.89-0.51 (m, 4H).

The following examples shown in Table 9 were prepared following similar procedures described above.

TABLE 9

| Example No. | Structure | IUPAC Name | Exact Mass [M + H]+ |
|---|---|---|---|
| 7B | 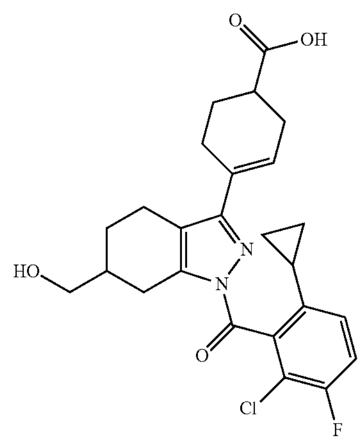 [SMILES: O=C(O)C1CC=C(c2nn(C(=O)c3c(C4CC4)ccc(F)c3Cl)c3c2CCC(CO)C3)CC1] | 4-((R or S)-1-(2-chloro-6-cyclopropyl-3-fluorobenzoyl)-6-(hydroxymethyl)-4,5,6,7-tetrahydro-1H-indaozl-3-yl)cyclohex-3-ene-1-carboxylic acid | 473 |
| 7C | 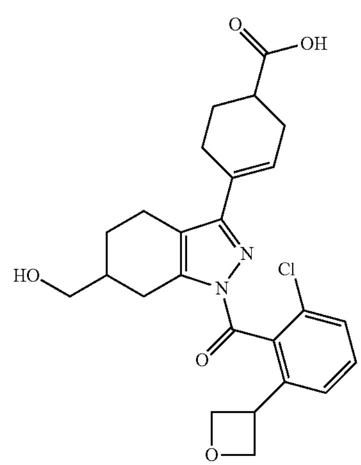 [SMILES: O=C(O)C1CC=C(c2nn(C(=O)c3c(Cl)cccc3C3COC3)c3c2CCC(CO)C3)CC1] | 4-((R or S)-1-(2-chloro-6-(oxetan-3-yl)benzoyl)-6-(hydroxymethyl)-4,5,6,7-tetrahydro-1H-indaozl-3-yl)cyclohex-3-ene-1-carboxylic acid | 471 |

TABLE 9-continued
| Example No. | Structure | IUPAC Name | Exact Mass [M + H]+ |
|---|---|---|---|
| 7D | 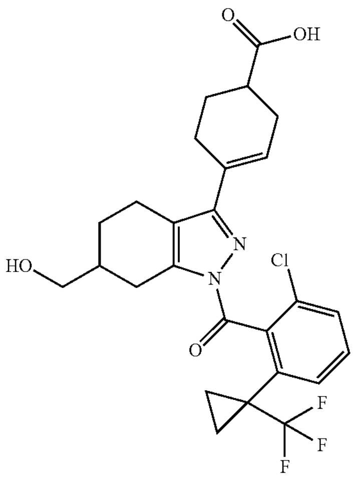 [SMILES: O=C(O)C1CC=C(c2nn(C(=O)c3c(Cl)cccc3C3(C(F)(F)F)CC3)c3c2CCC(CO)C3)CC1] | 4-((R or S)-1-(2-chloro-6-(1-(trifluoromethyl)cyclopropyl)benzoyl)-6-(hydroxymethyl)-4,5,6,7-tetrahydro-1H-indazol-3-yl)cyclohex-3-ene-1-carboxylic acid | 523 |
Example 8A
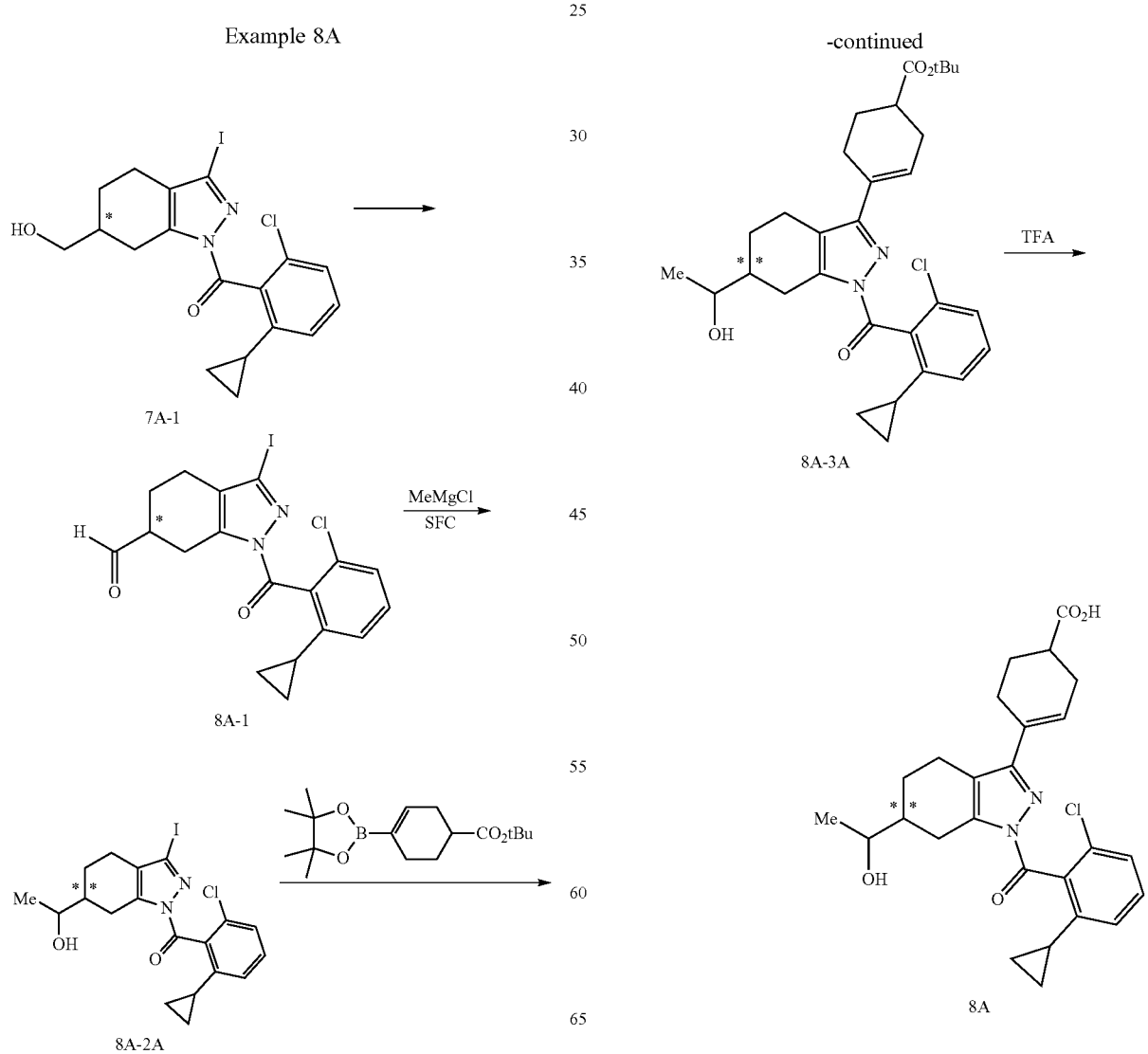

4-((R or S)-1-(2-chloro-6-cyclopropylbenzoyl)-6-
((R or S)-1-hydroxyethyl)-4,5,6,7-tetrahydro-1H-
indazol-3-yl)cyclohex-3-ene-1-carboxylic Acid Step 1. Preparation of (R or S)-1-(2-chloro-6-cyclo-
propylbenzoyl)-3-iodo-4,5,6,7-tetrahydro-1H-inda-
zole-6-carbaldehyde (8A-1)

To an oven dried microwave vial equipped with magnetic stir bar under an atmosphere of $N_2$, (R or S)-(2-chloro-6-cyclopropylphenyl)(6-(hydroxymethyl)-3-iodo-4,5,6,7-tetrahydro-1H-indazol-1-yl)methanone 7A-1 (1300 mg, 2.85 mmol, 1 equiv), DCM (7.12 mL, 0.3 M), DMSO (2.37 mL, 0.3 M), and ethyldiisopropylamine (1.5 mL, 8.54 mmol, 3 equiv) were added. The reaction mixture was cooled to −20° C. followed by the addition of sulfur trioxide pyridine complex (1.36 g, 8.54 mmol, 3 equiv). The reaction mixture was stirred 2 h while maintaining the temperature between −40° C. and −15° C. The reaction was then quenched with 1:1 $NaHCO_3$:$H_2O$ (25 mL), and diluted with DCM (25 mL). The layers were separated, and the aqueous layer was extracted with DCM (3×25 mL). The combined organic layers were washed with 1N HCl, sat. $NaHCO_3$, and brine. The solution was dried over $Na_2SO_4$, filtered through celite, and concentrated in vacuo to afford the title compound. MS: 455 (M+1).

Step 2. Preparation of (2-chloro-6-cyclopropylphe-
nyl)((R or S)-6-((R or S)-1-hydroxyethyl)-3-iodo-4,
5,6,7-tetrahydro-1H-indazol-1-yl)methanone and
(2-chloro-6-cyclopropylphenyl)((R or S)-6-((R or
S)-1-hydroxy ethyl)-3-iodo-4,5,6,7-tetrahydro-1H-
indazol-1-yl)methanone (8A-2A)

To an oven dried microwave vial equipped with magnetic stir bar under an atmosphere of $N_2$, (R or S)-1-(2-chloro-6-cyclopropylbenzoyl)-3-iodo-4,5,6,7-tetrahydro-1H-indazole-6-carbaldehyde (500 mg, 1.1 mmol, 1 equiv), and THF (3.66 mL, 0.3 M) were added. The reaction mixture was cooled to −78° C. followed by the addition of methyl magnesium chloride (0.4 mL, 1.21 mmol, 1.1 equiv). The reaction mixture was stirred for 1 h while maintaining the temperature between −78° C. and −60° C. The reaction was then quenched with saturated $NH_4Cl$ (25 mL), and diluted with EtOAc (25 mL). The layers were separated, and the aqueous layer was extracted with EtOAc (3×25 mL). The combined organic layers were washed with brine. The solution was dried over $Na_2SO_4$, concentrated in vacuo, and purified using $SiO_2$ gel chromatography to yield a mixture of diastereomers. MS: 471 (M+1).
The mixture of stereoisomers were purified by chiral SFC (ID column, 20%/80% MeOH/0.25% DEA/$CO_2$) to afford Isomer 8A-2A (faster eluting): MS: 471 (M+1). Isomer 8A-2B (slower eluting): MS: 471 (M+1).

Step 3. Preparation of tert-butyl 4-((R or S)-1-(2-
chloro-6-cyclopropylbenzoyl)-6-((R or S)-1-hy-
droxyethyl)-4,5,6,7-tetrahydro-1H-indazol-3-yl)cy-
clohex-3-ene-1-carboxylate (8A-3A)

To an oven dried microwave vial equipped with magnetic stir bar under an atmosphere of $N_2$, (2-chloro-6-cyclopropylphenyl)((R or S)-6-((R or S)-1-hydroxyethyl)-3-iodo-4,5,6,7-tetrahydro-1H-indazol-1-yl)methanone Isomer 8A-2A (35 mg, 0.07 mmol, 1 equiv), 2$^{nd}$ Gen Sphos Precatalyst (5.36 mg, 7.44 µmol, 0.1 equiv), racemic tert-butyl 4-(4,4,5,5-tetramethyl-1,3,2-dioxaborolan-2-yl)cyclohex-3-en-ecarboxylate (68.8 mg, 0.22 mmol, 3 equiv), and dioxane (372 µL, 0.2 M) were added, followed by potassium phosphate tribasic (223 µL, 1M, 3 equiv). The reaction mixture was heated to 80° C. for 24 h, and then cooled to room temperature. The crude reaction mixture was diluted with EtOAc (50 mL), filtered through celite, and concentrated in vacuo. The resulting oil was purified using $SiO_2$ gel chromatography to afford the title compound. MS: 525 (M+1).

Step 4. Preparation of 4-((R or S)-1-(2-chloro-6-
cyclopropylbenzoyl)-6-((R or S)-1-hydroxyethyl)-4,
5,6,7-tetrahydro-1H-indazol-3-yl)cyclohex-3-ene-1-
carboxylic Acid (8A)

To an oven dried microwave vial equipped with magnetic stir bar under an atmosphere of $N_2$, tert-butyl 4-((R or S)-1-(2-chloro-6-cyclopropylbenzoyl)-6-((R or S)-1-hydroxyethyl)-4,5,6,7-tetrahydro-1H-indazol-3-yl)cyclohex-3-ene-1-carboxylate (50 mg, 0.095 mmol, 1 equiv), and DCM (714 µL, 0.1 M) were added, followed by trifluoroacetic acid (238 µL, 0.1 M). The reaction mixture was stirred at room temperature for 1 h, and concentrated in vacuo. The resulting oil was purified using mass directed reverse phase chromatography to afford the title compound. MS: 469 (M+1). $^1$H NMR (DMSO-d6) δ (ppm): 7.36-7.26 (m, 2H), 6.99 (m, 1H), 6.16 (m, 1H), 3.58 (m, 1H), 3.26 (m, 1H), 2.73 (m, 1H), 2.57 (m, 1H), 2.52-2.38 (m, 2H), 2.33 (m, 1H), 2.25 (m, 1H), 2.12 (m, 1H), 2.08-2.02 (m, 2H), 1.91-1.78 (m, 2H), 1.71-1.35 (m, 4H), 1.18-1.08 (m, 3H), 0.81 (m, 1H), 0.74-0.54 (m, 3H).

Example 8B

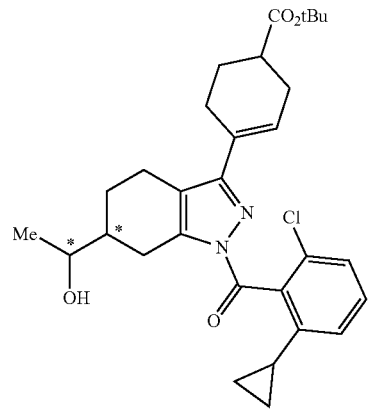 [SMILES: CC(O)C1CCc2c(C3=CCC(C(=O)OC(C)(C)C)CC3)nn(C(=O)c3c(Cl)cccc3C3CC3)c2C1]

4-((R or S)-1-(2-chloro-6-cyclopropylbenzoyl)-6-
((R or S)-1-hydroxyethyl)-4,5,6,7-tetrahydro-1H-
indazol-3-yl)cyclohex-3-ene-1-carboxylic Acid Step 1. Preparation of tert-butyl 4-((R or S)-1-(2-
chloro-6-cyclopropylbenzoyl)-6-((R or S)-1-hy-
droxyethyl)-4,5,6,7-tetrahydro-1H-indazol-3-yl)cy-
clohex-3-ene-1-carboxylate (8A-3B)

To an oven dried microwave vial equipped with magnetic stir bar under an atmosphere of $N_2$, (2-chloro-6-cyclopropylphenyl)((R or S)-6-((R or S)-1-hydroxyethyl)-3-iodo-4,5,6,7-tetrahydro-1H-indazol-1-yl)methanone Isomer 8A-2B (150 mg, 0.32 mmol, 1 equiv), $2^{nd}$ Gen Sphos Precatalyst (22.9 mg, 0.03 mmol, 0.1 equiv), racemic tert-butyl 4-(4,4,5,5-tetramethyl-1,3,2-dioxaborolan-2-yl)cyclohex-3-en-ecarboxylate (295 mg, 0.95 mmol, 3 equiv), and dioxane (1.6 mL, 0.2 M) were added, followed by potassium phosphate tribasic (956 µL, 1M, 3 equiv). The reaction mixture was heated to 80° C. for 24 h, and then cooled to room temperature. The crude reaction mixture was diluted with EtOAc (50 mL), filtered through celite, and concentrated in vacuo. The resulting oil was purified using $SiO_2$ gel chromatography to afford the title compound. MS: 525 (M+1).

Step 2. Preparation of 4-((R or S)-1-(2-chloro-6-cyclopropylbenzoyl)-6-((R or S)-1-hydroxyethyl)-4,5,6,7-tetrahydro-1H-indazol-3-yl)cyclohex-3-ene-1-carboxylic Acid (8B)

To an oven dried microwave vial equipped with magnetic stir bar under an atmosphere of $N_2$, tert-butyl 4-((R or S)-1-(2-chloro-6-cyclopropylbenzoyl)-6-((R or S)-1-hydroxyethyl)-4,5,6,7-tetrahydro-1H-indazol-3-yl)cyclohex-3-ene-1-carboxylate (100 mg, 0.19 mmol, 1 equiv), and DCM (1.43 mL, 0.1 M) were added, followed by trifluoroacetic acid (476 L, 0.1 M). The reaction mixture was stirred at room temperature for 1 h, and concentrated in vacuo. The resulting oil was purified using mass directed reverse phase chromatography to afford the title compound. MS: 469 (M+1). $^1$H NMR (DMSO-d6) δ (ppm): 7.36-7.26 (m, 2H), 6.99 (m, 1H), 6.16 (m, 1H), 3.58 (m, 1H), 3.26 (m, 1H), 2.73 (m, 1H), 2.57 (m, 1H), 2.52-2.38 (m, 2H), 2.33 (m, 1H), 2.25 (m, 1H), 2.12 (m, 1H), 2.08-2.02 (m, 2H), 1.91-1.78 (m, 2H), 1.71-1.35 (m, 4H), 1.18-1.08 (m, 3H), 0.81 (m, 1H), 0.74-0.54 (m, 3H).

Example 9A

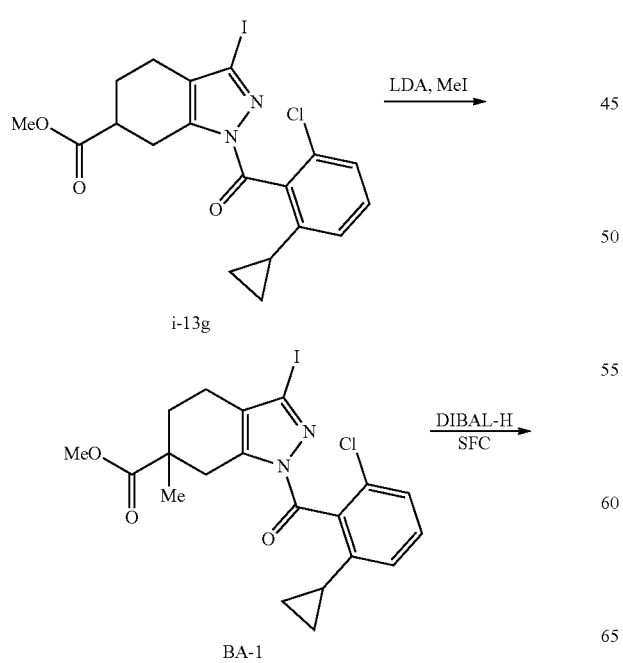

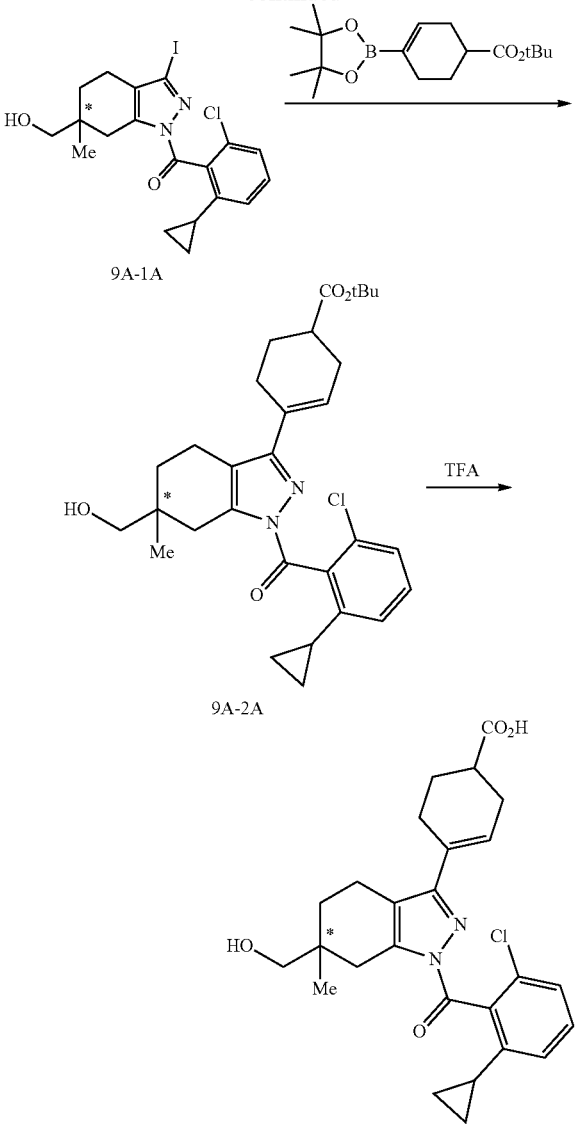

4-((R or S)-1-(2-chloro-6-cyclopropylbenzoyl)-6-(hydroxymethyl)-6-methyl-4,5,6,7-tetrahydro-1H-indazol-3-yl)cyclohex-3-ene-1-carboxylic Acid Step 1. Preparation of methyl-1-(2-chloro-6-cyclopropylbenzoyl)-3-iodo-6-methyl-4,5,6,7-tetrahydro-1H-indazole-6-carboxylate (BA-1)

To an oven dried round bottom flask equipped with magnetic stir bar under an atmosphere of $N_2$, methyl 1-(2-chloro-6-cyclopropylbenzoyl)-3-iodo-4,5,6,7-tetrahydro-1H-indazole-6-carboxylate (240 mg, 0.495 mmol, 1 equiv), and THF (2.48 mL, 0.2 M) were added. The reaction flask was cooled to −78° C., followed by the addition of lithium diisopropyl amide (0.5 mL, 2 M in THF, 0.99 mmol, 2.00 equiv). The reaction mixture was stirred for 30 minutes followed by the addition of methyl iodide (281 mg, 1.98 mmol, 4 equiv). The reaction mixture was slowly warmed to room temperature over 16 h, and then quenched with saturated $NH_4Cl$ (25 mL) and diluted with EtOAc (25 mL). The layers were separated, and the resulting aqueous layer was extracted with EtOAc (3×25 mL). The combined organic layers were washed with brine, dried over Na$_2$SO$_4$, and concentrated in vacuo. The crude oil was purified using SiO$_2$ gel chromatography to yield racemic methyl-1-(2-chloro-6-cyclopropylbenzoyl)-3-iodo-6-methyl-4,5,6,7-tetrahydro-1H-indazole-6-carboxylate. MS: 499 (M+1).

Step 2. Preparation of (R or S)-(2-chloro-6-cyclopropylphenyl)(6-(hydroxymethyl)-3-iodo-6-methyl-4,5,6,7-tetrahydro-1H-indazol-1-yl)methanone (9A-1A)

To an oven dried round bottom flask equipped with magnetic stir bar under an atmosphere of N$_2$, racemic methyl-1-(2-chloro-6-cyclopropylbenzoyl)-3-iodo-6-methyl-4,5,6,7-tetrahydro-1H-indazole-6-carboxylate (600 mg, 1.2 mmol, 1 equiv), and THF (4 mL, 0.3 M) were added. The reaction flask was cooled to −78° C., followed by the addition of diisobutyl aluminum hydride (3.6 mL, 1M in THF, 3.6 mmol, 3.00 equiv). The reaction mixture was slowly warmed to 0° C. over 2 h, and then quenched with 1N HCl (25 mL) and diluted with EtOAc (25 mL). The crude reaction was then warmed to room temperature over 1 h. The layers were separated, and the aqueous layer was extracted with EtOAc (3×25 mL). The combined organic layers were washed with brine, dried over Na$_2$SO$_4$, and concentrated in vacuo. The crude oil was purified using SiO$_2$ gel to afford the title compound. MS: 471 (M+1).

The mixture of stereoisomers were purified by chiral SFC (AD-H column, 20%/80% MeOH/0.25% DMEA/CO$_2$) to afford Isomer 9A-1A (faster eluting): MS: 471 (M+1). Isomer 9A-1B (slower eluting): MS: 471 (M+1).

Step 3. Preparation of tert-butyl 4-((R or S)-1-(2-chloro-6-cyclopropylbenzoyl)-6-(hydroxymethyl)-6-methyl-4,5,6,7-tetrahydro-1H-indazol-3-yl)cyclohex-3-ene-1-carboxylate (9A-2A)

To an oven dried microwave vial equipped with magnetic stir bar under an atmosphere of N$_2$, (R or S)-(2-chloro-6-cyclopropylphenyl)(6-(hydroxymethyl)-3-iodo-6-methyl-4,5,6,7-tetrahydro-1H-indazol-1-yl)methanone Isomer 9A-1A (150 mg, 0.32 mmol, 1 equiv), 2$^{nd}$ Gen Sphos Precatalyst (22.9 mg, 0.03 mmol, 0.1 equiv), racemic tert-butyl 4-(4,4,5,5-tetramethyl-1,3,2-dioxaborolan-2-yl)cyclohex-3-enecarboxylate (295 mg, 0.95 mmol, 3 equiv), and dioxane (1.6 mL, 0.2 M) were added, followed by potassium phosphate tribasic (956 μL, 1M, 3 equiv). The reaction mixture was heated to 80° C. for 24 h, and then cooled to room temperature. The crude reaction mixture was diluted with EtOAc (50 mL), filtered through celite, and concentrated in vacuo. The resulting oil was purified using SiO$_2$ gel chromatography to afford the title compound. MS: 525 (M+1).

Step 3. Preparation of 4-((R or S)-1-(2-chloro-6-cyclopropylbenzoyl)-6-(hydroxymethyl)-6-methyl-4,5,6,7-tetrahydro-1H-indazol-3-yl)cyclohex-3-ene-1-carboxylic Acid (9A)

To an oven dried microwave vial equipped with magnetic stir bar under an atmosphere of N$_2$, tert-butyl 4-((R or S)-1-(2-chloro-6-cyclopropylbenzoyl)-6-(hydroxymethyl)-6-methyl-4,5,6,7-tetrahydro-1H-indazol-3-yl)cyclohex-3-ene-1-carboxylate (150 mg, 0.29 mmol, 1 equiv), and DCM (2.1 mL, 0.1 M) were added, followed by trifluoroacetic acid (714 μL, 0.1 M). The reaction mixture was stirred at room temperature for 1 h, and concentrated in vacuo. The resulting oil was purified using mass directed reverse phase chromatography to afford the title compound. MS: 469 (M+1). $^1$H NMR (DMSO-d6) δ (ppm): 12.15 (s, 1H), 7.5-7.30 (m, 2H), 7.00 (t, J=6.54 Hz, 1H), 6.22 (s, 1H), 4.70 (s, 1H), 3.31-3.22 (m, 3H), 2.91 (m, 1H), 2.76 (m, 1H), 2.58-2.37 (m, 3H), 2.34 (m, 1H), 2.26 (m, 1H), 2.23 (m, 1H), 2.03 (m, 1H), 1.86 (m, 1H), 1.57 (m, 2H), 1.45 (m, 1H), 0.89 (d, J=5.88 Hz, 3H), 0.78 (m, 1H), 0.68 (m, 1H), 0.62 (m, 1H), 0.52 (m, 1H).

Example 9B

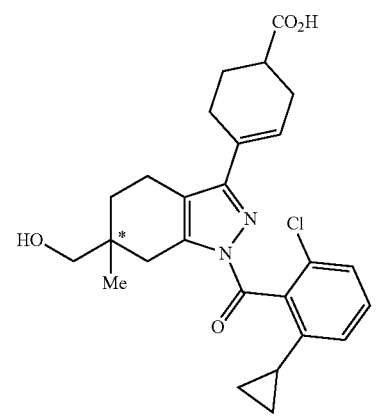 [SMILES: CC1(CO)CCc2c(C3=CCC(C(=O)O)CC3)nn(C(=O)c3c(Cl)cccc3C3CC3)c2C1]

4-((R or S)-1-(2-chloro-6-cyclopropylbenzoyl)-6-(hydroxymethyl)-6-methyl-4,5,6,7-tetrahydro-1H-indazol-3-yl)cyclohex-3-ene-1-carboxylic Acid Step 1. Preparation of tert-butyl 4-((R or S)-1-(2-chloro-6-cyclopropylbenzoyl)-6-(hydroxymethyl)-6-methyl-4,5,6,7-tetrahydro-1H-indazol-3-yl)cyclohex-3-ene-1-carboxylate (9A-2B)

To an oven dried microwave vial equipped with magnetic stir bar under an atmosphere of N$_2$, (R or S)-(2-chloro-6-cyclopropylphenyl)(6-(hydroxymethyl)-3-iodo-6-methyl-4,5,6,7-tetrahydro-1H-indazol-1-yl)methanone Isomer 9A-1B (150 mg, 0.32 mmol, 1 equiv), 2nd Gen Sphos Precatalyst (22.9 mg, 0.03 mmol, 0.1 equiv), racemic tert-butyl 4-(4,4,5,5-tetramethyl-1,3,2-dioxaborolan-2-yl)cyclohex-3-enecarboxylate (295 mg, 0.95 mmol, 3 equiv), and dioxane (1.6 mL, 0.2 M) were added, followed by potassium phosphate tribasic (956 μL, 1M, 3 equiv). The reaction mixture was heated to 80° C. for 24 h, and then cooled to room temperature. The crude reaction mixture was diluted with EtOAc (50 mL), filtered through celite, and concentrated in vacuo. The resulting oil was purified using SiO$_2$ gel chromatography to afford the title compound. MS: 525 (M+1).

Step 2. Preparation of 4-((R or S)-1-(2-chloro-6-cyclopropylbenzoyl)-6-(hydroxymethyl)-6-methyl-4,5,6,7-tetrahydro-1H-indazol-3-yl)cyclohex-3-ene-1-carboxylic Acid (9B)

To an oven dried microwave vial equipped with magnetic stir bar under an atmosphere of N$_2$, tert-butyl 4-((R or S)-1-(2-chloro-6-cyclopropylbenzoyl)-6-(hydroxymethyl)-6-methyl-4,5,6,7-tetrahydro-1H-indazol-3-yl)cyclohex-3-ene-1-carboxylate (150 mg, 0.29 mmol, 1 equiv), and DCM (2.1 mL, 0.1 M) were added, followed by trifluoroacetic acid (714 μL, 0.1 M). The reaction mixture was stirred at room temperature for 1 h, and concentrated in vacuo. The resulting oil was purified using mass directed reverse phase chromatography to afford the title compound. MS: 469 (M+1). $^1$H NMR (DMSO-d6) δ (ppm): 12.15 (s, 1H), 7.5-7.30 (m, 2H), 7.00 (t, J=6.54 Hz, 1H), 6.22 (s, 1H), 4.70 (s, 1H), 3.31-3.22 (m, 3H), 2.91 (m, 1H), 2.76 (m, 1H), 2.58-2.37 (m, 3H), 2.34 (m, 1H), 2.26 (m, 1H), 2.23 (m, 1H), 2.03 (m, 1H), 1.86 (m, 1H), 1.57 (m, 2H), 1.45 (m, 1H), 0.89 (d, J=5.88 Hz, 3H), 0.78 (m, 1H), 0.68 (m, 1H), 0.62 (m, 1H), 0.52 (m, 1H).

Example 10A

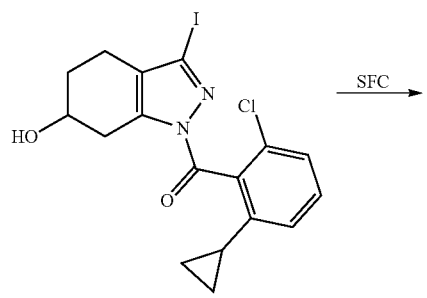

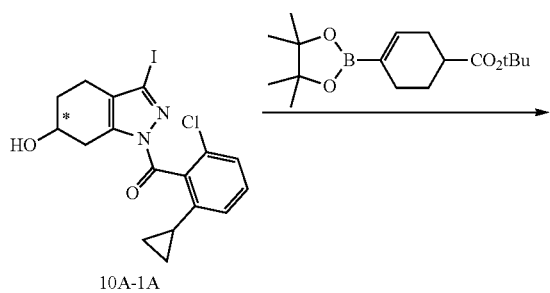

10A-1A

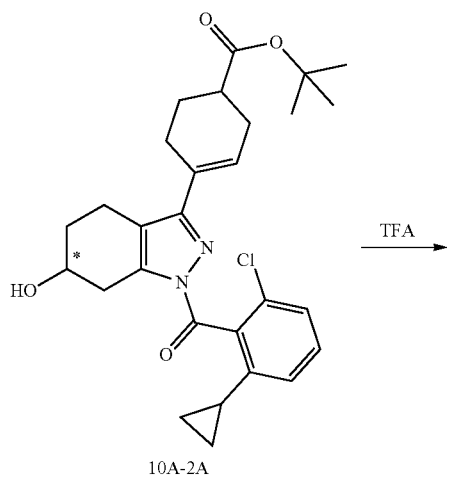

10A-2A

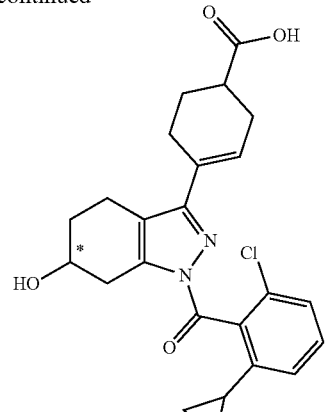

10A

4-((R or S)-1-(2-chloro-6-cyclopropylbenzoyl)-6-hydroxy-4,5,6,7-tetrahydro-1H-indazol-3-yl)cyclohex-3-ene-1-carboxylic Acid (10A)

Step 1. Preparation of (S)-(2-chloro-6-cyclopropylphenyl)(6-hydroxy-3-iodo-4,5,6,7-tetrahydro-1H-indazol-1-yl)methanone and (R)-(2-chloro-6-cyclopropylphenyl)(6-hydroxy-3-iodo-4,5,6,7-tetrahydro-1H-indazol-1-yl)methanone (10A-1A)

The mixture of the two stereoisomers of (2-chloro-6-cyclopropylphenyl)(6-hydroxy-3-iodo-4,5,6,7-tetrahydro-1H-indazol-1-yl)methanone was purified by chiral SFC (Chiralpak IB, 20%/80% methanol+0.25% dimethyl ethyl amine/CO₂) to afford Intermediate 10A-1A (faster eluting): MS: 443 (M+1). Intermediate 10A-1B (slower eluting): MS: 443 (M+1).

Step 2. Preparation of tert-butyl 4-(1-(2-chloro-6-cyclopropylbenzoyl)-6-hydroxy-4,5,6,7-tetrahydro-1H-indazol-3-yl)cyclohex-3-ene-1-carboxylate (10A-2A)

A mixture of (2-chloro-6-cyclopropylphenyl)(6-hydroxy-3-iodo-4,5,6,7-tetrahydro-1H-indazol-1-yl)methanone Intermediate 10A-1A (105 mg, 0.237 mmol), tert-butyl 4-(4,4,5,5-tetramethyl-1,3,2-dioxaborolan-2-yl)cyclohex-3-enecarboxylate (219 mg, 0.712 mmol), PdCl₂(dppf)-CH₂Cl₂ (38.7 mg, 0.047 mmol), potassium acetate (69.8 mg, 0.712 mmol), and THF (1898 μL) was purged with argon for 5 minutes. Water (474 μL) was then added to the mixture and the resulting solution was heated to 80° C. overnight. The reaction was cooled and the mixture was purified by silica gel chromatography (0-100% EtOAc/Hexanes) to afford the title compound. MS: 497 (M+1).

Step 3. Preparation of 4-((S)-1-(2-chloro-6-cyclopropylbenzoyl)-6-hydroxy-4,5,6,7-tetrahydro-1H-indazol-3-yl)cyclohex-3-ene-1-carboxylic Acid (10A)

A mixture of tert-butyl 4-(1-(2-chloro-6-cyclopropylbenzoyl)-6-hydroxy-4,5,6,7-tetrahydro-1H-indazol-3-yl)cyclohex-3-ene-1-carboxylate (100 mg, 0.201 mmol), TFA (310 μL, 4.02 mmol), and DCM (1 mL) was allowed to stir at room temperature for 1 hr. The reaction was concentrated and the residue redissolved in methanol. The mixture was filtered and purified by mass triggered reverse phase HPLC (ACN/water with 0.1% TFA modifier) to afford the title compound. MS: 441 (M+1). $^1$H NMR (500 MHz, DMSO-d6) δ 7.41-31 (m, 2H), 7.02 (d, J=7.7, 1H), 6.21 (s, 1H), 4.12-4.03 (m, 2H), 3.36-3.24 (m, 1H), 3.01-2.86 (m, 1H), 2.71-2.53 (m, 2H), 2.47-2.16 (m, 5H), 2.15-2.00 (m, 1H), 1.95-1.65 (m, 3H), 1.65-1.45 (m, 2H), 0.90-0.53 (m, 4H).

Example 10B

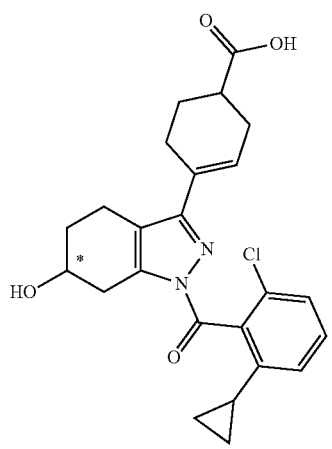 [SMILES: O=C(O)C1CC=C(c2nn(C(=O)c3c(Cl)cccc3C3CC3)c3c2CCC(O)C3)CC1]

4-((R or S)-1-(2-chloro-6-cyclopropylbenzoyl)-6-hydroxy-4,5,6,7-tetrahydro-1H-indazol-3-yl)cyclohex-3-ene-1-carboxylic Acid 4-((R or S)-1-(2-chloro-6-cyclopropylbenzoyl)-6-hydroxy-4,5,6,7-tetrahydro-1H-indazol-3-yl)cyclohex-3-ene-1-carboxylic acid (10B) was prepared in an analogous fashion to that described above using Intermediate 10A-1B to yield the corresponding title compound. MS: 441 (M+1). $^1$H NMR (500 MHz, DMSO-d6) δ 7.44-7.30 (m, 2H), 7.02 (d, J=7.5, 1H), 6.21 (s, 1H), 4.13-4.02 (m, 1H), 3.38-3.23 (m, 1H), 3.00-2.88 (m, 1H), 2.68-2.56 (m, 2H), 2.47-2.15 (m, 5H), 2.16-1.99 (m, 1H), 1.93-1.86 (m, 1H), 1.86-1.68 (m, 2H), 1.64-1.46 (m, 2H), 0.90-0.54 (m, 4H).

Example 11A

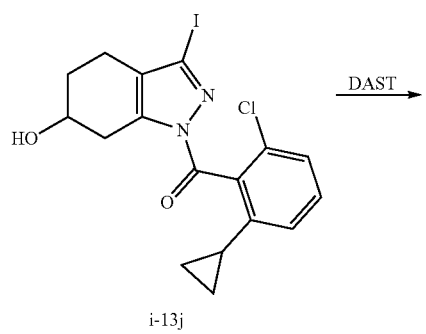

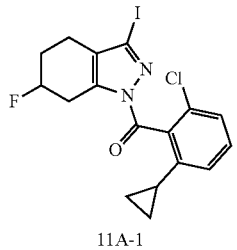

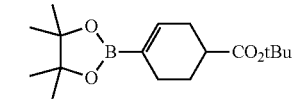

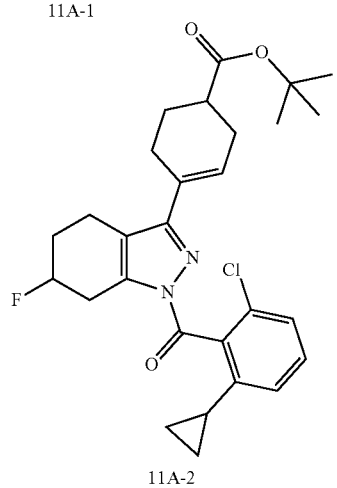

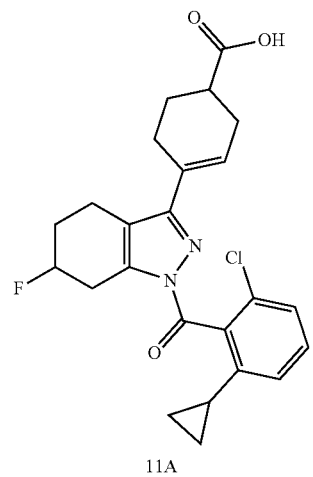

4-(1-(2-chloro-6-cyclopropylbenzoyl)-6-fluoro-4,5,6,7-tetrahydro-1H-indazol-3-yl)cyclohex-3-ene-1-carboxylic Acid Step 1. Preparation of (2-chloro-6-cyclopropylphenyl)(6-fluoro-3-iodo-4,5,6,7-tetrahydro-1H-indazol-1-yl)methanone (11A-1)

To a mixture of (2-chloro-6-cyclopropylphenyl)(6-hydroxy-3-iodo-4,5,6,7-tetrahydro-1H-indazol-1-yl)methanone (200 mg, 0.452 mmol) and CH$_2$Cl$_2$ (4518 μL) was added DAST (597 μL, 4.52 mmol) and the reaction was allowed to stir at room temperature overnight. The mixture was diluted with EtOAc. The organic layer was separated and washed twice with aqueous NaHCO$_3$ and once with brine. The combined organic layers were dried with Na$_2$SO$_4$, filtered and the solvent was evaporated under reduced pressure. The residue was purified by silica gel chromatography (0-100% EtOAc/hexane) to afford the title compound. MS: 445 (M+1).

Step 2. Preparation of tert-butyl 4-(1-(2-chloro-6-cyclopropylbenzoyl)-6-fluoro-4,5,6,7-tetrahydro-1H-indazol-3-yl)cyclohex-3-ene-1-carboxylate (11A-2)

A mixture of (2-chloro-6-cyclopropylphenyl)(6-fluoro-3-iodo-4,5,6,7-tetrahydro-1H-indazol-1-yl)methanone (33 mg, 0.074 mmol), tert-butyl 4-(4,4,5,5-tetramethyl-1,3,2-dioxaborolan-2-yl)cyclohex-3-enecarboxylate (45.7 mg, 0.148 mmol), PdCl$_2$(dppf)-CH$_2$Cl$_2$ (18.18 mg, 0.022 mmol), potassium acetate (21.85 mg, 0.223 mmol), and THF (594 µL) was purged with argon for 5 minutes. Water (148 µL) was then added and the solution was heated to 80° C. overnight. The mixture was cooled and diluted with EtOAc. The organic layer was separated and washed twice with aqueous NaHCO$_3$ and once with brine. The combined organic layers were dried with Na$_2$SO$_4$, filtered and the solvent was evaporated under reduced pressure to give crude product which was used directly in the next step. MS: 499 (M+1).

Step 3. Preparation of 4-(1-(2-chloro-6-cyclopropylbenzoyl)-6-fluoro-4,5,6,7-tetrahydro-1H-indazol-3-yl)cyclohex-3-ene-1-carboxylic Acid (11A)

A mixture of tert-butyl 4-(1-(2-chloro-6-cyclopropylbenzoyl)-6-fluoro-4,5,6,7-tetrahydro-1H-indazol-3-yl)cyclohex-3-ene-1-carboxylate (37 mg, 0.074 mmol), DCM (1 mL) and TFA (0.5 mL) was allowed to stir at room temperature for 3 hrs. The reaction concentrated and the residue redissolved in methanol. The mixture was filtered and purified by mass triggered reverse phase HPLC (ACN/water with 0.1% TFA modifier) to afford the title compound. MS: 443 (M+1). $^1$H NMR (600 MHz, DMSO-d6) δ 7.41-7.26 (m, 2H), 7.00 (s, 1H), 6.20 (s, 1H), 5.23 (d, J=47.9, 1H), 3.46-3.26 (m, 3H), 2.68-2.56 (m, 2H), 2.39-1.96 (m, 5H), 1.96-1.73 (m, 2H), 1.63-1.41 (m, 2H), 0.88-0.47 (m, 4H).

Example 12A 4-(1-(2-chloro-6-(1-(trifluoromethyl)cyclopropyl) benzoyl)-4,5,6,7-tetrahydro-1H-pyrazolo[4,3-b]pyridin-3-yl)cyclohex-3-ene-1-carboxylic Acid Step 1. Preparation of tert-butyl 1-(2-chloro-6-(1-(trifluoromethyl)cyclopropyl)benzoyl)-3-iodo-1,5,6,7-tetrahydro-4H-pyrazolo[4,3-b]pyridine-4-carboxylate (12A-1)

To a mixture of tert-butyl 3-iodo-1,5,6,7-tetrahydro-4H-pyrazolo[4,3-b]pyridine-4-carboxylate (300 mg, 0.859 mmol), DMAP (315 mg, 2.58 mmol), TEA (359 µL, 2.58 mmol), and DCE (2864 µL) was added 2-chloro-6-(1-(trifluoromethyl)cyclopropyl)benzoyl chloride (426 mg, 1.504 mmol). The resulting solution was heated to 70° C. and allowed to stir overnight. The reaction was cooled and diluted with EtOAc. The organic layer was separated and washed twice with aqueous NaHCO$_3$ and once with brine. The combined organic layers were dried with Na$_2$SO$_4$, filtered and the solvent was evaporated under reduced pressure. The residue was purified by silica gel chromatography (0-100% EtOAc/Hexane) to afford the title compound. MS: 596 (M+1).

Step 2. Preparation of tert-butyl 3-(4-(tert-butoxycarbonyl)cyclohex-1-en-1-yl)-1-(2-chloro-6-(1-(trifluoromethyl)cyclopropyl)benzoyl)-1,5,6,7-tetrahydro-4H-pyrazolo[4,3-b]pyridine-4-carboxylate (12A-2)

A mixture of tert-butyl 1-(2-chloro-6-(1-(trifluoromethyl)cyclopropyl)benzoyl)-3-iodo-1,5,6,7-tetrahydro-4H-pyrazolo[4,3-b]pyridine-4-carboxylate (74 mg, 0.124 mmol), tert-butyl 4-(4,4,5,5-tetramethyl-1,3,2-dioxaborolan-2-yl)cyclohex-3-enecarboxylate (77 mg, 0.248 mmol), PdCl$_2$(dppf)-CH$_2$Cl$_2$ (20.29 mg, 0.025 mmol), and potassium acetate (36.6 mg, 0.373 mmol) in THF (331 µL) was thoroughly purged with argon for 5 min. Water (83 µL) was then added to the mixture and the resulting solution was heated to 80° C. overnight.

The reaction was cooled and diluted with EtOAc. The organic layer was separated and washed twice with aqueous NaHCO$_3$ and once with brine. The combined organic layers were dried with Na$_2$SO$_4$, filtered and the solvent was evaporated under reduced pressure. The residue was purified by silica gel chromatography (0-100% EtOAc/Hexane) to afford the title compound. MS: 650 (M+1).

Step 3. Preparation of 4-(1-(2-chloro-6-(1-(trifluoromethyl)cyclopropyl)benzoyl)-4,5,6,7-tetrahydro-1H-pyrazolo[4,3-b]pyridin-3-yl)cyclohex-3-ene-1-carboxylic Acid (12A)

To a mixture of tert-butyl 3-(4-(tert-butoxycarbonyl)cyclohex-1-en-1-yl)-1-(2-chloro-6-(1-(trifluoromethyl)cyclopropyl)benzoyl)-1,5,6,7-tetrahydro-4H-pyrazolo[4,3-b]pyridine-4-carboxylate (70 mg, 0.108 mmol) in DCM (808 µL) was added TFA (269 µL). The solution was stirred at room temperature for 3 h. The reaction was concentrated and the residue was brought up in methanol. The mixture was filtered and purified by mass triggered reverse phase HPLC (ACN/water with 0.1% TFA modifier) to afford the title compound. MS: 494 (M+1). $^1$H NMR (600 MHz, DMSO-d6) δ 7.59-7.46 (m, 3H), 6.33 (s, 1H), 3.12-2.99 (m, 4H), 2.43-2.29 (m, 2H), 2.29-2.19 (m, 1H), 2.15-1.70 (m, 5H), 1.52-1.41 (m, 1H), 1.33-1.24 (m, 1H), 1.16-1.02 (m, 2H), 0.70 (s, 1H).

Example 13A

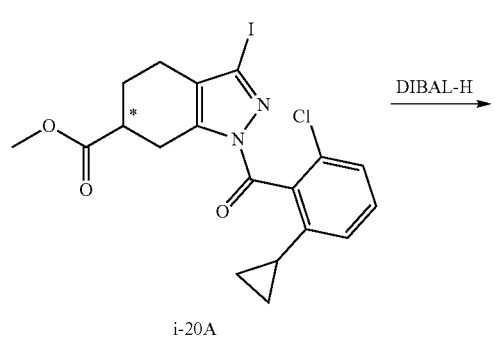

(R or S)-4-((R or S)-1-(2-chloro-6-cyclopropylbenzoyl)-6-(hydroxymethyl)-4,5,6,7-tetrahydro-1H-indazol-3-yl)-1-methylcyclohex-3-ene-1-carboxylic Acid

Step 1. Preparation of (R)-(2-chloro-6-cyclopropylphenyl)(6-(hydroxymethyl)-3-iodo-4,5,6,7-tetrahydro-1H-indazol-1-yl)methanone (CA-1)

To an oven dried microwave vial equipped with magnetic stir bar under an atmosphere of N$_2$, methyl (R or S)-1-(2-chloro-6-cyclopropylbenzoyl)-3-iodo-4,5,6,7-tetrahydro-1H-indazole-6-carboxylate i-20A (1 g, 2.06 mmol, 1 equiv) and DCM (6.9 mL, 0.3 M) were added. The reaction mixture was cooled to −78° C., and diisobutylaluminum hydride (6.19 mL, 1 M in THF, 3 equiv) was added. The reaction mixture was warmed to 0° C. over 1 h, and then quenched with 1 HCl (25 mL), and diluted with EtOAc (50 mL). The mixture was stirred vigorously for 1 h at room temperature. The layers were separated, the aqueous layer was extracted with EtOAc (3×50 mL), the combined organic layers were washed with brine, filtered through celite, and then concentrated in vacuo. The resulting oil was purified using SiO$_2$ gel chromatography to afford the title compound. MS: 457 (M+1).

Step 2. Preparation of tert-butyl (R or S)-4-((R or S)-1-(2-chloro-6-cyclopropylbenzoyl)-6-(hydroxymethyl)-4,5,6,7-tetrahydro-1H-indazol-3-yl)-1-methylcyclohex-3-ene-1-carboxylate (13A-1A)

To an oven dried microwave vial equipped with magnetic stir bar under an atmosphere of N$_2$, (R or S)-(2-chloro-6-cyclopropylphenyl)(6-(hydroxymethyl)-3-iodo-4,5,6,7-tetrahydro-1H-indazol-1-yl)methanone CA-1 (150 mg, 0.33 mmol, 1 equiv), Chloro(2-dicyclohexylphosphino-2',6'-dimethoxy-1,1'-biphenyl)[2-(2'-amino-1,1'-biphenyl)]palladium(II) (23.7 mg, 0.03 mmol, 0.1 equiv), racemic tert-butyl 1-methyl-4-(4,4,5,5-tetramethyl-1,3,2-dioxaborolan-2-yl)cyclohex-3-enecarboxylate (318 mg, 0.99 mmol, 3 equiv), and dioxane (1.64 mL, 0.2 M) were added, followed by potassium phosphate tribasic (985 µL, 1M, 3 equiv). The reaction mixture was heated to 80° C. for 24 h, and then cooled to room temperature. The crude reaction mixture was diluted with EtOAc (50 mL), filtered through celite, and concentrated in vacuo. The resulting oil was purified using SiO$_2$ gel chromatography to afford the title compound. MS: 525 (M+1).

The mixture of stereoisomers were purified by chiral SFC (OJ-H column, 20%/80% MeOH/0.25% DMEA/CO$_2$) to afford Isomer 13A-1A (faster eluting): MS: 525 (M+1). Isomer 13A-1B (slower eluting): MS: 525 (M+1).

Step 2. Preparation of (R or S)-4-((R or S)-1-(2-chloro-6-cyclopropylbenzoyl)-6-(hydroxymethyl)-4,5,6,7-tetrahydro-1H-indazol-3-yl)-1-methylcyclohex-3-ene-1-carboxylic Acid (13A)

To an oven dried microwave vial equipped with magnetic stir bar under an atmosphere of N$_2$, tert-butyl (R or S)-4-((R or S)-1-(2-chloro-6-cyclopropylbenzoyl)-6-(hydroxymethyl)-4,5,6,7-tetrahydro-1H-indazol-3-yl)-1-methylcyclohex-3-ene-1-carboxylate (Core Peak A, Diastereomer A) Isomer 13A-1A (45 mg, 0.09 mmol, 1 equiv), and DCM (643 L, 0.1 M) were added, followed by trifluoroacetic acid (214 µL, 0.1 M). The reaction mixture was stirred at room temperature for 1 h, and concentrated in vacuo. The resulting oil was purified using mass directed reverse phase chromatography to afford the title compound. MS: 469 (M+1). $^1$H NMR (DMSO-d6) δ (ppm): 12.13 (s, 1H), 7.36-7.30 (m, 2H), 6.99 (t, J=7.41 Hz, 1H), 6.14 (s, 1H), 4.65 (m, 1H), 3.43 (m, 2H), 2.63-2.47 (m, 4H), 2.15 (m, 1H), 2.04-1.97 (m, 3H), 1.92-1.82 (m, 3H), 1.57 (d, J=8.69 Hz, 1H), 1.47 (t, J=9.52 Hz, 1H), 1.32 (m, 1H), 1.08 (s, 3H), 0.80 (m, 1H), 0.70 (m, 1H), 0.62 (m, 1H), 0.56 (m, 1H).

Example 13B

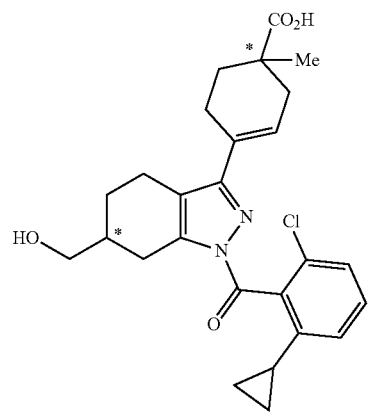 [SMILES: CC1(C(=O)O)CC=C(c2nn(C(=O)c3c(Cl)cccc3C3CC3)c3c2CCC(CO)C3)CC1]

(R or S)-4-((R or S)-1-(2-chloro-6-cyclopropylbenzoyl)-6-(hydroxymethyl)-4,5,6,7-tetrahydro-1H-indazol-3-yl)-1-methylcyclohex-3-ene-1-carboxylic Acid Step 1. Preparation of (R or S)-4-((R or S)-1-(2-chloro-6-cyclopropylbenzoyl)-6-(hydroxymethyl)-4,5,6,7-tetrahydro-1H-indazol-3-yl)-1-methylcyclohex-3-ene-1-carboxylic Acid (13B)

To an oven dried microwave vial equipped with magnetic stir bar under an atmosphere of N$_2$, tert-butyl (R or S)-4-((R or S)-1-(2-chloro-6-cyclopropylbenzoyl)-6-(hydroxymethyl)-4,5,6,7-tetrahydro-1H-indazol-3-yl)-1-methylcyclohex-3-ene-1-carboxylate Isomer 13A-1B (45 mg, 0.09 mmol, 1 equiv), and DCM (643 µL, 0.1 M) were added, followed by trifluoroacetic acid (214 µL, 0.1 M). The reaction mixture was stirred at room temperature for 1 h, and concentrated in vacuo. The resulting oil was purified using mass directed reverse phase chromatography to afford title compound. MS: 469 (M+1). $^1$H NMR (DMSO-d6) δ (ppm): 12.13 (s, 1H), 7.36-7.30 (m, 2H), 6.99 (t, J=7.41 Hz, 1H), 6.14 (s, 1H), 4.65 (m, 1H), 3.43 (m, 2H), 2.63-2.47 (m, 4H), 2.15 (m, 1H), 2.04-1.97 (m, 3H), 1.92-1.82 (m, 3H), 1.57 (d, J=8.69 Hz, 1H), 1.47 (t, J=9.52 Hz, 1H), 1.32 (m, 1H), 1.08 (s, 3H), 0.80 (m, 1H), 0.70 (m, 1H), 0.62 (m, 1H), 0.56 (m, 1H).

Example 14A

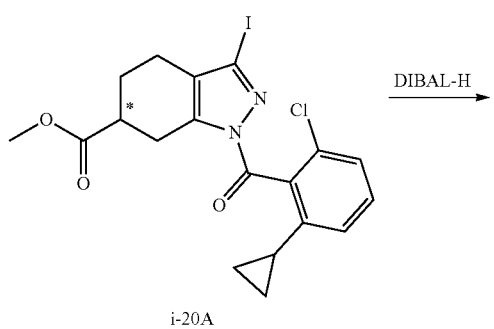

i-20A

-continued

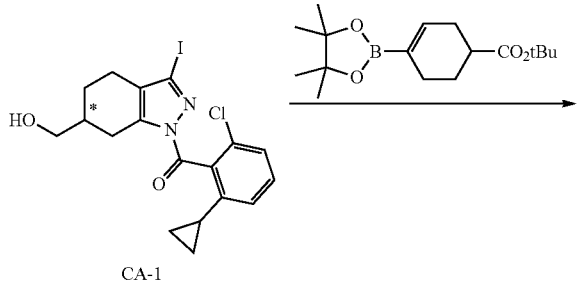

CA-1

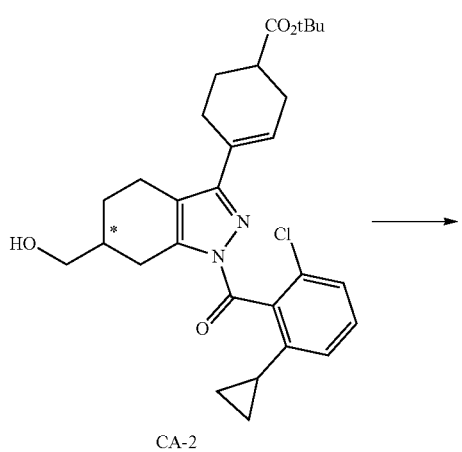

CA-2

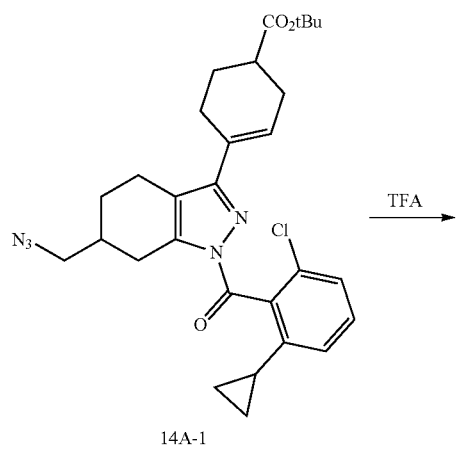

14A-1

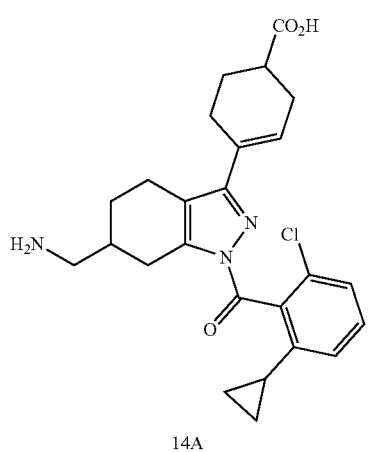 [SMILES: NCC1CCc2c(C3=CCC(C(=O)O)CC3)nn(C(=O)c3c(Cl)cccc3C3CC3)c2C1 ; "14A"]

14A 4-((R or S)-6-(aminomethyl)-1-(2-chloro-6-cyclopropylbenzoyl)-4,5,6,7-tetrahydro-1H-indazol-3-yl)cyclohex-3-ene-1-carboxylic Acid Step 1. Preparation of (R)-(2-chloro-6-cyclopropylphenyl)(6-(hydroxymethyl)-3-iodo-4,5,6,7-tetrahydro-1H-indazol-1-yl)methanone (CA-1)

To an oven dried microwave vial equipped with magnetic stir bar under an atmosphere of $N_2$, methyl (R or S)-1-(2-chloro-6-cyclopropylbenzoyl)-3-iodo-4,5,6,7-tetrahydro-1H-indazole-6-carboxylate i-20A (1 g, 2.06 mmol, 1 equiv) and DCM (6.9 mL, 0.3 M) were added. The reaction mixture was cooled to −78° C., and diisobutylaluminum hydride (6.19 mL, 1 M in THF, 3 equiv) was added. The reaction mixture was warmed to 0° C. over 1 h, and then quenched with 1 HCl (25 mL), and diluted with EtOAc (50 mL). The mixture was stirred vigorously for 1 h at room temperature. The layers were separated, the aqueous layer was extracted with EtOAc (3×50 mL), the combined organic layers were washed with brine, filtered through celite, and then concentrated in vacuo. The resulting oil was purified using $SiO_2$ gel chromatography to afford the title compound. MS: 457 (M+1).

Step 2. Preparation of tert-butyl 4-((R or S)-1-(2-chloro-6-cyclopropylbenzoyl)-6-(hydroxymethyl)-4,5,6,7-tetrahydro-1H-indazol-3-yl)cyclohex-3-ene-1-carboxylate (CA-2)

To an oven dried microwave vial equipped with magnetic stir bar under an atmosphere of $N_2$, (R or S)-(2-chloro-6-cyclopropylphenyl)(6-(hydroxymethyl)-3-iodo-4,5,6,7-tetrahydro-1H-indazol-1-yl)methanone (150 mg, 0.33 mmol, 1 equiv), Chloro(2-dicyclohexylphosphino-2',6'-dimethoxy-1,1'-biphenyl)[2-(2'-amino-1,1'-biphenyl)]palladium(II) (23.7 mg, 0.03 mmol, 0.1 equiv), racemic tert-butyl 4-(4,4,5,5-tetramethyl-1,3,2-dioxaborolan-2-yl)cyclohex-3-enecarboxylate (202 mg, 0.66 mmol, 2 equiv), and dioxane (1.64 mL, 0.2 M) were added, followed by potassium phosphate tribasic (985 µL, 1M, 3 equiv). The reaction mixture was heated to 80° C. for 24 h, and then cooled to room temperature. The crude reaction mixture was diluted with EtOAc (50 mL), filtered through celite, and concentrated in vacuo. The resulting oil was purified using $SiO_2$ gel chromatography to afford the title compound. MS: 511 (M+1).

Step 3. Preparation of tert-butyl 4-((R or S)-6-(azidomethyl)-1-(2-chloro-6-cyclopropylbenzoyl)-4,5,6,7-tetrahydro-1H-indazol-3-yl)cyclohex-3-ene-1-carboxylate (14A-1)

To an oven dried microwave vial equipped with magnetic stir bar under an atmosphere of $N_2$, tert-butyl 4-((R or S)-1-(2-chloro-6-cyclopropylbenzoyl)-6-(hydroxymethyl)-4,5,6,7-tetrahydro-1H-indazol-3-yl)cyclohex-3-ene-1-carboxylate (100 mg, 0.2 mmol, 1 equiv), and DCM (2 mL, 0.1 M) were added, followed by triphenylphosphine (100 mg, 0.4 mmol, 2 equiv), imidazole (27 mg, 0.4 mmol, 2 equiv), and iodine (75 mg, 0.3 mmol, 1.5 equiv), in that order. The reaction mixture was stirred at room temperature for 1 h, diluted with DCM (25 mL), filtered through Celite, and concentrated in vacuo. The resulting crude oil was taken up in NMP (1.6 mL, 0.1M), and sodium azide (32 mg, 0.49 mmol, 3 equiv) was added. The reaction mixture was stirred at room temperature for 2 h, and then purified using SiO$_2$ gel chromatography to afford title compound. MS: 536 (M+1).

Step 2. Preparation of 4-((R or S)-6-(aminomethyl)-1-(2-chloro-6-cyclopropylbenzoyl)-4,5,6,7-tetrahydro-1H-indazol-3-yl)cyclohex-3-ene-1-carboxylic Acid (14A)

To an oven dried microwave vial equipped with magnetic stir bar under an atmosphere of N$_2$, tert-butyl (racemic)-4-((R or S)-6-(azidomethyl)-1-(2-chloro-6-cyclopropylbenzoyl)-4,5,6,7-tetrahydro-1H-indazol-3-yl)cyclohex-3-ene-1-carboxylate (77 mg, 0.14 mmol, 1 equiv), and DCM (2 mL, 0.1 M) were added, followed by trifluoroacetic acid (359 µL, 0.1 M). The reaction mixture was stirred at room temperature for 1 h, and then concentrated in vacuo. The resulting crude oil was taken up in THF (575 µL, 0.1M), and water (144 µL, 0.1 M), and then triphenylphosphine (75 mg, 0.29 mmol, 2 equiv) was added. The reaction mixture was stirred at room temperature for 2 h, and then purified using mass directed reverse phase chromatography to afford title compound. MS: 454 (M+1). $^1$H NMR (DMSO-d6) δ (ppm): 12.16 (s, 1H), 7.87-7.81 (m, 3H), 7.37-7.31 (m, 2H), 7.01 (t, J=6.26 Hz, 1H), 6.19 (m, 1H), 3.44-3.39 (m, 2H), 2.94-2.89 (m, 2H), 2.73 (m, 1H), 2.64 (d, J=15.95 Hz, 1H), 2.53 (m, 1H), 2.34 (m, 1H), 2.28-2.21 (m, 2H), 2.12 (m, 1H), 2.04 (m, 1H), 1.93 (m, 1H), 1.87 (m, 1H), 1.56 (m, 1H), 1.39 (m, 1H), 0.79 (m, 1H), 0.70 (m, 1H), 0.64 (m, 1H), 0.58 (m, 1H).

Example 15A

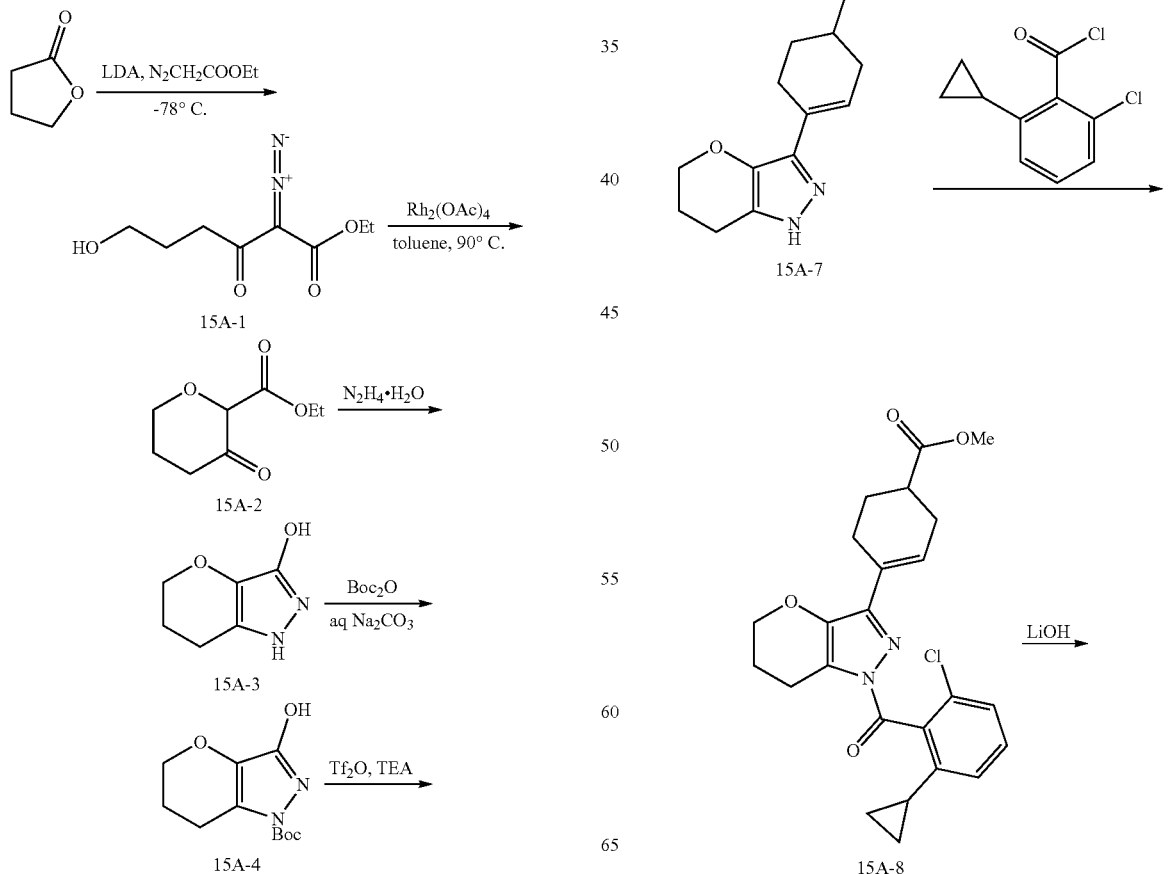
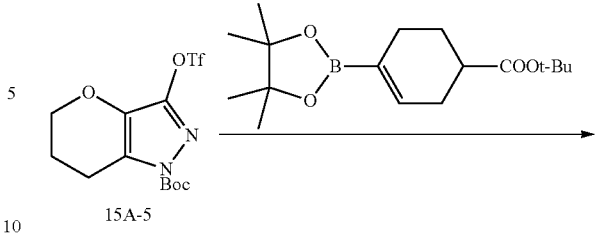
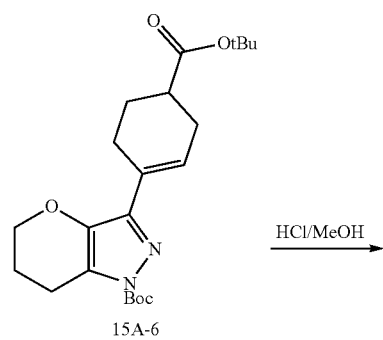
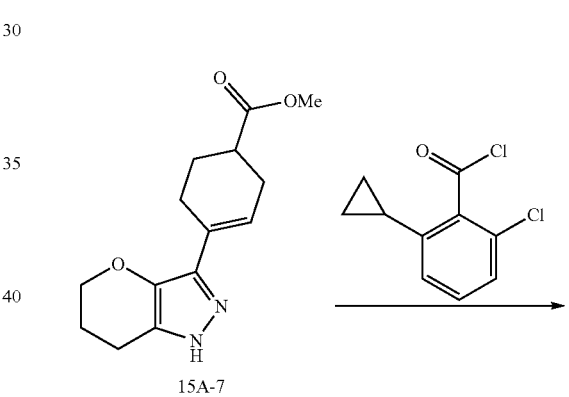
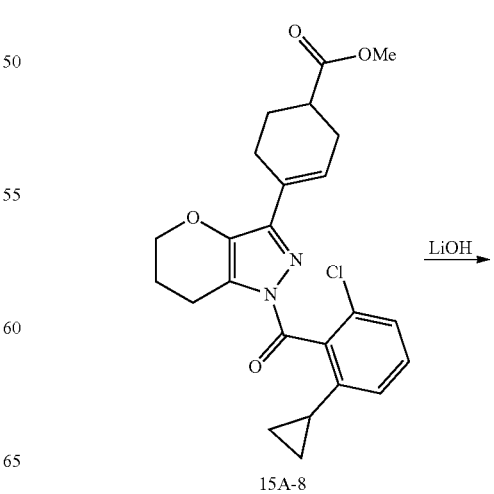

-continued

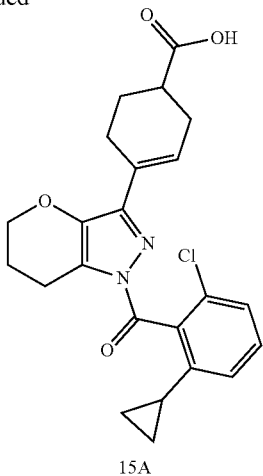

15A 4-(1-(2-chloro-6-cyclopropylbenzoyl)-1,5,6,7-tetra-hydropyrano[3,2-c]pyrazol-3-yl)cyclohex-3-ene-1-carboxylic Acid Step 1: Preparation of ethyl 2-diazo-6-hydroxy-3-oxohexanoate (15A-1)

Ethyl diazoacetate (21.87 g, 192 mmol) was added drop wise over 5 min to a cold solution of LDA (100 mL, 200 mmol) in THF (600 mL) under an atmosphere of nitrogen, the temperature being maintained at −78° C. The orange-brown solution was stirred at −78° C. for 15 min and this was followed by drop wise addition of dihydrofuran-2(3H)-one (15.0 g, 174 mmol) at −78° C. The solution was stirred at −78° C. for 2 h, before dropwise addition of acetic acid (40 mL). The reaction mixture was allowed to warm to 0° C., water (100 mL) was added, and then the mixture extracted with DCM (300 mL×3). The combined organic extracts were washed brine (50 mL), dried (MgSO$_4$), and evaporated. The crude product was purified by flash chromatography on silica gel (petroleum ether:EtOAc=10:1-2:1) to give the title compound. $^1$H NMR (400 MHz, CDCl$_3$) δ 4.26-4.33 (m, 2H), 3.60-3.70 (m, 2H), 2.97 (t, J=6.9 Hz, 2H), 1.88-1.93 (m, 2H), 1.30-1.34 (m, 3H).

Step 2: Preparation of ethyl 3-oxotetrahydro-2H-pyran-2-carboxylate (15A-2)

Solution of ethyl 2-diazo-6-hydroxy-3-oxohexanoate (2.00 g, 9.99 mmol) in toluene (100 mL) was added over 35 min to a suspension of rhodium(ii) acetate dimer (0.088 g, 0.200 mmol) in toluene (100 mL) at 90° C. The mixture was then stirred at 90° C. for 1 h. The reaction mixture was concentrated to give the title compound. $^1$H NMR (400 MHz, CDCl$_3$) δ 10.37 (s, 1H), 4.29-4.40 (m, 2H), 3.93-4.01 (m, 1H), 2.34-2.43 (m, 1H), 1.93-2.02 (m, 1H), 1.33-1.44 (m, 3H).

Step 3: Preparation of 1,5,6,7-tetrahydropyrano[3,2-c]pyrazol-3-ol (15A-3)

Hydrazine hydrate (0.324 mL, 10.34 mmol) was added to a stirred mixture of methyl 3-oxotetrahydro-2H-pyran-2-carboxylate (1.09 g, 6.89 mmol) in EtOH (15 mL), and the mixture was stirred at room temperature for 1 h. The mixture was concentrated to give the title compound. MS: 141 (M+1).

Step 4: Preparation of tert-butyl 3-hydroxy-6,7-dihydropyrano[3,2-c]pyrazole-1(5H)-carboxylate (15A-4)

(BOC)$_2$O (2.36 mL, 10.17 mmol) was added to a stirred mixture of 1,5,6,7-tetrahydropyrano[3,2-c]pyrazol-3-ol (950 mg, 6.78 mmol) and Na$_2$CO$_3$ (1.08 g, 10.17 mmol) in MeOH (15 mL) and water (3 mL) at 10° C. and the mixture was stirred at room temperature for 12 h. The mixture was filtered and the filter cake was washed with ethanol (50 mL). The filtrate was concentrated to dryness. The residue was purified by silica gel flash chromatography, eluting with CH$_2$Cl$_2$/MeOH=100:1-20:1 to give the title compound. $^1$H NMR (400 MHz, DMSO-d$_6$) δ 3.97-4.06 (m, 2H), 2.81 (t, J=6.3 Hz, 2H), 1.83-1.93 (m, 2H), 1.49 (s, 9H).

Step 5: Preparation of tert-butyl 3-(((trifluoromethyl)sulfonyl)oxy)-6,7-dihydropyrano[3,2-c]pyrazole-1(5H)-carboxylate (15A-5)

Tf$_2$O (0.387 mL, 2.289 mmol) was added to the mixture of TEA (0.319 mL, 2.289 mmol) and tert-butyl 3-hydroxy-6,7-dihydropyrano[3,2-c]pyrazole-1(5H)-carboxylate (500 mg, 2.081 mmol) in DCM (5 mL), the resultant mixture was stirred at room temperature for 1.5 h. The mixture was concentrated and the residue was purified by silica gel flash chromatography, eluting with petroleum ether/EtOAc=25:1-15:1 to give the title compound. MS: 373 (M+1). $^1$H NMR (400 MHz, CDCl$_3$) δ 4.10-4.25 (m, 2H), 3.00 (t, J=6.4 Hz, 2H), 1.96-2.13 (m, 2H), 1.63 (s, 9H).

Step 6: Preparation of tert-butyl 3-(4-(tert-butoxycarbonyl)cyclohex-1-en-1-yl)-6,7-dihydropyrano[3,2-c]pyrazole-1(5H)-carboxylate (15A-6)

PdCl$_2$(dppf) (0.138 g, 0.188 mmol) was added to the mixture of K$_2$CO$_3$ (1.039 g, 7.52 mmol) and tert-butyl 3-(((trifluoromethyl)sulfonyl)oxy)-6,7-dihydropyrano[3,2-c]pyrazole-1(5H)-carboxylate (1.40 g, 3.76 mmol) and tert-butyl 4-(4,4,5,5-tetramethyl-1,3,2-dioxaborolan-2-yl)cyclohex-3-enecarboxylate (1.275 g, 4.14 mmol) in dioxane (25 mL) and water (3.0 mL), the resultant mixture was stirred at 70° C. for 10 h. The mixture was cooled, diluted with ethyl acetate (50 mL), washed with brine (10 mL), dried (Na$_2$SO$_4$), filtered and the solvent was evaporated under reduced pressure. The residue was purified by silica gel flash chromatography, eluting with petroleum ether/EtOAc=10:1-2:1 to give the title compound. MS: 405 (M+1).

Step 7: methyl 4-(1,5,6,7-tetrahydropyrano[3,2-c]pyrazol-3-yl)cyclohex-3-ene-1-carboxylate (15A-7)

HCl/MeOH (~4 M, 5 mL, 20.0 mmol) was added to the solution of tert-butyl 3-(4-(tert-butoxycarbonyl)cyclohex-1-en-1-yl)-6,7-dihydropyrano[3,2-c]pyrazole-1 (5H)-carboxylate (150 mg, 0.371 mmol) in MeOH (10 mL). The resultant mixture was stirred at room temperature for 30 h. The reaction mixture was concentrated to give the title compound. MS: 263 (M+1).

Step 8: Preparation of methyl 4-(1-(2-chloro-6-cyclopropylbenzoyl)-1,5,6,7-tetrahydropyrano[3,2-c]pyrazol-3-yl)cyclohex-3-ene-1-carboxylate (15A-8)

2-chloro-6-cyclopropylbenzoyl chloride (73 mg, 0.339 mmol) was added to a stirred mixture of DMAP (34 mg, 0.278 mmol), TEA (0.138 mL, 0.988 mmol) and methyl 4-(1,5,6,7-tetrahydropyrano[3,2-c]pyrazol-3-yl)cyclohex-3-ene-1-carboxylate (50 mg, 0.191 mmol) in THF (5 mL) at room temperature and the mixture was stirred at 65° C. for 12 h. The mixture was evaporated under reduced pressure. The residue was purified by silica gel flash chromatography, eluting with petroleum ether/EtOAc=10:1-3:1 to give the title compound. MS: 441 (M+1).

Step 9: Preparation of 4-(1-(2-chloro-6-cyclopropylbenzoyl)-1,5,6,7-tetrahydropyrano[3,2-c]pyrazol-3-yl)cyclohex-3-enecarboxylic Acid (15A)

LiOH.H$_2$O (100 mg, 2.38 mmol) was added to the solution of methyl 4-(1-(2-chloro-6-cyclopropylbenzoyl)-1,5,6,7-tetrahydropyrano[3,2-c]pyrazol-3-yl)cyclohex-3-enecarboxylate (43 mg, 0.098 mmol) in MeOH (3 mL) and water (0.5 mL), the resultant mixture was stirred at room temperature for 5 h. The mixture was neutralized with aq. HCl (6 M) to pH~7. The solvent was evaporated under reduced pressure. The residue was purified by preparative HPLC, eluting with acetonitrile/water+0.1% HCOOH, to give the title compound. $^1$H NMR (400 MHz, MeOD) δ 7.21-7.37 (m, 2H), 7.01 (d, J=7.7 Hz, 1H), 6.71 (brs, 1H), 4.22 (d, J=2.9 Hz, 2H), 3.18 (t, J=6.4 Hz, 2H), 2.25-2.58 (m, 4H), 1.95-2.15 (m, 3H), 1.57-1.78 (m, 2H), 0.80-0.90 (m, 1H), 0.66-0.79 (m, 2H), 0.51-0.62 (m, 1H).

Example 16A

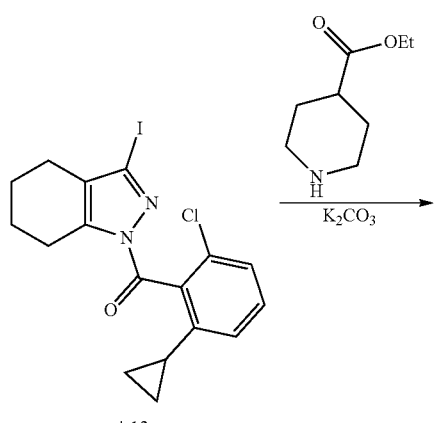

i-13a

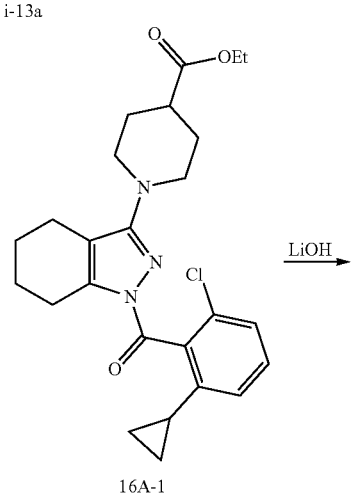

16A-1

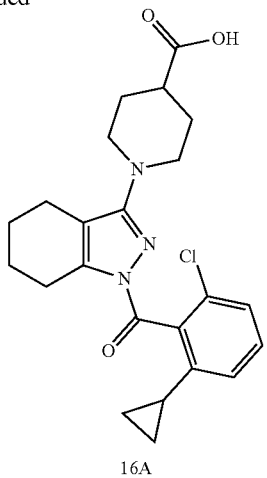

16A

Step 1. Preparation of ethyl 1-(1-(2-chloro-6-cyclopropylbenzoyl)-4,5,6,7-tetrahydro-1H-indazol-3-yl)piperidine-4-carboxylate (16A-1)

To a mixture of (2-chloro-6-cyclopropylphenyl)(3-iodo-4,5,6,7-tetrahydro-1H-indazol-1-yl)methanone (500 mg, 1.3 mmol), ethyl piperidine-4-carboxylate (2004 mg, 12.8 mmol) and K$_2$CO$_3$ (440 mg, 3.2 mmol) in DMF (5 mL) was added Chloro-(2-Dicyclohexylphosphino-2',6'-diisopropoxy-1,1'-biphenyl)[2-(2-aminoethyl)phenyl]palladium (II)-methyl-t-butyl ether adduct (312 mg, 0.4 mmol). The reaction mixture was stirred at 100° C. for 8 h under N$_2$. It was cooled and concentrated. The residue was extracted with ethyl acetate (50 mL). The combined organic fractions were washed with brine (10 mL), dried (Na$_2$SO$_4$), filtered and the solvent was evaporated under reduced pressure. The residue was purified with column chromatography on silica, eluting with (petroleum ether:EtOAc=10:1) to give the title compound. MS: 456 (M+1). $^1$H NMR (400 MHz, CDCl$_3$,) δ 7.17-7.10 (m, 2H), 6.83 (d, J=5.9 Hz, 1H), 4.05 (q, J=7.0 Hz, 2H), 3.56-3.41 (m, 2H), 3.16-2.99 (m, 2H), 2.62 (t, J=11.3 Hz, 2H), 2.38 (brs, 2H), 2.31 (t, J=11.0 Hz, 1H), 1.80-1.66 (m, 8H), 1.18 (d, J=5.9 Hz, 3H), 0.81-0.74 (m, 1H), 0.72-0.59 (m, 2H), 0.54 (d, J=3.9 Hz, 1H).

Step 2. Preparation of 1-(1-(2-chloro-6-cyclopropylbenzoyl)-4,5,6,7-tetrahydro-1H-indazol-3-yl)piperidine-4-carboxylic Acid (16A)

To a solution of ethyl 1-(1-(2-chloro-6-cyclopropylbenzoyl)-4,5,6,7-tetrahydro-1H-indazol-3-yl)piperidine-4-carboxylate (50 mg, 0.1 mmol) in 1,4-dioxane (1 mL)/water (0.5 mL) was added lithium hydroxide hydrate (23 mg, 0.5 mmol). It was stirred at 30° C. for 2 h. The mixture was cooled and acidified to pH=1. The mixture was extracted with ethyl acetate (20 mL). The combined organic fractions were washed with brine (10 mL), dried (Na$_2$SO$_4$), filtered and the solvent was evaporated under reduced pressure. The crude product was purified by prep-HPLC to give the title compound. MS: 428 (M+1). $^1$H NMR (400 MHz, CDCl$_3$) δ 7.22-7.15 (m, 2H), 6.88 (d, J=6.7 Hz, 1H), 3.61-3.47 (m, 2H), 3.19-3.09 (m, 2H), 2.74 (t, J=11.9 Hz, 2H), 2.44 (brs, 3H), 1.91-1.73 (m, 9H), 0.90-0.53 (m, 4H).

Example 17A

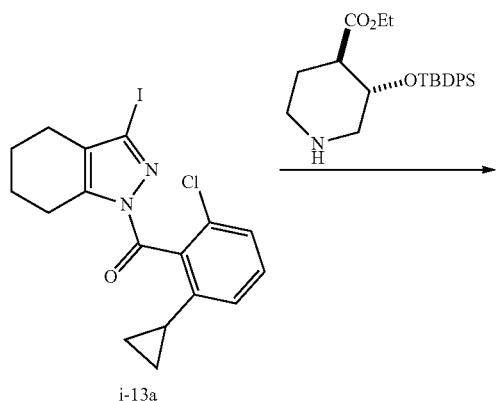

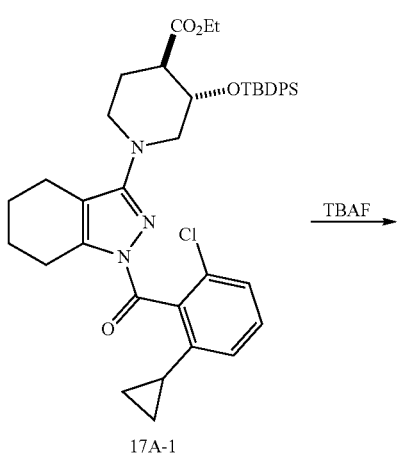

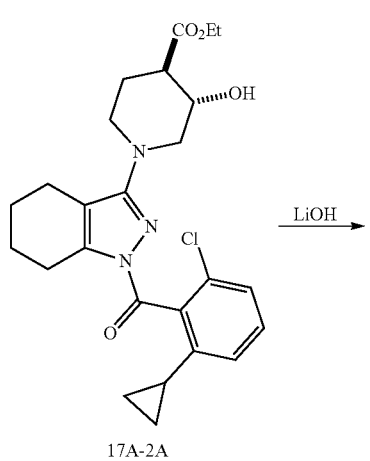

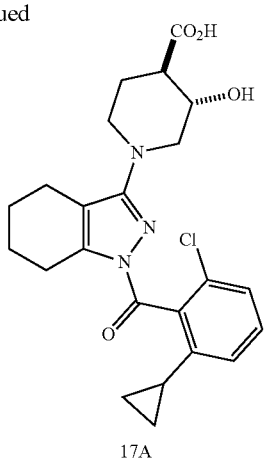

17A

Trans-(3R or S,4R or S)-1-(1-(2-chloro-6-cyclopropylbenzoyl)-4,5,6,7-tetrahydro-1H-indazol-3-yl)-3-hydroxypiperidine-4-carboxylic Acid Step 1. Preparation of ethyl-trans-3-((tert-butyldiphenylsilyl)oxy)-1-(1-(2-chloro-6-cyclopropylbenzoyl)-4,5,6,7-tetrahydro-1H-indazol-3-yl)piperidine-4-carboxylate (17A-1)

To an oven dried microwave vial equipped with magnetic stir bar under an atmosphere of $N_2$, (2-chloro-6-cyclopropylphenyl)(3-iodo-4,5,6,7-tetrahydro-1H-indazol-1-yl)methanone i-13a (500 mg, 1.17 mmol, 1.0 equiv), trans-ethyl 3-((tert-butyldiphenylsilyl)oxy)piperidine-4-carboxylate (WO 2014/028600) (724 mg, 1.76 mmol, 1.5 equiv), copper(I) iodide (67 mg, 0.35 mmol, 0.3 equiv), 2-((2,6-dimethoxyphenyl)amino)-2-oxoacetic acid (158 mg, 0.7 mmol, 0.6 equiv), and potassium phosphate tribasic (746 mg, 3.52 mmol, 3 equiv) were added, followed by the addition of DMSO (11.7 mL, 0.1 M). The reaction mixture was stirred at 80° C. for 24 h. The resulting solution was purified using $SiO_2$ gel chromatography to afford desired product. MS: 710 (M+1).

Step 2. Preparation of ethyl trans-(3R or S,4R or S)-1-(1-(2-chloro-6-cyclopropylbenzoyl)-4,5,6,7-tetrahydro-1H-indazol-3-yl)-3-hydroxypiperidine-4-carboxylate and trans-ethyl (3R or S,4R or S)-1-(1-(2-chloro-6-cyclopropylbenzoyl)-4,5,6,7-tetrahydro-1H-indazol-3-yl)-3-hydroxypiperidine-4-carboxylate (17A-2A)

To an oven dried microwave vial equipped with magnetic stir bar under an atmosphere of $N_2$, ethyl-trans-3-((tert-butyldiphenylsilyl)oxy)-1-(1-(2-chloro-6-cyclopropylbenzoyl)-4,5,6,7-tetrahydro-1H-indazol-3-yl)piperidine-4-carboxylate (270 mg, 0.38 mmol, 1.0 equiv), tetrabutyl ammonium fluoride (TBAF, 760 μL, 0.76 mmol, 1 M in THF), and THF (1.9 mL, 0.1 M) were added. The reaction mixture was stirred at room temperature for 2 h. The resulting solution was purified using $SiO_2$ gel chromatography to yield mixture of isomers. MS: 472 (M+1).

The mixture of stereoisomers were purified by chiral SFC (OJ-H column, 35%/65% MeOH+0.25% DMEA/$CO_2$) to afford Isomer 17A-2A (faster eluting): MS: 472 (M+1). Isomer 17A-2B (slower eluting): MS: 472 (M+1).

121

Step 3. Preparation of Trans-(3R or S,4R or S)-1-(1-(2-chloro-6-cyclopropylbenzoyl)-4,5,6,7-tetrahydro-1H-indazol-3-yl)-3-hydroxypiperidine-4-carboxylic Acid (17A)

To an oven dried microwave vial equipped with magnetic stir bar under an atmosphere of $N_2$, ethyl trans-(3R or S,4R or S)-1-(1-(2-chloro-6-cyclopropylbenzoyl)-4,5,6,7-tetrahydro-1H-indazol-3-yl)-3-hydroxypiperidine-4-carboxylate 17A-2A (55 mg, 0.12 mmol, 1 equiv), THF (770 µL, 0.1 M) and water (388 µL, 0.1 M) were added, followed by lithium hydroxide (8.4 mg, 0.35 mmol, 3 equiv). The reaction mixture was stirred at room temperature for 3 h, and then concentrated in vacuo. The resulting oil was purified using mass directed reverse phase chromatography to afford title compound. MS: 444 (M+1). $^1$H NMR (DMSO-d6) δ (ppm): 7.27 (dd, J=15.85, 7.88 Hz, 2H), 6.93 (d, J=7.37 Hz, 1H), 3.54-3.49 (m, 2H), 3.37 (m, 1H), 3.00-2.93 (m, 2H), 2.49-2.43 (m, 3H), 2.40 (m, 1H), 2.30 (m, 1H), 2.11 (m, 1H), 1.76-1.58 (m, 5H), 1.51 (m, 1H), 0.80 (m, 1H), 0.72 (m, 1H), 0.62-0.58 (m, 2H).

Example 17B

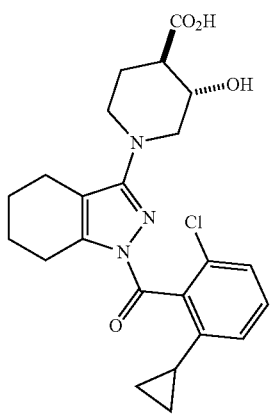 [SMILES: O=C(O)[C@@H]1CCN(c2nn(C(=O)c3c(Cl)cccc3C3CC3)c3c2CCCC3)C[C@H]1O]

Trans-(3R or S,4R or S)-1-(1-(2-chloro-6-cyclopropylbenzoyl)-4,5,6,7-tetrahydro-1H-indazol-3-yl)-3-hydroxypiperidine-4-carboxylic Acid To an oven dried microwave vial equipped with magnetic stir bar under an atmosphere of $N_2$, ethyl trans-(3R or S,4R or S)-1-(1-(2-chloro-6-cyclopropylbenzoyl)-4,5,6,7-tetrahydro-1H-indazol-3-yl)-3-hydroxypiperidine-4-carboxylate 17A-2B (55 mg, 0.12 mmol, 1 equiv), THF (770 µL, 0.1 M) and water (388 µL, 0.1 M) were added, followed by lithium hydroxide (8.4 mg, 0.35 mmol, 3 equiv). The reaction mixture was stirred at room temperature for 3 h, and then concentrated in vacuo. The resulting oil was purified using mass directed reverse phase chromatography to afford the title compound. MS: 444 (M+1). $^1$H NMR (DMSO-d6) δ (ppm): 7.27 (dd, J=15.85, 7.88 Hz, 2H), 6.93 (d, J=7.37 Hz, 1H), 3.54-3.49 (m, 2H), 3.37 (m, 1H), 3.00-2.93 (m, 2H), 2.49-2.43 (m, 3H), 2.40 (m, 1H), 2.30 (m, 1H), 2.11 (m, 1H), 1.76-1.58 (m, 5H), 1.51 (m, 1H), 0.80 (m, 1H), 0.72 (m, 1H), 0.62-0.58 (m, 2H).

122

Example 18A

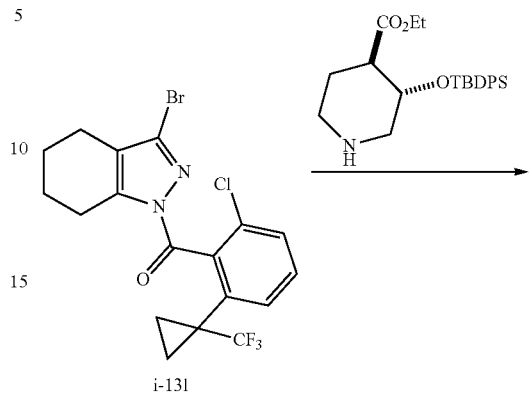

i-131

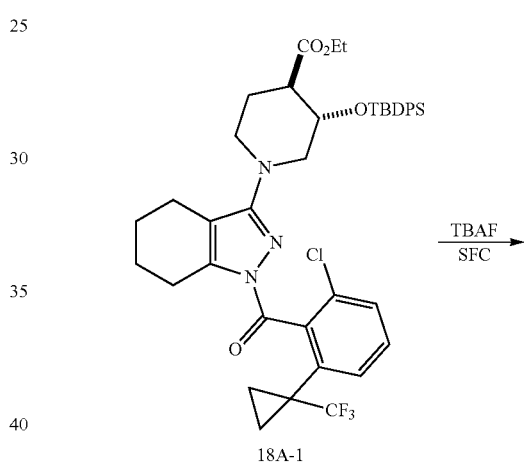

18A-1

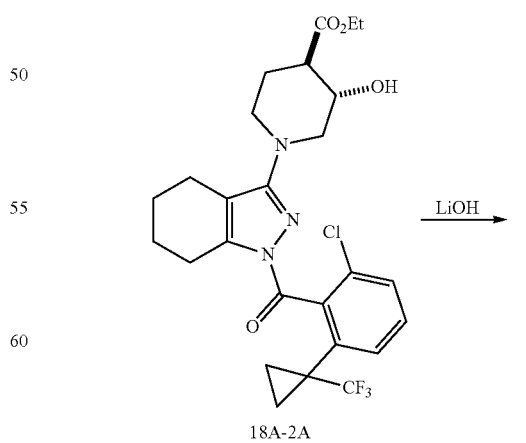

18A-2A

-continued

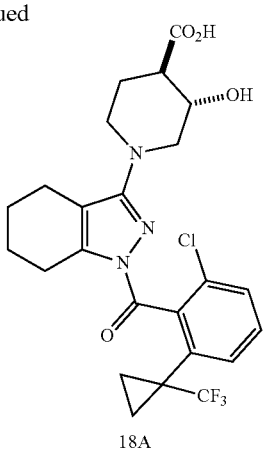

18A

Trans-(3R or S,4R or S)-1-(1-(2-chloro-6-(1-(trifluoromethyl)cyclopropyl)benzoyl)-4,5,6,7-tetrahydro-1H-indazol-3-yl)-3-hydroxypiperidine-4-carboxylic Acid Step 1. Preparation of ethyl trans-3-((tert-butyldiphenylsilyl)oxy)-1-(1-(2-chloro-6-(1-(trifluoromethyl)cyclopropyl)benzoyl)-4,5,6,7-tetrahydro-1H-indazol-3-yl)piperidine-4-carboxylate (18A-1)

To an oven dried microwave vial equipped with magnetic stir bar under an atmosphere of $N_2$, (2-chloro-6-cyclopropylphenyl)(3-iodo-4,5,6,7-tetrahydro-1H-indazol-1-yl) methanone i-131 (250 mg, 0.56 mmol, 1.0 equiv), trans-ethyl 3-((tert-butyldiphenylsilyl)oxy)piperidine-4-carboxylate (WO 2014/028600) (345 mg, 0.84 mmol, 1.5 equiv), chloro(2-dicyclohexylphosphino-2',6'-diisopropoxy-1,1'-biphenyl)[2-(2'-amino-1,1'-biphenyl)]palladium(II) (81 mg, 0.11 mmol, 0.2 equiv), and cesium carbonate (546 mg, 1.68 mmol, 3 equiv) were added, followed by dioxane (2.8 mL, 0.1 M). The reaction mixture was stirred at 80° C. for 24 h. The resulting solution was purified using $SiO_2$ gel chromatography to afford desired product. MS: 778 (M+1).

Step 2. Preparation of ethyl trans-(3R or S,4R or S)-1-(1-(2-chloro-6-(1-(trifluoromethyl)cyclopropyl) benzoyl)-4,5,6,7-tetrahydro-1H-indazol-3-yl)-3-hydroxypiperidine-4-carboxylate (18A-2A)

To an oven dried microwave vial equipped with magnetic stir bar under an atmosphere of $N_2$, ethyl trans-3-((tert-butyldiphenylsilyl)oxy)-1-(1-(2-chloro-6-(1-(trifluoromethyl)cyclopropyl)benzoyl)-4,5,6,7-tetrahydro-1H-indazol-3-yl)piperidine-4-carboxylate (650 mg, 0.84 mmol, 1.0 equiv), tetrabutyl ammonium fluoride (TBAF, 2.5 mL, 2.5 mmol, 1 M in THF), and THF (4.2 mL, 0.1 M) were added. The reaction mixture was stirred at room temperature for 2 h. The resulting solution was purified using $SiO_2$ gel chromatography to yield mixture of isomers. MS: 540 (M+1).

The mixture of stereoisomers were purified by chiral SFC (Phenomenex Lux-2 column, 15%/85% MeOH+0.25% DMEA/$CO_2$) to afford Isomer 18A-2A (faster eluting): MS: 540 (M+1). Isomer 18A-2B (slower eluting): MS: 540 (M+1).

Step 3. Preparation of Trans-(3R or S,4R or S)-1-(1-(2-chloro-6-(1-(trifluoromethyl)cyclopropyl)benzoyl)-4,5,6,7-tetrahydro-1H-indazol-3-yl)-3-hydroxypiperidine-4-carboxylic Acid (18A)

To an oven dried microwave vial equipped with magnetic stir bar under an atmosphere of $N_2$, ethyl trans-(3R or S,4R or S)-1-(1-(2-chloro-6-(1-(trifluoromethyl)cyclopropyl)benzoyl)-4,5,6,7-tetrahydro-1H-indazol-3-yl)-3-hydroxypiperidine-4-carboxylate 18A-2A (125 mg, 0.23 mmol, 1 equiv), THF (1.85 mL, 0.1 M) and water (463 μL, 0.1 M) were added, followed by lithium hydroxide (16.6 mg, 0.69 mmol, 3 equiv). The reaction mixture was stirred at room temperature for 3 h, and then concentrated in vacuo. The resulting oil was purified using mass directed reverse phase chromatography to afford title compound. MS: 512 (M+1). $^1$H NMR (DMSO-d6) δ (ppm): 7.27 (dd, J=15.85, 7.88 Hz, 2H), 6.93 (d, J=7.37 Hz, 1H), 3.54-3.49 (m, 2H), 3.37 (m, 1H), 3.00-2.93 (m, 2H), 2.49-2.43 (m, 3H), 2.40 (m, 1H), 2.30 (m, 1H), 2.11 (m, 1H), 1.76-1.58 (m, 5H), 1.51 (m, 1H), 0.80 (m, 1H), 0.72 (m, 1H), 0.62-0.58 (m, 2H).

Example 18B

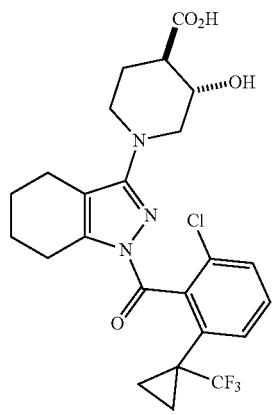 [SMILES: O=C(O)[C@@H]1CCN(c2nn(C(=O)c3c(Cl)cccc3C3(C(F)(F)F)CC3)c3c2CCCC3)C[C@H]1O]

Trans-(3R or S,4R or S)-1-(1-(2-chloro-6-(1-(trifluoromethyl)cyclopropyl)benzoyl)-4,5,6,7-tetrahydro-1H-indazol-3-yl)-3-hydroxypiperidine-4-carboxylic Acid To an oven dried microwave vial equipped with magnetic stir bar under an atmosphere of $N_2$, ethyl trans-(3R or S,4R or S)-1-(1-(2-chloro-6-(1-(trifluoromethyl)cyclopropyl)benzoyl)-4,5,6,7-tetrahydro-1H-indazol-3-yl)-3-hydroxypiperidine-4-carboxylate 18A-2B (125 mg, 0.23 mmol, 1 equiv), THF (1.85 mL, 0.1 M) and water (463 μL, 0.1 M) were added, followed by lithium hydroxide (16.6 mg, 0.69 mmol, 3 equiv). The reaction mixture was stirred at room temperature for 3 h, and then concentrated in vacuo. The resulting oil was purified using mass directed reverse phase chromatography to afford desired product. MS: 512 (M+1). $^1$H NMR (DMSO-d6) δ (ppm): 7.27 (dd, J=15.85, 7.88 Hz, 2H), 6.93 (d, J=7.37 Hz, 1H), 3.54-3.49 (m, 2H), 3.37 (m, 1H), 3.00-2.93 (m, 2H), 2.49-2.43 (m, 3H), 2.40 (m, 1H), 2.30 (m, 1H), 2.11 (m, 1H), 1.76-1.58 (m, 5H), 1.51 (m, 1H), 0.80 (m, 1H), 0.72 (m, 1H), 0.62-0.58 (m, 2H).

Example 19A

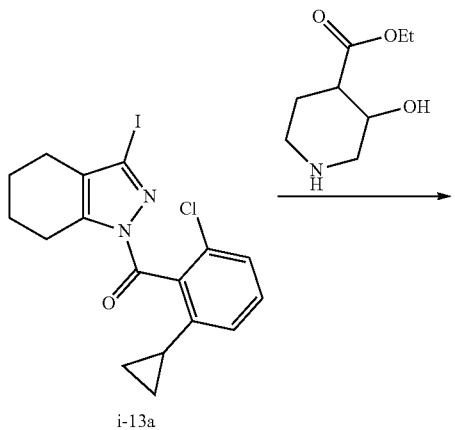

i-13a

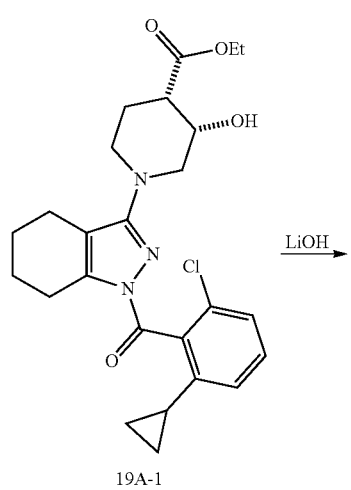

19A-1

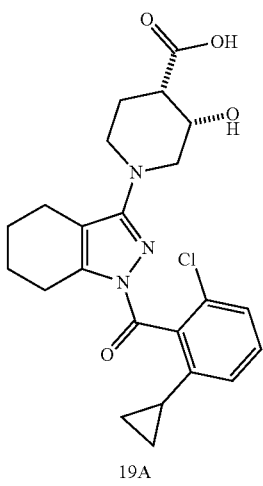

19A cis 1-(1-(2-chloro-6-cyclopropylbenzoyl)-4,5,6,7-tetrahydro-1H-indazol-3-yl)-3-hydroxypiperidine-4-carboxylic Acid Step 1. Preparation of cis-ethyl 1-(1-(2-chloro-6-cyclopropylbenzoyl)-4,5,6,7-tetrahydro-1H-indazol-3-yl)-3-hydroxypiperidine-4-carboxylate (19A-1)

To a solution of (2-chloro-6-cyclopropylphenyl)(3-iodo-4,5,6,7-tetrahydro-1H-indazol-1-yl)methanone (250 mg, 0.586 mmol) in toluene (5 mL) was added ethyl 3-hydroxypiperidine-4-carboxylate (200 mg, 1.15 mmol) and $Cs_2CO_3$ (400 mg, 1.23 mmol), the resulting mixture was purged with $N_2$. Chloro[2-(dicyclohexylphosphino)-3,6-dimethoxy-2',4',6'-triisopropyl-1,1'-biphenyl][2-(2-aminoethyl)phenyl]palladium(II) (30 mg, 0.038 mmol) was then added under $N_2$ atmosphere and the resulting suspension was stirred at 120° C. overnight. The reaction was then cooled and concentrated. The residue was purified by preparative TLC (petroleum ether:EtOAc=5:1 and then DCM:THF=20:1) to give the title compound. MS: 472 (M+1). 1H NMR (400 MHz, MeOD) δ 7.26-7.33 (m, 1H), 7.20-7.25 (m, 1H), 6.99 (d, J=7.8 Hz, 1H), 4.09-4.21 (m, 3H), 3.56-3.68 (m, 2H), 3.08 (brs 2H), 2.83 (d, J=13.3 Hz, 1H), 2.60-2.70 (m, 1H), 2.45-2.59 (m, 3H), 1.98-2.10 (m, 1H), 1.87 (brs, 2H), 1.64-1.81 (m, 3H), 1.24 (t, J=7.0 Hz, 3H), 0.99 (d, J=6.7 Hz, 1H), 0.82-0.90 (m, 2H), 0.58-0.78 (m, 3H).

Step 2: Preparation of cis 1-(1-(2-chloro-6-cyclopropylbenzoyl)-4,5,6,7-tetrahydro-1H-indazol-3-yl)-3-hydroxypiperidine-4-carboxylic Acid (19A)

To a solution of cis ethyl 1-(1-(2-chloro-6-cyclopropylbenzoyl)-4,5,6,7-tetrahydro-1H-indazol-3-yl)-3-hydroxypiperidine-4-carboxylate (8 mg, 0.017 mmol) in THF (2 mL) and water (1 mL) was added aq LiOH (10 µL, 0.050 mmol, 5.0 M), the resulting mixture was stirred at room temperature for 2 h, adjusted to pH 7 with 1 M HCl and purified by preparative HPLC to afford the title compound. MS: 444 (M+1). $^1$H NMR (400 MHz, MeOD) δ 7.20-7.32 (m, 2H), 6.99 (d, J=7.4 Hz, 1H), 4.19 (s, 1H), 3.54-3.71 (m, 2H), 3.32-3.37 (m, 1H), 3.08 (brs, 2H), 2.83 (d, J=12.9 Hz, 1H), 2.60-2.70 (m, 1H), 2.53 (d, J=5.9 Hz, 3H), 1.98-2.12 (m, 1H), 1.64-1.93 (m, 6H), 0.79-0.91 (m, 1H), 0.55-0.77 (m, 3H).

Biological Assay

The compounds of the invention inhibit RORgammaT activity. Activation of RORgammaT activity can be measured using, e.g., biochemical TR-FRET assay. In such an assay, interaction of cofactor-derived peptides with human RORgammaT-Ligand Binding Domain (LBD) can be measured. The TR-FRET technique is a sensitive biochemical proximity assay that will give information concerning the interaction of a ligand with the LBD, in the presence of cofactor-derived peptides (Zhou et al., Methods 25:54-61, 2001).

To identify novel antagonists of RORgammaT, an assay was developed which employs the interaction of RORgammaT with its co-activator peptide SRC1_2. This peptide mimics the recruitment of co-activators to RORgammaT through its interaction with the LXXLL (e.g., NR box) motifs (Xie et al., J. Immunol. 175: 3800-09, 2005; Kurebayashi et al., Biochem. Biophys. Res. Commun. 315: 919-27, 2004; Jin et al., Mol. Endocrinology 24:923-29, 2010). The RORγ-Ligand Binding Domain TR-FRET Assay was run according to the following protocol.

HIS-tagged RORγ-LBD protein was recombinantly expressed in *Escherichia coli*. The RORγ-LBD protein was purified by Ni2+-affinity resin. Purified protein was then diluted in assay buffer (50 mM Tris pH 7.0, 50 mM KCl, 1 mM EDTA, 0.1 mM DTT, 100 mg/ml bovine serum albumin, delipidated) to obtain a RORγ-LBD final concentration of 3 nM. Europium tagged anti-HIS antibody was also added to this solution (1.25 nM). Separately, SF9 cells not expressing any recombinant protein were lysed (32,000 cells per ml in 25 mM Tris, 50 mM NaCl) and the previously frozen lysate was added to the diluted RORγ-LBD solution at a ratio of 0.75 ml SF9 lysate per 15 ml of diluted RORγ-LBD.

Compounds to be tested were injected to the 384-well assay plate using Acoustic Droplet Ejection technology by Echo 550 liquid handler (Labcyte, Calif.).

A stock of biotinylated-LXXLL peptide from coactivator SRC1 (Biotin-SPSSHSSLTERHKILHRLLQEGSP) (SEQ ID NO: 1) and APC-conjugated streptavidin (final concentrations 100 nM and 8 nM respectively) were also added to each well.

The final assay mixture was incubated overnight at 4° C., warmed to room temperature and the fluorescence signal was measured on an Envision plate reader: (Excitation filter=340 nm; APC emission=665 nm; Europium emission=615 nm; dichroic mirror=D400/D630; delay time=100 μs, integration time=200 μs). IC50 values for test compounds were calculated from the quotient of the fluorescence signal at 665 nm divided by the fluorescence signal at 615 nm.

The $IC_{50}$ values for representative compounds of the invention are set forth below.

| Example No. | Fret $IC_{50}$ (nM) |
|---|---|
| 1A | 22 |
| 1B | 73 |
| 1C | 130 |
| 1D | 38 |
| 1E | 33 |
| 1F | 1171 |
| 2A-A | 56 |
| 2A-B | 102 |
| 2B-A | 728 |
| 2B-B | 978 |
| 2C-A | 676 |
| 2C-B | 1050 |
| 3A | 1809 |
| 3B | 334 |
| 4A | 14 |
| 5A | 354 |
| 6A | 173 |
| 7A | 9 |
| 7B | 14 |
| 7C | 15 |
| 7D | 5 |
| 8A | 1801 |
| 8B | 475 |
| 9A | 3990 |
| 9B | 1986 |
| 10A | 57 |
| 10B | 32 |
| 11A | 16 |
| 12A | 255 |
| 13A | 11 |
| 13B | 34 |
| 14A | 1196 |
| 15A | 56 |
| 16A | 149 |
| 17A | 19 |
| 17B | 681 |

-continued

| Example No. | Fret $IC_{50}$ (nM) |
|---|---|
| 18A | 598 |
| 18B | 10 |
| 19A | 1197 |

INCORPORATION BY REFERENCE

The entire disclosure of each of the patent documents and scientific articles referred to herein is incorporated by reference for all purposes.

EQUIVALENTS

The invention may be embodied in other specific forms without departing from the spirit or essential characteristics thereof. The foregoing embodiments are therefore to be considered in all respects illustrative rather than limiting the invention described herein. Scope of the invention is thus indicated by the appended claims rather than by the foregoing description, and all changes that come within.

What is claimed is:

1. A compound according to Formula I:

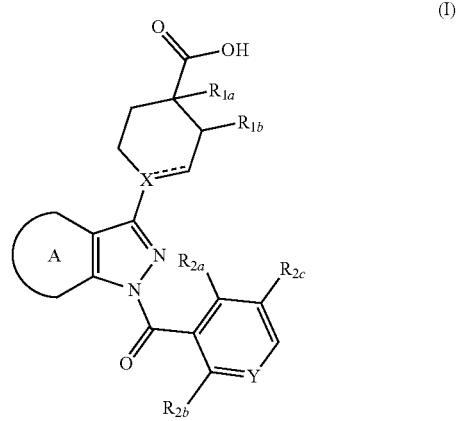

wherein:
Ring A is selected from:

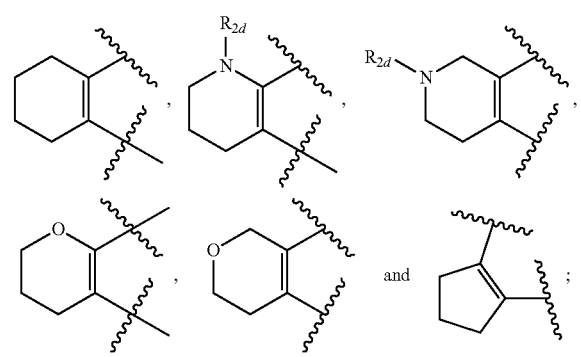

each optionally substituted with one or two substituents independently selected from OH, halogen, $(C_{1-4})$alkyl and $(C=O)O(C_{1-4})$alkyl, wherein a carbon in the $(C_{1-4})$alkyl chain may bond to a carbon on Ring A and form a spirocyclic moiety, wherein (C$_{1-4}$)alkyl is optionally substituted with OH, methylpyrrolidinyl, NH$_2$ or oxo;

X is N or C, wherein when X is N then the dashed line is absent and when X is C the dashed line represents a double bond;

Y is N or CH;

R$_{1a}$ is H or (C$_{1-4}$)alkyl;

R$_{1b}$ is H, OH or (C$_{1-4}$)alkyl;

R$_{2a}$ is Cl or (C$_{1-4}$)alkyl;

R$_{2b}$ is cyclopropyl, cyclobutyl, oxetanyl or azetidinyl, each optionally substituted with (C$_{1-4}$)alkyl, F, CF$_3$, CHF$_2$ or CN;

R$_{2c}$, is H or F; and

R$_{2d}$ is H or (C$_{1-4}$)alkyl;

or a pharmaceutically acceptable salt thereof.

2. A compound according to claim 1, wherein X is C.
3. A compound according to claim 2, wherein Y is CH.
4. A compound according to claim 3, wherein R$_{1a}$ is H.
5. A compound according to claim 4, wherein R$_{1b}$ is H or OH.
6. A compound according to claim 3, wherein R$_{2a}$ is Cl.
7. A compound according to claim 6, wherein R$_{2b}$ is cyclopropyl optionally substituted with CF$_3$.
8. A compound according to claim 7, wherein R$_{2c}$ is H.
9. A compound according to Claim 1, wherein R$_{2d}$ is H.
10. A compound according to claim 1, wherein Ring A is

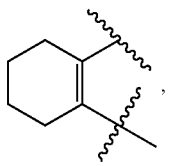 [SMILES: *C1=C(*)CCCC1]

optionally substituted with one or two substituents independently selected from halogen and (C$_{1-4}$)alkyl, wherein the (C$_{1-4}$)alkyl is optionally substituted with OH or NH$_2$.

11. A compound according to claim 1, wherein:
Ring A is selected from:

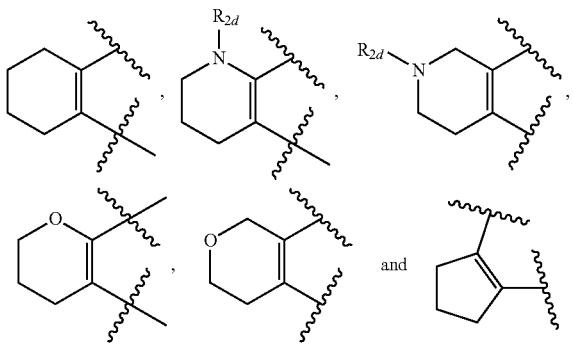

each optionally substituted with one or two substituents independently selected from OH, F, (C$_{1-4}$)alkyl and (C=O)O(C$_{1-4}$)alkyl, wherein a carbon in the (C$_{1-4}$) alkyl chain may bond to a carbon on Ring A and form a spirocyclic moiety, wherein (C$_{1-4}$)alkyl is optionally substituted with OH, methylpyrrolidinyl, NH$_2$ or oxo;

X is N or C, wherein when X is N then the dashed line is absent and when X is C the dashed line represents a double bond;

Y is N or CH;

R$_{1a}$ is H or methyl;

R$_{1b}$ is H, OH or methyl;

R$_{2a}$ is Cl or methyl;

R$_{2b}$ is cyclopropyl, cyclobutyl, oxetanyl or azetidinyl, each optionally substituted with methyl, F, CF$_3$, CHF$_2$ and CN;

R$_{2c}$, is H or F; and

R$_{2d}$ is H or (C$_{1-4}$)alkyl;

or a pharmaceutically acceptable salt thereof.

12. A compound according to claim 1, wherein the compound is represented by Formula II:

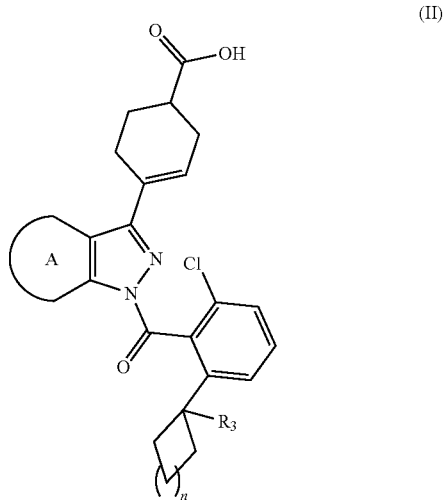

(II)

wherein:

Ring A is selected from:

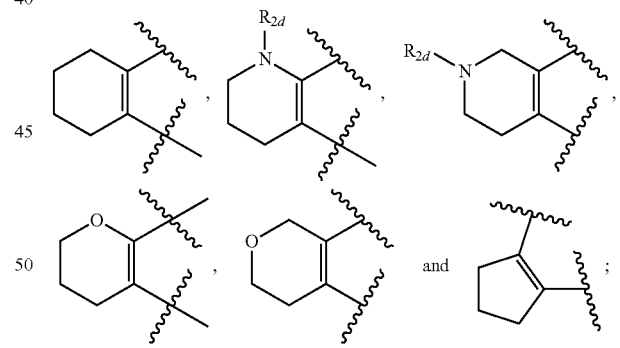

each optionally substituted with one or two substituents independently selected from OH, F, (C$_{1-4}$)alkyl and (C=O)O(C$_{1-4}$)alkyl, wherein a carbon in the (C$_{1-4}$) alkyl chain may bond to a carbon on Ring A and form a spirocyclic moiety, wherein (C$_{1-4}$)alkyl is optionally substituted with OH, methylpyrrolidinyl, NH$_2$ or oxo;

n is 0 or 1;

R$_{2d}$ is H or (C$_{1-4}$)alkyl; and

R$_3$ is methyl, F, CF$_3$, CHF$_2$ or CN;

or a pharmaceutically acceptable salt thereof.

13. A compound according to claim 1, wherein the compound is represented by Formula III:

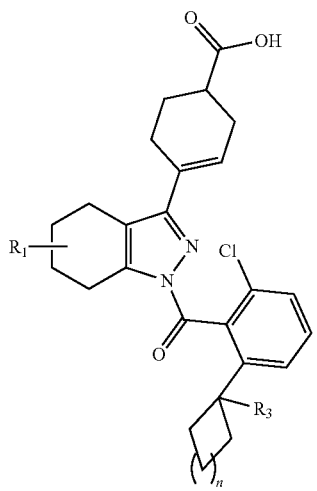

(III)

wherein:
R₁ is independently selected from OH, F, (C$_{1-4}$)alkyl and (C=O)O(C$_{1-4}$)alkyl, wherein a carbon in the (C$_{1-4}$) alkyl chain may bond to a carbon on the cyclohexyl ring and form a spirocyclic moiety, wherein (C$_{1-4}$)alkyl is optionally substituted with OH, methylpyrrolidinyl, NH₂ or oxo;
n is 0 or 1; and
R₃ is methyl, F, CF₃, CHF₂ or CN;
or a pharmaceutically acceptable salt thereof.

14. A compound according to claim 13, wherein the compound is in the form of a free acid.

15. A compound selected from:
4-(1-(2-chloro-6-cyclopropylbenzoyl)-4,5,6,7-tetrahydro-1H-indazol-3-yl)cyclohex-3-ene-1-carboxylic acid;
4-{1-[(2-chloro-6-cyclopropylphenyl)carbonyl]-1,4,5,7-tetrahydropyrano[3,4-c]pyrazol-3-yl}cyclohex-3-ene-1-carboxylic acid;
4-{1-[(2-chloro-6-cyclopropylphenyl)carbonyl]-1,4,5,6-tetrahydrocyclopenta[c]pyrazol-3-yl}cyclohex-3-ene-1-carboxylic acid;
4- (1-{[(2-chloro-6-methylcyclopropyl)phenyl)]carbonyl}-1,4,5,7-tetrahydropyrano[3,4-c]pyrazol-3-yl)cyclohex-3-ene-1-carboxylic acid;
4-(1-{[2-chloro-6-(1-methylcyclopropyl)phenyl]carbonyl}1,4,5,6-tetrahydrocyclopenta[c]pyrazol-3-yl)cyclohex-3-ene-1-carboxylic acid;
4-(1 -{[2-chloro-6-(1 -cyanocyclobutyl)phenyl]carbonyl}-1,4,5 ,6-tetrahydrocyclopenta[c]pyrazol-3-yl)cyclohex-3-ene-1-carboxylic acid;
(S)-4-(1-(2-Chloro-6-cyclobutylbenzoyl)-1,4,5,7-tetrahydropyrano[3,4-c]pyrazol-3-yl)cyclohex-3-ene-1-carboxylic acid;
(R)-4-(1-(2-Chloro-6-cyclobutylbenzoyl)-1,4,5,7-tetrahydropyrano[3,4-c]pyrazol-3-yl)cyclohex-3-ene-1-carboxylic acid;
(1R or S)-4-(1-{[2-chloro-6-(1-cyanocyclopropyl)phenyl]carbonyl}-1,4,5,7-tetrahydropyrano[3,4-c]pyrazol-3-yl)cyclohex-3-ene-1-carboxylic acid;
(1R or S)-4-(1{[2-chloro-6-(1-cyanocyclobutyl)phenyl]carbonyl}-1,4,5,7-tetrahydropyrano[3,4-c]pyrazol-3-yl)cyclohex-3-ene-1-carboxylic acid;
4-((R or S)-1-(2-chloro-6-cyclopropylbenzoyl)-4-methyl-4,5,6,7-tetrahydro-1H-indazol-3-yl) cyclohex-3-ene-1-carboxylic acid;
4-((R or S)-1-(2-chloro-6-cyclopropylbenzoyl)-6-(methoxycarbonyl)-4,5,6,7-tetrahydro-1H-indazol-3-yl)cyclohex-3-ene-1-carboxylic acid;
4-(1'-(2-chloro-6-cyclopropylbenzoyl)-2-oxo-1',4,4',5,5',7'-hexahydro-2H-spiro[furan-3,6'-indazol]-3'-yl)cyclohex-3-ene-1-carboxylic acid;
4-((R or S)-1-(2-chloro-6-cyclopropylbenzoyl)-6-(hydroxymethyl)-4,5,6,7-tetrahydro-1H-indazol-3-yl)cyclohex-3-ene-1-carboxylic acid;
4-((R or S)-1-(2-chloro-6-cyclopropylbenzoyl)-6-(hydroxymethyl)-4,5,6,7-tetrahydro-1H-indazol-3-yl)cyclohex-3-ene-1-carboxylic acid;
4-((R or S)-1-(2-chloro-6-cyclopropyl-3-fluorobenzoyl)-6-(hydroxymethyl)-4,5,6,7-tetrahydro-1H-indazol-3-yl)cyclohex-3-ene-1-carboxylic acid;
4-((R or S)-1-(2-chloro-6-(oxetan-3-yObenzoyl)-6-(hydroxymethyl)-4,5,6,7-tetrahydro-1H-indazol-3-yl)cyclohex-3-ene-1-carboxylic acid;
4-((R or S)-1-(2-chloro-6-(1-(trifluoromethyl)cyclopropyl)benzoyl)-6-(hydroxymethyl)-4,5,6,7-tetrahydro-1H-indazol-3-yl)cyclohex-3-ene-1-carboxylic acid;
4-((R or S)-1-(2-chloro-6-cyclopropylbenzoyl)-6-((R or S)-1-hydroxyethyl)-4,5,6,7-tetrahydro-1H-indazol-3-yl)cyclohex-3-ene-1-carboxylic acid;
4-((R or S)-1-(2-chloro-6-cyclopropylbenzoyl)-6-(hydroxymethyl)-6-methyl-4,5,6,7-tetrahydro-1H-indazol-3-yl)cyclohex-3-ene-1-carboxylic acid;
4-((R or S)-1-(2-chloro-6-cyclopropylbenzoyl)-6-hydroxy-4,5,6,7-tetrahydro-1H-indazol-3-yl)cyclohex-3-ene-1-carboxylic acid;
4-(1-(2-chloro-6-cyclopropylbenzoyl)-6-fluoro-4,5,6,7-tetrahydro-1H-indazol-3-yl)cyclohex-3-ene-1-carboxylic acid;
4-(1-(2-chloro-6-(1-(trifluoromethyl)cyclopropyl)benzoyl)-4,5,6,7-tetrahydro-1H-pyrazolo[4,3-b]pyridin-3-yl)cyclohex-3-ene-1-carboxylic acid;
(R or S)-4-((R or S)-1-(2-chloro-6-cyclopropylbenzoyl)-6-(hydroxymethyl)-4,5,6,7-tetrahydro-1H-indazol-3-yl)-1-methylcyclohex-3-ene-1-carboxylic acid;
4-((R or S)-6-(aminomethyl)-1-(2-chloro-6-cyclopropylbenzoyl)-4,5,6,7-tetrahydro-1H-indazol-3-yl)cyclohex-3-ene-1-carboxylic acid;
4-(1-(2-chloro-6-cyclopropylbenzoyl)-1,5,6,7-tetrahydropyrano[3,2-c]pyrazol-3-yl)cyclohex-3-ene-1-carboxylic acid;
1-(1-(2-chloro-6-cyclopropylbenzoyl)-4,5,6,7-tetrahydro-1H-indazol-3-yl)piperidine-4-carboxylic acid;
Trans-(3R or S,4R or S)-1-(1-(2-chloro-6-cyclopropylbenzoyl)-4,5,6,7-tetrahydro-1H-indazol-3-yl)-3-hydroxypiperidine-4-carboxylic acid;
Trans-(3R or S,4R or S)-1-(1-(2-chloro-6-(1-(trifluoromethyl)cyclopropyl)benzoyl)-4,5,6,7-tetrahydro-1H-indazol-3 -yl)-3 -hydroxypiperidine-4 -carboxylic acid; and
cis 1-(1-(2-chloro-6-cyclopropylbenzoyl)-4,5,6,7-tetrahydro-1H-indazol-3-yl)-3-hydroxypiperidine-4-carboxylic acid;
or a pharmaceutically acceptable salt thereof.

16. A pharmaceutical composition comprising a compound of claim 1 or a pharmaceutically acceptable salt thereof, and one or more pharmaceutically acceptable carriers.

17. A pharmaceutical composition comprising a compound of claim 15 or a pharmaceutically acceptable salt thereof, and one or more pharmaceutically acceptable carriers.

18. A method of treating a disorder selected from the group consisting of an autoimmune disorder and an inflammatory disorder, comprising administering to a subject in need thereof a therapeutically effective amount of a compound of claim 1 to treat the disorder.

19. The method of claim 18, wherein the disorder is an autoimmune disorder.

20. The method of claim 19, wherein the autoimmune disorder is rheumatoid arthritis, psoriasis, Crohn's disease, inflammatory bowel disease, multiple sclerosis, ankylosing spondylitis, systemic lupus erythematosus, chronic graft-versus-host disease, acute graft-versus-host disease, Celiac Sprue, idiopathic thrombocytopenic thrombotic purpura, myasthenia gravis, Sjogren's syndrome, scleroderma, ulcerative colitis, or epidermal hyperplasia.

21. The method of claim 18, wherein the disorder is an inflammatory disorder.

22. A method of inhibiting the activity of a RORγ, comprising exposing a RORγto an effective amount of a compound of claim 1 to inhibit the activity of said RORγ.

23. The method of claim 20, wherein the compound is a compound of claim 13.

\* \* \* \* \*